US012746238B2

(12) United States Patent
Jackson et al.

(10) Patent No.: US 12,746,238 B2
(45) Date of Patent: *Sep. 29, 2026

(54) SELECTED COMPOUNDS FOR TARGETED DEGRADATION OF BRD9

(71) Applicant: C4 THERAPEUTICS, INC., Watertown, MA (US)

(72) Inventors: Katrina L. Jackson, Weston, MA (US); Christopher G. Nasveschuk, Stoneham, MA (US); Rhamy Zeid, Arlington, MA (US); Ning Yin, Lexington, MA (US); Gesine Kerstin Veits, Somerville, MA (US); Moses Moustakim, Cambridge, MA (US); Jeremy L. Yap, Sudbury, MA (US); Minsheng He, Andover, MA (US); Robert T. Yu, Arlington, MA (US); Matthew J. Schnaderbeck, Methuen, MA (US); Kathleen Neville, Watertown, MA (US); Siyi Jiang, Watertown, MA (US); Meiqi Li, Watertown, MA (US); Qianwei Liu, Watertown, MA (US); Manjie Zheng, Watertown, MA (US); Jia Li, Watertown, MA (US); Liwei Zhang, Watertown, MA (US)

(73) Assignee: C4 THERAPEUTICS, INC., Watertown, MA (US)

( * ) Notice: Subject to any disclaimer, the term of this patent is extended or adjusted under 35 U.S.C. 154(b) by 372 days.

This patent is subject to a terminal disclaimer.

(21) Appl. No.: 18/600,097

(22) Filed: Mar. 8, 2024

(65) Prior Publication Data

US 2024/0245677 A1 Jul. 25, 2024

Related U.S. Application Data

(63) Continuation of application No. PCT/US2022/043129, filed on Sep. 9, 2022.

(60) Provisional application No. 63/328,660, filed on Apr. 7, 2022, provisional application No. 63/285,392, filed on Dec. 2, 2021, provisional application No. 63/242,430, filed on Sep. 9, 2021.

(51) Int. Cl.
*A61K 31/496* (2006.01)
*A61P 35/00* (2006.01)

(52) U.S. Cl.
CPC ............ *A61K 31/496* (2013.01); *A61P 35/00* (2018.01)

(58) Field of Classification Search
CPC ....... A61K 31/496; A61K 45/06; A61P 35/00; A61P 29/00; C07D 401/14
See application file for complete search history.

(56) References Cited

U.S. PATENT DOCUMENTS

| | | | |
|---|---|---|---|
| 5,635,517 | A | 6/1997 | Muller et al. |
| 6,306,663 | B1 | 10/2001 | Kenten et al. |
| 10,646,575 | B2 | 5/2020 | Phillips et al. |
| 10,660,968 | B2 | 5/2020 | Phillips et al. |
| 10,849,982 | B2 | 12/2020 | Phillips et al. |
| 10,905,768 | B1 | 2/2021 | Phillips et al. |
| 11,185,592 | B2 | 11/2021 | Phillips et al. |
| 11,254,672 | B2 | 2/2022 | Norcross et al. |
| 11,319,318 | B2 | 5/2022 | Martin et al. |
| 11,401,256 | B2 | 8/2022 | Norcross et al. |
| 11,407,732 | B1 | 8/2022 | Henderson et al. |
| 11,414,416 | B1 | 8/2022 | Ruppel et al. |
| 11,459,335 | B2 | 10/2022 | Phillips et al. |
| 11,524,949 | B2 | 12/2022 | Phillips et al. |
| 11,560,381 | B1 | 1/2023 | Ruppel et al. |
| 11,584,748 | B2 | 2/2023 | Nasveschuk et al. |
| 11,623,929 | B2 | 4/2023 | Nasveschuk et al. |
| 11,673,902 | B2 | 6/2023 | Nasveschuk et al. |
| 11,691,972 | B2 | 7/2023 | Nasveschuk et al. |
| 11,753,397 | B2 | 9/2023 | Henderson et al. |
| 11,787,802 | B2 | 10/2023 | Norcross et al. |
| 11,802,131 | B2 | 10/2023 | Norcross et al. |
| 11,992,531 | B2 | 5/2024 | Phillips et al. |
| 12,048,747 | B2 | 7/2024 | Phillips et al. |
| 12,048,748 | B2 | 7/2024 | Phillips et al. |
| 12,049,464 | B2 | 7/2024 | Nasveschuk et al. |
| 12,076,405 | B2 | 9/2024 | Phillips et al. |
| 12,091,397 | B2 | 9/2024 | Norcross et al. |
| 2014/0302523 | A1 | 10/2014 | Crews et al. |
| 2014/0356322 | A1 | 12/2014 | Crews et al. |
| 2015/0291562 | A1 | 10/2015 | Crew et al. |

(Continued)

FOREIGN PATENT DOCUMENTS

| | | | |
|---|---|---|---|
| WO | WO 2013/097052 | A1 | 7/2013 |
| WO | WO 2016/065139 | A1 | 4/2016 |

(Continued)

OTHER PUBLICATIONS

Bartlett et al. "The evolution of thalidomide and its IMiD derivatives as anticancer agents," Nat Rev Cancer, 4(4):314-322, Apr. 1, 2004.
Berndsen et al. "New insights into ubiquitin E3 ligase mechanism," Nat. Struct. Mol. Biol. Nature America, Inc., 21:4, 301-307, Apr. 4, 2014.
Bondeson et al. "Catalytic in vivo protein knockdown by small-molecule PROTACs" Nature Chemical Biology, 11:611-617, Jun. 10, 2015.
Brien, G. L. et al. Targeted degradation of BRD9 reverses oncogenic gene expression in synovial sarcoma, Elife e41305, Biochemistry and Chemical Biology, pp. 1-26, Nov. 15, 2018.

(Continued)

*Primary Examiner* — Rebecca L Anderson
*Assistant Examiner* — David M Shim
(74) *Attorney, Agent, or Firm* — Knowles Intellectual Property Strategies, LLC

(57) ABSTRACT

Selected BRD9 protein degradation compounds and morphic forms thereof are provided for the treatment of disorders mediated by BRD9, including but not limited to abnormal cellular proliferation.

21 Claims, 48 Drawing Sheets

(56) References Cited

U.S. PATENT DOCUMENTS

| | | | | |
|---|---|---|---|---|
| 2016/0022642 | A1 | 1/2016 | Crews et al. | |
| 2016/0045607 | A1 | 2/2016 | Crew et al. | |
| 2016/0046661 | A1 | 2/2016 | Gray et al. | |
| 2016/0058872 | A1 | 3/2016 | Crew et al. | |
| 2016/0176916 | A1 | 6/2016 | Bradner et al. | |
| 2016/0272639 | A1 | 9/2016 | Crew et al. | |
| 2018/0085465 | A1 | 3/2018 | Bradner et al. | |
| 2019/0247509 | A1* | 8/2019 | Buckley ................. | A61K 47/55 |
| 2021/0198256 | A1 | 7/2021 | Nasveschuk et al. | |
| 2022/0372016 | A1 | 11/2022 | Phillips et al. | |
| 2023/0019060 | A1 | 1/2023 | Nasveschuk et al. | |
| 2023/0082430 | A1 | 3/2023 | Henderson et al. | |
| 2023/0145336 | A1 | 5/2023 | Nasveschuk et al. | |
| 2023/0190760 | A1 | 6/2023 | Proia et al. | |
| 2023/0233692 | A1 | 7/2023 | Henderson et al. | |
| 2023/0279023 | A1 | 9/2023 | Phillips et al. | |
| 2023/0339902 | A1 | 10/2023 | Nasveschuk et al. | |
| 2023/0357180 | A1 | 11/2023 | Phillips et al. | |
| 2023/0372496 | A1 | 11/2023 | Nasveschuk et al. | |
| 2023/0416251 | A1 | 12/2023 | Nasveschuk et al. | |
| 2024/0018118 | A1 | 1/2024 | Nasveschuk et al. | |
| 2024/0018156 | A1 | 1/2024 | Nasveschuk et al. | |
| 2024/0051953 | A1 | 2/2024 | Nasveschuk et al. | |
| 2024/0076300 | A1 | 3/2024 | Nasveschuk et al. | |
| 2024/0109889 | A1 | 4/2024 | Norcross et al. | |
| 2024/0158418 | A1 | 5/2024 | Nasveschuk et al. | |
| 2024/0199581 | A1 | 6/2024 | Nasveshuk et al. | |
| 2024/0199638 | A1 | 6/2024 | Norcross et al. | |

FOREIGN PATENT DOCUMENTS

| | | | |
|---|---|---|---|
| WO | WO 2016/105518 | A1 | 6/2016 |
| WO | WO 2016/197032 | A1 | 12/2016 |
| WO | WO 2017/024317 | A2 | 2/2017 |
| WO | WO 2017/079267 | A1 | 5/2017 |
| WO | WO 2017/161119 | A1 | 9/2017 |
| WO | WO 2017/180417 | A1 | 10/2017 |
| WO | WO 2017/197046 | A1 | 11/2017 |
| WO | WO 2017/201069 | A1 | 11/2017 |
| WO | WO 2017/223452 | A1 | 12/2017 |
| WO | WO 2018/052945 | A1 | 3/2018 |
| WO | WO 2018/052949 | A1 | 3/2018 |
| WO | WO 2018/118947 | A1 | 6/2018 |
| WO | WO 2018/119357 | A1 | 6/2018 |
| WO | WO 2018/119441 | A1 | 6/2018 |
| WO | WO 2018/119448 | A1 | 6/2018 |
| WO | WO 2018/144649 | A1 | 8/2018 |
| WO | WO 2019/060742 | A1 | 3/2019 |
| WO | WO 2019/152440 | A1 | 8/2019 |
| WO | WO 2019/246423 | A1 | 12/2019 |
| WO | WO 2019/246430 | A1 | 12/2019 |
| WO | WO 2020/051235 | A1 | 3/2020 |
| WO | WO 2020/106915 | A1 | 5/2020 |
| WO | WO 2020/160192 | A1 | 8/2020 |
| WO | WO 2020/160193 | A2 | 8/2020 |
| WO | WO 2020/160196 | A1 | 8/2020 |
| WO | WO 2020/172655 | A1 | 8/2020 |
| WO | WO 2021/022163 | A2 | 2/2021 |
| WO | WO 2021/053495 | A1 | 3/2021 |
| WO | WO 2021/055295 | A1 | 3/2021 |
| WO | WO 2021/155100 | A1 | 8/2021 |
| WO | WO 2021/178920 | A1 | 9/2021 |

OTHER PUBLICATIONS

Clark, Peter G. K. et al. "LP99: Discovery and Synthesis of the First Selective BRD7/9 Bromodomain Inhibitor," Angewandte Chemie Int. Ed. Weinheim Bergstr Ger., 54, 6217-6221, Apr. 13, 2015.

C4 Therapeutics Presentation Phillips—"Small Molecule Driven Targeted Protein Degradation", ChemBio in the Hub 47, Cambridge, MA, 47 pages, Oct. 22, 2018.

C4 Therapeutics Presentation Fisher—"Targeted Protein Degradation", Targeted Protein Degradation Summit, Boston, MA, 39 pages, Oct. 24-25, 2018.

C4 Therapeutics Presentation Fisher—"Degrader Drugs: From cellular activity to in vivo pharmacology Discovery on Target," Boston, MA, 21 pages, Sep. 18, 2019.

C4 Therapeutics Presentation Nasveschuk—"Degrader Drug Space: What Rules?" HT-ADME Conference Cambridge, MA, 20 pages, Jun. 20, 2019.

C4 Therapeutics Press Release—Reports Third Quarter 2023 Financial Results and Recent Business Highlights; 2023, Nov. 1, 2023.

C4 Therapeutics CFT8634: An Oral BRD9 BiDAC™ Degrader, TPD Summit slides, Oct. 31, 2023.

C4 Therapeutics Agulnik, Mark et al. "Initial Results From A Phase 1 Study of CFT8634, A Novel Bifunctional Degradation Activating Compound (or BIDAC™ Degrader) of BRD9, in Synovial Sarcoma and SMARCB1-Null Tumors" CTOS poster, Nov. 1, 2023.

Chamberlain et al. "Structure of the human cereblon-DDB1-lenalidomide complex reveals basis for responsiveness to thalidomide analogs" Nature Structural and Molecule Biology, Nature American, Inc., 21(9):803-809, Aug. 10, 2014.

Corson et al. "Design and applications of bifunctional small molecules: Why two heads are better than one" ACS Chemical Biology, 3(11): 677-692, Oct. 23, 2008.

Fischer et al. "Structure of the DDB1-CRBN E3 ubiquitin ligase in complex with thalidomide" Nature, Macmillan Publisher Limited, 512:49-53, Jul. 16, 2014.

Fischer et al. "The Molecular Basis of $CRL4^{DDB2/CSA}$ Ubiquitin Ligase Architecture, Targeting, and Activation," Cell, 147:1024-1039, Nov. 23, 2011.

International Application No. PCT/US22/43129, filed Sep. 9, 2022; International Search Report and Written Opinion dated Nov. 22, 2022, 14 pages.

Karim, Rezaul M.D. et al. "Structural Basis of Inhibitor Selectivity in the BRD7/9 Subfamily of Bromodomains," Journal of Medicinal Chemistry, 63(6), 3227-3237, Feb. 24, 2020.

Lu et al. "Hijacking the E3 Ubiquitin Ligase Cereblon to Efficiently Target BRD4" Chemistry and Biology, 22(6):755-763, Jun. 4, 2015.

Martin, Laetitia J. et al. Structure-Based Design of an in Vivo Active Selective BRD9 Inhibitor, Journal of Medicinal Chemistry, 59(10), 4462-4475, Feb. 25, 2016.

Mcdaniel, Keith F. et al. Discovery of N-(4-(2,4-Difluorophenoxy)-3-(6-methyl-7-oxo-6,7-dihydro-1H-pyrrolo[2,3-c]pyridin-4-yl)phenyl)ethanesulfonamide (ABBV-075/Mivebresib), a Potent and Orally Available Bromodomain and Extraterminal Domain (BET) Family Bromodomain Inhibitor, Journal of Medicinal Chemistry, 60, 20, 8369-8384, Sep. 26, 2017.

Michel, B. C. et al. A noncanonical SWI/SNF complex is a synthetic lethal target in cancers driven by BAF complex perturbation, Nat Cell Biol 20, 1-11, Nov. 5, 2018.

Pérez-Salvia, M. et al. "Bromodomain inhibitors and cancer therapy: From structures to applications" Epigenetics, 12(5): 323-339, Dec. 2, 2016.

Pubchem, SID 386724358, [retrieved on Jul. 7, 2021] Retrieved from the Internet: <URL: https://pubchem.ncbi.nim.nih.gov/substance/386724358> Available Date: Nov. 2, 2019.

Zengerle et al. "Selective Small Molecule Induced Degradation of the BET Bromodomain Protein BRD4" ACS Chem. Biol., 10:1770-1777, Jun. 2, 2015.

Zoppi, Vittoria et al. "Iterative Design and Optimization of Initially Inactive Proteolysis Targeting Chimeras (PROTACs) Identify VZ185 as a Potent, Fast, and Selective von Hippel-Lindau (VHL) Based Dual Degrader Probe of BRD9 and BRD7," Journal of Medicinal Chemistry, 62(2), 699-726, Dec. 12, 2018.

U.S. Appl. No. 18/240,231, filed Aug. 30, 2023, Henderson et al.

U.S. Appl. No. 18/642,602, filed Apr. 22, 2024, Phillips et al.

U.S. Appl. No. 18/774,794, filed Jul. 16, 2024, Phillips et al.

U.S. Appl. No. 18/774,801, filed Jul. 16, 2024, Phillips et al.

U.S. Appl. No. 18/775,662, filed Jul. 17, 2024, Phillips et al.

U.S. Appl. No. 18/797,261, filed Aug. 7, 2024, Henderson et al.

U.S. Appl. No. 18/806,363, filed Aug. 15, 2024, Norcross et al.

* cited by examiner

XRPD overlay of polymorphs and pseudo-polymorphs

Degradation of BRD4 by Compound in HEK293T.92 Cell Line

Growth Inhibition of SW982 Treated with Compound 1 for 144 Hours

Viability of HepG2 Cell Following 72-Hour Treatment with Compound 1

SELECTED COMPOUNDS FOR TARGETED DEGRADATION OF BRD9

CROSS-REFERENCE TO RELATED APPLICATIONS

This application is a continuation of U.S. International Patent Application No. PCT/US2022/043129, filed in the U.S. Receiving Office on Sep. 9, 2022, which claims the benefit of U.S. Provisional Application 63/242,430 filed Sep. 9, 2021, U.S. Provisional Application 63/285,392 filed Dec. 2, 2021, and U.S. Provisional Application 63/328,660 filed Apr. 7, 2022. The entirety of each of these applications is incorporated by reference for all purposes.

FIELD OF THE INVENTION

This invention provides selected BRD9 degrading compounds for therapeutic applications as described further herein.

BACKGROUND

Bromodomain containing proteins (BRD) such as BRD9 are proteins that recognize acetylated lysine residues such as those on the N-terminals of histones. BRDs are evolutionarily conserved and present in diverse nuclear proteins comprising HATs (GCN5, PCAF), ATP-dependent chromatin-remodeling complexes (BAZ1B), helicases (SMARCA), methyltransferases (MLL, ASH1L), transcriptional coactivators (TRIM/TIF1, TAFs) transcriptional mediators (TAF1), nuclear-scaffolding proteins (PB1), and the BET family. (Muller S, Filippakopoulos P, Knapp S., Bromodomains as therapeutic targets, Expert Rev Mol Med. 2011, 13(29)). Bromodomain containing proteins have a number of functions that mediate transcription and coactivation, and thus are involved in cellular proliferation.

Bromodomain-containing protein 9 (BRD9) is a component of the non-canonical BRG1/BRM-associated factor (ncBAF) chromatin remodeling complex. SMARCB1 is a component of the canonical BRG1/BRM associated factor (cBAF) with potent tumor suppressor function. Studies have shown that BRD9 is preferentially used by cancer cells that harbor SMARCB1 abnormalities such as malignant rhabdoid tumors and several specific types of sarcoma. Synovial Sarcoma is a rare, soft tissue malignancy, it is characterized by the presence of a unique chromosomal translocation, resulting in the formation of the fusion gene SS18-SSX. In synovial sarcoma, SS18-SSX fusion presence drives the disruption of SMARCB1 function, resulting in BRD9 dependence. In SMARCB1 deleted solid tumors (e.g., malignant rhabdoid tumor, epithelioid sarcoma, chordoma, etc.), SMARCB1 loss drives disruption of SMARCB1 function, resulting in BRD9 dependence. BRD9-containing complexes bind to both active promoters and enhancers, where they contribute to gene expression. Loss of BRD9 results in gene expression changes related to apoptosis regulation, translation, and development regulation. BRD9 is essential for the proliferation of SMARCB1-deficient cancer cell lines, suggesting it can be a therapeutic target for these lethal cancers. (Xiaofeng Wang et. al., "BRD9 defines a SWI/SNF sub-complex and constitutes a specific vulnerability in malignant rhabdoid tumors," Nature Communications, 2019, 10 (1881)). BRD9 is also a critical target required in acute myeloid leukemia, "Nature Chemical Biology, 2016, 101038/nchembio.2115." In addition to the role of BRD9 as a functional dependency in certain cancers, BRD9 also plays a pivotal role in immune cells as a regulator of regulatory T cells (Tregs) via transcriptional control of Foxp3 target genes, "BioRxiv, 10.1101/2020.02.26.964981.

Studies have also shown that the newly identified noncanonical BAF (ncBAF) complex is a distinct entity made up of a unique combination of sub-units as compared to the canonical BAF (cBAF) and polybromo (pBAF) complexes. (Alpsoy, A. & Dykhuizen, E. C. Glioma tumor suppressor candidate region gene 1 (GLTSCR1) and its paralog GLTSCR1-like form SWI/SNF chromatin remodeling subcomplexes. *J Biol Chem* 293, 3892-3903 (2018)). Notably, BRD9 incorporates selectively into the noncanonical BAF (ncBAF) complex while SMARCB1 is absent. In a SMARCB1 perturbed setting (for example, cBAF complex eviction, deletion, truncation, or inactivation), the cBAF complex function is compromised leading to a unique so-called synthetic lethal dependency on ncBAF complex function. In turn, BRD9 is essential for ncBAF complex function and thus BRD9 is a unique dependency in SMARCB1 perturbed cancers (Michel, B. C. et al. A non-canonical SWI/SNF complex is a synthetic lethal target in cancers driven by BAF complex perturbation. *Nat Cell Biol* 20, 1-11 (2018) and Brien, G. L. et al. Targeted degradation of BRD9 reverses oncogenic gene expression in synovial sarcoma. *Elife* 7, e41305 (2018)).

Bromodomain-containing protein 7 (BRD7) is also a subunit of PBAF SWI/SNF with structural similarity to BRD9. Publications describing BRD7 and ligands to BRD7 and BRD9 include: a paper by Pérez-Salvia M. et al, titled "Bromodomain inhibitors and cancer therapy: From structures to applications" Epigenetics. 2017; 12(5): 323-339; 99; and a paper by Clark P. G. K., et al., titled "Discovery and Synthesis of the First Selective BRD7/9 Bromodomain Inhibitor" Angew Chem Weinheim Bergstr Ger. 2015, 127 (21): 6315-6319.

Because of BRD9's role in cancer proliferation there has been interest in the development of BRD9 inhibitors for the treatment of cancers including those described in: WO 2014/114721, WO 2016/077375, WO 2016/077378, WO 2016/139361, WO 2019/152440, a paper by Martin L. J. et. al., (*Journal of Medicinal Chemistry* 2016, 59, 4462-4475) titled "Structure-Based Design of an in Vivo Active Selective BRD9 Inhibitor"; a paper by Theodoulou N. H. et. al., (*Journal of Medicinal Chemistry* 2015, 59, 1425-1439) titled "Discovery of I-BRD9, a selective Cell Active Chemical Probe for Bromodomain Containing Protein 9 Inhibition"; and a paper by Clack P. et. al., (*Angewandte Chemie,* 2015, 127, 6315-6319).

Research has also been reported on protein degrading compounds that have an E3 ligase binding portion and a BRD9 binding portion wherein the BRD9 binding ligand binds to BRD9 and brings it to the ligase for ubiquitination followed by degradation by the proteasome. See, for example, WO 2017/223452, WO 2019/152440, WO 2019/246423, WO 2019/246430, WO 2020/051235, WO 2020/106915, WO 2020/160192, WO 2020/160193, WO 2020/160196, WO 2020/160198, WO 2021/022163, WO 2021/055295, U.S. Pat. Nos. 11,285,218 and 11,414,416.

C4 Therapeutics' WO 2021/178920 describes compounds for the targeted degradation of BRD9 and their use to treat a range of disorders.

In light of the serious disorders mediated by BRD9, and notably cancer, there remains a significant need for new compounds and methods that treat disorders mediated by BRD9.

SUMMARY OF THE INVENTION

Compound 1 is a small pharmaceutical molecule that binds with high affinity to BRD9 and cereblon E3 ligase, which results in the efficient ubiquitination of BRD9 by cereblon and degradation by the proteasome.

(Compound 1)

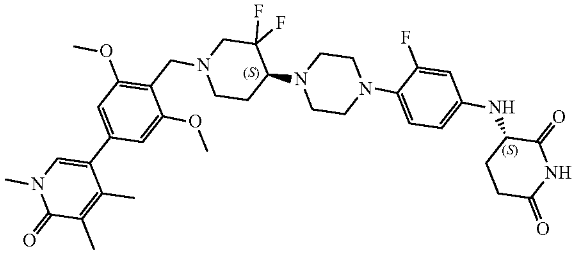

Compound 1, (S)-3-((4-(4-((S)-1-(2,6-dimethoxy-4-(1,4,5-trimethyl-6-oxo-1,6-dihydropyridin-3-yl)benzyl)-3,3-difluoropiperidin-4-yl)piperazin-1-yl)-3-fluorophenyl)amino)-piperidine-2,6-dione, was first disclosed in WO 2021/178920 filed by C4 Therapeutics, Inc. Compound 1 rapidly, selectively, and durably degrades BRD9 resulting in potent activity in cancer cells, for example including but not limited to, synovial sarcoma and SMARCB1 perturbed cancer. Compound 1 exhibits a high degree of selectivity for BRD9 degradation over the degradation of other bromodomain containing proteins. For example, Compound 1 has a DC50 (e.g., degradation of 50% of the protein) of greater than 1 μM when tested against BRD4, an important transcriptional and epigenetic regulator, and BRD7 (see Example 2), whereas the DC50 of Compound 1 against BRD9 is in the range of 2-75 nM. This strong selectivity is maintained over long time periods. While Compound 1 effectively degrades BRD9 in 2 hours or less it does not appreciably degrade BRD4 and BRD7 when assayed over 24 hours. In certain embodiments Compound 1 is selective for the treatment of SMARCB1 perturbed human cancer lines (for example Compound 1 is active in Yamato-SS, HS-SY-II, and A204 cell lines while being inactive in SW982 cell lines). As a result of this selectivity Compound 1 can provide anticancer effect while having minimal effects on normal cells.

Compound 1 can be administered in an effective amount to treat a range of tumors that are mediated by BRD9. Advantageously, it can be administered orally, in contrast to many anti-cancer therapies that have to be administered intravenously. In certain nonlimiting embodiments, Compound 1 is administered orally once, twice, or three times a day to a patient with a BRD9 mediated disorder such as a cancer. Non-limiting examples of twice a day doses include a dose of at least about 0.1 mg, 0.5 mg, 1 mg, 2 mg, 4 mg, 8 mg, 10 mg, 25 mg, 50 mg, 80 mg, 110 mg, 120 mg, 150 mg, 175 mg or 200 mg up to 250-300 mg, per dose. In other embodiments, the dosage is not more than about 1 mg, 2 mg, 4 mg, 8 mg, 10 mg, 25 mg, 50 mg, 80 mg, 110 mg, 120 mg, 150 mg, 175 mg or 200 mg, 250 mg or 300 mg. In other embodiments Compound 1 is administered once a day to a patient with a BRD9 mediated disorder. Non-limiting examples of once a day doses include a dose of at least about 15 mg, 30 mg, 50 mg, 80 mg, 120, 150 or 200 mg per dose.

In other embodiments, an effective amount of the active agent is administered once a day including but not limited to at a dose of at least about 0.1 mg, 0.5 mg, 1 mg, 2 mg, 4 mg, 8 mg, 10 mg, 25 mg, 50 mg, 80 mg, 110 mg, 120 mg, 150 mg, 175 mg or 200 mg up to 250-300 mg, per dose.

Treatment of BRD9 mediated disorders with Compound 1 provides advantages over traditional treatment with a BRD9 inhibitor. For example Compound 1 can a) overcome resistance in certain cases; b) prolong the kinetics of drug effect by destroying BRD9 thus requiring resynthesis of the protein even after the compound has been metabolized; c) target all functions of BRD9 at once rather than a specific catalytic activity or binding event; d) exhibit improved selectivity (for example BRD9 degradation vs BRD7 degradation); and/or e) have increased potency compared to inhibitors due to the possibility of Compound 1 acting catalytically. These advantages may also be achieved by treating the BRD9 mediated disorder with Compound 1 and an additional therapeutic agent.

The invention provides an improved and advantageous method for the synthesis of Compound 1. Advantages of the method for the synthesis according to the present invention include better scalability and reproducibility of the synthesis of Compound 1, easier isolation and separation of Compound 1, and higher yield and purity of Compound 1 achieved by using the method according to the present invention.

A novel advantageous highly stable morphic form of Compound 1 has been discovered. This morphic form (Form N) stands out from over a dozen other crystalline Compound 1 morphic forms because of its superior properties, including for example, improved flowability, scalability, stability, and/or hygroscopicity. Compound 1 Form N can be administered to a patient in need thereof to treat a BRD9-mediated disorder as a neat chemical, for example a powder filled capsule, or as part of a pharmaceutical composition. Other morphic forms of Compound 1 are also described herein, including for example a new urea cocrystal of Compound 1.

The invention also provides a method for the manufacture of new advantageous morphic Form N. Morphic Form N is a particularly stable morphic form of Compound 1 and may be obtained by equilibration of other morphic forms of the invention, such as Pattern A or G, in a solvent, such as acetone or acetone/water mixtures.

Compound 1 was investigated with fourteen acids and two coformers (co-crystallizing agents) in acetone, methanol, ethyl acetate, and acetonitrile. Compound 1 did not form a crystalline solid with any of the tested acids. However, Compound 1 did form a highly crystalline cocrystal with urea. This cocrystal has been assigned Form P and is shown in FIG. 22. The Compound 1: Urea cocrystal has a stoichiometry of about 2 molecules of Compound 1 per molecule of urea. Form P is highly stable, scalable, and reproducible. Morphic Form P is distinguished by high crystallinity and good chemical stability.

Non-limiting examples of new methods that are presented herein that include Compound 1 or a morphic form of Compound 1, for example Compound 1 Form N, include:

1. The treatment of a disorder mediated by BRD9, for example synovial sarcoma, malignant rhabdoid tumor, atypical teratoid rhabdoid tumor, cribriform neuroepithelial tumor, renal medullary carcinoma, epithelioid sarcoma, epithelioid malignant peripheral nerve sheath tumor, schwannomas in familial schwannomatosis, chordoma, myoepithelial carcinoma, sinonasal carcinoma, or a SMARCB1 perturbed cancer, comprising administering an effective amount of a morphic form of Compound 1, for example Compound 1 Form N, to a patient in need thereof.
2. The treatment of a disorder mediated by BRD9 comprising administering an effective amount of Compound 1 or a morphic form of Compound 1, for example Compound 1 Form N, or a pharmaceutically acceptable salt thereof to a patient in need thereof, wherein the disorder mediated by BRD9 is selected from epithelioid sarcoma, epithelioid malignant peripheral nerve sheath tumor, schwannomas in familial schwannomatosis, atypical malignant teratoid rhabdoid tumor, and cribriform neuroepithelial tumor.

3. The treatment of a unresectable disorder mediated by BRD9, for example an unresectable, relapsed, and/or refractory SMARCB1-perturbed cancer, comprising administering an effective amount of Compound 1 or a morphic form of Compound 1, for example Compound 1 Form N, or a pharmaceutically acceptable salt thereof to a patient in need thereof, wherein the disorder mediated by BRD9 is selected from epithelioid sarcoma, epithelioid malignant peripheral nerve sheath tumor, schwannomas in familial schwannomatosis, atypical malignant teratoid rhabdoid tumor, and cribriform neuroepithelial tumor.

4. The treatment of a disorder mediated by BRD9 comprising administering an effective amount of Compound 1 or a morphic form of Compound 1, for example Compound 1 Form N, or a pharmaceutically acceptable salt thereof and an effective amount of an additional therapeutically active agent to a patient in need thereof, wherein the additional therapeutically active agent is selected from ixazomib, anlotinib, itacitinib, cixutumumab, ixabepilone, exatecan mesylate, brostallicin, tazemetostat, and sapanisertib.

5. The treatment of a disorder mediated by BRD9 comprising administering an effective amount of Compound 1 or a morphic form of Compound 1, for example Compound 1 Form N, or a pharmaceutically acceptable salt thereof and an effective amount of a combination with additional therapeutically active agent to a patient in need thereof, wherein the combination of additional therapeutically active agents are selected from an active agent as described herein with any of the two or three additional combination agents:

a. sintilimab, doxorubicin, and ifosfamide;
b. cixutumumab and doxorubicin;
c. cixutumumab and temsirolimus;
d. lurbinectedin and irinotecan;
e. sorafenib and dacarbazine;
f. pazopanib and gemcitabine;
g. doxorubicin and ribociclib;
h. tazemetostat, itraconazole, and rifampin;
i. cyclophosphamide and fludarabine;
j. ifosfamide, carboplatin, and etoposide;
k. doxorubicin, vincristine, and cyclophosphamide;
l. doxorubicin hydrochloride, etoposide, and ifosfamide; and
m. trofosfamide, idarubicin, and etoposide.

6. The treatment of a soft tissue sarcoma comprising administering an effective amount of a morphic form of Compound 1, for example Compound 1 Form N, to a patient in need thereof.

7. The treatment of clear cell renal cell carcinoma comprising administering an effective amount of Compound 1 or a morphic form of Compound 1, for example Compound 1 Form N, or a pharmaceutically acceptable salt thereof to a patient in need thereof.

8. The treatment of interferon-mediated inflammation comprising administering an effective amount of Compound 1 or a morphic form of Compound 1, for example Compound 1 Form N, or a pharmaceutically acceptable salt thereof to a patient in need thereof.

9. A method of reducing the risk of recurrence of disorder mediated by BRD9, for example, a soft tissue sarcoma or synovial sarcoma, comprising administering an effective amount of Compound 1 or a morphic form of Compound 1, for example Compound 1 Form N, or a pharmaceutically acceptable salt thereof, to a patient in need thereof.

10. A method for preventing recurrence of a soft tissue sarcoma comprising administering an effective amount of Compound 1 or a morphic form of Compound 1, for example Compound 1 Form N, or a pharmaceutically acceptable salt thereof, to a patient in need thereof.

Other diastereomers of Compound 1, or its pharmaceutically acceptable salt, can also be used in the methods described above to treat the disorders described herein. In certain embodiments the compound for use in treating a disorder described herein is selected from:

(Compound 1)

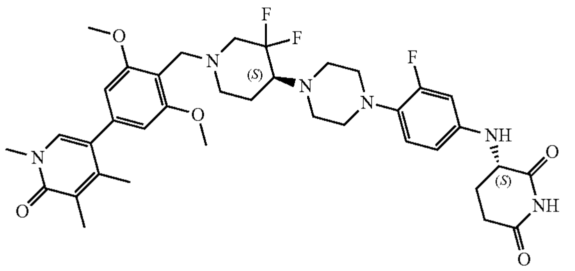

(Compound 2)

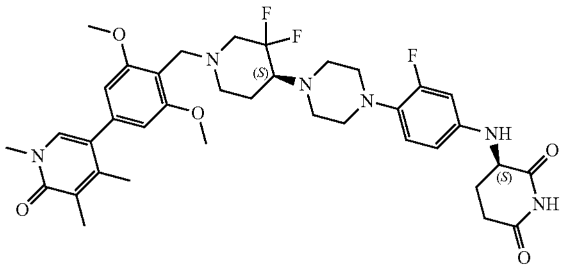

(Compound 3)

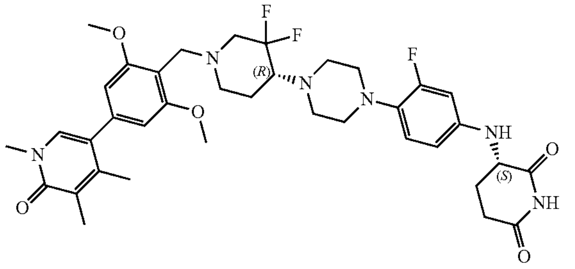

(Compound 4)

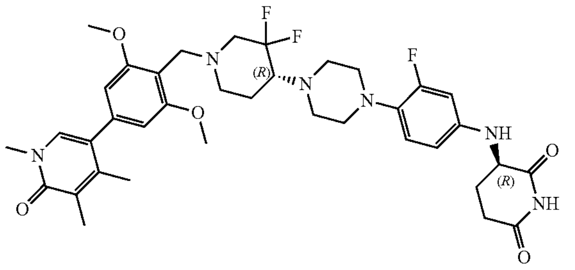

-continued (Compound 5)

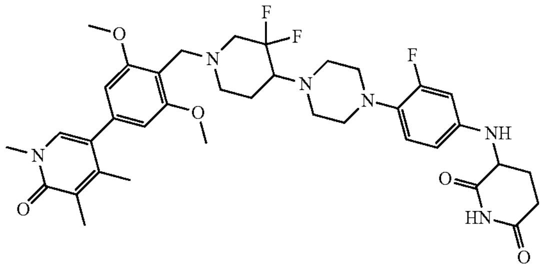

or a pharmaceutically acceptable salt thereof.

In certain embodiments, a method of treatment is provided comprising administering an effective amount of a morphic form of Compound 1 to a patient in need thereof, for example a human, optionally in a pharmaceutically acceptable carrier. For example, in certain embodiments, a morphic form of Compound 1 is administered to a human to treat a cancer, for example synovial sarcoma, advanced synovial sarcoma, or metastatic synovial sarcoma. In certain embodiments a morphic form of Compound 1 is administered to a patient with a SS18-SSX translocation cancer. In certain embodiments a morphic form of Compound 1 is administered to a patient with a SMARCB1 perturbed cancer. In certain embodiments a morphic form of Compound 1 is administered to a patient with a metastatic SMARCB1 perturbed cancer or advanced SMARCB1 cancer. In certain embodiments a morphic form of Compound 1 is administered to a patient with epithelioid sarcoma. In certain embodiments a morphic form of Compound 1 is administered orally two or more times a day. In certain of any of the above aspects, the morphic form is Form N.

In certain embodiments a morphic form of Compound 1 (including but not limited to Form N) is used to treat a rhabdoid tumor. In certain embodiments the rhabdoid tumor is a tumor occurring in the central nervous system, soft tissue, viscera, or the kidney, for example an atypical malignant teratoid rhabdoid tumor occurring in the central nervous system, soft tissue, viscera, or the kidney. In certain embodiments a morphic form of Compound 1 is administered to a patient with a malignant rhabdoid tumor.

In certain embodiments an effective amount of Compound 1 is administered to a patient in need thereof with a locally advanced or metastatic SMARCB1-perturbed cancer which is relapsed and/or refractory and unresectable. In certain embodiments an effective amount of Compound 1 is administered to a patient in need thereof with a locally advanced SMARCB1-perturbed cancer which is relapsed and/or refractory and unresectable and/or metastatic.

Other aspects of the present invention provide a compound as described herein, or an enantiomer, diastereomer, or stereoisomer thereof, or pharmaceutically acceptable salt, hydrate, or solvate thereof, or a pharmaceutical composition, for use in the manufacture of a medicament for treating or preventing a BRD9 mediated disorder.

In certain embodiments, a compound described herein is useful to treat a disorder comprising an abnormal cellular proliferation, such as a tumor or cancer, wherein BRD9 is an oncogenic protein or a signaling mediator of an abnormal cellular proliferative pathway and its degradation decreases abnormal cell growth.

Other features and advantages of the present application will be apparent from the following detailed description.

DETAILED DESCRIPTION OF THE INVENTION

I. Definitions

Figure 1:
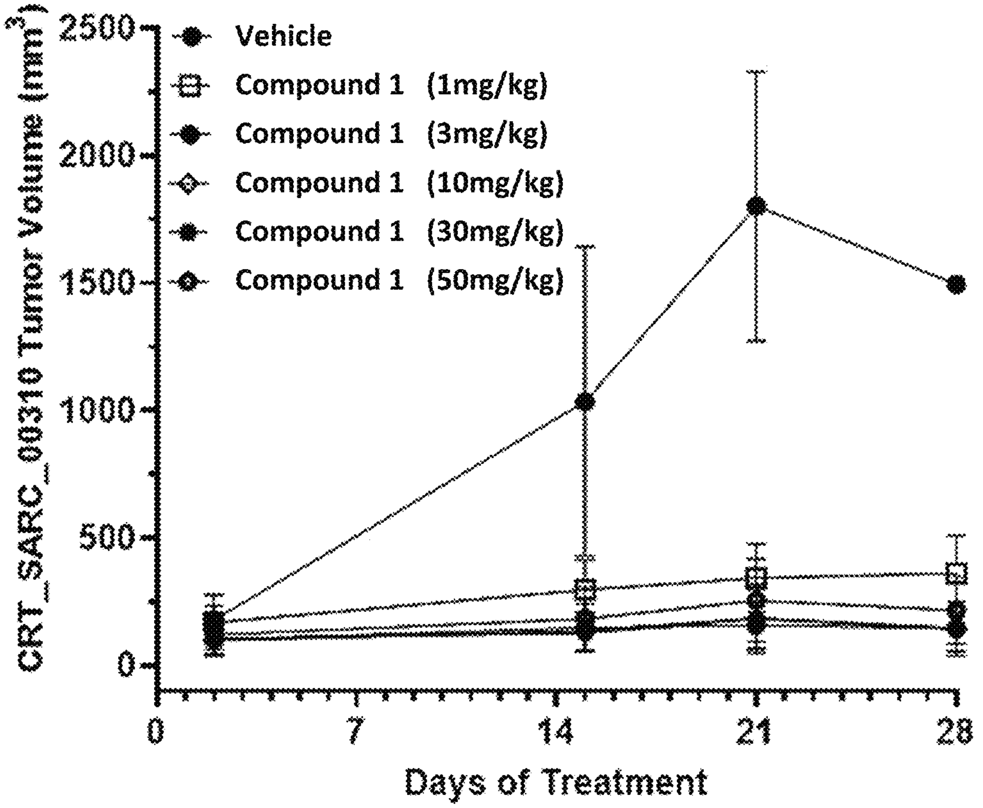
FIG. 1 is a graph demonstrating the effect of Compound 1 at various doses on female NOG (NOD/Shi-scid IL2rgnull) mice bearing an established CRT_SARC_00310 synovial sarcoma PDX. The mice were administered Compound 1 (1, 3, 10, 30, or 50 mg/kg/day) by oral gavage as indicated in the figure legend. Tumors were measured using the Aspect Imaging M3 MRI and tumor volumes quantified as $mm^3$ using VivoQuant software. Data are expressed as mean tumor volumes±SEM. The experimental procedure is provided in Example 3.

Compounds are described using standard nomenclature. Unless defined otherwise, all technical and scientific terms used herein have the same meaning as is commonly understood by one of skill in the art to which this invention belongs.

The compounds in any of the Formulas described herein may be in the form of a racemate, enantiomer, mixture of enantiomers, diastereomer, mixture of diastereomers, tautomer, N-oxide, isomer; such as rotamer, as if each is specifically described unless specifically excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^{2}H$, $^{3}H$, $^{11}C$, $^{13}C$, $^{14}C$, $^{15}N$, $^{17}O$, $^{18}O$, $^{18}F$ $^{31}P$, $^{32}P$, $^{35}S$, $^{36}Cl$, and $^{125}I$ respectively. In one non-limiting embodiment, isotopically labelled compounds can be used in metabolic studies (with, for example $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any compound described herein. In one non-limiting embodiment, the substitution of a hydrogen atom for a deuterium atom occurs within one or more groups of the molecule. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The compound of the present invention may form a solvate with a solvent (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO (dimethyl sulfoxide). A solvate can be in a liquid or solid form.

A dash ("-") that is not between two letters or symbols is used to indicate a point of attachment for a substituent. For example, $-(C{=}O)NH_2$ is attached through carbon of the carbonyl ($C{=}O$) group.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein, means an amount which provides a therapeutic or prophylactic benefit.

As used herein "endogenous" refers to any material from or produced inside an organism, cell, tissue or system.

As used herein, the term "exogenous" refers to any material introduced from or produced outside an organism, cell, tissue or system.

By the term "modulating," as used herein, is meant mediating a detectable increase or decrease in the level of a response in a patient compared with the level of a response in the patient in the absence of a treatment or compound, and/or compared with the level of a response in an otherwise identical but untreated patient. The term encompasses perturbing and/or affecting a native signal or response thereby mediating a beneficial therapeutic response in a patient, preferably, a human.

"Parenteral" administration of a pharmaceutical composition includes, e.g., subcutaneous (s.c.), intravenous (i.v.), intramuscular (i.m.), intrasternal injection, or infusion techniques.

To "treat" a disease as the term is used herein, means to reduce the frequency or severity of at least one sign or symptom of a disease or disorder experienced by a patient (i.e. palliative treatment) or to decrease a cause or effect of the disease or disorder (i.e. disease-modifying treatment).

Throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, "pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, "pharmaceutically acceptable salt" is a derivative of the disclosed compound in which the parent compound is modified by making an inorganic or organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable carrier" means a carrier or excipient that is useful in preparing a pharmaceutical composition/combination that is generally safe, non-toxic and neither biologically nor otherwise inappropriate for administration to a patient, typically a human. In one embodiment, an excipient is used that is acceptable for veterinary use.

A "patient" or "subject" is a human or non-human animal in need of treatment or prevention of any of the disorders as specifically described herein, for example that is modulated by a natural (wild-type) or modified (non-wild type) protein that can be degraded according to the present invention, resulting in a therapeutic effect. As described further herein, the word patient or subject typically refers to a human patient or subject unless it is clear from the context or wording that the disclosure is meant to include a non-human animal. Typically, the patient is a human. In an alternative embodiment, the patient or subject is a non-human animal in need of such therapy and responsive thereto.

A "therapeutically effective amount" of a pharmaceutical composition/combination of this invention means an amount effective, when administered to a patient, typically a human patient, to provide a therapeutic benefit such as an amelioration of symptoms or reduction or diminution of the disease itself.

"Unresectable cancer", and unless otherwise noted, refers to a solid tumor that cannot be completely removed. In an alternative embodiment unresectable cancer is a solid tumor that can only be partially removed by surgery.

Unless otherwise defined, all technical and scientific terms used herein have the same meaning as commonly understood by one of ordinary skill in the art to which this application belongs. In the specification, singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

II. Compound 1 Morphic Forms

Compound 1 as a free base was investigated in a variety of crystallization conditions. Unless specified otherwise the starting material in each experiment is Form E. Conditions tested included equilibration at 25° C. and 50° C., equilibration under temperature cycling between 5° C. and 50° C., crystallization from hot saturated solutions by slow and fast cooling, precipitation by addition of anti-solvent, slow evaporation, fast evaporation, vapor diffusion experiments and heat-cool DSC. Relative stability of identified polymorphs was investigated by competitive water activity study, competitive equilibration experiments, variable temperature XRPD and variable humidity XRPD. The morphic forms were evaluated for their bulk stability, hygroscopicity and behaviors under compression and ball-milling.

Including the salts described in Section III 15 crystalline morphic forms were discovered, including 6 anhydrates, named as Form G, Form H, Form I, Form J, Form M, Form O, 8 hydrates, named as Form A, Form B, Form C, Form D, Form E, Form F, Form K, and Form N, and 1 hetero-solvate, named as Form L.

Figure 18:
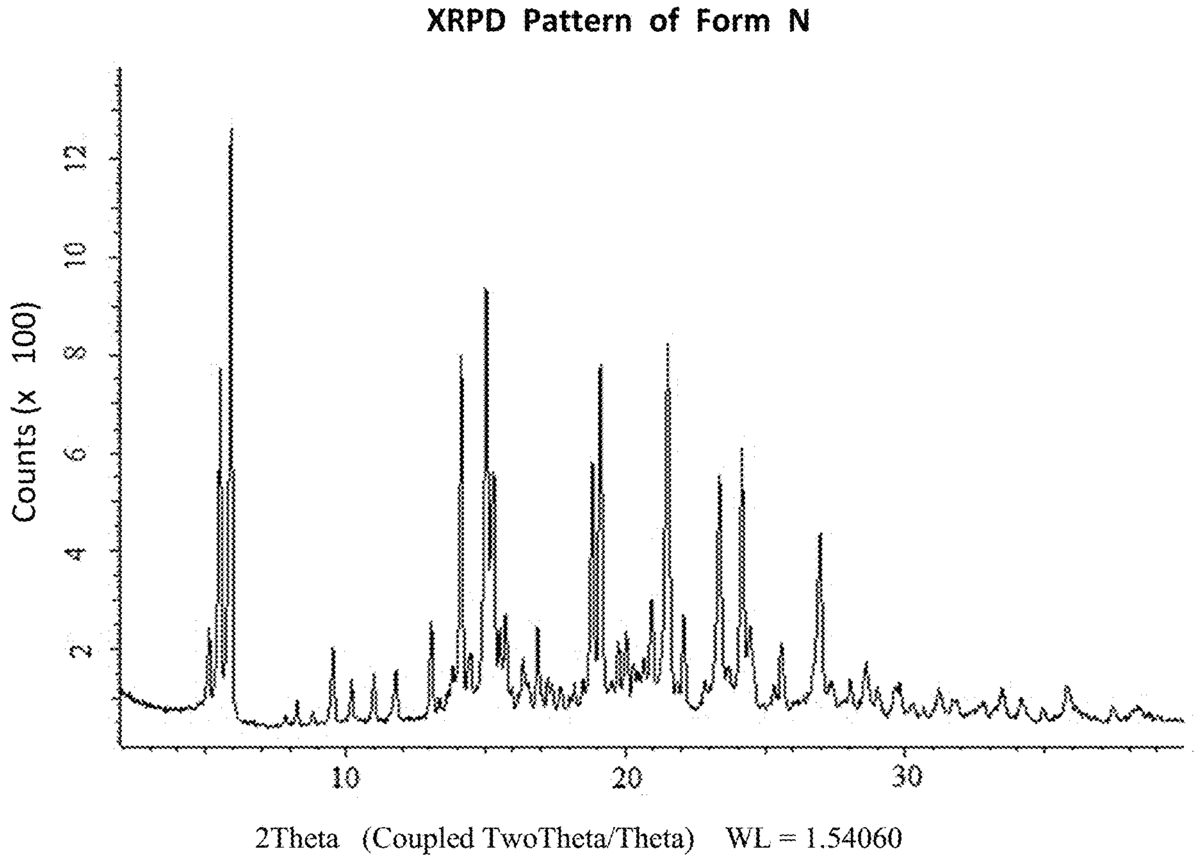
FIG. 18 depicts the XRPD pattern of Compound 1 Form N: The Compound 1 Form N XRPD pattern exhibits sharp peaks, indicating the sample was composed of crystalline material.
Figure 19:
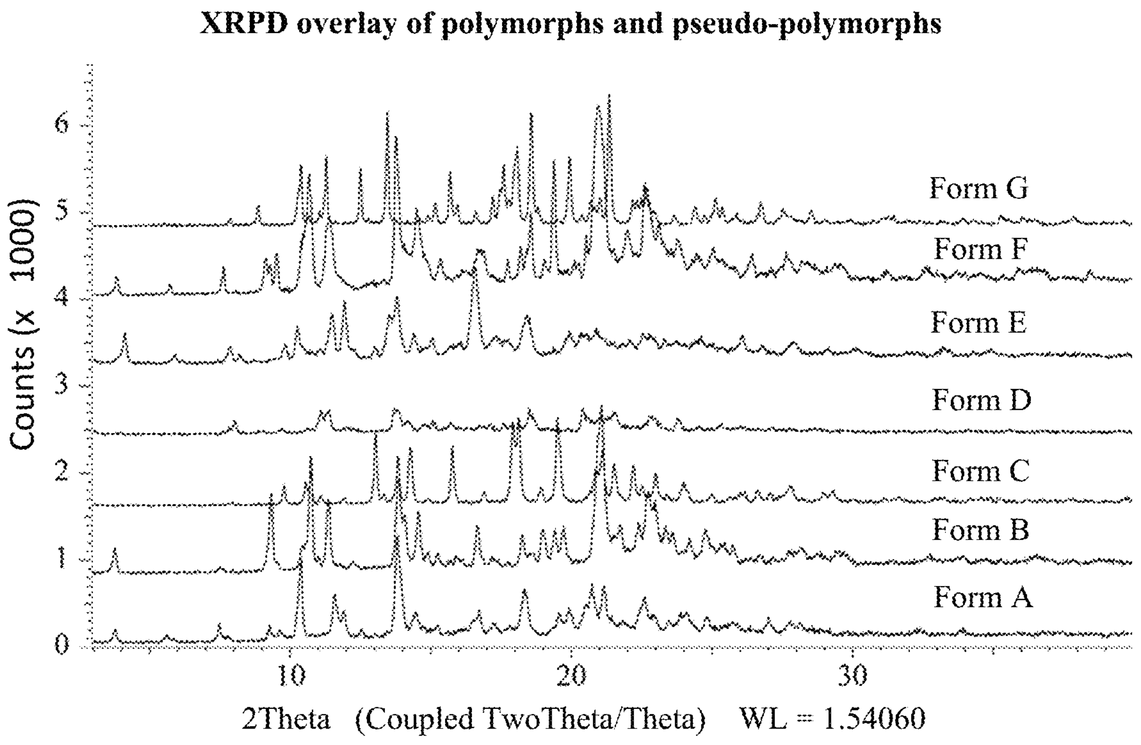
FIG. 19 depicts the overlay of polymorphs and psuedopolymorphs A, B, C, D, E, F, and G.
Figure 20:
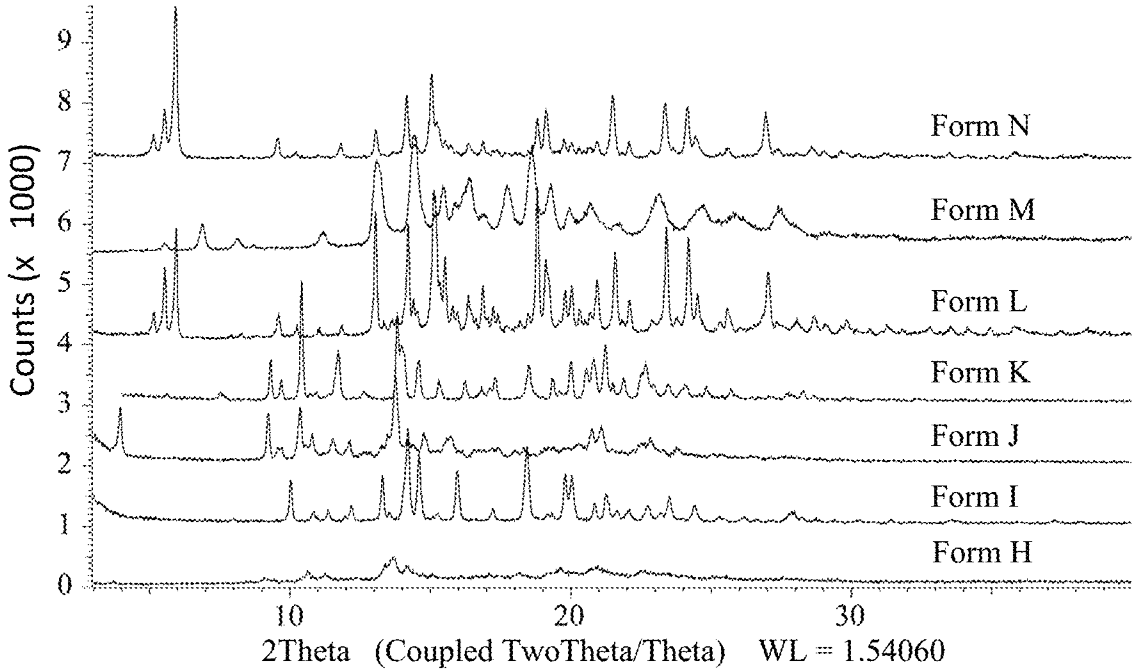
FIG. 20 depicts the overlay of polymorphs and psuedopolymorphs H, I, J, K, L, M, and N.

Form N is a hydrate. In certain embodiments Form N is an isomorphic crystal structure to hetero-solvate Form L. It is the stable hydrate when water activity is $<0.7$. Form N is of high crystallinity. It contains about 1.7% water by KF. DSC shows a dehydration peak at $T_{onset}$ of about 150.6° C.±20° C. After dehydration, it shows a recrystallization peak at $T_{onset}$ of about 162.5° C. Then it melts at about 217.8° C.±20° C. with an enthalpy of about 65 J/g. TGA shows about 0.60 weight loss at about 100° C.±20° C. and about 1.8% weight loss from about 100° C.±20° C. to about 170° C.±20° C. The hydration and dehydration behavior of Form N was investigated by variable humidity XRPD. No form change was observed in a whole humidity range. The XRPD of Form N is provided in FIG. 18.

Form N is characterized by an XRPD pattern with peaks within +/−0.4° 2theta of the peaks listed in Peak List #1.

Peak List #1

| Angle | d Value | Net Intensity | Gross Intensity | Rel. Intensity |
|---|---|---|---|---|
| 39.051° | 2.30470 Å | 72.2357 | 610.275 | 0.9% |
| 35.419° | 2.53231 Å | 88.5880 | 632.929 | 1.2% |
| 37.847° | 2.37526 Å | 100.964 | 640.479 | 1.3% |
| 36.766° | 2.44254 Å | 107.157 | 639.160 | 1.4% |
| 36.449° | 2.46304 Å | 111.967 | 650.538 | 1.5% |
| 26.096° | 3.41193 Å | 120.246 | 903.946 | 1.6% |
| 7.874° | 11.21957 Å | 128.610 | 575.119 | 1.7% |
| 38.719° | 2.32375 Å | 131.147 | 672.853 | 1.7% |
| 30.655° | 2.91412 Å | 147.312 | 783.858 | 1.9% |
| 33.196° | 2.69657 Å | 143.872 | 752.868 | 1.9% |
| 38.140° | 2.35766 Å | 155.244 | 697.401 | 2.0% |
| 18.033° | 4.91511 Å | 162.521 | 944.050 | 2.1% |
| 26.370° | 3.37712 Å | 167.361 | 949.218 | 2.2% |
| 30.267° | 2.95058 Å | 186.655 | 831.938 | 2.4% |
| 8.847° | 9.98761 Å | 194.971 | 661.259 | 2.5% |
| 36.096° | 2.48635 Å | 224.474 | 767.717 | 2.9% |
| 32.779° | 2.72992 Å | 230.334 | 852.470 | 3.0% |
| 31.804° | 2.81136 Å | 240.544 | 878.139 | 3.1% |
| 38.347° | 2.34542 Å | 236.235 | 779.095 | 3.1% |
| 37.437° | 2.40032 Å | 268.281 | 800.863 | 3.5% |
| 13.358° | 6.62289 Å | 276.675 | 915.974 | 3.6% |
| 34.934° | 2.56634 Å | 273.737 | 812.531 | 3.6% |
| 8.282° | 10.66735 Å | 329.828 | 786.383 | 4.3% |
| 13.649° | 6.48241 Å | 331.178 | 992.907 | 4.3% |
| 19.534° | 4.54084 Å | 330.153 | 1160.80 | 4.3% |
| 15.951° | 5.55179 Å | 350.431 | 1122.66 | 4.6% |
| 17.710° | 5.00412 Å | 352.428 | 1128.88 | 4.6% |
| 22.851° | 3.88860 Å | 349.586 | 1140.28 | 4.6% |
| 25.334° | 3.51278 Å | 362.156 | 1163.84 | 4.7% |
| 31.205° | 2.86398 Å | 367.963 | 1004.47 | 4.8% |
| 16.573° | 5.34477 Å | 371.727 | 1153.39 | 4.9% |
| 18.196° | 4.87161 Å | 374.104 | 1163.40 | 4.9% |
| 34.136° | 2.62444 Å | 391.468 | 956.534 | 5.1% |
| 21.855° | 4.06350 Å | 397.538 | 1204.55 | 5.2% |
| 27.376° | 3.25528 Å | 400.269 | 1160.88 | 5.2% |
| 17.248° | 5.13702 Å | 406.576 | 1188.64 | 5.3% |
| 17.397° | 5.09338 Å | 403.554 | 1184.33 | 5.3% |
| 33.469° | 2.67521 Å | 413.943 | 1012.23 | 5.4% |
| 18.498° | 4.79271 Å | 429.355 | 1231.50 | 5.6% |
| 29.643° | 3.01128 Å | 428.612 | 1080.85 | 5.6% |
| 29.014° | 3.07502 Å | 434.407 | 1111.73 | 5.7% |
| 20.466° | 4.33606 Å | 483.898 | 1319.60 | 6.3% |
| 28.055° | 3.17802 Å | 490.056 | 1223.48 | 6.4% |
| 29.804° | 2.99536 Å | 498.893 | 1150.17 | 6.5% |
| 10.223° | 8.64595 Å | 561.355 | 1079.41 | 7.3% |
| 23.660° | 3.75733 Å | 590.018 | 1399.51 | 7.7% |
| 35.796° | 2.50649 Å | 595.708 | 1140.70 | 7.8% |
| 20.294° | 4.37231 Å | 606.738 | 1442.97 | 7.9% |
| 28.608° | 3.11780 Å | 669.357 | 1372.97 | 8.7% |
| 11.025° | 8.01870 Å | 669.779 | 1201.85 | 8.8% |
| 13.831° | 6.39759 Å | 677.682 | 1352.47 | 8.9% |
| 16.361° | 5.41354 Å | 704.642 | 1484.06 | 9.2% |
| 20.655° | 4.29680 Å | 725.186 | 1559.52 | 9.5% |
| 11.805° | 7.49050 Å | 736.678 | 1280.79 | 9.6% |
| 14.479° | 6.11245 Å | 837.779 | 1553.09 | 10.9% |
| 25.591° | 3.47815 Å | 944.466 | 1739.40 | 12.3% |
| 19.761° | 4.48920 Å | 973.187 | 1806.86 | 12.7% |
| 20.044° | 4.42627 Å | 1044.04 | 1879.87 | 13.6% |
| 9.558° | 9.24594 Å | 1051.16 | 1546.64 | 13.7% |
| 5.141° | 17.17545 Å | 1076.05 | 1712.43 | 14.1% |
| 15.540° | 5.69779 Å | 1148.12 | 1909.34 | 15.0% |
| 24.457° | 3.63672 Å | 1162.30 | 1975.93 | 15.2% |
| 16.880° | 5.24826 Å | 1199.81 | 1982.92 | 15.7% |
| 15.741° | 5.62520 Å | 1334.66 | 2101.75 | 17.4% |
| 13.070° | 6.76813 Å | 1340.64 | 1955.87 | 17.5% |
| 22.083° | 4.02199 Å | 1413.10 | 2211.24 | 18.5% |
| 20.943° | 4.23842 Å | 1606.44 | 2437.18 | 21.0% |
| 26.968° | 3.30353 Å | 2580.23 | 3352.18 | 33.7% |
| 15.306° | 5.78413 Å | 3347.27 | 4100.54 | 43.7% |
| 23.360° | 3.80502 Å | 3413.42 | 4217.66 | 44.6% |
| 18.823° | 4.71060 Å | 3594.28 | 4407.98 | 47.0% |
| 24.162° | 3.68048 Å | 3907.63 | 4721.39 | 51.1% |
| 5.542° | 15.93507 Å | 4461.49 | 5057.82 | 58.3% |
| 19.119° | 4.63847 Å | 5005.79 | 5827.90 | 65.4% |
| 14.153° | 6.25272 Å | 5126.60 | 5822.70 | 67.0% |
| 21.518° | 4.12630 Å | 5150.06 | 5968.00 | 67.3% |
| 15.049° | 5.88221 Å | 5886.77 | 6629.91 | 76.9% |
| 5.925° | 14.90480 Å | 7653.51 | 8208.12 | 100.0% |

1. In certain embodiments Compound 1 Form N is characterized by an XRPD pattern which has at least three peaks selected from 5.1, 5.5, 5.9, 9.6, 13.1, 14.2, 14.5 15.0, 15.3, 15.5, 15.7, 16.9, 18.8, 19.1, 19.8, 20.0, 20.9, 21.5, 22.1, 23.4, 24.2, 24.5, 25.6, and 27.0+/−0.4° 2theta.
2. The morphic form of embodiment 1, wherein Compound 1 Form N is characterized by an XRPD pattern which has at least three peaks selected from 5.1, 5.5, 5.9, 9.6, 13.1, 14.2, 14.5 15.0, 15.3, 15.5, 15.7, 16.9, 18.8, 19.1, 19.8, 20.0, 20.9, 21.5, 22.1, 23.4, 24.2, 24.5, 25.6, and 27.0+/−0.3° 2theta.
3. The morphic form of embodiment 1, wherein Compound 1 Form N is characterized by an XRPD pattern which has at least three peaks selected from 5.1, 5.5, 5.9, 9.6, 13.1, 14.2, 14.5 15.0, 15.3, 15.5, 15.7, 16.9, 18.8, 19.1, 19.8, 20.0, 20.9, 21.5, 22.1, 23.4, 24.2, 24.5, 25.6, and 27.0+/−0.2° 2theta.
4. The morphic form of any one of embodiments 1-3, wherein there are at least four peaks selected from the listed peaks.
5. The morphic form of any one of embodiments 1-3, wherein there are at least five peaks selected from the listed peaks.
6. The morphic form of any one of embodiments 1-3, wherein there are at least six peaks selected from the listed peaks.
7. The morphic form of any one of embodiments 1-3, wherein there are at least seven peaks selected from the listed peaks.
8. The morphic form of any one of embodiments 1-3, wherein there are at least eight peaks selected from the listed peaks.
9. The morphic form of any one of embodiments 1-3, wherein there are at least nine peaks selected from the listed peaks.
10. The morphic form of any one of embodiments 1-3, wherein there are at least ten peaks selected from the listed peaks.
11. The morphic form of any one of embodiments 1-10, wherein the XRPD includes a peak at 5.9+/−0.2° 2theta.
12. The morphic form of any one of embodiments 1-11, wherein the XRPD includes a peak at 15.0+/−0.2° 2theta.
13. The morphic form of any one of embodiments 1-12, wherein the XRPD includes a peak at 21.5+/−0.2° 2theta.
14. The morphic form of any one of embodiments 1-13, wherein the XRPD includes a peak at 14.2+/−0.2° 2theta.
15. The morphic form of any one of embodiments 1-14, wherein the XRPD includes a peak at 19.1+/−0.2° 2theta.
16. The morphic form of any one of embodiments 1-15, wherein the XRPD includes a peak at 5.5+/−0.2° 2theta.

17. The morphic form of any one of embodiments 1-16, wherein the XRPD includes a peak at 24.2+/−0.2° 2theta.
18. The morphic form of any one of embodiments 1-17, wherein the XRPD includes a peak at 18.8+/−0.2° 2theta.

Other Morphic Forms

Figure 5:
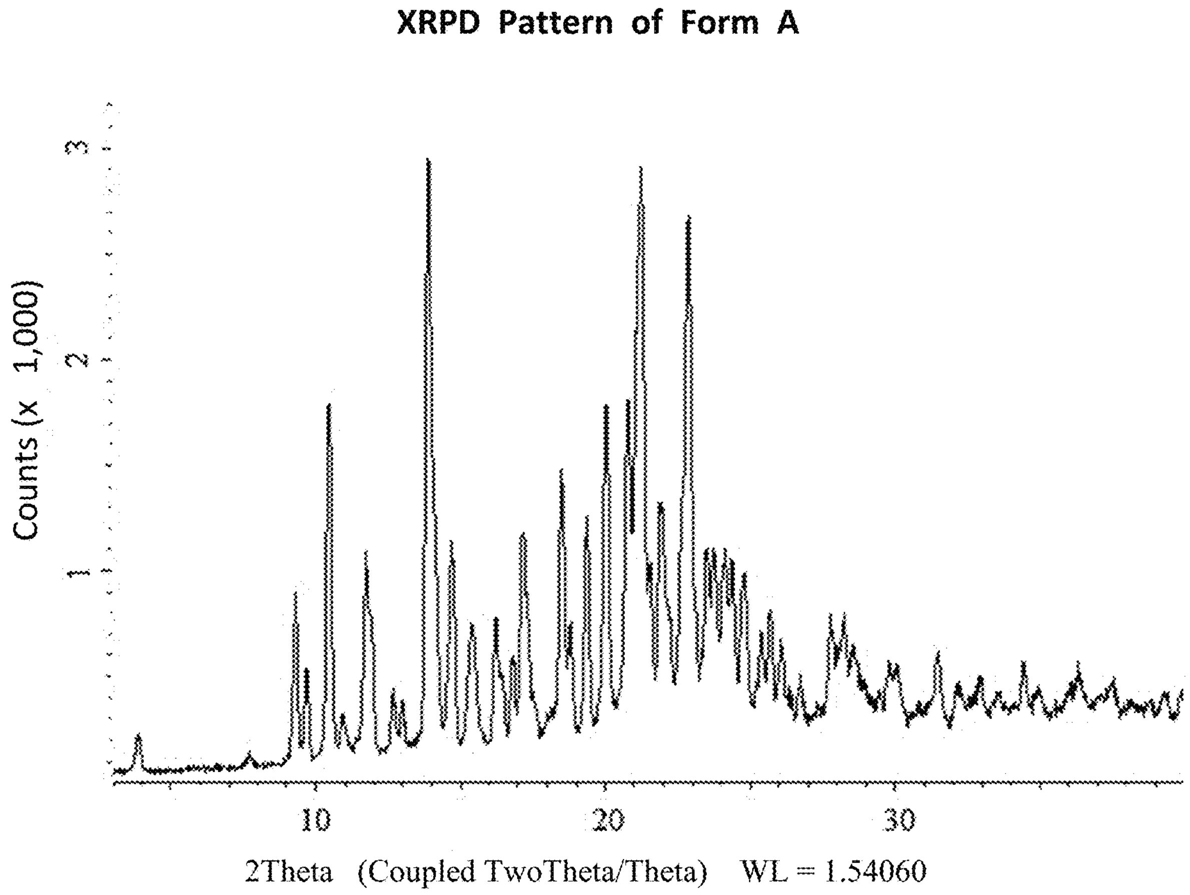
FIG. 5 depicts the XRPD pattern of Compound 1 Form A. The Form A XRPD pattern exhibits sharp peaks, indicating the sample was composed of crystalline material.

Form A is a hydrate. It was obtained from equilibration experiments at 25° C. in EtOH, equilibration experiments under temperature cycling between 5° C. and 50° C. in toluene, acetone/water (v:v=76:24). Form A is of high crystallinity. It contains about 3.8% water by KF. DSC shows a dehydration peak starting from about 30.0° C. and a melting peak at $T_{onset}$ of about 150.2° C. with an enthalpy of about 20 J/g. TGA shows about 4.2% weight loss at about 100° C. The hydration and dehydration behavior of Form A was investigated by variable temperature XRPD and variable relative humidity XRPD. Results of variable temperature XRPD show that Form A converts to a metastable anhydrate Form J after dehydration and Form J converts back to Form A when cooled to about 25° C. Results of variable relative humidity XRPD show that Form A coverts to a metastable anhydrate Form J after dehydration and Form A also converts to a metastable hydrate Form K when exposure to about or above 70% RH. Form K converts back to Form A when exposure to about 40% relative humidity (RH). Form A shows reversible hydration-dehydration behavior. The XRPD of Form A is provided in FIG. 5.

Figure 6:
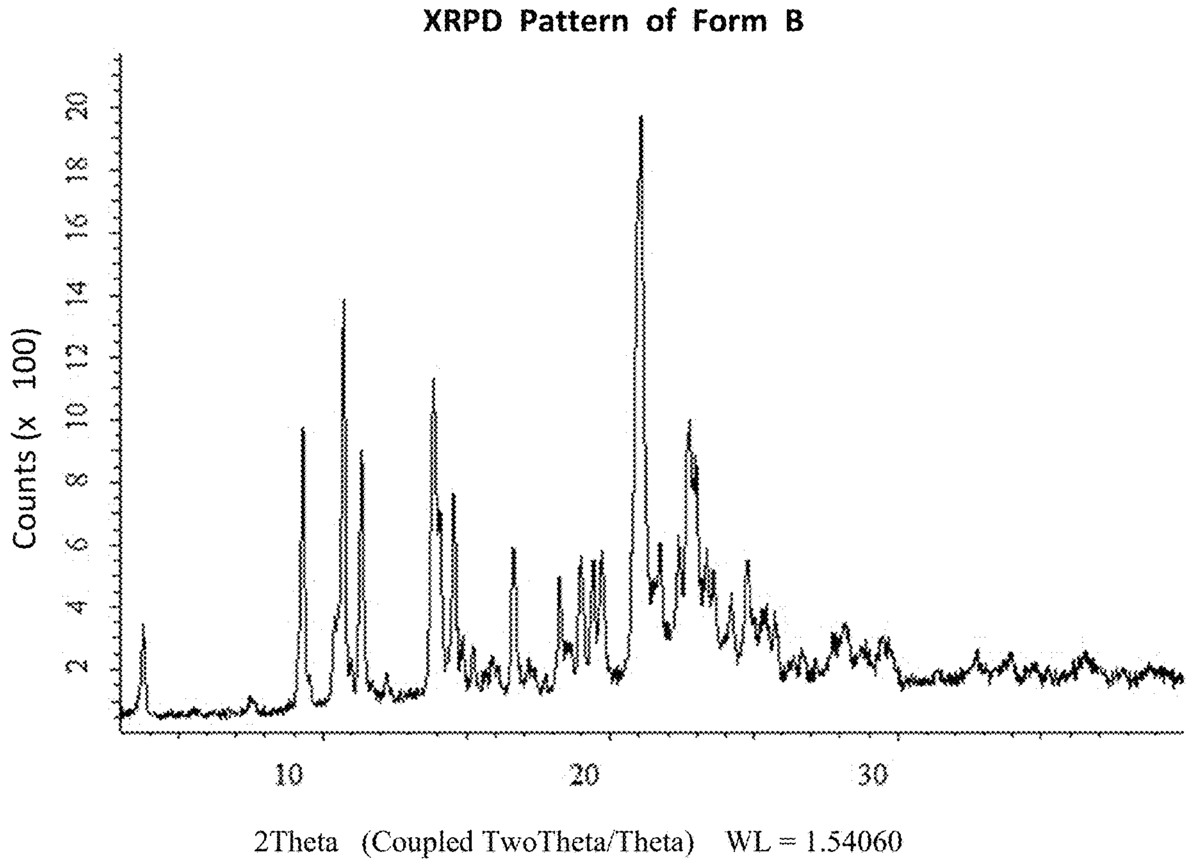
FIG. 6 depicts the XRPD pattern of Compound 1 Form B.

Form B is a hydrate. It was obtained from equilibration experiments at about 25° C. in acetone, ACN, 2-MeTHF, acetone/water (v:v=76:24) etc., equilibration experiments at about 50° C. in acetone, 2- and MeTHF, equilibration experiments under temperature cycling in acetone, ACN, 1,4-dioxane/heptane (v:v=1:1), fast evaporation experiments in ACN, slow cooling experiments in acetone, and fast cooling experiments in acetone. Form B, is of high crystallinity. It contains about 8.5% water by KF. DSC shows a dehydration peak from about 30.0° C. and an exothermic peak at $T_{onset}$ of about 94.6° C. Then it melts at $T_{onset}$ of about 153.1° C. with an enthalpy of about 29 J/g. TGA shows about 6.5% weight loss at about 100° C. $^1$H-NMR shows about 0.9% residual ACN. The hydration and dehydration behavior of Form B was investigated by variable temperature XRPD. Results show that the hydration-dehydration behavior of Form B is non-reversible and it converts to an anhydrate Form H after dehydration. The XRPD of Form B is provided in FIG. 6.

Figure 7:
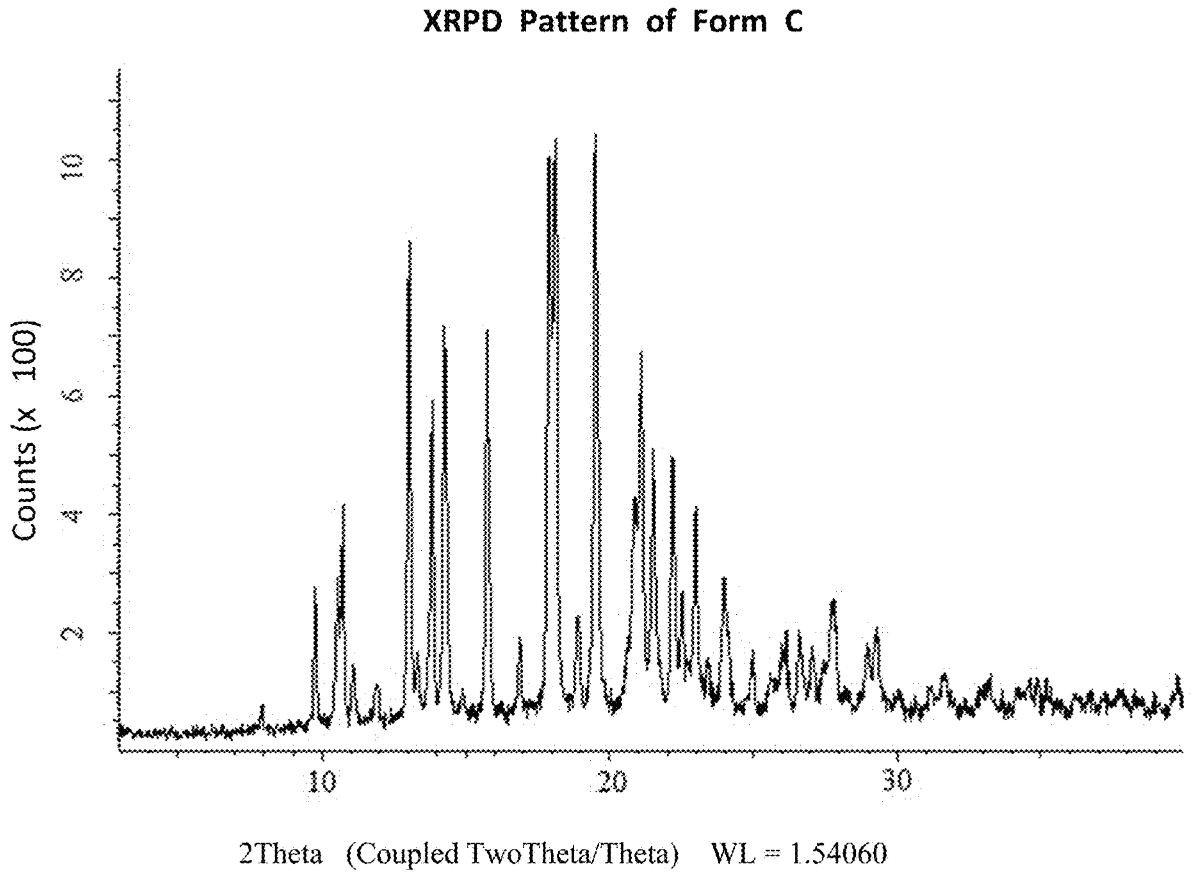
FIG. 7 depicts the XRPD pattern of Compound 1 Form C.

Form C is a hydrate. It was obtained from salt formation with weak acids. Form C is of high crystallinity. It contains about 7.4% water by KF. DSC shows a dehydration peak from about 30.0° C. and a melting peak at $T_{onset}$ of about 155.5° C. and an enthalpy of about 22 J/g after dehydration. TGA shows about 3.5% weight loss at about 100° C. $^1$H-NMR shows no detectable residual solvent. The hydration and dehydration behavior of Form C was investigated by variable temperature XRPD. Results show that Form C converts to a metastable anhydrate Form I and Form I converts back to Form C when cooled to about 25° C. So, Form C shows reversible hydration-dehydration behavior. The XRPD of Form C is provided in FIG. 7.

Figure 8:
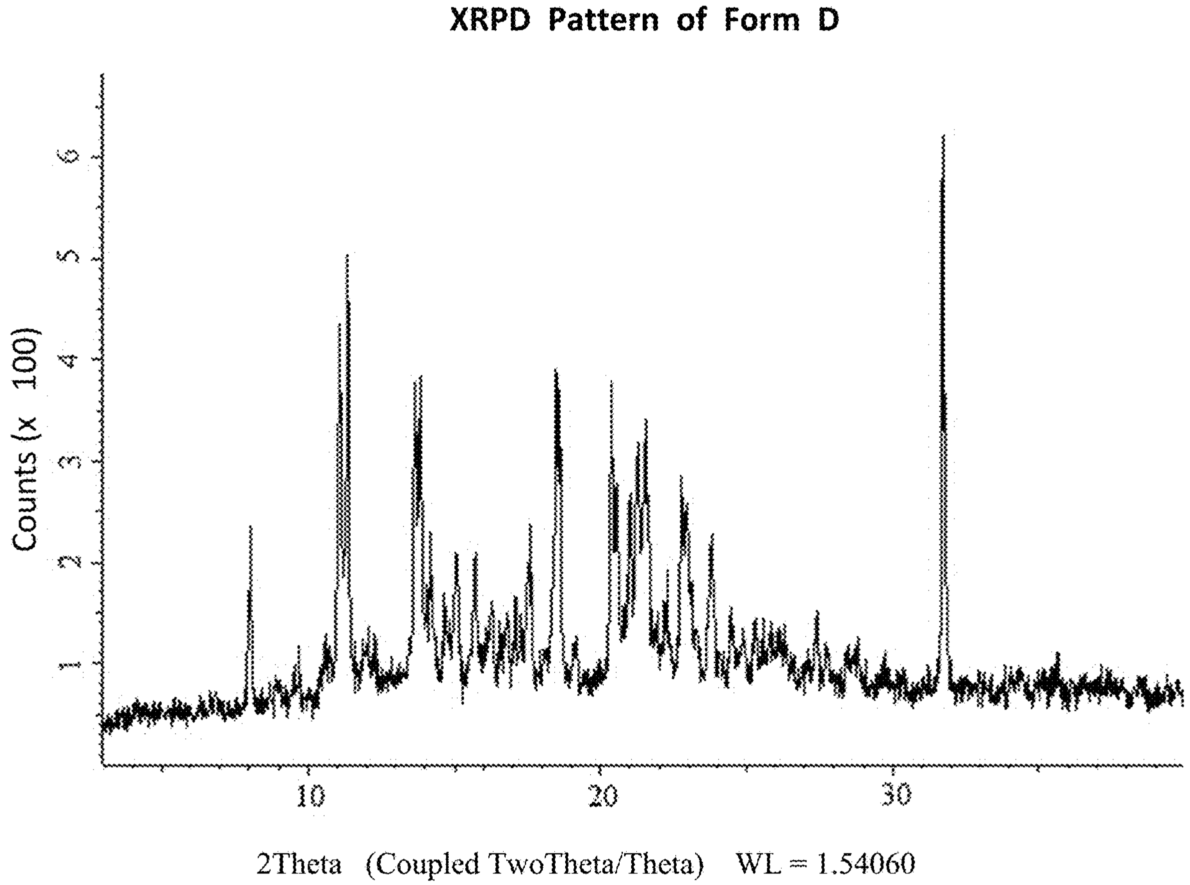
FIG. 8 depicts the XRPD pattern of Compound 1 Form D.

Form D is a hydrate. It was obtained from dissociation of the urea co-crystal Form P in aqueous media. Form D is of high crystallinity. DSC shows a dehydration peak from 30.0° C. and a melting peak at $T_{onset}$ of about 152.9° C. with an enthalpy of about 22 J/g. TGA shows 6.8% weight loss at about 100° C. $^1$H-NMR shows no detectable residual solvent. Form D is a metastable form. The XRPD of Form D is provided in FIG. 8.

Figure 9:
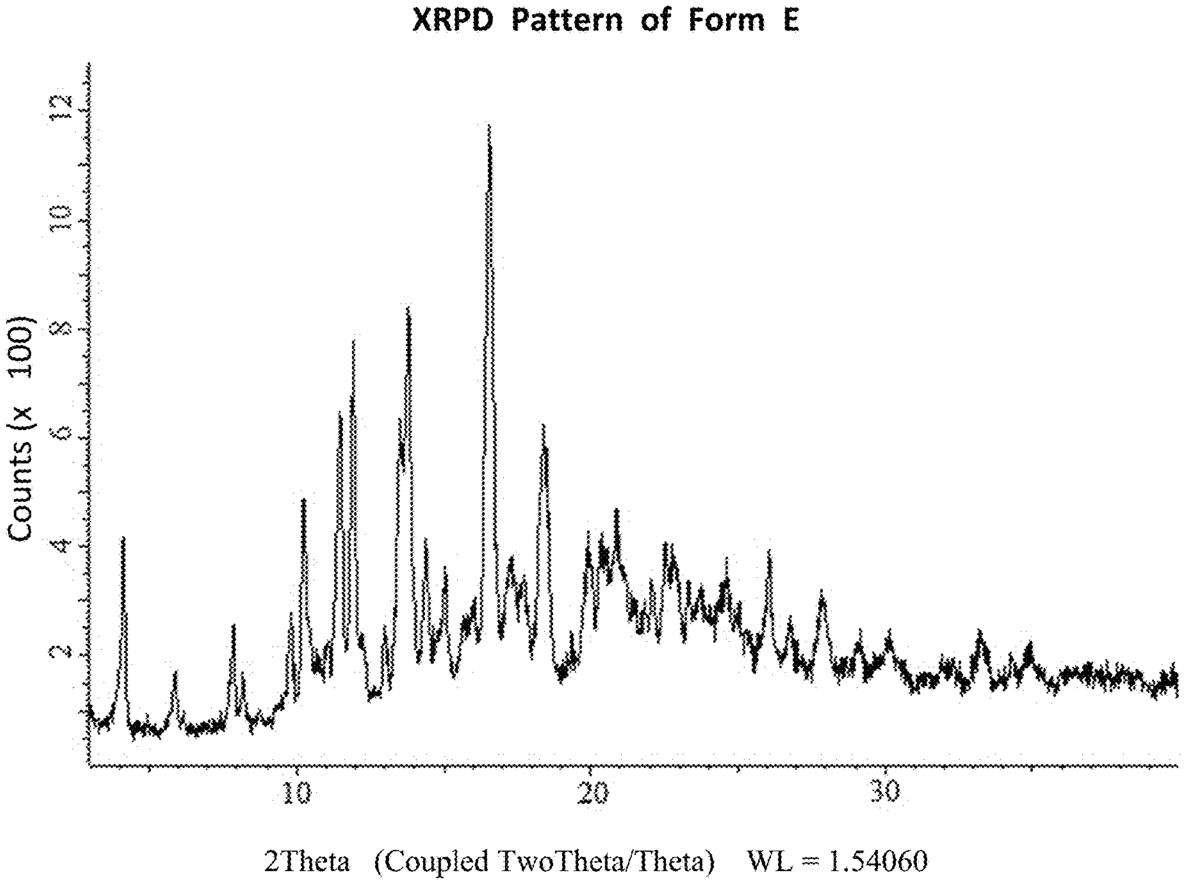
FIG. 9 depicts the XRPD pattern of Compound 1 Form E.

Form E is a hydrate. Form E is of high crystallinity. It contains about 4.1% water by KF. DSC shows a dehydration peak from about 30.0° C. and an exothermic peak at $T_{onset}$ of about 92.2° C. Then it melts at $T_{onset}$ of about 155.4° C. with an enthalpy of about 30 J/g. TGA shows about 1.4% weight loss at about 80° C. $^1$H-NMR shows no detectable residual solvent. In certain embodiments Form E is a metastable form. The XRPD of Form E is provided in FIG. 9.

Figure 10:
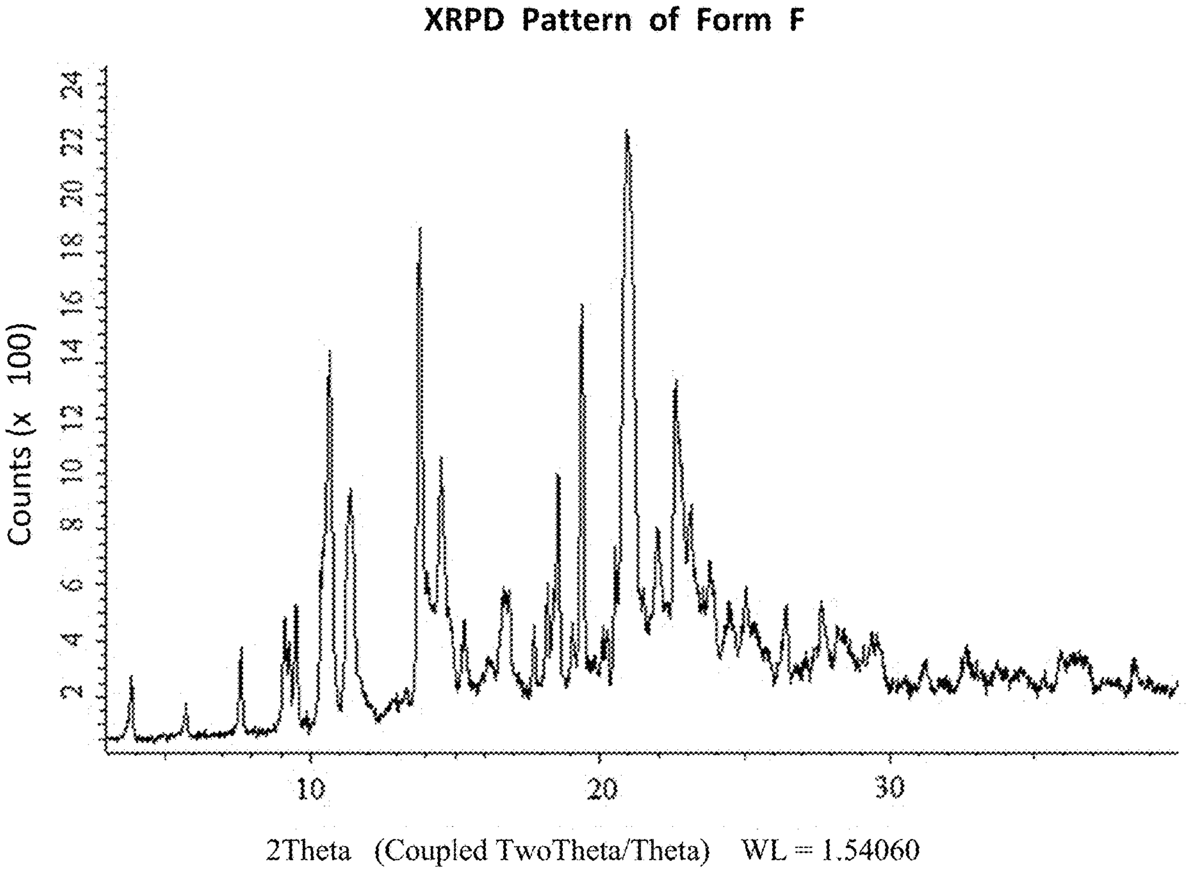
FIG. 10 depicts the XRPD pattern of Compound 1 Form F.

Form F is a hydrate. It was obtained from equilibration experiments at about 25° C. in EA etc., equilibration experiments at about 50° C. in EA, ACN, equilibration experiments under temperature cycling in EtOH, EA, THF/heptane (v:v=1:1), slow evaporation experiments in EA, slow cooling experiments in EtOH, fast cooling experiments in EtOH and EA, anti-solvent addition experiments in 1,4-dioxane/heptane, DCM/MTBE systems. Form F is of high crystallinity. It contains about 7.0% water by KF. DSC shows a dehydration peak from about 30.0° C. and a small endothermic peak at $T_{onset}$ of about 109.7° C. Then it melts at $T_{onset}$ of about 155.1° C. with an enthalpy of about 29 J/g. TGA shows about 6.1% weight loss at about 100° C. $^1$H-NMR shows about 0.8% residual ethanol. The hydration and dehydration behavior of Form F was investigated by variable temperature XRPD. Results show that the hydration-dehydration behavior of Form F is non-reversible and it converts to an anhydrate Form H after dehydration. The XRPD of Form F is provided in FIG. 10.

Figure 11:
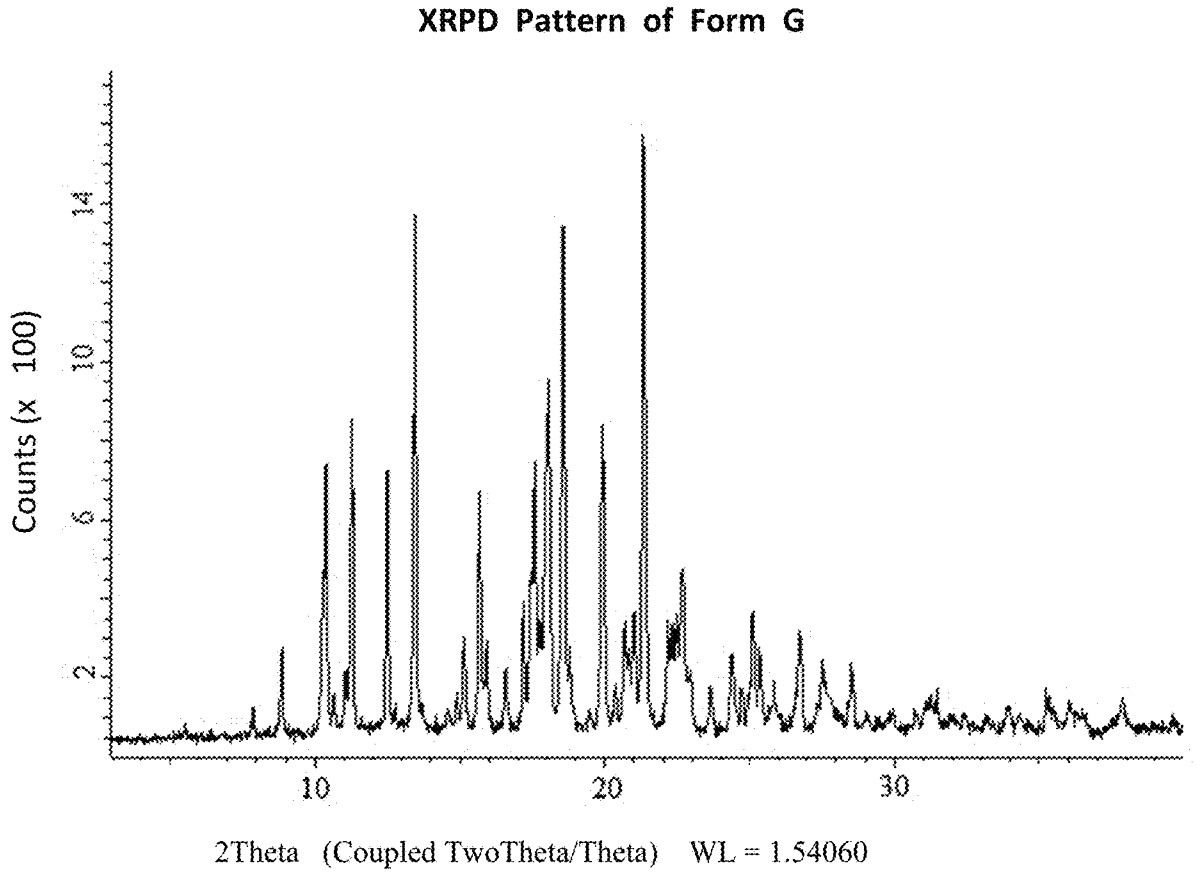
FIG. 11 depicts the XRPD pattern of Compound 1 Form G.

Form G is an anhydrate. It was obtained from equilibration experiments at about 50° C. in toluene. Form G is of high crystallinity. DSC shows a melting peak at $T_{onset}$ of about 196.5° C. and an enthalpy of about 72 J/g. TGA shows 0.5% weight loss at about 190° C. $^1$H-NMR shows no detectable residual solvent. UPLC shows its chemical purity is about 99.2%. Its chiral purity is about 98.0%. The XRPD of Form G is provided in FIG. 11.

Figure 12:
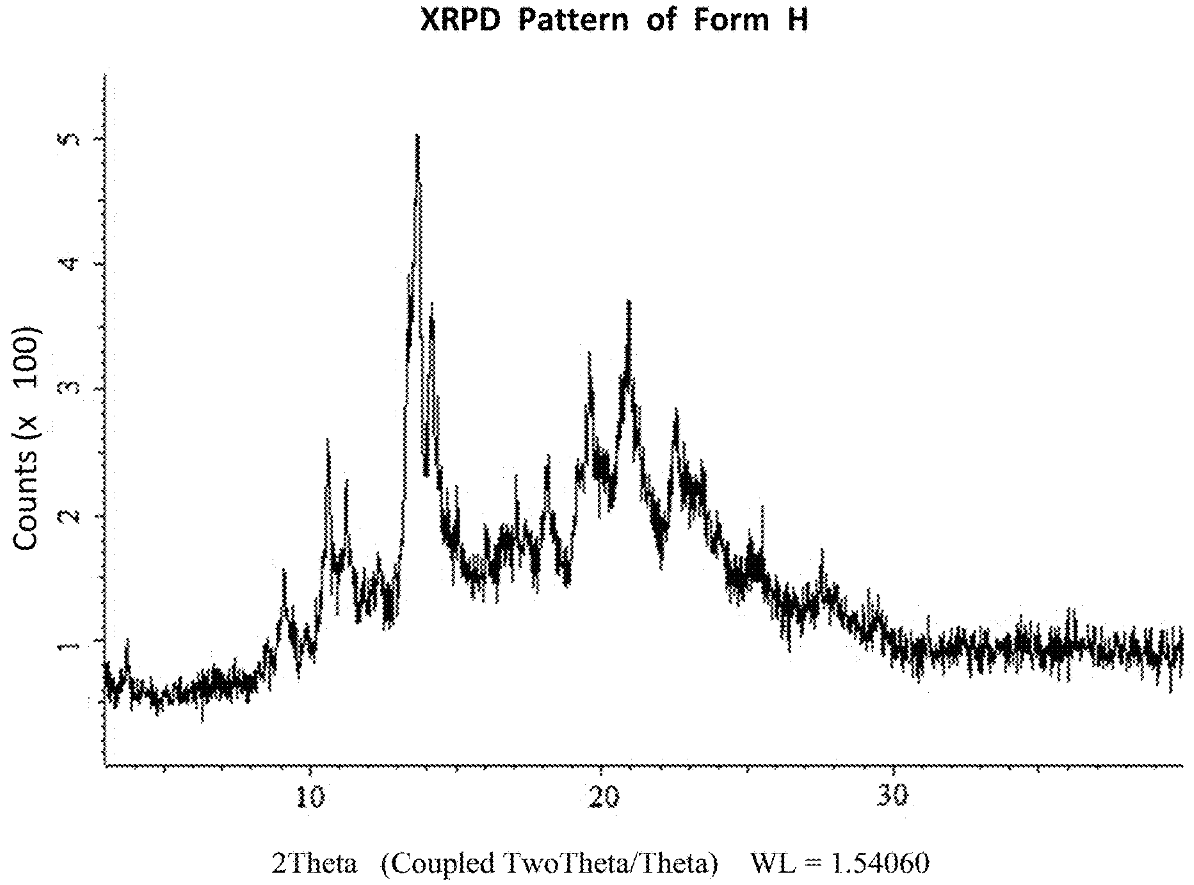
FIG. 12 depicts the XRPD pattern of Compound 1 Form H.

Form H is an anhydrate. It was obtained from dehydration of Form F. Form H is of low crystallinity. DSC shows a melting peak at $T_{onset}$ of about 149.5° C. with an enthalpy of about 23 J/g. The XRPD of Form H is provided in FIG. 12.

Figure 13:
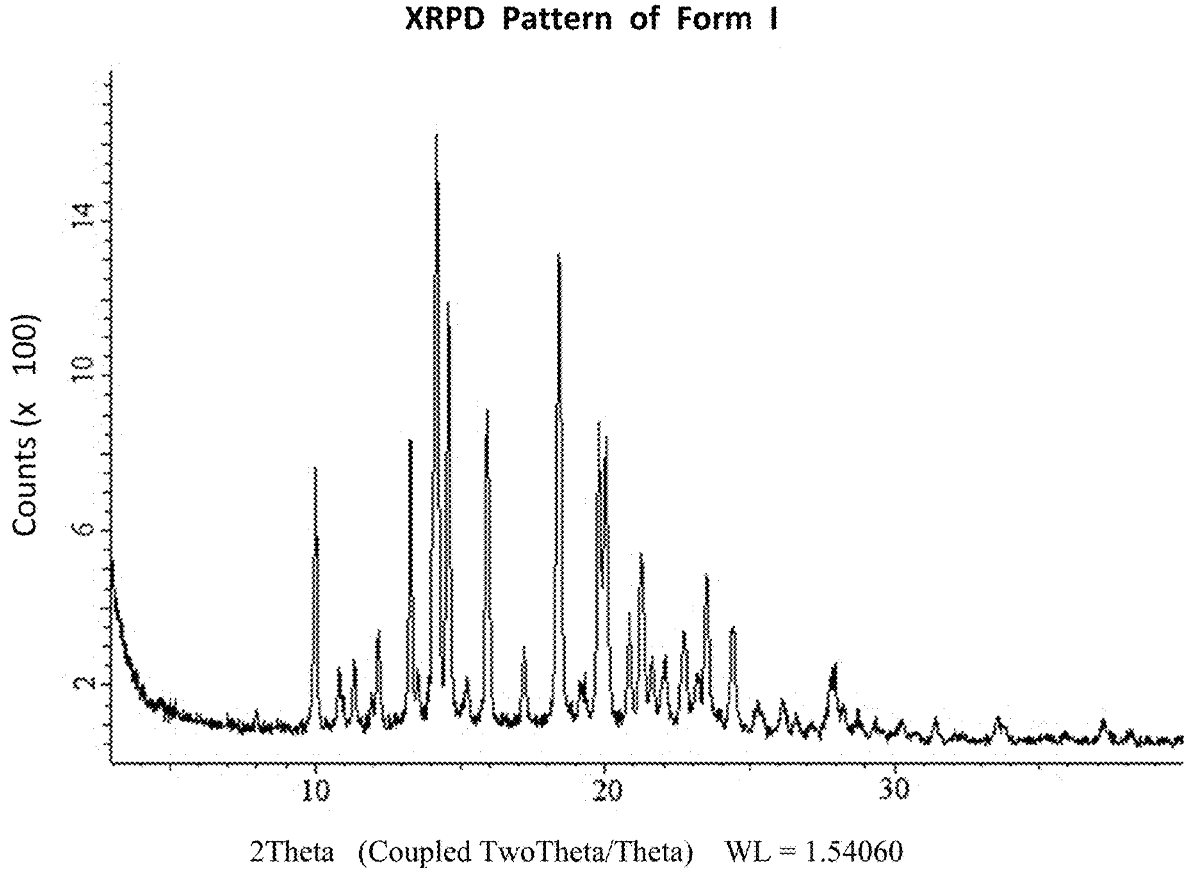
FIG. 13 depicts the XRPD pattern of Compound 1 Form I.

Form I is an anhydrate obtained after dehydration of Form C at about 110° C. In certain embodiments Form I is not stable. It converts to Form C when cooled to about 25° C. The XRPD of Form I is provided in FIG. 13.

Figure 14:
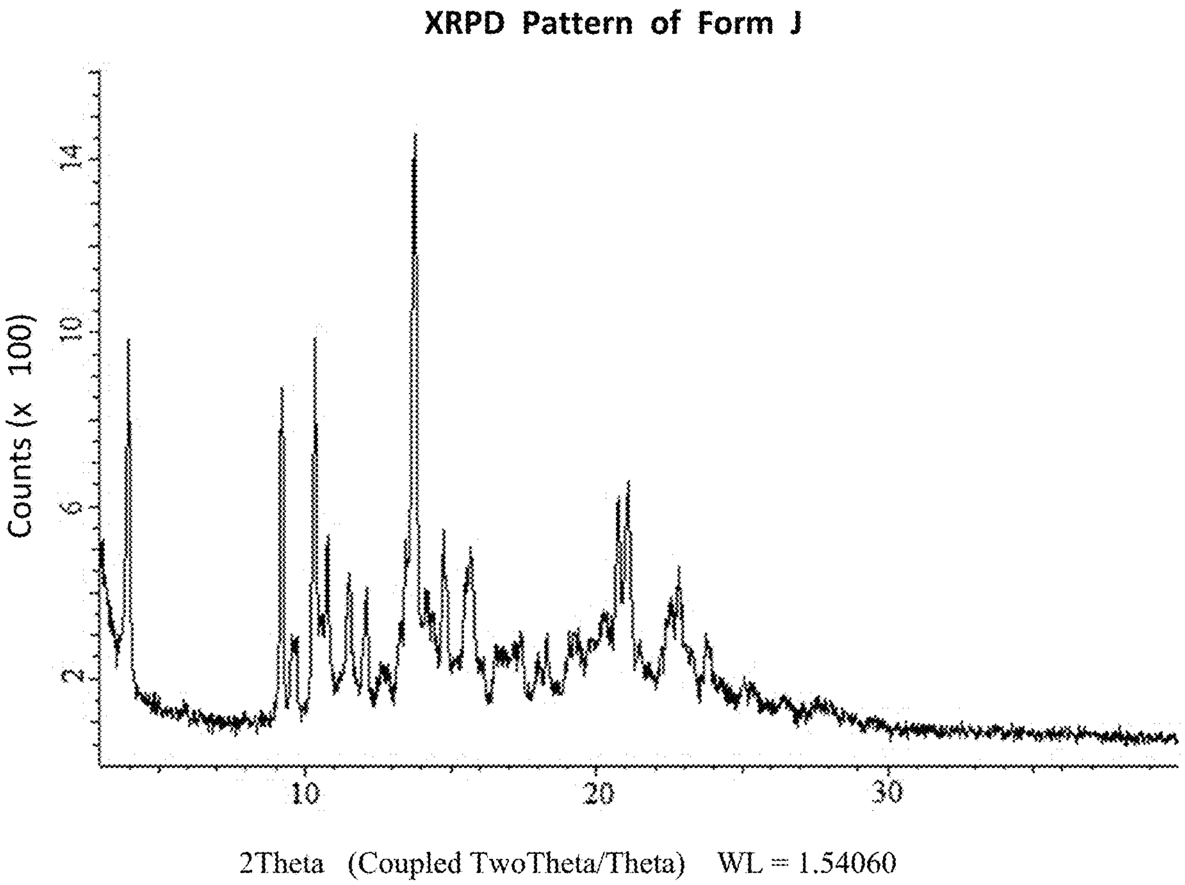
FIG. 14 depicts the XRPD pattern of Compound 1 Form J.

Form J is an anhydrate. It was obtained from dehydration of Form A when heated to about 110° C. or exposure to about 0% RH. In certain embodiments Form J is not stable. It converts to Form A when exposure to ambient condition (about 25-30° C., about 30-50% RH). The XRPD of Form J is provided in FIG. 14.

Figure 15:
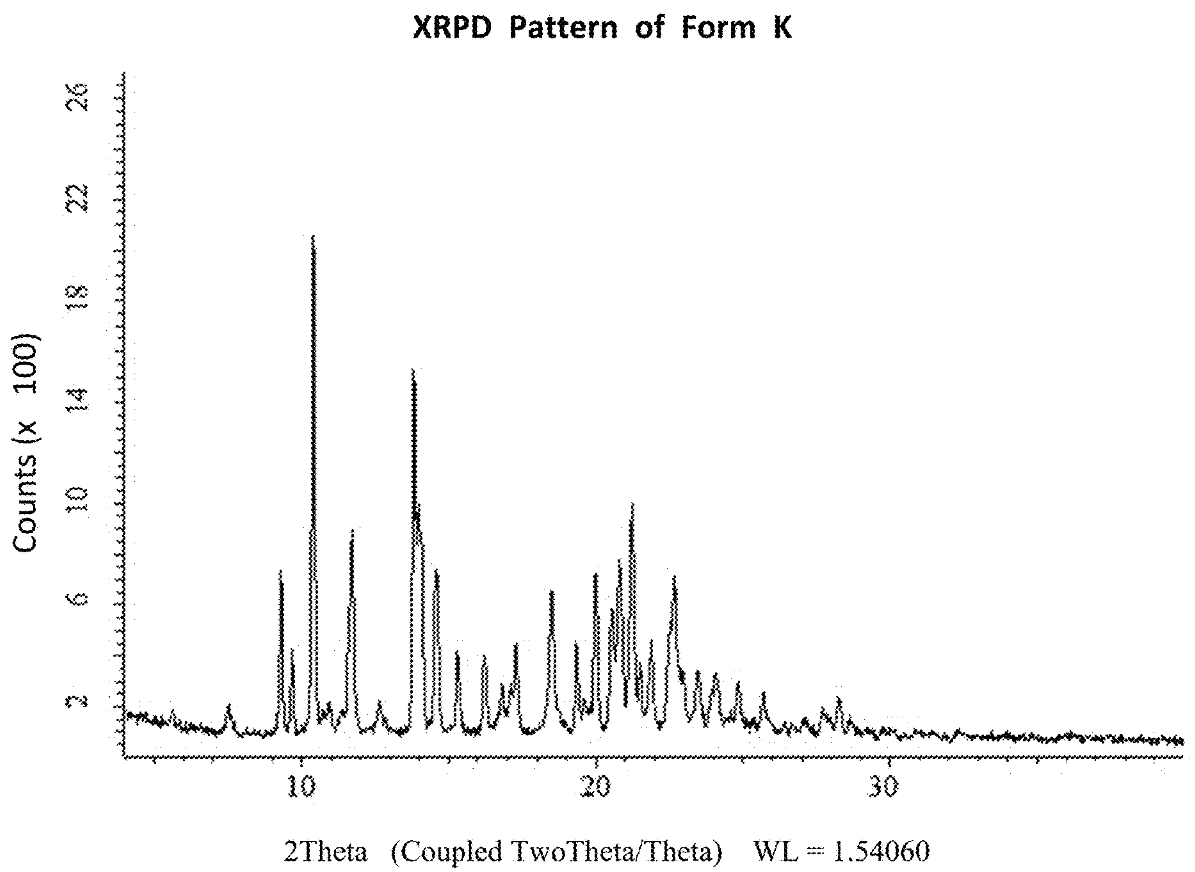
FIG. 15 depicts the XRPD pattern of Compound 1 Form K.

Form K is a hydrate. It was obtained after exposed Form A to about or above 70% RH. It can be obtained from equilibration experiments at about 25° C. in MeOH, DMSO/water (v:v=23:77)., equilibration experiments at about 50° C. in acetone/water (v:v=36:64), DMSO/water (v:v=23:77), equilibration experiments under temperature cycling between about 5° C. and 50° C. in acetone/water (v:v=36:64). In certain embodiments Form K is not stable. It converts to Form A under ambient condition (about 25-30° C., about 30-50% RH). The XRPD of Form K is provided in FIG. 15.

Figure 16:
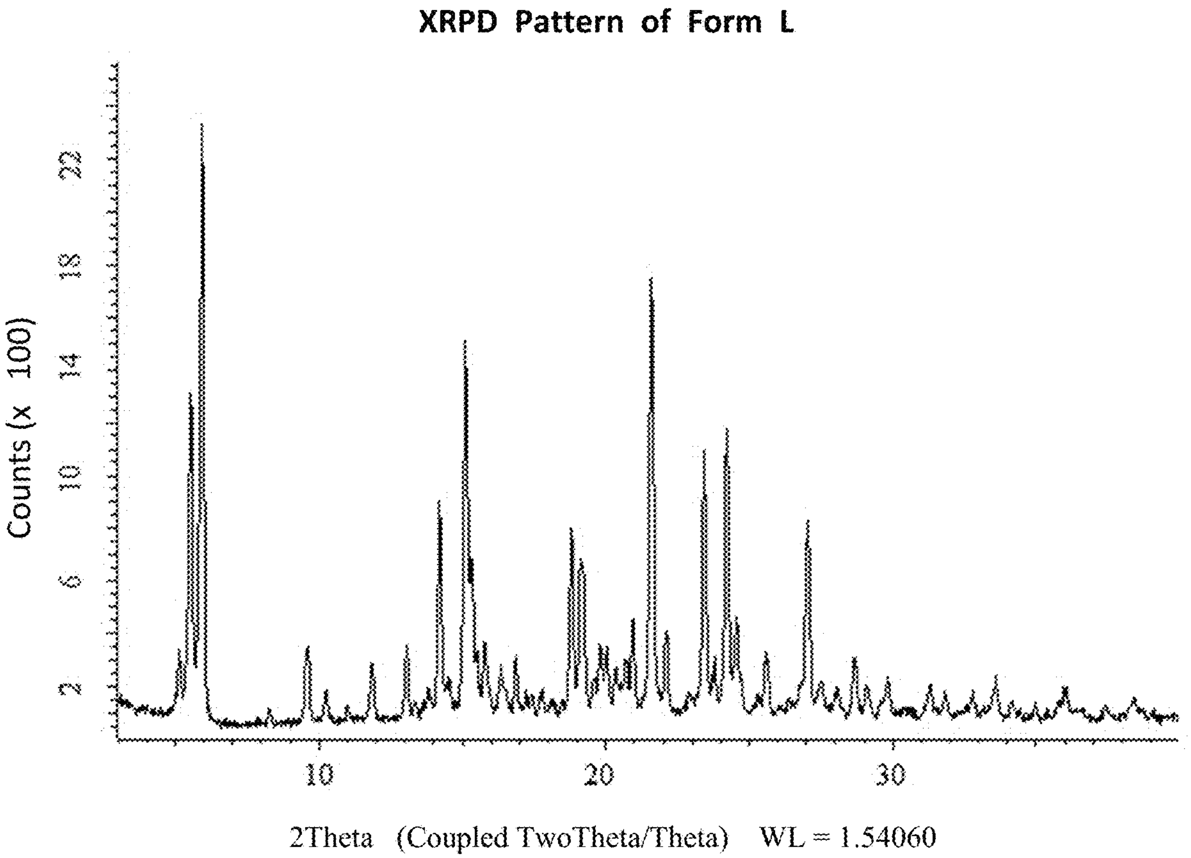
FIG. 16 depicts the XRPD pattern of Compound 1 Form L.

Form L is a hetero-solvate. It was obtained from equilibration experiments at about 25° C. in 2-MeTHF. Form L is of high crystallinity. It contains about 6.5% water by KF and 7.3% (0.65 equiv.) 2-MeTHF by $^1$H-NMR. DSC shows a dehydration-desolvation peak at $T_{onset}$ of about 149.2° C.

and an exothermic peak at $T_{onset}$ of about 166.8° C. Then it melts at about 221.2° C. with an enthalpy of about 60 J/g. TGA shows 9.0% weight loss at about 180° C. Form L converts to anhydrate Form M after dehydration and desolvation by heating. The XRPD of Form L is provided in FIG. 16.

Figure 17:
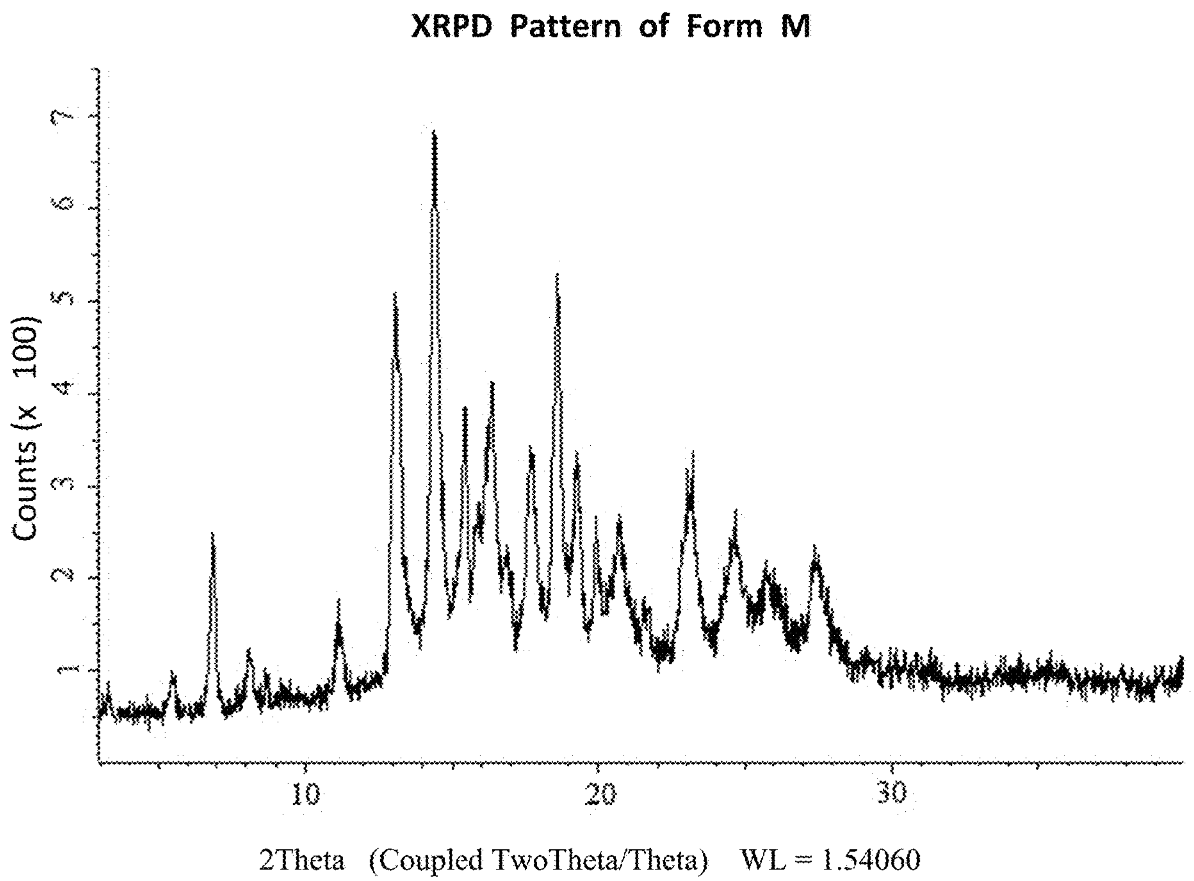
FIG. 17 depicts the XRPD pattern of Compound 1 Form M.

Form M is an anhydrate. It was obtained from dehydration-desolvation of Form L by heating. Form M is of medium crystallinity. DSC shows a melting peak at $T_{onset}$ of about 218.6° C. and an enthalpy of about 64 J/g. TGA shows 0.5% weight loss at about 200° C. $^1$H-NMR shows about 0.6% residual 2-MeTHF. Its chiral purity is about 96.9%. The XRPD of Form M is provided in FIG. 17.

Form O is an anhydrate. It was precipitated from supersaturated solution in acetone during single crystal cultivation. Form O is used for single crystal analysis, see Example 1. The simulated XRPD of Form O is different from the measured powder XRPD Form under ambient condition. The experimental XRPD Form is in accordance with that of the Form B. And DSC of the samples used for single crystal analysis also showed a dehydration thermal event. From single crystal structure of Form O, obvious channel structures exist in its crystal structure. So highly possible the channel structures in Form O is filled with water molecules after exposure to ambient condition. In certain embodiments Form O is unstable. It converts to hydrate Form B under ambient condition.

Comparison of Form A and Form N

Hygroscopicity of Form A and Form N was investigated by DVS at 25° C. Form A is slightly hygroscopic and shows about 2.0% water uptake from 40% RH to 70% RH. Form A converted to Form K after the DVS test. Form K is a metastable hydrate. It reverted back to Form A after exposure to ambient condition. Form N is slightly hygroscopic and shows about 1.0% water uptake from 40% RH to 80% RH. No form change and no obvious crystallinity decrease were observed after the DVS test.

Feasibility of formulation processes was evaluated with compression and ball-milling experiments. The hydrate Form A showed good tolerance to compression process with no form change and no obvious crystallinity decrease even under 10 MPa. However, the hydrate Form N is sensitive to pressure. It showed crystallinity decrease even compressed under 2 MPa. Considering manually grinding may exert shear force, ball milling experiment was conducted for both Form A and Form N. They showed no obvious crystallinity decrease after ball milling for 5 min.

Both Form A and Form N are physically and chemically stable after being stressed at 25° C./92% RH in an open vial, 40° C./75% RH in an open vial or 60° C. in a closed vial for 1 week. No form change and no obvious degradation were observed after bulk stability study. For hydrate Form N, investigation of drying condition was also conducted. No form change and no degradation were observed after drying at 50° C. under vacuum for 2 days.

Form N shows good crystallinity, physical stability, chemical stability and slight hygroscopicity from 40% RH to 80% RH.

III. Compound 1 Salt Investigation

Compound 1 was investigated with a variety of salts to find additional morphic forms and cocrystals. This salt and cocrystal investigation for Compound 1 was performed with free form Pattern A*. This is a hydrate with medium crystallinity. Based on its pKa(s) of 5.2 and 2.9 calculated by Marvin Sketch (a computer program that estimates pKa), 14 acids and 2 coformers were selected as salt and cocrystal forming agents. Acetone, methanol, ethyl acetate and acetonitrile were used as evaluation solvents. Five crystallization methods, including equilibration, fast cooling, slow evaporation, addition of anti-solvent and re-equilibration, were applied to obtain salt or cocrystal hits. From these investigations only one crystalline form—a urea cocrystal Form P was identified.

In addition, amorphous sulfate salt, amorphous MSA salt, amorphous TFA salt and amorphous p-toluenesulfonate salt were obtained based on $^1$H-NMR results. Even though multiple crystallization methods were applied including cooling, addition of anti-solvent and re-equilibration, no crystalline salt hit was obtained.

This urea cocrystal Form P shows high crystallinity, reasonable stoichiometry and good reproducibility.

The urea cocrystal Form P was prepared using the method reported in Example 7. The urea cocrystal Form P, was evaluated for chemical purity, stoichiometry, crystallinity, thermal properties, stability, solubility and hygroscopicity in comparison of the free form Pattern A*.

Chemical and Physicochemical Properties

The free form Pattern A* is a hydrate. The free form Pattern A*, is of medium crystallinity. It contains about 4.0% water by KF. It dehydrates from 30° C. and shows a melting onset at 154.0° C. with an enthalpy of 22 J/g by DSC. It shows about 4.0% weight loss at about 110° C. by TGA. No residual solvent was detected by $^1$H-NMR.

The urea cocrystal Form P is a hydrate. The urea cocrystal Form P, is of high crystallinity. It contains about 5.4% water by KF. The stoichiometric ratio of free form to urea is 1:0.5 by $^1$H-NMR. No chemical shift was observed on $^1$H-NMR spectrum, indicating that this complex is a cocrystal. It dehydrates starting from 30° C. and shows a melting onset at about 140.2° C.±20° C. It decomposes upon melting. It shows about 4.4% weight loss at about 114° C.±20° C. by TGA.

The urea cocrystal Form P was evaluated for bulk stability in comparison with the free form Pattern A*. A bulk stability study was conducted using three conditions for one week including 25° C./92% RH in an open container, 40° C./75% RH in an open container and 60° C. in a tight container. Both the free form Pattern A* and the urea cocrystal Form P show good chemical stability in these conditions. The free form Pattern A* is physically stable after stressed at 40° C./75% RH. However, it showed agglomeration after stressed at 25° C./92% RH and also showed crystallinity decrease after stressed at 60° C. For the urea cocrystal Form P, it is physically stable after stressed at 25° C./92% RH and 40° C./75% RH but shows slight discoloration after stressed at 60° C.

The urea cocrystal Form P was evaluated for photostability in comparison with the free form Pattern A*. Photostability study was conducted under 1.2 million lux-hrs at 25° C. in an open container. ~1% degradation was observed for both the free form Pattern A* and the urea cocrystal Form P after exposure to light, but no form changed was detected.

Solubility studies were conducted for the free form Pattern A*, and the urea cocrystal Form P, in aqueous media including pH 1.0 HCl solution (0.1N), pH 4.5 acetate buffer (50 mM), SGF (pH 1.8), FeSSIF-v1 (pH 5.0) and FaSSIF-v1 (pH 6.5) after equilibration at 37° C. for 2 h and 24 h, respectively.

Both the free form Pattern A* and the urea cocrystal Form P show good solubility (>2 mg/mL) in pH 1.0 HCl solution and in SGF, medium solubility (~0.1 to 0.3 mg/mL) in pH 4.5 acetate buffer and FeSSIF-v1 and low solubility (close to LOQ) in FaSSIF-v1. The urea cocrystal Form P shows comparable solubility as that of the free form Pattern A*, which may be due to dissociation to free form during solubility tests.

Hygroscopicity of the free base Pattern A* and the urea cocrystal Form P were evaluated by DVS at 25° C.

The free form Pattern A*, is slightly hygroscopic below 60% RH. It then absorbs water and becomes hygroscopic at 95% RH (about 6.0% water uptake) at 25° C. One additional peak and a slight crystallinity decrease was observed after the DVS test.

The urea cocrystal Form P is slightly hygroscopic (1.6% water uptake) below 90% RH and becomes hygroscopic (3.1% water uptake) in 95% RH. No form change and no crystallinity decrease were observed after the DVS test.

Form P is characterized by an XRPD pattern with peaks within +/−0.4° 2theta of the peaks listed in Peak List #2.

Peak List #2

| Angle | d Value | Net Intensity | Gross Intensity | Rel. Intensity |
|---|---|---|---|---|
| 5.741° | 15.38099 Å | 43.1221 | 183.426 | 0.8% |
| 31.251° | 2.85984 Å | 81.3450 | 719.294 | 1.6% |
| 38.212° | 2.35335 Å | 103.462 | 794.862 | 2.0% |
| 12.622° | 7.00749 Å | 132.004 | 510.491 | 2.6% |
| 35.841° | 2.50347 Å | 151.386 | 860.005 | 3.0% |
| 36.278° | 2.47425 Å | 171.416 | 883.382 | 3.4% |
| 12.948° | 6.83192 Å | 197.834 | 586.500 | 3.9% |
| 34.451° | 2.60117 Å | 197.520 | 876.003 | 3.9% |
| 33.339° | 2.68534 Å | 219.654 | 852.597 | 4.3% |
| 32.271° | 2.77173 Å | 230.086 | 842.976 | 4.5% |
| 7.443° | 11.86830 Å | 234.525 | 396.803 | 4.6% |
| 37.208° | 2.41452 Å | 249.427 | 958.690 | 4.9% |
| 12.210° | 7.24297 Å | 254.933 | 618.206 | 5.0% |
| 27.734° | 3.21402 Å | 283.353 | 1152.48 | 5.5% |
| 28.213° | 3.16052 Å | 293.495 | 1142.34 | 5.7% |
| 30.914° | 2.89023 Å | 331.875 | 1000.22 | 6.5% |
| 29.790° | 2.99671 Å | 340.794 | 1097.92 | 6.7% |
| 25.916° | 3.43525 Å | 348.952 | 1264.13 | 6.8% |
| 28.756° | 3.10209 Å | 360.190 | 1181.79 | 7.1% |
| 38.950° | 2.31048 Å | 364.067 | 1032.47 | 7.1% |
| 10.744° | 8.22792 Å | 384.782 | 672.705 | 7.5% |
| 26.106° | 3.41065 Å | 387.562 | 1300.01 | 7.6% |
| 29.463° | 3.02920 Å | 392.444 | 1171.72 | 7.7% |
| 9.644° | 9.16402 Å | 424.267 | 656.956 | 8.3% |
| 28.902° | 3.08673 Å | 426.342 | 1239.83 | 8.4% |
| 9.073° | 9.73940 Å | 447.104 | 655.817 | 8.8% |
| 27.283° | 3.26615 Å | 478.985 | 1363.99 | 9.4% |
| 11.670° | 7.57711 Å | 493.312 | 832.669 | 9.7% |
| 25.430° | 3.49972 Å | 497.168 | 1416.81 | 9.7% |
| 15.947° | 5.55298 Å | 498.428 | 969.702 | 9.8% |
| 22.482° | 3.95147 Å | 504.981 | 1373.81 | 9.9% |
| 24.682° | 3.60414 Å | 641.823 | 1561.24 | 12.6% |
| 26.717° | 3.33398 Å | 653.210 | 1553.68 | 12.8% |
| 24.446° | 3.63832 Å | 700.502 | 1618.06 | 13.7% |
| 25.111° | 3.54343 Å | 746.760 | 1667.36 | 14.6% |
| 16.607° | 5.33397 Å | 753.472 | 1253.00 | 14.8% |
| 7.705° | 11.46552 Å | 807.116 | 976.339 | 15.8% |
| 14.559° | 6.07914 Å | 856.396 | 1300.99 | 16.8% |
| 16.946° | 5.22786 Å | 888.912 | 1413.99 | 17.4% |
| 23.468° | 3.78770 Å | 1012.43 | 1913.14 | 19.8% |
| 19.819° | 4.47619 Å | 1062.72 | 1775.33 | 20.8% |
| 14.882° | 5.94812 Å | 1083.18 | 1536.62 | 21.2% |
| 14.206° | 6.22969 Å | 1224.71 | 1657.76 | 24.0% |
| 18.564° | 4.77586 Å | 1241.13 | 1863.51 | 24.3% |
| 22.060° | 4.02625 Å | 1272.46 | 2123.04 | 24.9% |
| 19.349° | 4.58375 Å | 1458.04 | 2135.37 | 28.6% |
| 15.396° | 5.75072 Å | 1488.18 | 1952.40 | 29.1% |
| 23.979° | 3.70813 Å | 1619.22 | 2530.57 | 31.7% |
| 20.747° | 4.27794 Å | 1763.94 | 2540.28 | 34.5% |
| 22.163° | 4.00763 Å | 1820.69 | 2676.00 | 35.7% |
| 17.764° | 4.98911 Å | 1991.81 | 2571.09 | 39.0% |
| 23.126° | 3.84292 Å | 2024.28 | 2915.63 | 39.6% |
| 20.057° | 4.42341 Å | 3186.59 | 3915.84 | 62.4% |
| 11.232° | 7.87127 Å | 3381.24 | 3697.94 | 66.2% |
| 13.891° | 6.37004 Å | 4125.51 | 4546.68 | 80.8% |
| 21.303° | 4.16758 Å | 5105.56 | 5916.56 | 100.0% |

1. In certain embodiments Compound 1 urea cocrystal Form P is characterized by an XRPD pattern which has at least three peaks selected from 21.3, 13.9, 11.2, 20.1, 23.1, 17.8, 22.2, 20.7, 24.0, 15.4, 19.4, 22.1, 18.6, 14.2, 14.9, 19.8, 23.5, 17.0, 15.6, 7.7, 16.6, 25.1, 24.4, 26.7, and 24.7+/−0.4° 2theta.
2. The morphic form of embodiment 1, wherein Compound 1 urea cocrystal Form P is characterized by an XRPD pattern which has at least three peaks selected from 21.3, 13.9, 11.2, 20.1, 23.1, 17.8, 22.2, 20.7, 24.0, 15.4, 19.4, 22.1, 18.6, 14.2, 14.9, 19.8, 23.5, 17.0, 15.6, 7.7, 16.6, 25.1, 24.4, 26.7, and 24.7+/−0.3° 2theta.
3. The morphic form of embodiment 1, wherein Compound 1 urea cocrystal Form P is characterized by an XRPD pattern which has at least three peaks selected from 21.3, 13.9, 11.2, 20.1, 23.1, 17.8, 22.2, 20.7, 24.0, 15.4, 19.4, 22.1, 18.6, 14.2, 14.9, 19.8, 23.5, 17.0, 15.6, 7.7, 16.6, 25.1, 24.4, 26.7, and 24.7+/−0.2° 2theta.
4. The morphic form of any one of embodiments 1-3, wherein there are at least four peaks selected from the listed peaks.
5. The morphic form of any one of embodiments 1-3, wherein there are at least five peaks selected from the listed peaks.
6. The morphic form of any one of embodiments 1-3, wherein there are at least six peaks selected from the listed peaks.
7. The morphic form of any one of embodiments 1-3, wherein there are at least seven peaks selected from the listed peaks.
8. The morphic form of any one of embodiments 1-3, wherein there are at least eight peaks selected from the listed peaks.
9. The morphic form of any one of embodiments 1-3, wherein there are at least nine peaks selected from the listed peaks.
10. The morphic form of any one of embodiments 1-3, wherein there are at least ten peaks selected from the listed peaks.
11. The morphic form of any one of embodiments 1-10, wherein the XRPD includes a peak at 21.3+/−0.2° 2theta.
12. The morphic form of any one of embodiments 1-11, wherein the XRPD includes a peak at 13.9+/−0.2° 2theta.
13. The morphic form of any one of embodiments 1-12, wherein the XRPD includes a peak at 11.2+/−0.2° 2theta.
14. The morphic form of any one of embodiments 1-13, wherein the XRPD includes a peak at 20.1+/−0.2° 2theta.
15. The morphic form of any one of embodiments 1-14, wherein the XRPD includes a peak at 23.1+/−0.2° 2theta.

16. The morphic form of any one of embodiments 1-15, wherein the XRPD includes a peak at 17.8+/−0.2° 2theta.
17. The morphic form of any one of embodiments 1-16, wherein the XRPD includes a peak at 22.2+/−0.2° 2theta.
18. The morphic form of any one of embodiments 1-17, wherein the XRPD includes a peak at 20.7+/−0.2° 2theta.

Non-Limiting BRD9 Degradation Embodiments

In certain embodiments, the compound of the presentation invention is characterized as having a BRD binding ($K_i$) of less than 200 nM. In certain embodiments, the compound of the presentation invention is characterized as having a BRD binding ($K_i$) of less than 100 nM.

In certain embodiments, the compound of the presentation invention is characterized as having a FP-E3 binding ($K_d$) of less than 2000 nM. In certain embodiments, the compound of the presentation invention is characterized as having a FP-E3 binding ($K_d$) of less than 1000 nM.

In certain embodiments, the compound of the presentation invention is characterized as having BRD9 degradation of less than 10 nM at 2 hours and/or a $K_{endo}$ of less than 10% after 17 hours.

In certain embodiments, the compound of the presentation invention is characterized as having BRD9 degradation kinetics $K_{pc}$ of less than 20 nM.

In certain embodiments, the compound of the presentation invention is characterized as having BRD7 degradation of greater than >999 nM and/or an $E_{max}$ of greater than 95% after 24 hours.

In certain embodiments, the compound of the presentation invention is characterized as having a BRD4 degradation of more than 1000 nM and less than 5000 nM and/or an $E_{max}$ of >60% and less than 90% after 24 hours.

In certain embodiments, the compound of the presentation invention is characterized as having IKZF1/SALL4/GSPT1 degradation $IC_{50}$ of >999 nM.

In certain embodiments, the compound of the presentation invention is characterized as having HEPG2 viability of >999 nM. In certain embodiments, the compound of the presentation invention is characterized as having HEPG2 viability of >10,000 nM.

In certain embodiments, the compound of the presentation invention is characterized as having SW982 viability ($GI_{50}$) of >1000 nM. In certain embodiments, the compound of the presentation invention is characterized as having SW982 viability ($GI_{50}$) of >10,000 nM.

In certain embodiments, the compound of the presentation invention is characterized as having a hERG $IC_{50}$ of >30 μM. In certain embodiments, the compound of the presentation invention is characterized as having a hERG $IC_{50}$ of >60 μM.

IV. Methods of Treatment

A compound as described herein can be used in an effective amount to treat a patient, typically a human patient, in need thereof with a disorder mediated by BRD9.

Another aspect of the present invention provides a compound as described herein, or an enantiomer, diastereomer, or stereoisomer thereof, or pharmaceutically acceptable salt, hydrate, or solvate thereof, or a pharmaceutical composition, for use in the manufacture of a medicament for treating or preventing cancer or more generally abnormal cellular proliferation in a patient, for example a human, in need thereof, wherein the cancer or abnormally proliferating cell comprises an activated BRD9 or wherein there is a need of BRD9 inhibition for the treatment or prevention of cancer.

In certain embodiments, the method comprises administering an effective amount of the active compound or its salt as described herein, optionally including a pharmaceutically acceptable excipient, carrier, or adjuvant (i.e., a pharmaceutically acceptable composition), or optionally in combination or alternation with another therapeutically active agent or combination of agents, to a patient in need thereof.

In certain embodiments, the present invention provides a method of treating any of the disorders described herein, in a patient in need thereof.

In other embodiments, the patient is administered an additional therapeutic agent. In other embodiments, the compound as described herein, and the additional therapeutic agent are administered simultaneously or sequentially.

In certain embodiments, the application provides a method of preventing any of the disorders described herein, in a patient in need thereof. In certain embodiments, the patient is a human.

In certain embodiments a compound of the present invention is used to treat a refractory disorder, for example a refractory cancer. In certain embodiments a compound of the present invention is used to treat a relapsed disorder, for example a relapsed cancer. In further embodiments a compound of the present invention is used to treat a refractory and reflapsed disorder, for example a refractory and relapsed cancer. In further embodiments a compound of the present invention is used to treat a multiply drug resistant disorder, for example a multiply drug resistant cancer.

In certain embodiments a compound of the present invention is used to treat a SMARCB1-perturbed cancer, for example a SMARCB1-perturbed solid tumor.

In certain embodiments the SMARCB1-perturbed cancer is characterized by the presence of SS18-SSX fusion proteins resulting in altered SMARCB1 functionality (e.g.: synovial sarcoma). In certain embodiments the SMARCB1-perturbed cancer is characterized by being SMARBC1 null by NGS or IHC/FISH (SMARCB1 deleted tumors)

In certain embodiments the BRD9 mediated disorder is synovial sarcoma, malignant rhabdoid tumor, atypical teratoid or rhabdoid tumor, epithelioid sarcoma, renal medullary carcinoma, epithelioid malignant peripheral nerve sheath tumor, myoepithelial carcinoma, extraskeletal myxoid chondrosarcoma, chordoma, pancreatic undifferentiated rhabdoid carcinoma, sinonasal basaloid carcinoma, or rhabdoid carcinoma of the gastrointestinal tract.

In certain embodiments the BRD9 mediated disorder is a poorly differentiated chordoma.

In certain embodiments the BRD9 mediated disorder is a rare soft tissue malignancy.

In certain embodiments the BRD9 mediated disorder is a synovial sarcoma.

In certain embodiments the BRD9 mediated disorder is a malignant rhabdoid tumor.

In certain embodiments the BRD9 mediated disorder is an atypical teratoid or rhabdoid tumor.

In certain embodiments the BRD9 mediated disorder is an epithelioid sarcoma.

In certain embodiments the BRD9 mediated disorder is a renal medullary carcinoma.

In certain embodiments the BRD9 mediated disorder is an epithelioid malignant peripheral nerve sheath tumor.

In certain embodiments the BRD9 mediated disorder is a myoepithelial carcinoma.

In certain embodiments the BRD9 mediated disorder is an extraskeletal myxoid chondrosarcoma.

In certain embodiments the BRD9 mediated disorder is a chordoma.

In certain embodiments the BRD9 mediated disorder is a pancreatic undifferentiated rhabdoid carcinoma.

In certain embodiments the BRD9 mediated disorder is a sinonasal basaloid carcinoma.

In certain embodiments the BRD9 mediated disorder is a sinonasal carcinoma.

In certain embodiments the BRD9 mediated disorder is a rhabdoid carcinoma of the gastrointestinal tract.

In certain embodiments the BRD9 mediated disorder is a malignant rhabdoid tumor located in or on the brain or spinal cord.

In certain embodiments the BRD9 mediated disorder is a cribriform neuroepithelial tumor located in or on the brain, for example the periventricular region or medulla.

In certain embodiments the BRD9 mediated disorder is a renal medullary carcinoma located in or on the kidney.

In certain embodiments the BRD9 mediated disorder is an epithelioid sarcoma located in or on the skin, subcantaneous tissue, extremities, deep tissue, perineum, or proximal limb girdles.

In certain embodiments the BRD9 mediated disorder is classic epitheloid sarcoma.

In certain embodiments the BRD9 mediated disorder is proximal epitheloid sarcoma.

In certain embodiments the BRD9 mediated disorder is an epithelioid malignant peripheral nerve sheath tumor located in or on the dermis, subcutaneous tissue, or deep soft tissue.

In certain embodiments the BRD9 mediated disorder is a schwannoma in familial schwannomatosis located in or on a peripheral nerve or spinal nerve root.

In certain embodiments the BRD9 mediated disorder is a chordoma located in or on the skull base, spine, or cervical and spheno-occipital origin common in children.

In certain embodiments the BRD9 mediated disorder is a myoepithelial carcinoma located in or on a soft tissue or viscera.

In certain embodiments the BRD9 mediated disorder is a sinonasal carcinoma located in or on the sinonasal region.

In certain embodiments the BRD9 mediated disorder is a synovial sarcoma located in or on deep soft tissues of extremities or another location.

In certain embodiments the BRD9 mediated disorder is a atypical teratoid rhabdoid tumor located in or on the kidney, a soft tissue, or viscera.

As inhibitors of BRD9, the compounds and compositions of this application are particularly useful for treating or lessening the severity of a disease, condition, or disorder where a bromodomain protein is implicated in the disease, condition, or disorder.

In one aspect, the present invention provides a method for treating or lessening the severity of a disease, condition, or disorder where a bromodomain protein is implicated in the disease state.

Another aspect of the present invention provides a method of inhibiting or decreasing the amount of bromodomain protein in a patient in need thereof comprising administering an effective amount of a compound as described herein or an enantiomer, diastereomer, or stereoisomer thereof, or pharmaceutically acceptable salt, hydrate, or solvate thereof, and optionally a pharmaceutically acceptable carrier.

Another aspect of the present invention provides a method of treating a bromodomain protein mediated disorder, the method comprising administering to a patient in need thereof an effective amount of a compound as described herein, or an enantiomer, diastereomer, or stereoisomer thereof, or pharmaceutically acceptable salt, hydrate, or solvate thereof; and optionally a pharmaceutically acceptable carrier.

Another aspect of the present invention provides a method of treating or preventing a proliferative disease. The method comprises administering an effective amount of a pharmaceutical composition comprising a compound as described herein, or an enantiomer, diastereomer, or stereoisomer thereof, or pharmaceutically acceptable salt, hydrate, or solvate thereof and optionally a pharmaceutically acceptable carrier to a patient in need thereof.

In some embodiments, the disease is mediated by BRD9. In other embodiments, BRD9 plays a role in the initiation or development of the disease.

In certain embodiments, the BRD9 mediated disorder comprises a benign growth, metastasis, neoplasm, tumor, solid tumor, rhabdoid tumor, malignant rhabdoid tumor, carcinoma, leukemia, cancer, abnormal cellular proliferation, graft-versus-host rejection, an amyloid-based proteinopathy, a proteinopathy, fibrotic disorder, inflammation, arthritis, pulmonary disorders, and immune disorders.

In certain embodiments, the disorder treated by the present invention is a SS18-SSX fusion protein related disorder. In certain embodiments, the disorder treated by the present invention is a SS18 protein related disorder. In certain embodiments, the disorder treated by the present invention is a SSX protein related disorder.

In certain embodiments, the disease or disorder is cancer or a proliferation disease.

In certain embodiments, the BRD9 mediated disorder is an abnormal cell proliferation, including, but not limited to, a tumor or cancer, or a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder.

In certain embodiments, the hematological cancer is acute myelogenous leukemia (AML), acute lymphoblastic leukemia (ALL), lymphoblastic T-cell leukemia, chronic myelogenous leukemia (CML), chronic lymphocytic leukemia (CLL), hairy-cell leukemia, chronic neutrophilic leukemia (CNL), acute lymphoblastic T-cell leukemia, acute monocytic leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukemia (MLL), erythroleukemia, malignant lymphoma, Hodgkins lymphoma, non-Hodgkins lymphoma, lymphoblastic T-cell lymphoma, Burkitt's lymphoma, follicular lymphoma, B cell acute lymphoblastic leukemia, diffuse large B cell lymphoma, Myc and B-Cell Leukemia (BCL)2 and/or BCL6 rearrangements/overexpression [double- and triple-hit lymphoma], myelodysplastic/myeloproliferative neoplasm, mantle cell lymphoma including bortezomib resistant mantle cell lymphoma.

Solid tumors that can be treated with the compounds described herein include, but are not limited to lung cancers, including small cell lung cancer (SCLC) and non-small cell lung cancer (NSCLC), breast cancers including inflammatory breast cancer, ER-positive breast cancer including tamoxifen resistant ER-positive breast cancer, and triple negative breast cancer, colon cancers, midline carcinomas, liver cancers, renal cancers, prostate cancers including castrate resistant prostate cancer (CRPC), brain cancers including gliomas, glioblastomas, neuroblastoma, and medulloblastoma including MYC-amplified medulloblastoma, colorectal cancers, Wilm's tumor, Ewing's sarcoma, rhabdomyosarcomas, ependymomas, head and neck cancers, melanomas, squamous cell carcinomas, ovarian cancers, pancreatic cancers including pancreatic ductal adenocarcinomas (PDAC) and pancreatic neuroendocrine tumors (PanNET), osteosarcomas, giant cell tumors of bone, thyroid cancers, bladder cancers, urothelial cancers, vulval cancers, cervical cancers, endometrial cancers, mesotheliomas, esophageal cancers, salivary gland cancers, gastric cancers, nasopharangeal cancers, buccal cancers, cancers of the mouth, GIST (gastrointestinal stromal tumors), NUT-midline carcinomas, testicular cancers, squamous cell carcinomas, hepatocellular carcinomas (HCC), MYCN driven solid tumors, and NUT midline carcinomas (NMC).

In further embodiments, the disease or disorder is sarcoma of the bones, muscles, tendons, cartilage, nerves, fat, or blood vessels.

In further embodiments, the disease or disorder is soft tissue sarcoma, bone sarcoma, or osteosarcoma.

In further embodiments, the disease or disorder is angiosarcoma, fibrosarcoma, liposarcoma, leiomyosarcoma, Karposi's sarcoma, osteosarcoma, gastrointestinal stromal tumor, synovial sarcoma, Pleomorphic sarcoma, chondrosarcoma, Ewing's sarcoma, reticulum cell sarcoma, meningiosarcoma, botryoid sarcoma, rhabdomyosarcoma, or embryonal rhabdomyosarcoma.

In certain embodiments the disorder is a bone, muscle, tendon, cartilage, nerve, fat, or blood vessel sarcoma.

In further embodiments, the disease or disorder is multiple myeloma.

In further embodiments, the disease or disorder is synovial sarcoma. The connection between synovial sarcoma and BRD9 has been described in the literature. For example, the paper by Brien et al., titled "Targeted degradation of BRD9 reverses oncogenic gene expression in synovial sarcoma" describes the high sensitivity of synovial sarcoma tumours to administration of BRD9 degraders. Similarly, the paper by Michel et al, titled "A non-canonical SWI/SNF complex is a synthetic lethal target in cancers driven by BAF complex perturbation" describes the role of BAF in synovial sarcoma and BRD9's role in synovial sarcoma proliferation.

In certain embodiments, the BRD9 mediated disorder is an inflammatory disease, including but not limited to asthma, chronic peptic ulcers, tuberculosis, rheumatoid arthritis, periodontitis, ulcerative colitis, Crohn's disease, or hepatitis.

In other embodiments, the disease or disorder is inflammation, arthritis, rheumatoid arthritis, spondyiarthropathies, gouty arthritis, osteoarthritis, juvenile arthritis, and other arthritic conditions, neuroinflammation, allergy, pain, neuropathic pain, fever, pulmonary disorders, lung inflammation, adult respiratory distress chronic pulmonary inflammatory disease, and chronic obstructive pulmonary disease (COPD), liver disease and nephritis, gastrointestinal conditions, inflammatory bowel disease, Crohn's disease, gastritis, irritable bowel syndrome, ulcerative colitis, ulcerative diseases, gastric ulcers, autoimmune disease, graft vs. host reaction and allograft rejections, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, clear cell renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, peripheral neuropathy, or B-Cell Lymphoma.

In other embodiments, the present invention provides a method for treating or preventing clear cell renal cell carcinoma, the method comprising administering to a patient in need thereof an effective amount of a compound as described herein, or an enantiomer, diastereomer, or stereoisomer thereof, or pharmaceutically acceptable salt, hydrate, or solvate thereof; and optionally a pharmaceutically acceptable carrier. In one aspect, the method for treating or preventing clear cell renal cell carcinoma comprises administering an effective amount of Compound 1 or a morphic form of Compound 1, for example Compound 1 Form N, or a pharmaceutically acceptable salt thereof to a patient in need thereof.

In other embodiments, the pharmaceutical composition comprising the compound as described herein and the additional therapeutic agent are administered simultaneously or sequentially.

In other embodiments, the disease or disorder is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, solid tumors, hematological cancers or solid cancers.

In some embodiments, said method is used to treat or prevent a condition selected from autoimmune diseases, inflammatory diseases, proliferative and hyperproliferative diseases, and immunologically-mediated diseases. In other embodiments, said condition is selected from a proliferative disorder. In other embodiments, the present invention provides a method for treating or preventing interferon-associated inflammation, the method comprising administering to a patient in need thereof an effective amount of a compound as described herein, or an enantiomer, diastereomer, or stereoisomer thereof, or pharmaceutically acceptable salt, hydrate, or solvate thereof; and optionally a pharmaceutically acceptable carrier. In one aspect, the method comprises administering an effective amount of Compound 1 or a morphic form of Compound 1, for example Compound 1 Form N, or a pharmaceutically acceptable salt thereof to a patient in need thereof.

In certain embodiments, the BRD9 mediated disorder is an immune disorder, including but not limited to, autoimmune disorders such as Addison disease, Celiac disease, dermatomyositis, Graves disease, thyroiditis, multiple sclerosis, pernicious anemia, reactive arthritis, lupus, or type I diabetes.

One aspect of this application provides compounds that are useful for the treatment of diseases, disorders, and conditions characterized by excessive or abnormal cell proliferation. Such diseases include, but are not limited to, a proliferative or hyperproliferative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term “cancer” includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term “cancer” refers to any cancer caused by the proliferation of malignant neoplastic cells, such as a tumor, neoplasm, carcinoma, sarcoma, leukemia, lymphoma and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers, such as oral, laryngeal, nasopharyngeal and esophageal, genitourinary cancers, such as prostate, bladder, renal, uterine, ovarian, testicular, lung cancer, such as small-cell and non-small cell, breast cancer, pancreatic cancer, melanoma and other skin cancers, stomach cancer, brain tumors, tumors related to Gorlin's syndrome, such as medulloblastoma or meningioma, and liver cancer.

Additional exemplary forms of cancer include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiarly adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more compound as described herein, in the manufacture of a medicament for the treatment of cancer, including without limitation the various types of cancer disclosed herein.

In some embodiments, the compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compound as described herein is useful for treating hematopoietic disorders, in particular, acute-myelogenous leukemia (AML), chronic-myelogenous leukemia (CML), acute-promyelocytic leukemia, and acute lymphocytic leukemia (ALL).

In one embodiment, a compound or its corresponding pharmaceutically acceptable salt, or isotopic derivative, as described herein can be used in an effective amount to treat a host, for example a human, with a lymphoma or lymphocytic or myelocytic proliferation disorder or abnormality. For example, a compound as described herein can be administered to a host suffering from a Hodgkin's Lymphoma or a Non-Hodgkin's Lymphoma. For example, the host can be suffering from a Non-Hodgkin's Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); diffuse small-cleaved cell lymphoma (DSCCL); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; Langerhans cell histiocytosis; or Waldenstrom's Macroglobulinemia.

In another embodiment, a compound or its corresponding pharmaceutically acceptable salt, or isotopic derivative, as described herein can be used in an effective amount to treat a patient, for example a human, with a Hodgkin's lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin's Lymphoma; or Nodular Lymphocyte Predominant HL.

This application further embraces the treatment or prevention of cell proliferative disorders such as hyperplasia, dysplasia and pre-cancerous lesion. Dysplasia is the earliest form of pre-cancerous lesion recognizable in a biopsy by a pathologist. The compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

In certain embodiments, a method of reducing the risk of recurrence of a disorder mediated by BRD9 is provided comprising administering an effective amount of Compound 1, or a morphic form of Compound 1, or a pharmaceutically acceptable salt thereof, to a patient in need thereof, for example a human, optionally in a pharmaceutically acceptable carrier. For example, in certain embodiments, a morphic form of Compound 1 is administered to a human to treat a cancer, for example, a soft tissue sarcoma, synovial sarcoma, advanced synovial sarcoma, or metastatic synovial sarcoma.

In certain embodiments, a method of reducing the risk of relapse of a disorder mediated by BRD9 is provided comprising administering an effective amount of Compound 1, or a morphic form of Compound 1, or a pharmaceutically acceptable salt thereof, to a patient in need thereof, for example a human, optionally in a pharmaceutically acceptable carrier. For example, in certain embodiments, a morphic form of Compound 1 is administered to a human to treat a cancer, for example, a soft tissue sarcoma, synovial sarcoma, advanced synovial sarcoma, or metastatic synovial sarcoma.

In other embodiments, a method for preventing recurrence of a disorder mediated by BRD9 is provided comprising administering an effective amount of Compound 1, or a morphic form of Compound 1, or a pharmaceutically acceptable salt thereof, to a patient in need thereof, for example a human, optionally in a pharmaceutically acceptable carrier. For example, in certain embodiments, a morphic form of Compound 1 is administered to a human to treat a cancer, for example, a soft tissue sarcoma, synovial sarcoma, advanced synovial sarcoma, or metastatic synovial sarcoma.

In other embodiments, a method for preventing relapse of a disorder mediated by BRD9 is provided comprising administering an effective amount of Compound 1, or a morphic form of Compound 1, to a patient in need thereof, for example a human, optionally in a pharmaceutically acceptable carrier. For example, in certain embodiments, a morphic form of Compound 1 is administered to a human to treat a cancer, for example, a soft tissue sarcoma, synovial sarcoma, advanced synovial sarcoma, or metastatic synovial sarcoma.

In another embodiment, a method of reducing the risk of recurrence of multiple myeloma is provided comprising administering an effective amount of Compound 1, or a morphic form of Compound 1, or a pharmaceutically acceptable salt thereof, to a patient in need thereof, for example a human, optionally in a pharmaceutically acceptable carrier.

In other another aspect, the present invention provides a method for preventing recurrence of multiple myeloma comprising administering an effective amount of Compound 1, or a morphic form of Compound 1, or a pharmaceutically acceptable salt thereof, to a patient in need thereof, for example a human, optionally in a pharmaceutically acceptable carrier.

Other aspects of the present invention provide a compound as described herein, or an enantiomer, diastereomer, or stereoisomer thereof, or pharmaceutically acceptable salt, hydrate, or solvate thereof, or a morphic form thereof, or a pharmaceutical composition, for use in the manufacture of a medicament for reducing the risk of relapse or recurrence or preventing recurrence or relapse a BRD9 mediated disorder. In one aspect, the BRD9 mediated disorder is a soft tissue sarcoma, synovial sarcoma, advanced synovial sarcoma, or metastatic synovial sarcoma.

For methods of reducing the risk of recurrence or relapse of a BRD9 mediated disorder or cancer, or a method of preventing recurrence or relapse of a BRD9 mediated disorder or cancer, in accordance with the present invention, the amount of Compound 1, or a morphic form of Compound 1, or a pharmaceutically acceptable salt thereof, administered to the patient is the same as the amount used to initially treat said disorder or cancer. In another embodiment, the amount is less than the amount used to initially treat the disorder or cancer, for example, 25% less, 50% less, or 75% less. In one embodiment, the amount is 50% less than the amount used to initially treat the disorder or cancer.

In another aspect, for methods of reducing the risk of recurrence or relapse of a BRD9 mediated disorder or cancer, or a method of preventing recurrence or relapse of a BRD9 mediated disorder or cancer, in accordance with the present invention, the patient is administered the amount of Compound 1, or a morphic form of Compound 1, or a pharmaceutically acceptable salt thereof, for a period of time following completion of initial treatment for the BRD9 mediated disorder or cancer, wherein the period is between six months to three years. In one embodiment, the period is selected from six months, nine months, one year, eighteen months, two years, thirty months, and three years. In one aspect, the period is one year. In another aspect, the period is eighteen months. In yet another aspect, the period is two years.

As inhibitors of BRD9 protein, the compounds and compositions of this application are also useful in biological samples. One aspect of the application is inhibiting protein activity in a biological sample, which method comprises contacting said biological sample with a compound or composition as described herein. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein activity in a biological sample is useful for a variety of purposes that are known to one of skill in the art. Examples of such purposes include, but are not limited to, blood transfusion, organ-transplantation, and biological specimen storage.

Another aspect of this application is the study of BRD9 protein in biological and pathological phenomena; the study of intracellular signal transduction pathways mediated by such proteins; and the comparative evaluation of new protein inhibitors. Examples of such uses include, but are not limited to, biological assays such as enzyme assays and cell-based assays.

The activity of the compounds and compositions of the present application as BRD9 inhibitors may be assayed in vitro, in vivo, or in a cell line. In vitro assays include assays that determine inhibition of either the enzyme activity or ATPase activity of the activated protein. Alternate in vitro assays quantitate the ability of the inhibitor to bind to the bromodomain protein and may be measured either by radio labelling the inhibitor prior to binding, isolating the inhibitor/bromodomain complex and determining the amount of radio label bound, or by running a competition experiment where new inhibitors are incubated with the bromodomain bound to known radioligands. Detailed conditions for assaying a compound used in this application as an inhibitor of various bromodomain proteins are set forth in the Examples below.

In accordance with the foregoing, the present application further provides a method for preventing or treating any of the diseases or disorders described above in a patient in need of such treatment, which method comprises administering to said patient a therapeutically effective amount of a compound as described herein, or an enantiomer, diastereomer, or stereoisomer thereof, or pharmaceutically acceptable salt, hydrate, or solvate thereof. For any of the above uses, the required dosage will vary depending on the mode of administration, the particular condition to be treated and the effect desired.

In certain embodiments Compound 1 is used in a treatment described herein as a pharmaceutically acceptable salt.

Unresectable or Locally Advanced Cancers

In certain embodiments an effective amount of compound described herein for example Compound 1 is administered to a patient in need thereof with a locally advanced or metastatic SMARCB1-perturbed cancer which is relapsed and/or refractory and unresectable. In certain embodiments an effective amount of compound described herein for example Compound 1 is administered to a patient in need thereof with a locally advanced SMARCB1-perturbed cancer which is relapsed and/or refractory and unresectable and/or metastatic.

Unresectable cancers are cancers that cannot be removed (resected) by surgery. Many cancers can be either resectable or unresectable depending on the site of the tumor and the size of the tumor. In certain embodiments an unresectable cancer is treated with an effective amount of Compound 1 or a morphic form or pharmaceutical composition thereof. In other embodiments resectable cancer is treated with Compound 1 or a morphic form or pharmaceutical composition thereof wherein the treatment additionally optionally includes surgically removing the tumor.

Locally advanced cancers are cancers that have grown outside of the body part where the tumor started but have not yet spread (metastasized) to other parts of the body. In certain embodiments a locally advanced cancer is treated with an effective amount of Compound 1 or a morphic form or pharmaceutical composition thereof.

In certain embodiments an effective amount of Compound 1 is administered to a patient in need thereof with a locally advanced SMARCB1-perturbed cancer. In certain embodiments an effective amount of Compound 1 is administered to a patient in need thereof with a locally advanced SMARCB1-perturbed cancer which is unresectable. In certain embodiments an effective amount of Compound 1 is administered to a patient in need thereof with a locally advanced SMARCB1-perturbed cancer which is relapsed, refractory, and unresectable. In certain embodiments an effective amount of Compound 1 is administered to a patient in need thereof with a locally advanced SMARCB1-perturbed cancer which is relapsed and unresectable. In certain embodiments an effective amount of Compound 1 is administered to a patient in need thereof with a locally advanced SMARCB1-perturbed cancer which is refractory and unresectable.

In certain embodiments an effective amount of Compound 1 is administered to a patient in need thereof with an unresectable SMARCB1-perturbed cancer. In certain embodiments an effective amount of Compound 1 is administered to a patient in need thereof with a metastatic SMARCB1-perturbed cancer which is unresectable. In certain embodiments an effective amount of Compound 1 is administered to a patient in need thereof with a metastatic SMARCB1-perturbed cancer which is relapsed, refractory, and unresectable. In certain embodiments an effective amount of Compound 1 is administered to a patient in need thereof with a metastatic SMARCB1-perturbed cancer which is relapsed and unresectable. In certain embodiments an effective amount of Compound 1 is administered to a patient in need thereof with a metastatic SMARCB1-perturbed cancer which is refractory and unresectable.

In certain embodiments an effective amount of Compound 1 is administered to a patient in need thereof with a SMARCB1-perturbed cancer which is relapsed, refractory, and unresectable. In certain embodiments an effective amount of Compound 1 is administered to a patient in need thereof with a SMARCB1-perturbed cancer which is relapsed and unresectable. In certain embodiments an effective amount of Compound 1 is administered to a patient in need thereof with a SMARCB1-perturbed cancer which is refractory and unresectable.

In certain embodiments an effective amount of Compound 1 is administered to a patient in need thereof with a locally advanced synovial sarcoma. In certain embodiments an effective amount of Compound 1 is administered to a patient in need thereof with a locally advanced synovial sarcoma which is unresectable. In certain embodiments an effective amount of Compound 1 is administered to a patient in need thereof with a locally advanced synovial sarcoma which is relapsed, refractory, and unresectable. In certain embodiments an effective amount of Compound 1 is administered to a patient in need thereof with a locally advanced synovial sarcoma which is relapsed and unresectable. In certain embodiments an effective amount of Compound 1 is administered to a patient in need thereof with a locally advanced synovial sarcoma which is refractory and unresectable.

In certain embodiments an effective amount of Compound 1 is administered to a patient in need thereof with an unresectable synovial sarcoma. In certain embodiments an effective amount of Compound 1 is administered to a patient in need thereof with a metastatic synovial sarcoma which is unresectable. In certain embodiments an effective amount of Compound 1 is administered to a patient in need thereof with a metastatic synovial sarcoma which is relapsed, refractory, and unresectable. In certain embodiments an effective amount of Compound 1 is administered to a patient in need thereof with a metastatic synovial sarcoma which is relapsed and unresectable. In certain embodiments an effective amount of Compound 1 is administered to a patient in need thereof with a metastatic synovial sarcoma which is refractory and unresectable.

In certain embodiments an effective amount of Compound 1 is administered to a patient in need thereof with a synovial sarcoma which is relapsed, refractory, and unresectable. In certain embodiments an effective amount of Compound 1 is administered to a patient in need thereof with a synovial sarcoma which is relapsed and unresectable. In certain embodiments an effective amount of Compound 1 is administered to a patient in need thereof with a synovial sarcoma which is refractory and unresectable.

In certain embodiments an effective amount of Compound 1 is administered to a patient in need thereof with a locally advanced SMARCB1-null cancer. In certain embodiments an effective amount of Compound 1 is administered to a patient in need thereof with a locally advanced SMARCB1-null cancer which is unresectable. In certain embodiments an effective amount of Compound 1 is administered to a patient in need thereof with a locally advanced SMARCB1-null cancer which is relapsed, refractory, and unresectable. In certain embodiments an effective amount of Compound 1 is administered to a patient in need thereof with a locally advanced SMARCB1-null cancer which is relapsed and unresectable. In certain embodiments an effective amount of Compound 1 is administered to a patient in need thereof with a locally advanced SMARCB1-null cancer which is refractory and unresectable.

In certain embodiments an effective amount of Compound 1 is administered to a patient in need thereof with an unresectable SMARCB1-null cancer. In certain embodiments an effective amount of Compound 1 is administered to a patient in need thereof with a metastatic SMARCB1-null cancer which is unresectable. In certain embodiments an effective amount of Compound 1 is administered to a patient in need thereof with a metastatic SMARCB1-null cancer which is relapsed, refractory, and unresectable. In certain embodiments an effective amount of Compound 1 is administered to a patient in need thereof with a metastatic SMARCB1-null cancer which is relapsed and unresectable. In certain embodiments an effective amount of Compound 1 is administered to a patient in need thereof with a metastatic SMARCB1-null cancer which is refractory and unresectable.

In certain embodiments an effective amount of Compound 1 is administered to a patient in need thereof with a SMARCB1-null cancer which is relapsed, refractory, and unresectable. In certain embodiments an effective amount of Compound 1 is administered to a patient in need thereof with a SMARCB1-null cancer which is relapsed and unresectable. In certain embodiments an effective amount of Compound 1 is administered to a patient in need thereof with a SMARCB1-null cancer which is refractory and unresectable.

V. Combination Therapy

A compound described herein or a pharmaceutically acceptable salt thereof can be used in an effective amount, either alone or in combination, to treat a patient such as a human with a disorder as described herein or a BRD9 mediated disorder.

The disclosed compounds described herein can be used in an effective amount alone or in combination with another compound of the present invention or another therapeutically active agent or second therapeutic agent to treat a patient such as a human with a disorder, including but not limited to those described herein.

The term "therapeutically active agent" is used to describe an agent, other than the selected compound according to the present invention, which can be used in combination or alternation with a compound of the present invention to achieve a desired result of therapy. In one embodiment, the compound of the present invention and the therapeutically active agent are administered in a manner that they are active in vivo during overlapping time periods, for example, have time-period overlapping Cmax, Tmax, AUC or other pharmacokinetic parameter. In another embodiment, the compound of the present invention and the therapeutically active agent are administered to a patient in need thereof that do not have overlapping pharmacokinetic parameter, however, one has a therapeutic impact on the therapeutic efficacy of the other.

In one aspect of this embodiment, the therapeutically active agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDIO680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In certain embodiments the checkpoint inhibitor is selected from nivolumab/OPDIVO®; pembrolizumab/KEYTRUDA®; and pidilizumab/CT-011, MPDL3280A/RG7446; MEDI4736; MSB0010718C; BMS 936559, a PDL2/lg fusion protein such as AMP 224 or an inhibitor of B7-H3 (e.g., MGA271), B7-H4, BTLA, HVEM, TIM3, GAL9, LAG 3, VISTA, KIR, 2B4, CD160, CGEN-15049, CHK 1, CHK2, A2aR, B-7 family ligands, or a combination thereof.

In yet another embodiment, one of the active compounds described herein can be administered in an effective amount for the treatment of abnormal tissue of the female reproductive system such as breast, ovarian, endometrial, or uterine cancer, in combination or alternation with an effective amount of an estrogen inhibitor including, but not limited to, a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors.

Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138.

Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestratnt; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone.

Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853,423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990;

WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497, 5,880,137, WO 2012/048058 and WO 2007/087684.

In another embodiment, an active compounds described herein can be administered in an effective amount for the treatment of abnormal tissue of the male reproductive system such as prostate or testicular cancer, in combination or alternation with an effective amount of an androgen (such as testosterone) inhibitor including, but not limited to a selective androgen receptor modulator, a selective androgen receptor degrader, a complete androgen receptor degrader, or another form of partial or complete androgen antagonist. In one embodiment, the prostate or testicular cancer is androgen-resistant.

Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, the therapeutically active agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In one embodiment, the therapeutically active agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In one embodiment, the therapeutically active agent is an HER-2 inhibitor. Examples of HER-2 inhibitors include trastuzumab, lapatinib, ado-trastuzumab emtansine, and pertuzumab.

In one embodiment, the therapeutically active agent is a CD20 inhibitor. Examples of CD20 inhibitors include obinutuzumab, rituximab, fatumumab, ibritumomab, tositumomab, and ocrelizumab.

In one embodiment, the therapeutically active agent is a JAK3 inhibitor. Examples of JAK3 inhibitors include tasocitinib.

In one embodiment, the therapeutically active agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl] amino]-3-nitrophenyl]sulfonylbenzamide) (navitoclax), ABT-263 ((R)-4-(4-((4'-chloro-4,4-dimethyl-3,4,5,6-tetrahydro-[1, 1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In one embodiment, the therapeutically active agent is a kinase inhibitor. In one embodiment, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include, but are not limited to, Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)-N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E, 9S,9aR,10R,11aS)-6-[[bis(prop-2-enyl)amino] methylidene]-5-hydroxy-9-(methoxymethyl)-9a,11a-dimethyl-1,4,7-trioxo-2,3,3a,9,10,11-hexahydroindeno[4,5h]isochromen-10-yl] acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422).

Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo [h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, but are not limited to, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl] methyl dihydrogen phosphate), fostamatinib disodium salt (sodium (6-((5-fluoro-2-((3,4,5-trimethoxyphenyl)amino) pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), R09021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl) bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4] oxazin-3(4H)-one), piceatannol (3-Hydroxyresveratol), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

In one embodiment, the therapeutically active agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl] azetidin-3-ol), refametinib/BAY869766/RDEAl 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/$CH_{4987655}$ (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, the therapeutically active agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide;4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3(trifluoroMethyl)phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, the therapeutically active agent is an AKT inhibitor, including, but not limited to, MK-2206, GSK690693, Perifosine, (KRX-0401), GDC-0068, Triciribine, AZD5363, Honokiol, PF-04691502, and Miltefosine, a FLT-3 inhibitor, including, but not limited to, P406, Dovitinib, Quizartinib (AC220), Amuvatinib (MP-470), Tandutinib (MLN518), ENMD-2076, and KW-2449, or a combination thereof.

In one embodiment, the therapeutically active agent is an mTOR inhibitor. Examples of mTOR inhibitors include, but are not limited to, rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/$CH_{4987655}$ (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide).

In one embodiment, the therapeutically active agent is a RAS inhibitor. Examples of RAS inhibitors include but are not limited to Reolysin and siG12D LODER.

In one embodiment, the therapeutically active agent is a HSP inhibitor. HSP inhibitors include but are not limited to Geldanamycin or 17-N-Allylamino-17-demethoxygeldanamycin (17AAG), and Radicicol.

Additional therapeutically active compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an aurora kinase inhibitor, a PIK-1 modulator, an HDAC inhibitor, a c-MET inhibitor, a PARP inhibitor, a Cdk inhibitor, an IGFR-TK inhibitor, an anti-HGF antibody, a focal adhesion kinase inhibitor, a Map kinase kinase (mek) inhibitor, a VEGF trap antibody, pemetrexed, panitumumab, amrubicin, oregovomab, Lep-etu, nolatrexed, azd2171, batabulin, of atumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In certain embodiments Compound 1 is administered in combination with doxorubicin.

In certain embodiments Compound 1 is administered in combination with ifosfamide, carboplatin, and etoposide.

In certain embodiments Compound 1 is administered in combination with doxorubicin, vincristine, and cyclophosphamid.

In certain embodiments Compound 1 is administered in combination with tazemetostat.

In certain embodiments Compound 1 is administered in combination with pazopanib.

In certain embodiments the compound is administered in combination with ifosfamide.

In one embodiment, the therapeutically active agent is selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the therapeutically active agent is an anti-inflammatory agent, a chemotherapeutic agent, a radiotherapeutic, an additional therapeutic agent, or an immunosuppressive agent.

Suitable chemotherapeutic therapeutically active agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™).

Examples of additional suitable chemotherapeutic agents include, but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In some embodiments, the compound of the present invention is administered in combination with a chemotherapeutic agent (e.g., a cytotoxic agent or other chemical compound useful in the treatment of cancer). Examples of chemotherapeutic agents include alkylating agents, antimetabolites, folic acid analogs, pyrimidine analogs, purine analogs and related inhibitors, *vinca* alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Inti. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, NJ), ABRAXANE®, cremophor-free, albumin-engineered nanoparticle formulation of paclitaxel (American Pharmaceutical Partners, Schaumberg, IL), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; and pharmaceutically acceptable salts, acids or derivatives of any of the above. Two or more chemotherapeutic agents can be used in a cocktail to be administered in combination with the compound of the present invention. Suitable dosing regimens of combination chemotherapies are known in the ar. For example combination dosing regimes are described in Saltz et al., Proc. Am. Soc. Clin. Oncol. 18:233a (1999) and Douillard et al., Lancet 355(9209): 1041-1047 (2000).

Additional therapeutic agents that can be administered in combination with a Compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one embodiment, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

In one aspect of the present invention, the therapeutically active agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a SiP receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In some embodiments, the therapeutically active agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN® (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-1-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOURIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

The combination therapy may include a therapeutic agent which is a non-drug treatment. For example, the compound could be administered in addition to radiation therapy, cryotherapy, hyperthermia, and/or surgical excision of tumor tissue.

In certain embodiments the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

In certain embodiments the second therapeutic agent is administered on a different dosage schedule than the compound of the present invention. For example the second therapeutic agent may have a treatment holiday of 1 day, 2 days, 3 days, 4 days, 5 days, 6 days, 7 days, 8 days, 9 days, 10 days, 11 days, 12 days, 13 days, or 14 days per treatment cycle. In another embodiment the first therapeutic agent has a treatment holiday. For example the first therapeutic agent may have a treatment holiday of 1 day, 2 days, 3 days, 4 days, 5 days, 6 days, 7 days, 8 days, 9 days, 10 days, 11 days, 12 days, 13 days, or 14 days per treatment cycle. In certain embodiments both the first and second therapeutic have a treatment holiday.

In certain embodiments a monotherapy or combination described herein additionally comprises administering one or more additional therapeutic agents to decrease side effects of the therapy. For example, in certain embodiments Compound 1 or a combination comprising Compound 1 is administered concurrently, before, or after administration of an antineutropenia medication, antinausea medication, an antihistamine, and/or an antipain medication. Non-limiting examples of antineutropenia medications include growth factors for example a granulocyce colony stimulating factor (G-CSF). In certain embodiments a therapy in a table above is administered in combination with a G-CSF. G-CSF (or another active agent) can be given before, with after, or on different days than Compound 1.

Non-limiting examples of granulocyte colony stimulating factors include filgrastim (in the form of neupogen, zarxio, nivestym, or another form), CG-10639, and PEGF.

In certain embodiments the granulocyte colony stimulating factor is pegfilgrastim. In certain embodiments the granulocyte colony stimulating factor is Neulasta. In certain embodiments the granulocyte colony stimulating factor is selected from Ristempa, Tezmota, Fulphila, Pelgraz, Udenyca, Udenyca, Pelmeg, Ziextenzo, Grasustek, Ziextenzo, Lapelga, Neutropeg, Cegfila, Nyvepria, and Stimufend.

In certain embodiments the therapy described herein further comprises an antinausea medication. Non-limiting examples of antinauasea medications include aprepitant, dolasetron, granisetron, ondansetron, palonosetron, proclorperazine, promethazine, netupitant-palonosetron, rolapitant, lorazepam, metoclopramide, famotidine, dexamethasone, and ranitidine.

In certain embodiments the therapy described herein further comprises an antihistamine medication. Non-limiting examples of antihistamine medications include benadryl, cetirizine, loratadine, and fexofenadine.

In certain embodiments the therapy described herein further comprises an antipain medication. Non-limiting examples of antipain medications include tramadol, hydromorphone, methadone, morphine, oxycodone, hydrocodone, oxymorphone, fentanyl, and tapentadol.

In certain embodiments the therapy described herein further comprises an anticoagulation agent. Non-limiting examples of anticoagulation agents include argatroban, bivalirudin, dabigatran, desirudin, hirudin, dalteparin, enoxaparin, fondaparinux, heparin, heparin-unfractionated, apixaban, betrixaban, deoxaban, rivaroxaban, and warfarin.

VI. Pharmaceutical Composition

A compound described herein can be administered as the neat chemical, but are more typically administered as a pharmaceutical composition, that includes an effective amount for a patient, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In general, the compositions of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, or 750 mg of active compound, or its salt.

In certain embodiments the compound of the present invention is administered at a dose of about 1 mg, 2 mg, about 4 mg, about 8 mg, about 15 mg, about 30 mg, about 50 mg, about 80 mg, about 110 mg, about 120 mg, 150, 200, 250, 300, 350, 400, 450 or 500 mg, once or twice a day.

In an alternative embodiment patient can be treated with low dosage therapy. For example the pharmaceutical composition can be in a dosage form that contains from about 0.1 μg to about 2000 μg, from about 10 μg to about 1000 μg, from about 100 μg to about 800 μg, or from about 200 μg to about 600 μg of the active compound. Examples are dosage forms with at least 0.1, 1, 5, 10, 25, 50, 100, 200, 250, 300, 400, 500, 600, 700, or 750 mg of active compound, or its salt.

In some embodiments, compounds disclosed herein or used as described are administered once a day (QD), twice a day (BID), or three times a day (TID). In some embodiments, compounds disclosed herein or used as described are administered at least once a day or twice a day for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer.

In certain embodiments the compound of the present invention is administered once a day, twice a day, three times a day, or four times a day.

In certain embodiments the compound of the present invention is administered orally once a day. In certain embodiments the compound of the present invention is administered orally twice a day. In certain embodiments the compound of the present invention is administered orally three times a day. In certain embodiments the compound of the present invention is administered orally four times a day.

In certain embodiments the compound of the present invention is administered intravenously once a day. In certain embodiments the compound of the present invention is administered intravenously twice a day. In certain embodiments the compound of the present invention is administered intravenously three times a day. In certain embodiments the compound of the present invention is administered intravenously four times a day.

In some embodiments, compounds disclosed herein or used as described are administered once a day (QD), twice a day (BID), or three times a day (TID). In some embodiments, compounds disclosed herein or used as described are administered at least once a day for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer.

In certain embodiments the compound of the present invention is administered once a day, twice a day, three times a day, or four times a day.

In certain embodiments the compound of the present invention is administered orally once a day. In certain embodiments the compound of the present invention is administered orally twice a day. In certain embodiments the compound of the present invention is administered orally three times a day. In certain embodiments the compound of the present invention is administered orally four times a day.

In certain embodiments the compound of the present invention is administered intravenously once a day. In certain embodiments the compound of the present invention is administered intravenously twice a day. In certain embodiments the compound of the present invention is administered intravenously three times a day. In certain embodiments the compound of the present invention is administered intravenously four times a day.

In some embodiments, compounds disclosed herein or used as described are administered once a week (QW), twice a week (BIW), or three times a week (TIW). In some embodiments, compounds disclosed herein or used as described are administered at least once a week for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer.

In certain embodiments the compound of the present invention is administered once a week, twice a week, three times a week, four times a week, five times a week, six times a week, or seven times a week.

In certain embodiments the compound of the present invention is administered orally once a week. In certain embodiments the compound of the present invention is administered orally twice a week. In certain embodiments the compound of the present invention is administered orally three times a week. In certain embodiments the compound of the present invention is administered orally four times a week.

In certain embodiments the compound of the present invention is administered intravenously once a week. In certain embodiments the compound of the present invention is administered intravenously twice a week. In certain embodiments the compound of the present invention is administered intravenously three times a week. In certain embodiments the compound of the present invention is administered intravenously four times a week.

In some embodiments the compound of the present invention is administered with a treatment holiday in between treatment cycles. For example, the compound may have a treatment holiday of 1 day, 2 days, 3 days, 4 days, 5 days, 6 days, 7 days, 8 days, 9 days, 10 days, 11 days, 12 days, 13 days, or 14 days per treatment cycle.

The pharmaceutical composition may also include a molar ratio of the active compound and an additional active agent. For example, the pharmaceutical composition may contain a molar ratio of about 0.5:1, about 1:1, about 2:1, about 3:1 or from about 1.5:1 to about 4:1 of an anti-inflammatory or immunosuppressing agent.

These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

A pharmaceutically or therapeutically effective amount of the composition will be delivered to the patient. The precise effective amount will vary from patient to patient, and will depend upon the species, age, the subject's size and health, the nature and extent of the condition being treated, recommendations of the treating physician, and the therapeutics or combination of therapeutics selected for administration. The effective amount for a given situation can be determined by routine experimentation. For purposes of the disclosure, a therapeutic amount may for example be in the range of about 0.01 mg/kg to about 250 mg/kg body weight, more typically about 0.1 mg/kg to about 10 mg/kg, in at least one dose. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

In certain embodiments the dose ranges from about 0.01-100 mg/kg of patient bodyweight, for example about 0.01 mg/kg, about 0.05 mg/kg, about 0.1 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packed tablets, capsules, and powders in vials or ampoules. Also, the unit dosage form can be a capsule, tablet, cachet, or lozenge itself, or it can be the appropriate number of any of these in packaged form.

In certain embodiments the compound is administered as a pharmaceutically acceptable salt. Non-limiting examples of pharmaceutically acceptable salts include: acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

Thus, the composition of the disclosure can be administered as a pharmaceutical formulation including one suitable for oral (including buccal and sub-lingual), rectal, nasal, topical, transdermal, pulmonary, vaginal or parenteral (including intramuscular, intra-arterial, intrathecal, subcutaneous and intravenous), injections, inhalation or spray, intra-aortal, intracranial, subdermal, intraperitioneal, subcutaneous, or by other means of administration containing conventional pharmaceutically acceptable carriers. A typical manner of administration is oral, topical or intravenous, using a convenient daily dosage regimen which can be adjusted according to the degree of affliction.

Depending on the intended mode of administration, the pharmaceutical compositions can be in the form of solid, semi-solid or liquid dosage forms, such as, for example, tablets, suppositories, pills, capsules, powders, liquids, syrup, suspensions, creams, ointments, lotions, paste, gel, spray, aerosol, foam, or oil, injection or infusion solution, a transdermal patch, a subcutaneous patch, an inhalation formulation, in a medical device, suppository, buccal, or sublingual formulation, parenteral formulation, or an ophthalmic solution, or the like, preferably in unit dosage form suitable for single administration of a precise dosage.

Some dosage forms, such as tablets and capsules, are subdivided into suitably sized unit doses containing appropriate quantities of the active components, e.g., an effective amount to achieve the desired purpose. The compositions will include an effective amount of the selected drug in combination with a pharmaceutically acceptable carrier and, in addition, can include other pharmaceutical agents, adjuvants, diluents, buffers, and the like.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to adjuvants, binders, buffering agents, coloring agents, diluents, disintegrants, excipients, emulsifiers, flavorants, gels, glidents, lubricants, preservatives, stabilizers, surfactants, solubilizer, tableting agents, wetting agents or solidifying material.

Some carriers may be listed in more than one class, for example vegetable oil may be used as a lubricant in some formulations and a diluent in others.

Exemplary pharmaceutically acceptable carriers include sugars, starches, celluloses, powdered tragacanth, malt, gelatin; talc, petroleum jelly, lanoline, polyethylene glycols, alcohols, transdermal enhancers and vegetable oils. Optional active agents may be included in a pharmaceutical composition, which do not substantially interfere with the activity of the compound of the present invention.

Some excipients include, but are not limited, to liquids such as water, saline, glycerol, polyethylene glycol, hyaluronic acid, ethanol, and the like. The compound can be provided, for example, in the form of a solid, a liquid, spray dried material, a microparticle, nanoparticle, controlled release system, etc., as desired according to the goal of the therapy. Suitable excipients for non-liquid formulations are also known to those of skill in the art. A thorough discussion of pharmaceutically acceptable excipients and salts is available in Remington's Pharmaceutical Sciences, 18th Edition (Easton, Pennsylvania: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable, and which provides the formulation with the desired pH, i.e., a pH in the physiologically acceptable range. Examples of buffer solutions include saline, phosphate buffered saline, Tris buffered saline, Hank's buffered saline, and the like.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment provided is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

In certain embodiments the excipient is selected from butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The pharmaceutical compositions/combinations can be formulated for oral administration. For oral administration, the composition will generally take the form of a tablet, capsule, a softgel capsule or can be an aqueous or nonaqueous solution, suspension or syrup. Tablets and capsules are typical oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

Parenteral formulations can be prepared in conventional forms, either as liquid solutions or suspensions, solid forms suitable for solubilization or suspension in liquid prior to injection, or as emulsions. Typically, sterile injectable suspensions are formulated according to techniques known in the art using suitable carriers, dispersing or wetting agents and suspending agents. The sterile injectable formulation can also be a sterile injectable solution or a suspension in a acceptably nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered using a syringe, injector, pump, or any other device recognized in the art for parenteral administration.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, typical methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Formulations for buccal administration include tablets, lozenges, gels and the like. Alternatively, buccal administration can be effected using a transmucosal delivery system as known to those skilled in the art. The compounds of the disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like.

Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compositions of the disclosure can be formulated for aerosol administration, particularly to the respiratory tract and including intranasal administration. The compound may, for example generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve.

Alternatively, the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

Formulations suitable for rectal administration are typically presented as unit dose suppositories. These may be prepared by admixing the active compound with one or more conventional solid carriers, for example, cocoa butter, and then shaping the resulting mixture.

In certain embodiments, the pharmaceutical composition is suitable for topical application to the skin using a mode of administration and defined above.

In certain embodiments, the pharmaceutical composition is suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound.

In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Many methods and devices for drug delivery are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen O Y); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277,830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nano-particles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Therapeutically active agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multi-block copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of therapeutically active molecules" (PR Pharmaceuticals, Inc.); and U.S. Pat. No. 8,663,674 titled "Microparticle containing matrices for drug delivery" (Surmodics).

VII. General Synthesis

The compounds described herein can be prepared by methods known by those skilled in the art. In one non-limiting example, the disclosed compounds can be made using the schemes below.

Compounds of the present invention with stereocenters may be drawn without stereochemistry for convenience. One skilled in the art will recognize that pure enantiomers and diastereomers can be prepared by methods known in the art. Examples of methods to obtain optically active materials include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the enantiomer is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step in the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e. chirality) in the product, which may be achieved by chiral catalysts or chiral auxiliaries;

vi) diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer;

vii) first- and second-order asymmetric transformations—a technique whereby diastereomers from the racemate quickly equilibrate to yield a preponderance in solution of the diastereomer from the desired enantiomer of where preferential crystallization of the diastereomer from the desired enantiomer perturbs the equilibrium such that eventually in principle all the material is converted to the crystalline diastereomer from the desired enantiomers. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including vial chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is place in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through;

xiv) simulated moving bed chromatography is used in one embodiment. A wide variety of chiral stationary phases are commercially available.

VIII. Synthesis of Compounds of the Present Invention

In certain embodiments, the present invention provides a process of preparation of Compound 1 of formula:

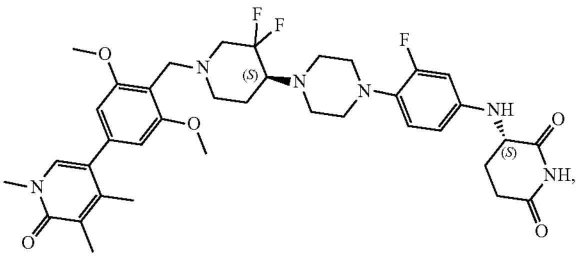

wherein the process comprises the steps of:

a. reacting tert-butyl piperazine-1-carboxylate with 1,2-difluoro-4-nitro-benzene in the presence of a first base in a first solvent to afford tert-butyl 4-(2-fluoro-4-nitro-phenyl) piperazine-1-carboxylate of formula:

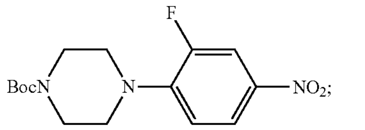 [SMILES: CC(C)(C)OC(=O)N1CCN(c2ccc([N+](=O)[O-])cc2F)CC1]

b. reacting tert-butyl 4-(2-fluoro-4-nitro-phenyl) piperazine-1-carboxylate of step (a) with a solution of a first organic or inorganic acid in a second solvent to afford 1-(2-fluoro-4-nitrophenyl)piperazine of formula:

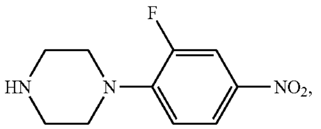 [SMILES: O=[N+]([O-])c1ccc(N2CCNCC2)c(F)c1]

or its acid-addition salt, wherein the acid-addition salt is formed through protonation of 1-(2-fluoro-4-nitrophenyl)piperazine with the first organic or inorganic acid;

c. reacting 1-(2-fluoro-4-nitrophenyl)piperazine or its acid-addition salt of step (b) with tert-butyl 3,3-difluoro-4-oxo-piperidine-1-carboxylate under reflux with toluene to remove water formed during the reaction and to afford 3,3-difluoro-4-(4-(2-fluoro-4-nitrophenyl) piperazin-1-yl)-3,6-dihydropyridine-1(2H)-carboxylate of formula:

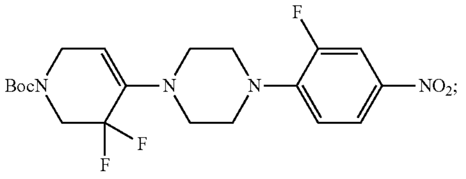 [SMILES: CC(C)(C)OC(=O)N1CC=C(N2CCN(c3ccc([N+](=O)[O-])cc3F)CC2)C(F)(F)C1]

d. reacting 3,3-difluoro-4-(4-(2-fluoro-4-nitrophenyl)piperazin-1-yl)-3,6-dihydropyridine-1(2H)-carboxylate of step (c) with a first reducing agent in a third solvent to afford tert-butyl-3,3-difluoro-4-[4-(2-fluoro-4-nitro-phenyl)piperazin-1-yl]piperidine-1-carboxylate of formula:

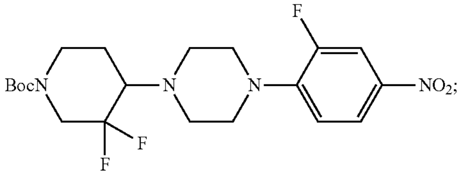 [SMILES: CC(C)(C)OC(=O)N1CCC(N2CCN(c3ccc([N+](=O)[O-])cc3F)CC2)C(F)(F)C1]

e. chiral separation of tert-butyl-3,3-difluoro-4-[4-(2-fluoro-4-nitro-phenyl)piperazin-1-yl]piperidine-1-carboxylate of step (d) by a chiral supercritical fluid chromatography to afford tert-butyl (R)-3,3-difluoro-4-(4-(2-fluoro-4-nitrophenyl)piperazin-1-yl)piperidine-1-carboxylate and tert-butyl (S)-3,3-difluoro-4-(4-(2-fluoro-4-nitrophenyl)piperazin-1-yl)piperidine-1-carboxylate of formulas:

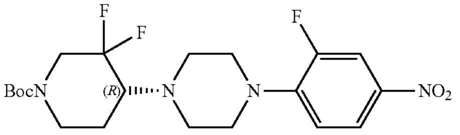

and

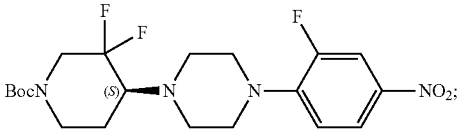

f. reducing the nitro group in tert-butyl (S)-3,3-difluoro-4-(4-(2-fluoro-4-nitrophenyl)piperazin-1-yl)piperidine-1-carboxylate of step (e) with a second reducing agent to convert the nitro group into an amino group and to afford tert-butyl 4-[4-(4-amino-2-fluoro-phenyl)piperazin-1-yl]-3,3-difluoro-piperidine-1-carboxylate of formula:

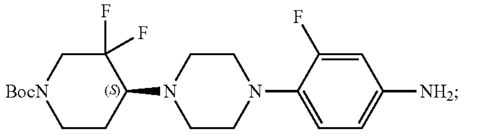

g. reacting tert-butyl 4-[4-(4-amino-2-fluoro-phenyl)piperazin-1-yl]-3,3-difluoro-piperidine-1-carboxylate of step (f) with 3-bromopiperidine-2,6-dione in the presence of a second base in a fourth solvent and in the presence of a phase transfer catalyst to afford tert-butyl (4S)-4-(4-(4-((2,6-dioxopiperidin-3-yl)amino)-2-fluorophenyl)piperazin-1-yl)-3,3-difluoropiperidine-1-carboxylate of formula:

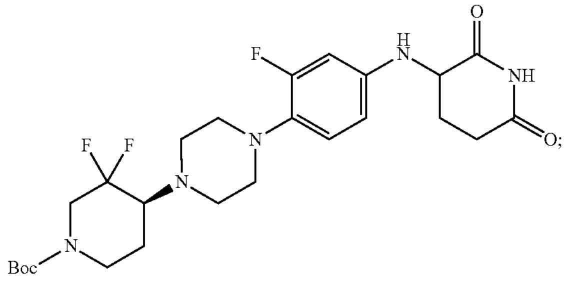

h. chiral separation of tert-butyl (4S)-4-(4-(4-((2,6-dioxopiperidin-3-yl)amino)-2-fluorophenyl)piperazin-1-yl)-3,3-difluoropiperidine-1-carboxylate of step (g) by a chiral high-performance liquid chromatography to afford tert-butyl (S)-4-(4-(4-(((S)-2,6-dioxopiperidin-3-yl)amino)-2-fluorophenyl)piperazin-1-yl)-3, 3-difluoropiperidine-1-carboxylate of formula:

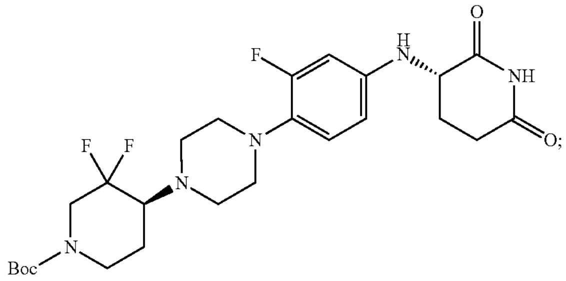 [SMILES: CC(C)(C)OC(=O)N1CC[C@H](N2CCN(c3ccc(N[C@H]4CCC(=O)NC4=O)cc3F)CC2)C(F)(F)C1]

and i. reacting tert-butyl (S)-4-(4-(4-(((S)-2,6-dioxopiperidin-3-yl)amino)-2-fluorophenyl)piperazin-1-yl)-3,3-difluoropiperidine-1-carboxylate of step (h) with a solution of a second organic or inorganic acid in a fifth solvent to afford (S)-3-((4-(4-((S)-3,3-difluoropiperidin-4-yl)piperazin-1-yl)-3-fluorophenyl)amino)piperidine-2,6-dione of formula:

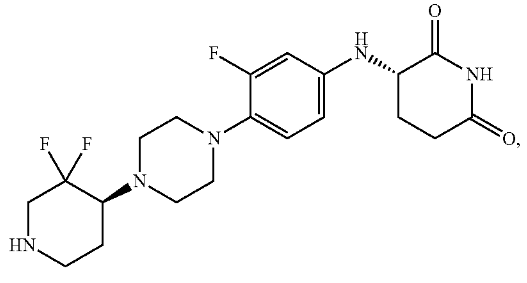 [SMILES: O=C1CC[C@H](Nc2ccc(N3CCN([C@H]4CCNCC4(F)F)CC3)c(F)c2)C(=O)N1]

or its acid-addition salt; and j. reacting (S)-3-((4-(4-((S)-3,3-difluoropiperidin-4-yl)piperazin-1-yl)-3-fluorophenyl)amino)piperidine-2,6-dione or its acid-addition salt of step (i) with 4-(1,4,5-trimethyl-6-oxo-1,6-dihydropyridin-3-yl)benzaldehyde in a sixth solvent in the presence of sodium triacetoxyborohydride to afford Compound 1.

Synthesis of 2,6-dimethoxy-4-(1,4,5-trimethyl-6-oxo-1,6-dihydropyridin-3-yl)benzaldehyde

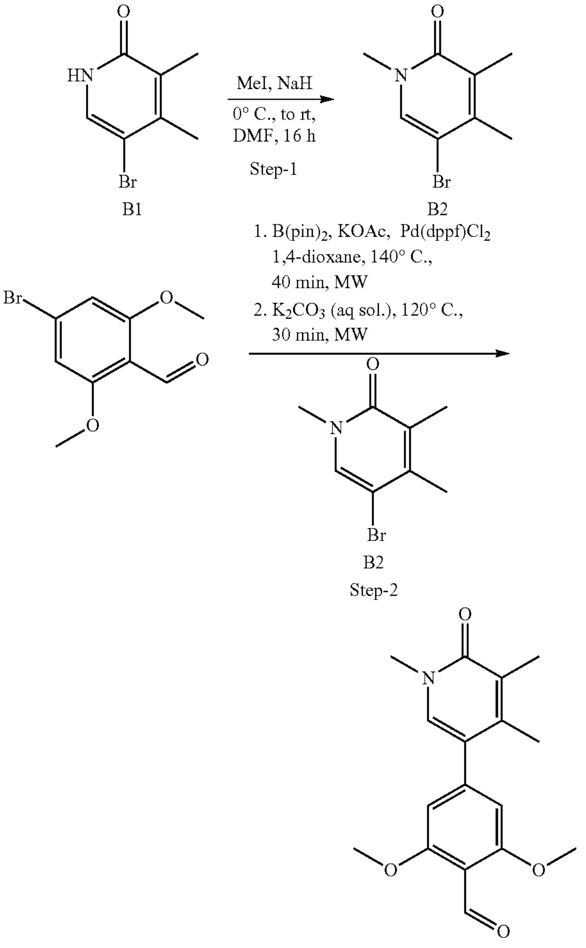

10

Step-1: Initially 5-bromo-3,4-dimethyl-1H-pyridin-2-one (2 g, 9.90 mmol) was dissolved in DMF (40.57 mL) and cooled to 0° C. before sodium hydride (475.09 mg, 19.80 mmol) was added in one portion and the mixture was stirred for 30 mins. Iodomethane (5.62 g, 39.59 mmol, 2.46 mL) was then added dropwise and the mixture was allowed to stir overnight at ambient temperature. The reaction was then quenched with ice water and the mixture was then extracted with ethyl acetate (3×50 mL), the combined organic layers were dried with brine (1×100 mL), $Na_2SO_4$, filtered and concentrated to a residue which was purified via flash column chromatography (hexanes:ethyl acetate 1:0 to 0:1) to afford 4-bromo-2,6-dimethoxy-benzaldehyde Intermediate-B2. Yield—1.35 g, 63%; LC-MS (ES$^+$): m/z 215.9 $[M+H]^+$.

Step-2: Initially cyclopentyl(diphenyl)phosphane;dichloropalladium;iron (59.71 mg, 81.61 μmol), 4-bromo-2,6-dimethoxy-benzaldehyde (200 mg, 816.09 μmol), bis(pinacolato) diboron (248.68 mg, 979.31 μmol), potassium acetate (240.28 mg, 2.45 mmol) were charged into a MW vial (2-5 mL) and suspended under an argon atmosphere in 1,4-dioxane (12.27 mL) and heated in a MW at 140° C. for 40 mins. To this suspension was then added 5-bromo-1,3,4-trimethyl-pyridin-2-one Intermediate-B2 (176.34 mg, 816.09 μmol) under argon along with potassium carbonate (2 M, 2 eq) and reheated at 120° C. for 30 mins before being checked by LCMS. Upon completion of the reaction, the mixture was filtered through a pad of celite and washed with DCM/ethyl acetate. The filtrate was washed with water (10 mL), brine (50 mL), dried over anhydrous $Na_2SO_4$, filtered and concentrated to a residue which was purified via flash column chromatography (hexanes:ethyl acetate 1:0 to 0:1) to afford 2,6-dimethoxy-4-(1,4,5-trimethyl-6-oxo-1,6-dihydropyridin-3-yl)benzaldehyde 10. Yield—245 mg, 99%; LC-MS (ES$^+$): m/z 302.2 $[M+H]^+$.

Synthesis of Compound 1

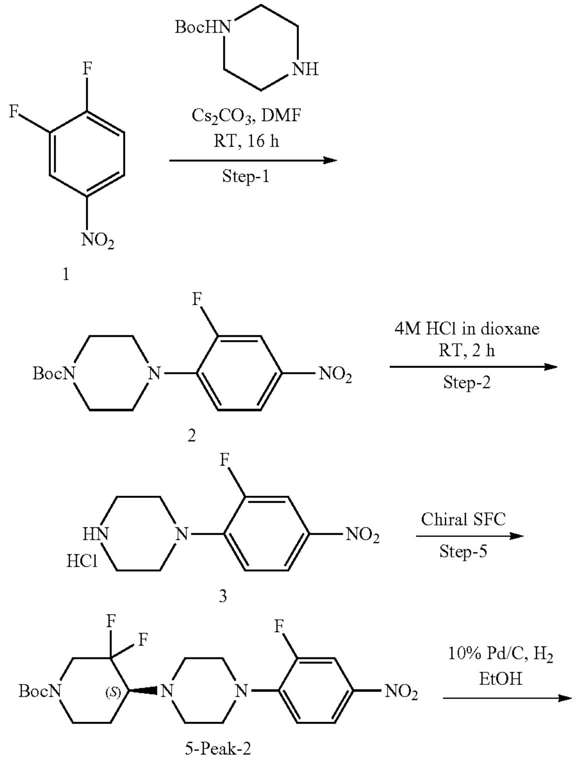

-continued

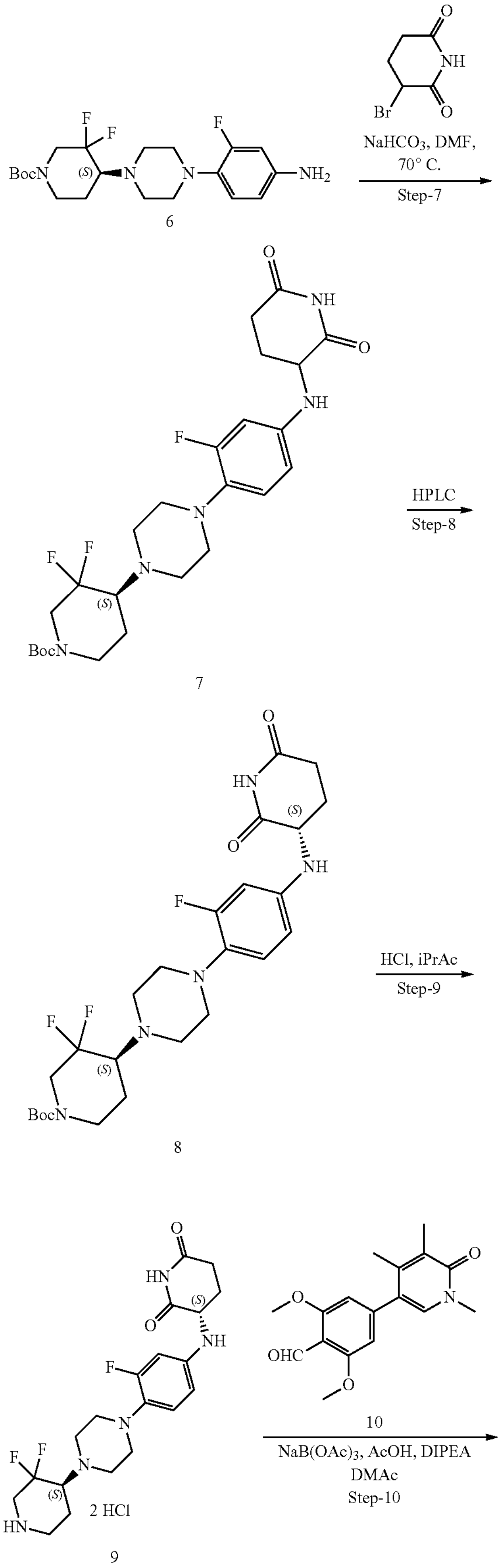

-continued

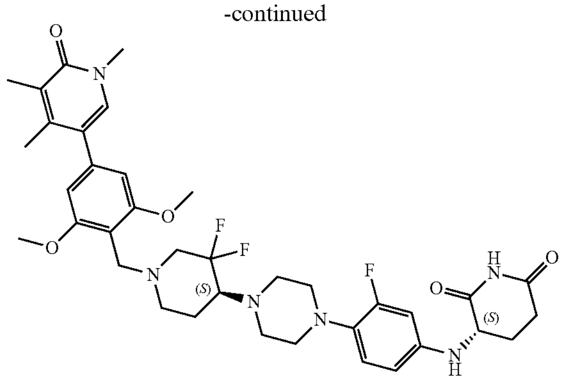

Compound 1

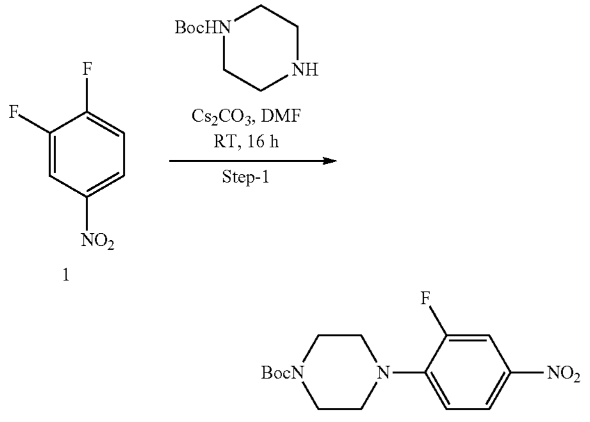

1

2

Step-1: To a stirred solution of compound tert-butyl piperazine-1-carboxylate (85.40 g, 536.82 mmol) in DMF (500 mL) was added cesium carbonate (262.4 g, 805.4 mmol) and stirred for 15 min before adding 1,2-difluoro-4-nitro-benzene 1 (100 g, 536.82 mmol). The reaction mixture stirred at RT for 16 h while monitoring by TLC. After completion, the reaction mass was quenched with ice flakes and the precipitated solid was filtered, dried under vacuum to afford tert-butyl 4-(2-fluoro-4-nitro-phenyl) piperazine-1-carboxylate 2 (152 g, 88.85% yield, 97.94% purity) as a yellow solid.

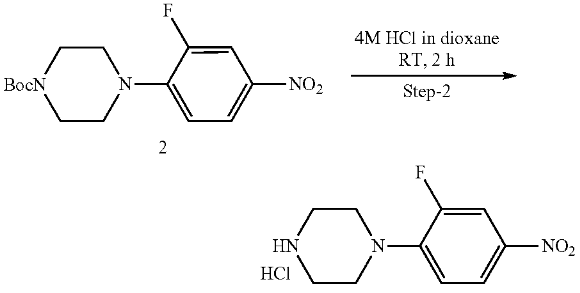

2

3

Step-2: To a stirred solution of tert-butyl 4-(2-fluoro-4-nitrophenyl)piperazine-1-carboxylate 2 (50.0 g, 153.69 mmol) in 20 ml dioxane was added 4M HCl in dioxane (30 ml) and reaction mixture stirred for 2 h at RT while monitoring by TLC. The solvent was evaporated to dryness under reduced pressure and crude solid was triturated with diethyl ether (75 ml) and n-pentane (100 ml) to afford 1-(2-fluoro-4-nitrophenyl) piperazine HCl salt 3 (36.0 g, 136.2 mmol, 88.62% yield, 99% purity). LCMS ($ES^+$): m/z 226.10 $[M+H]^+$

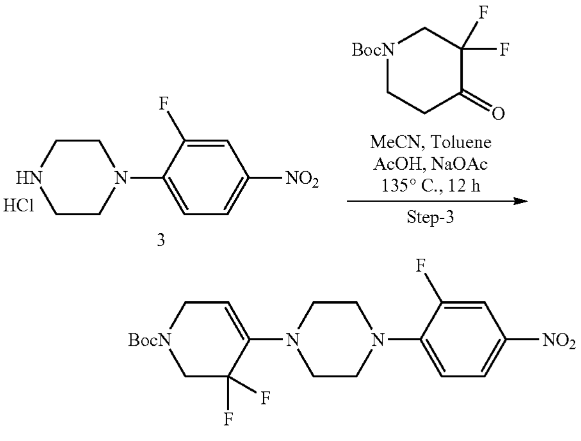

3

4

Step-3: To stirred solution of 1-(2-fluoro-4-nitro-phenyl) piperazine 3 (8.0 g, 35.52 mmol) in toluene (200 ml) and ACN (100 ml) was added NaOAc (7.28 g, 88.80 mmol), followed by AcOH (8 ml) and 4 Å molecular sieves (10 g) and stirred for 15 min. After 15 min, tert-butyl 3,3-difluoro-4-oxo-piperidine-1-carboxylate (11.49 g, 48.84 mmol, co-distilled with toluene before use) was added and the reaction mixture was allowed to reflux for 12 h, while monitoring by LCMS and TLC. After completion of the reaction, the reaction mixture was cooled to room temperature and filtered through a pad of celite. The filtrate was concentrated under vacuum to dryness to afford 3,3-difluoro-4-(4-(2-fluoro-4-nitrophenyl)piperazin-1-yl)-3,6-dihydropyridine-1(2H)-carboxylate 4 (12.2 g, 98.89% purity), which was used in the next step without any purification. LCMS ($ES^+$): m/z 443.75 $[M+H]^+$

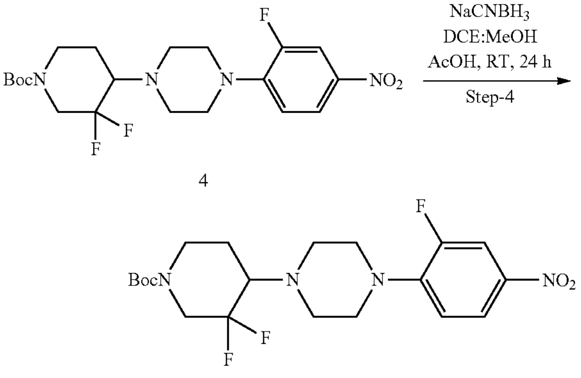

4

5

Step-4: A solution of 3,3-difluoro-4-(4-(2-fluoro-4-nitrophenyl)piperazin-1-yl)-3,6-dihydropyridine-1(2H)-carboxylate 4 (8 g, 18.08 mmol) in methanol (20 mL), DCE (20 mL) and AcOH (2 ml) was allowed to stir for 15 min before sodium cyanoborohydride (5.68 g, 90.41 mmol) was added. The reaction mixture was stirred for 24 h at room temperature, while monitoring by LCMS and TLC. Upon completion of the reaction, the reaction mixture was filtered through a pad of celite and the filtrate was concentrated under vacuum. The crude product was purified by column chromatography (100-200 mesh silica gel, 30% ethyl acetate in pet ether to 100% ethyl acetate) to afford tert-butyl-3,3-difluoro-4-[4-(2-fluoro-4-nitro-phenyl)piperazin-1-yl]piperidine-1-carboxylate 5 (7.2 g, 15.39 mmol, 85.11% yield, 98% purity). LCMS ($ES^+$): m/z 445.35 $[M+H]^+$

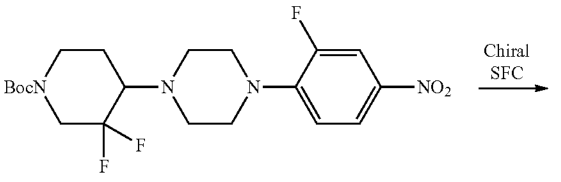

5

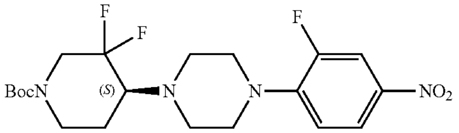

5-Peak-2

$[\alpha]^{25}_{D}$: -28.79

Step-5: 20 g of tert-butyl-3,3-difluoro-4-[4-(2-fluoro-4-nitro-phenyl)piperazin-1-yl]piperidine-1-carboxylate 5 was separated by SFC to afford 8.5 g of 5-Peak-1 (First eluted peak during SFC) and 8.5 g of 5-Peak-2 (Second eluted peak during SFC separation)

Preparative SFC Conditions:

Column/dimensions: Chiralpak-IC (30×250) mm, 5μ

% $CO_2$: 70%

% Co solvent: 30% (MeOH)

Total Flow: 100.0 g/min

Back Pressure: 100 bar

Temperature: 30° C.

UV: 220 nm

Instrument details: Make/Model: SFC-200

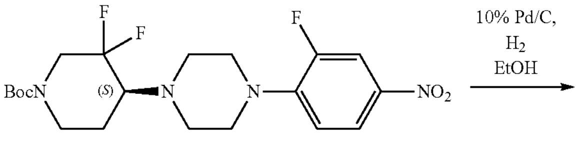

5-Peak-2

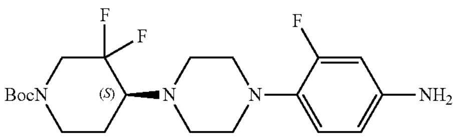

6

Step-6: To the stirred solution of tert-butyl 3,3-difluoro-4-(4-(2-fluoro-4-nitrophenyl)piperazin-1-yl)piperidine-1-carboxylate 5-Peak-2 (5 g, 11.25 mmol) in ethyl acetate (100 mL) was added 10% Palladium on carbon, wet (3.59 g, 33.75 mmol) at RT. The reaction mixture was stirred at RT under $H_2$ balloon pressure for 12 h and monitored by TLC. After the completion of the reaction, the reaction mixture was filtered through a pad of celite and washed with ethyl acetate (200 mL). The filtrate was concentrated to obtain the crude product which is triturated with pentane. The solid was then filtered and dried to afford tert-butyl 4-[4-(4-amino-2-fluoro-phenyl)piperazin-1-yl]-3,3-difluoro-piperidine-1-carboxylate 6.

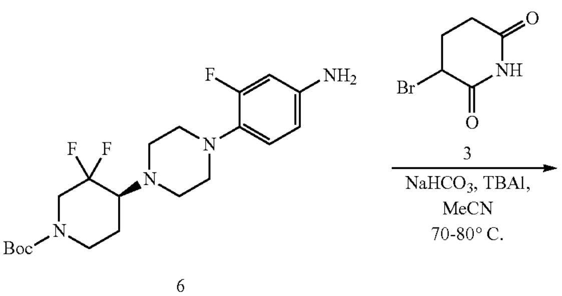

6

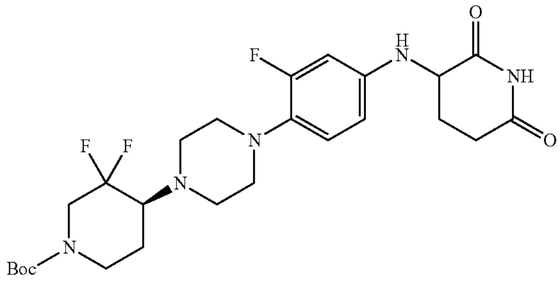

7

Step-7: To a nitrogen purged reactor was added 420 g of acetonitrile followed by 100.0 g of tert-butyl 4-(4-(4-amino-2-fluorophenyl)piperazin-1-yl)-3,3-difluoropiperidine-1-carboxylate 6 (0.241 mol, 1.00 eq). The mixture was stirred at 20-30° C. for 15-30 minutes before 60.8 g sodium bicarbonate (0.724 mol, 3.0 eq) was added, followed by 44.6 g of tetrabutylammonium iodide (0.121 mol, 0.50 eq). Then 3-bromopiperidine-2,6-dione 3 (92.7 g, 0.483 mol, 2.00 eq) was added and rinsed with 48 g of acetonitrile. The reaction was then heated to 75-85° C. for 21-30 hours under nitrogen atmosphere. The reaction was then cooled to 40-50° C. and sampled to ensure starting material was consumed (<1.0%). The reaction was then cooled to 20-30° C. and 1200 g of water was added. This mixture was stirred for 1-2 h under nitrogen, then filtered at 20-30° C. The wet cake was washed with 400 g of water and then dried under vacuum at 45-55° C. for 18-24 h (residual solvent by KF titration <5.0%) to afford tert-butyl (4S)-4-(4-(4-((2,6-dioxopiperidin-3-yl)amino)-2-fluorophenyl)piperazin-1-yl)-3,3-difluoropiperidine-1-carboxylate 7 (92.4% yield).

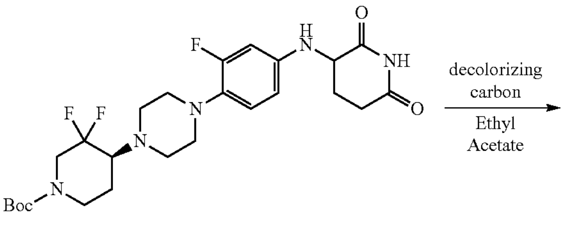

7

-continued

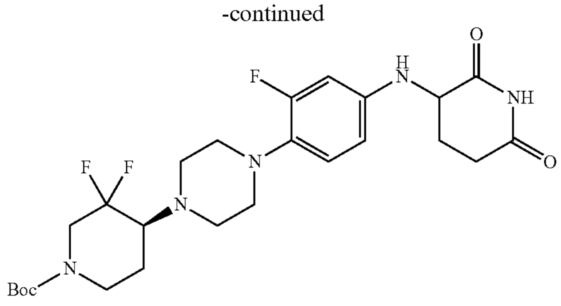

7

Step-7b: A nitrogen purged reactor was charged with tert-butyl (4S)-4-(4-(4-((2,6-dioxopiperidin-3-yl)amino)-2-fluorophenyl)piperazin-1-yl)-3,3-difluoropiperidine-1-carboxylate 7 (100.0 g, 0.190 mol) in ethyl acetate (11,000 g) at 20-30° C. The reactor walls were then rinsed with ethyl acetate (1000 g) and the solution stirred for 1-6 hours under nitrogen. Activated carbon (15 g) was then added and stirred at 20-30° C. for 3-8 hours. A column filled with 500 g of silica was then washed with ethyl acetate (500 g). The solution of 7 was passed through the column and eluted with ethyl acetate (14000 g) to afford tert-butyl (4S)-4-(4-(4-((2,6-dioxopiperidin-3-yl)amino)-2-fluorophenyl)piperazin-1-yl)-3,3-difluoropiperidine-1-carboxylate 7 (70-100% yield).

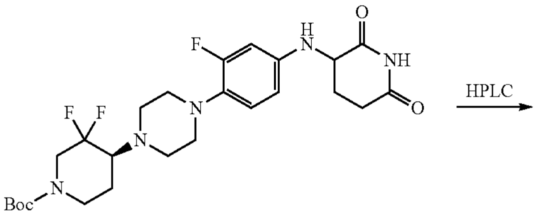

7

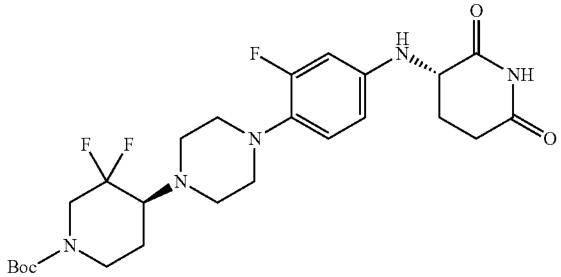

8

Step-8: A solution (containing about 57.8 g of tert-butyl (4S)-4-(4-(4-((2,6-dioxopiperidin-3-yl)amino)-2-fluorophenyl)piperazin-1-yl)-3,3-difluoropiperidine-1-carboxylate, 7) in ethyl acetate (10000 g) was purified by prep-HPLC (CHIRALPAK IG 10 m 250×50 mm column. Injection rate 200-300 mL/min). The product was eluted with 100% ethyl acetate (250 mL/min, retention time 5-10 minutes), and the purified fractions were collected and concentrated to 150 mL under vacuum at 40° C. The solution was then cooled to 15-25° C. and filtered. The reactor was washed with 60 g ethyl acetate and the rinsate filtered. The wet cake was then dried at 30-40° C. for 16-24 hours (residual ethyl acetate <2.0%) to give tert-butyl (S)-4-(4-(4-(((S)-2,6-dioxopiperidin-3-yl)amino)-2-fluorophenyl)piperazin-1-yl)-3,3-difluoropiperidine-1-carboxylate 8 (early eluting isomer, 30-60% yield).

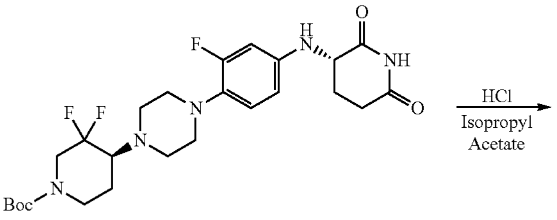

7

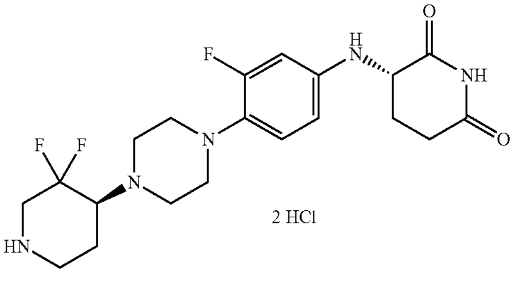

9

Step-9: 1000 g of isopropyl acetate was charged to a reactor and cooled to 0-20° C. Next, 170 g of HCl gas was charged to the reactor to produce a 14-18% solution of HCl in isopropyl acetate. In a second nitrogen purged reactor, 100 g of tert-butyl (S)-4-(4-(4-(((S)-2,6-dioxopiperidin-3-yl)amino)-2-fluorophenyl)piperazin-1-yl)-3,3-difluoropiperidine-1-carboxylate 8 was charged followed by 1000 g of isopropyl acetate. 1000 g of the HCl solution (14-18% wt) was then added to the reactor containing starting material solution. The reaction was stirred at 20-30° C. for 2-10 hours under nitrogen, until residual starting material was <0.5%. The headspace of the reaction was then purged with nitrogen gas for 1-2 hours at 20-30° C. and the slurry was filtered. The wet cake was washed with 500 g isopropyl acetate and the dried under vacuum at 45-55° C. for 12-224 hours (residual solvent <5.0%) to give (S)-3-((4-(4-((S)-3,3-difluoropiperidin-4-yl)piperazin-1-yl)-3-fluorophenyl)amino)piperidine-2,6-dione dihydrochloride 9 (75-100% yield).

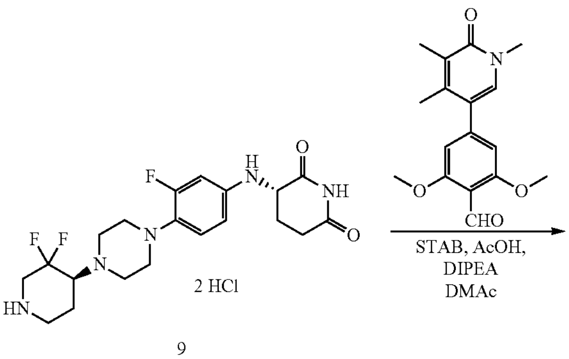

9

-continued

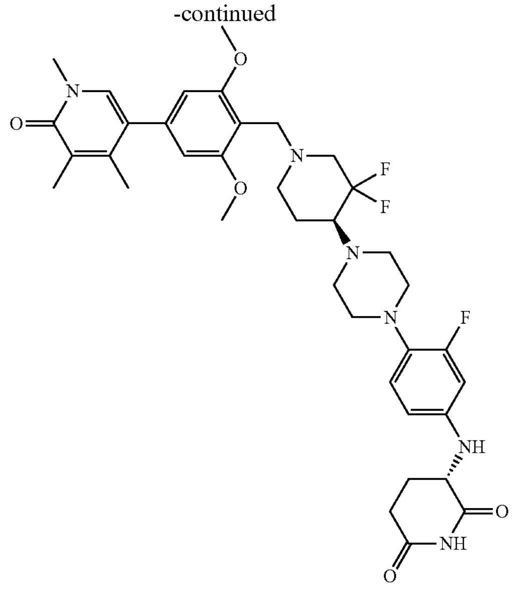

Compound 1

Step-10: To a nitrogen purged reactor was added 410 g of dimethylacetamide, followed by (S)-3-((4-(4-((S)-3,3-difluoropiperidin-4-yl)piperazin-1-yl)-3-fluorophenyl)amino) piperidine-2,6-dione dihydrochloride 9 (100.0 g). The reactor was cooled to −10-0° C. before diisopropylethylamine (116.7 g) was added. While maintaining the reaction at −10-0° C., 20 g of dimethylacetamide was used to rinse residual diisopropylethylamine. Next, 54.5 g of 4-(1,4,5-trimethyl-6-oxo-1,6-dihydropyridin-3-yl)benzaldehyde 10 was added followed by 48.2 g of acetic acid. 20 g of dimethylacetamide was used to rinse the pipe. The solution was stirred for 1-3 hours at −10-0° C. and then 127.6 g sodium triacetoxyborohydride was added and the reaction stirred for 16-20 hours under nitrogen atmosphere (residual starting material <1%). The reaction was then warmed to −5-5° C. and 1000 g of water was added. This mixture was stirred for 2-6 hours and then 103.8 g of diisopropylethylamine was added and stirred for an additional 1-3 hours. The mixture was then filtered at −5-5° C. and 700 g water was used to rinse the reactor. The wet cake was then charged to a reactor followed by 650 g of THF and 1200 g of 2-MeTHF at 20-30° C. The solution was stirred for 0.5-1 hour and then 500 g of 2 wt % $KH_2PO_4$ aqueous solution was then added and the solution and stirred at 20-30° C. for 0.5-1 hour. The solution was then stirred for 0.5-1 hour and the lower aqueous layer was removed. Then 700 g of purified water was added and the biphasic mixture was stirred for 0.5-1 hour, followed by removal of the lower aqueous layer. A third extraction with 700 g of water was performed. The organic layer containing product was charged to a reactor and the transfer pipe was rinsed with 2-MeTHF (200 g). The solution was concentrated to 1500 mL at 40° C. under vacuum. The solution was then cooled to 20-30° C. and 1.0 g of product was added to seed crystallization. The solution was stirred for 1-3 hours and then warmed to 40° C. and concentrated to 300 mL at 40° C. under reduced pressure. 1161 g of 2-MeTHF was then added and then the solution was concentrated to 500 mL at 40° C. under reduced pressure. 430 g of 2-MeTHF was then added and then the solution was concentrated to 500 mL at 40° C. under reduced pressure. The solution was then cooled to 20-30° C. and 1398 g of MTBE was then added over 4 hours. The solution was slowly cooled to −5-5° C. over 3-4 hours and then stirred at the same temperature for 1-3 hours. The suspension was then filtered at −5-5° C. under nitrogen and 29 g of MTBE was charged to rinse the reactor and filtered. In certain embodiments the resulting solid material is Form N. The solid was swept for 4-8 hours with nitrogen gas (residual MTBE<21%, residual 2-MeTHF<10%). A reactor was then charged with 12 g water and 464.5 g acetone and the solution (aqueous acetone solution) was then stirred for 0.5-1 h and collected. Under nitrogen atmosphere, the filter cake was then charged to the reactor followed by 120 g of aqueous acetone solution and stirred for 12-16 hours at 20-30° C. (residual MTBE<0.5%, residual 2MeTHF<0.5%). The solution was then filtered at 20-30° C. under nitrogen and 100 g aqueous acetone solution was used to rinse the reactor and filtered. The wet cake was then humidified dried at 35-45° C. for 20-28 hours to provide (S)-3-((4-(4-((S)-3,3-difluoro-1-(4-(1,4,5-trimethyl-6-oxo-1,6-dihydropyridin-3-yl)benzyl)piperidin-4-yl)piperazin-1-yl)-3-fluorophenyl) amino)piperidine-2,6-dione Compound 1 (target RH 40%, residual 2-MeTHF 1600 ppm, residual THE 0 ppm, residual DMAc 0 ppm residual MTBE 700 ppm) (55-85% yield).

IX. Additional Embodiments

1. In certain embodiments a method is provided for the treatment of an unresectable cancer mediated by BRD9 in a human, comprising administering to the human an effective amount of a compound of Formula:

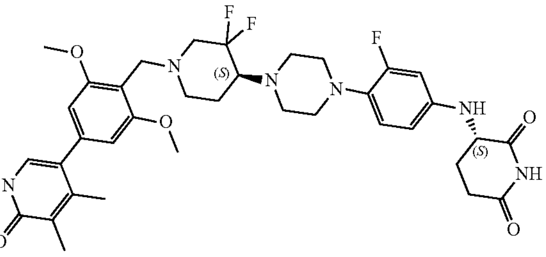

or a pharmaceutically acceptable salt thereof, is provided.

2. The method of embodiment 1, wherein the cancer is relapsed.
3. The method of embodiment 1 or 2, wherein the cancer is refractory.
4. The method of any one of embodiments 1-3, wherein the cancer is a SMARCB1-perturbed cancer.
5. The method of any one of embodiments 1-4, wherein the cancer is selected from synovial sarcoma, malignant rhabdoid tumor, atypical teratoid rhabdoid tumor, cribriform neuroepithelial tumor, renal medullary carcinoma, epithelioid sarcoma, epithelioid malignant peripheral nerve sheath tumor, schwannomas in familial schwannomatosis, chordoma, myoepithelial carcinoma, and sinonasal carcinoma.
6. The method of any one of embodiments 1-4, wherein the cancer is synovial sarcoma.
7. The method of any one of embodiments 1-4, wherein the cancer is a soft tissue sarcoma.
8. The method of any one of embodiments 1-4, wherein the cancer is a clear cell renal cell carcinoma.
9. The method of any one of embodiments 1-8, wherein one or more additional therapeutically active agents are administered.

10. In certain embodiments a method is provided for the treatment of a cancer mediated by BRD9 in a human, comprising administering to the human an effective amount of a compound of Formula:

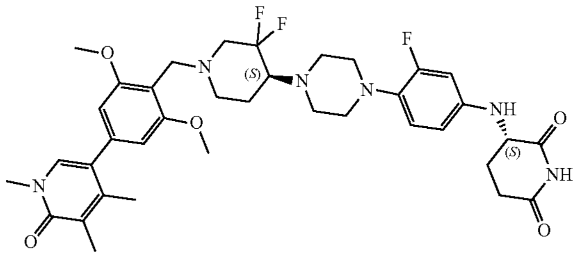

or a pharmaceutically acceptable salt thereof, wherein the cancer is an epithelioid malignant peripheral nerve sheath tumor, schwannomas in familial schwannomatosis, atypical malignant teratoid rhabdoid tumor, or cribriform neuroepithelial tumor.

11. The method of embodiment 10, wherein one or more additional therapeutically active agents are administered.

12. In certain embodiments a method is provided for the treatment of a cancer mediated by BRD9 in a human, comprising administering to the human an effective amount of a compound of Formula:

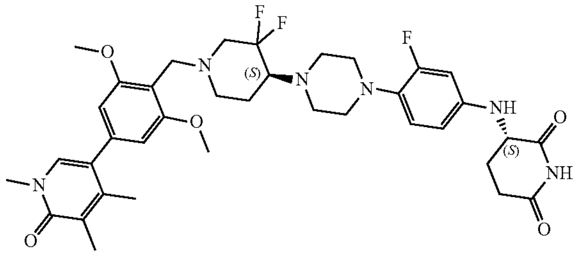

or a pharmaceutically acceptable salt thereof, wherein one or more additional therapeutic agents selected from ixazomib, anlotinib, itacitinib, cixutumumab, ixabepilone, exatecan mesylate, brostallicin, tazemetostat, and sapanisertib are also administered.

13. In certain embodiments a method is provided for the treatment of a cancer mediated by BRD9 in a human, comprising administering to the human an effective amount of a compound of Formula:

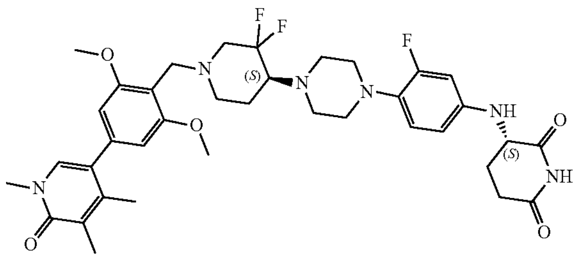

or a pharmaceutically acceptable salt thereof, wherein an additional chemotherapeutic regimen is administered and that regimen is selected from:

a. sintilimab, doxorubicin, and ifosfamide;
b. cixutumumab and doxorubicin;
c. cixutumumab and temsirolimus;
d. lurbinectedin and irinotecan;
e. sorafenib and dacarbazine;
f. pazopanib and gemcitabine;
g. doxorubicin and ribociclib;
h. tazemetostat, itraconazole, and rifampin;
i. cyclophosphamide and fludarabine;
j. ifosfamide, carboplatin, and etoposide;
k. doxorubicin, vincristine, and cyclophosphamide;
l. doxorubicin hydrochloride, etoposide, and ifosfamide; and
m. trofosfamide, idarubicin, and etoposide.

14. In certain embodiments a method is provided for the treatment of interferon-mediated inflammation in a human, comprising administering to the human an effective amount of a compound of Formula:

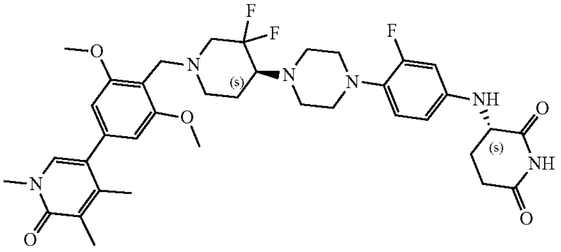 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof.

15. In certain embodiments a crystalline form is provided of a compound of structure:

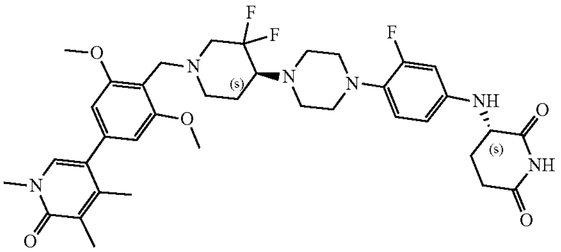 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

characterized by an X-ray powder diffraction (XRPD) pattern comprising at least three 2theta values selected from 5.5±0.4°, 5.9±0.4°, 14.2±0.4°, 15.0±0.4°, 15.3±0.4°, 18.8±0.4°, 19.1±0.4°, 21.5±0.4°, 23.4±0.4°, 24.2±0.4°, and 27.0±0.4°.

16. The crystalline form of embodiment 15, wherein the XRPD pattern comprises at least four 2theta values selected from 5.5±0.4°, 5.9±0.4°, 14.2±0.4°, 15.0±0.4°, 15.3±0.4°, 18.8±0.4°, 19.1±0.4°, 21.5±0.4°, 23.4±0.4°, 24.2±0.4°, and 27.0±0.4°.

17. The crystalline form of embodiment 15, wherein the XRPD pattern comprises at least five 2theta values selected from 5.5±0.2°, 5.9±0.2°, 14.2±0.2°, 15.0±0.2°, 15.3±0.2°, 18.8±0.2°, 19.1±0.2°, 21.5±0.2°, 23.4±0.2°, 24.2±0.2°, and 27.0±0.2°.

18. The crystalline form of embodiment 15, wherein the XRPD pattern comprises at least six 2theta values selected from 5.5±0.2°, 5.9±0.2°, 14.2±0.2°, 15.0±0.2°, 15.3±0.2°, 18.8±0.2°, 19.1±0.2°, 21.5±0.2°, 23.4±0.2°, 24.2±0.2°, and 27.0±0.2°.

19. The crystalline form of any of embodiments 15-18, wherein the XRPD pattern comprises at least the 2theta value of 5.9±0.2°.
20. The crystalline form of any of embodiments 15-19, wherein the XRPD pattern comprises at least the 2theta value of 15.0±0.2°.
21. The crystalline form of any of embodiments 15-20, wherein the XRPD pattern comprises at least the 2theta value of 21.5±0.2°.
22. The crystalline form of any of embodiments 15-21, wherein the XRPD pattern comprises at least the 2theta value of 14.2±0.2°.
23. The crystalline form of any of embodiments 15-22, wherein the XRPD pattern comprises at least the 2theta value of 19.1±0.2°.
24. The crystalline form of any of embodiments 15-23, wherein the XRPD pattern comprises at least the 2theta value of 5.5±0.2°.
25. The crystalline form of any of embodiments 15-24, wherein the XRPD pattern comprises at least the 2theta value of 24.2±0.2°.
26. The crystalline form of any of embodiments 15-25, wherein the XRPD pattern comprises at least the 2theta value of 18.8±0.2°.
27. The crystalline form of any of embodiments 15-26, characterized by an XRPD pattern having the characteristic 2θ values of FIG. 18.
28. The crystalline form of any of embodiments 15-27 that has differential scanning calorimetry (DSC) onset endotherms of about 151±20° C., about 162±20° C., and about 218±20° C.
29. The crystalline form of any of embodiments 15-27 that has differential scanning calorimetry (DSC) onset endotherms of about 151±10° C., about 162±10° C., and about 218±10° C.
30. In certain embodiments a pharmaceutical composition is provided comprising the crystalline form of any of embodiments 15-29 and a pharmaceutically acceptable excipient.
31. In certain embodiments a pharmaceutical composition is provided for the treatment of a BRD9-mediated disorder in a host in need thereof, comprising an effective amount of the crystalline form of any of embodiments 15-29 in a pharmaceutically acceptable excipient for solid dosage delivery.
32. The pharmaceutical composition of any of embodiments 30 and 31, further comprising one or more additional therapeutic agents.
33. In certain embodiments a pharmaceutical composition is provided that is prepared from a crystalline form of any one of embodiments 15-29.
34. In certain embodiments a method is provided for the treatment of a BRD9-mediated disorder comprising administering an effective amount of crystalline form of any of embodiments 15-29 or a pharmaceutical composition of any one of embodiments 31-33 to a host in need thereof.
35. The method of embodiment 34, wherein the host is a human.
36. The method of embodiment 35, wherein the disorder is a synovial sarcoma.
37. The method of embodiment 35, wherein the disorder is a poorly differentiated chordoma.
38. The method of embodiment 35, wherein the disorder is a rare soft tissue malignancy.
39. The method of embodiment 35, wherein the disorder is multiple myeloma.
40. The method of embodiment 35, wherein the disorder is acute myeloid leukemia.
41. The method of embodiment 35, wherein the disorder is a SMARCB1-perturbed cancer.
42. The method of embodiment 35, wherein the disorder is a malignant rhabdoid tumor or an atypical teratoid or rhabdoid tumor.
43. The method of embodiment 35, wherein the disorder is an epithelioid sarcoma.
44. The method of embodiment 35, wherein the disorder is a renal medullary carcinoma.
45. The method of embodiment 35, wherein the disorder is an epithelioid malignant peripheral nerve sheath tumor.
46. The method of embodiment 35, wherein the disorder is a myoepithelial carcinoma.
47. The method of embodiment 35, wherein the disorder is an extra-skeletal myxoid chondrosarcoma.
48. The method of embodiment 35, wherein the disorder is a chordoma.
49. The method of embodiment 35, wherein the disorder is pancreatic undifferentiated rhabdoid carcinoma.
50. The method of embodiment 35, wherein the disorder is a sinonasal basaloid carcinoma.
51. The method of embodiment 35, wherein the disorder is a malignant rhabdoid tumor located in or on the brain or spinal cord.
52. The method of embodiment 35, wherein the disorder is a cribriform neuroepithelial tumor located in or on the brain.
53. The method of embodiment 35, wherein the disorder is a renal medullary carcinoma located in or on the kidney.
54. The method of embodiment 35, wherein the disorder is an epithelioid sarcoma located in or on the skin, subcutaneous tissue, extremities, deep tissue, perineum, or proximal limb girdles.
55. The method of embodiment 35, wherein the disorder is classic epithelioid sarcoma.
56. The method of embodiment 35, wherein the disorder is proximal epithelioid sarcoma.
57. The method of embodiment 35, wherein the disorder is an epithelioid malignant peripheral nerve sheath tumor located in or on the dermis, subcutaneous tissue, or deep soft tissue.
58. The method of embodiment 35, wherein the disorder is a schwannoma in familial schwannomatosis located in or on a peripheral nerve or spinal nerve root.
59. The method of embodiment 35, wherein the disorder is a myoepithelial carcinoma located in or on a soft tissue or viscera.
60. The method of embodiment 35, wherein the disorder is a sinonasal carcinoma located in or on the sinonasal region.
61. The method of embodiment 35, wherein the disorder is a synovial sarcoma located in or on deep soft tissues of extremities.
62. The method of embodiment 35, wherein the disorder is an atypical teratoid rhabdoid tumor located in or on the kidney, a soft tissue, or viscera.
63. The method of embodiment 35, wherein the crystalline form is administered in combination with doxorubicin, ifosfamide, carboplatin, etoposide or cyclophosphamide.
64. In certain embodiments a crystalline form is provided of a compound of formula:

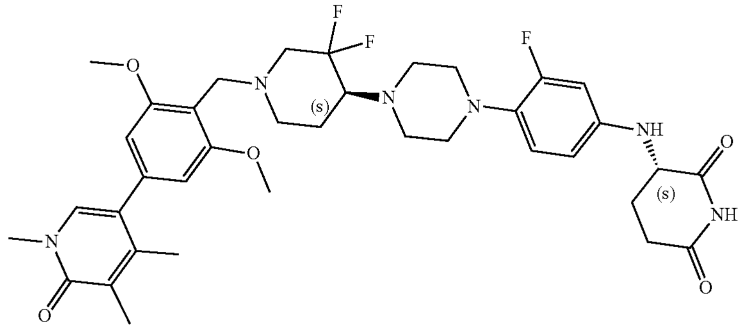

• 0.5 $CO(NH_2)_2$ characterized by an X-ray powder diffraction (XRPD) pattern comprising at least three 2theta values selected from 11.2±0.4°, 13.9±0.4°, 15.4±0.4°, 17.8±0.4°, 18.6±0.4°, 19.4±0.4°, 20.1±0.4°, 20.7±0.4°, 21.3±0.4°, 22.2±0.4°, 23.1±0.4°, and 24.0±0.4°.

Figure 22:
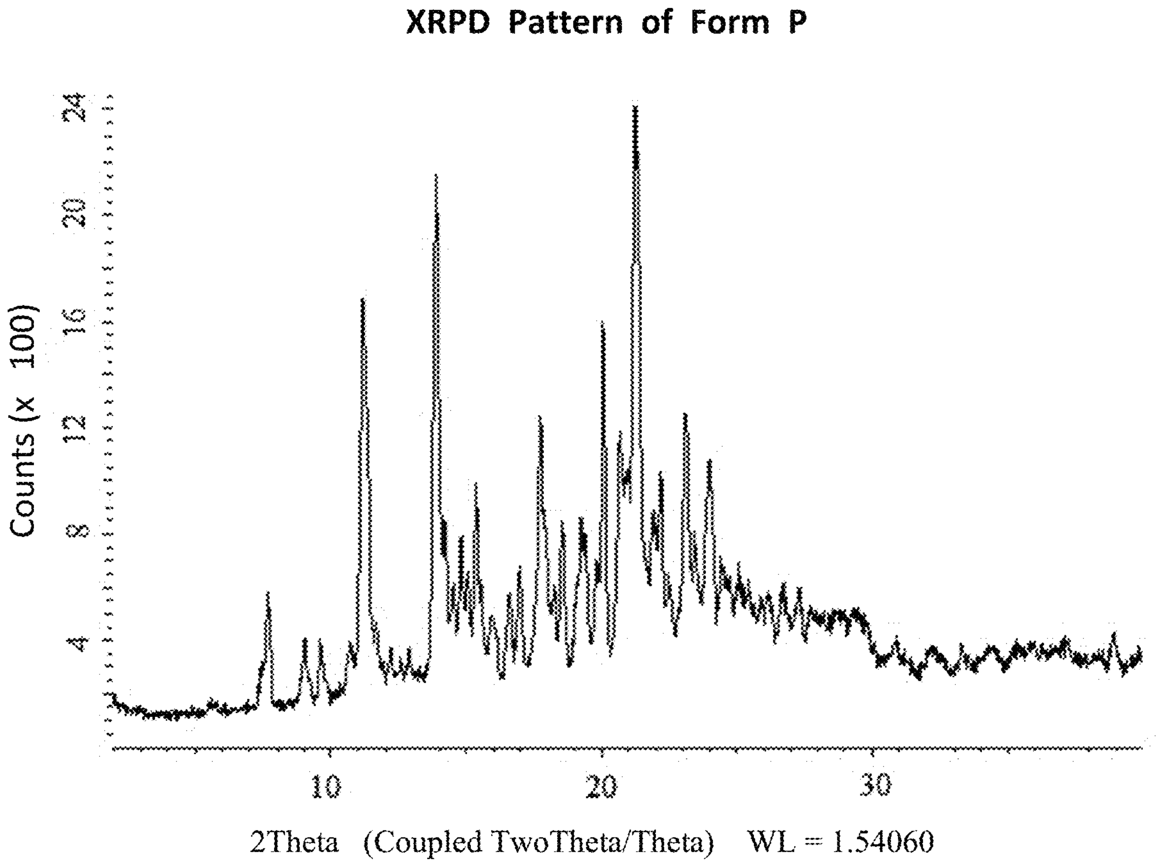
FIG. 22 depicts the XRPD pattern of Compound 1 Form P. Compound 1 Form P is a cocrystal with urea. The Compound 1 Form P XRPD pattern exhibits sharp peaks, indicating the sample was composed of crystalline material.
Figure 23:
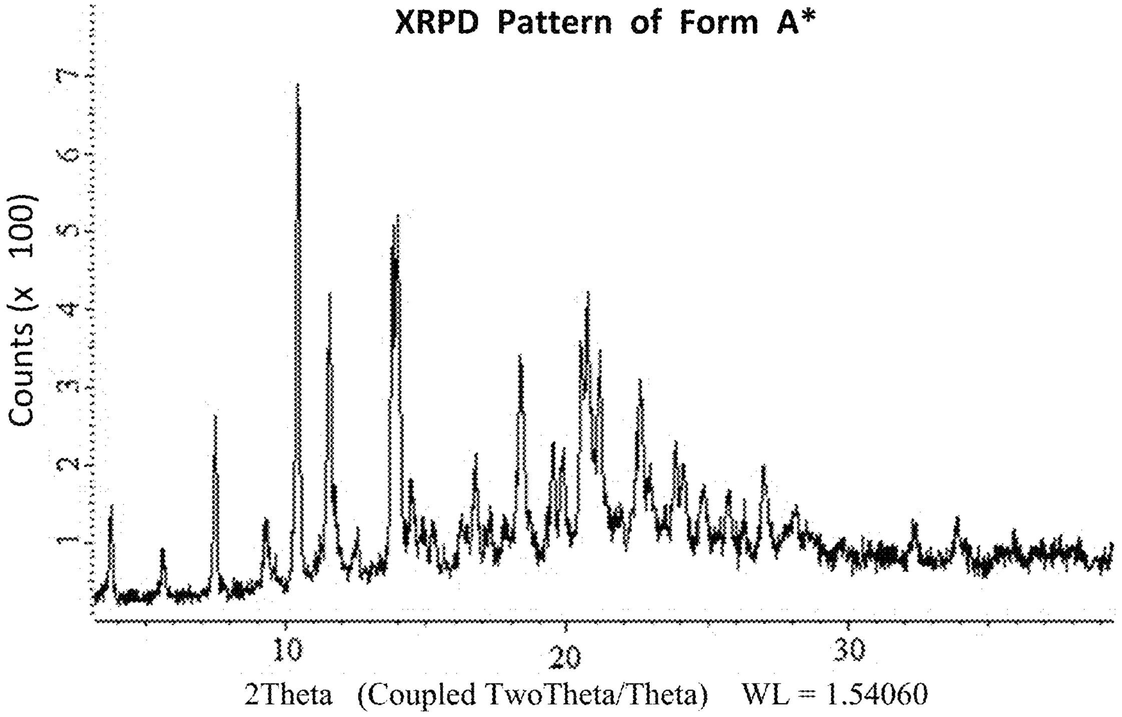
FIG. 23 depicts the XRPD pattern of Compound 1 Form A*. The Compound 1 Form A* XRPD pattern exhibits sharp peaks, indicating the sample was composed of crystalline material.
Figure 24:
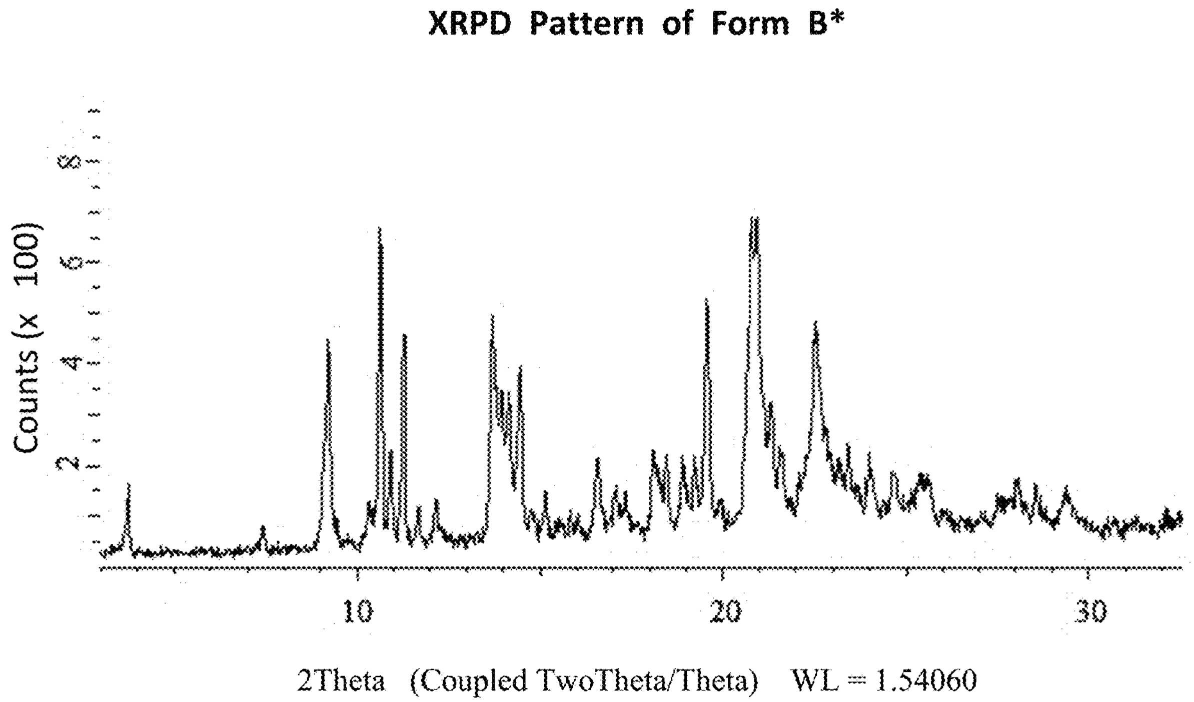
FIG. 24 depicts the XRPD pattern of Compound 1 Form B*.

65. The crystalline form of embodiment 64, wherein the XRPD pattern comprises at least four 2theta values selected from 11.2±0.4°, 13.9±0.4°, 15.4±0.4°, 17.8±0.4°, 18.6±0.4°, 19.4±0.4°, 20.1±0.4°, 20.7±0.4°, 21.3±0.4°, 22.2±0.4°, 23.1±0.4°, and 24.0±0.4°.
66. The crystalline form of embodiment 64, wherein the XRPD pattern comprises at least five 2theta values selected from 11.2±0.2°, 13.9±0.2°, 15.4±0.2°, 17.8±0.2°, 18.6±0.2°, 19.4±0.2°, 20.1±0.2°, 20.7±0.2°, 21.3±0.2°, 22.2±0.2°, 23.1±0.2°, and 24.0±0.2°.
67. The crystalline form of embodiment 64, wherein the XRPD pattern comprises at least six 2theta values selected from 11.2±0.2°, 13.9±0.2°, 15.4±0.2°, 17.8±0.2°, 18.6±0.2°, 19.4±0.2°, 20.1±0.2°, 20.7±0.2°, 21.3±0.2°, 22.2±0.2°, 23.1±0.2°, and 24.0±0.2°.
68. The crystalline form of any of embodiments 64-67, wherein the XRPD pattern comprises at least the 2theta value of 21.3±0.2°.
69. The crystalline form of any of embodiments 64-68, wherein the XRPD pattern comprises at least the 2theta value of 13.9±0.2°.
70. The crystalline form of any of embodiments 64-69, wherein the XRPD pattern comprises at least the 2theta value of 11.2±0.2°.
71. The crystalline form of any of embodiments 64-70, wherein the XRPD pattern comprises at least the 2theta value of 20.1±0.2°.
72. The crystalline form of any of embodiments 64-71, wherein the XRPD pattern comprises at least the 2theta value of 23.1±0.2°.
73. The crystalline form of any of embodiments 64-72, wherein the XRPD pattern comprises at least the 2theta value of 17.8±0.2°.
74. The crystalline form of any of embodiments 64-73, wherein the XRPD pattern comprises at least the 2theta value of 22.2±0.2°.
75. The crystalline form of any of embodiments 64-74, wherein the XRPD pattern comprises at least the 2theta value of 20.7±0.2°.
76. The crystalline form of any of embodiments 64-75, characterized by an XRPD pattern having the characteristic 2θ values of FIG. 22.
77. The crystalline form of any of embodiments 64-76, that has differential scanning calorimetry (DSC) onset endotherms of about 140±20° C.
78. The crystalline form of any of embodiments 64-77, that has differential scanning calorimetry (DSC) onset endotherms of about 140±10° C.
79. In certain embodiments a pharmaceutical composition is provided comprising the crystalline form of any of embodiments 64-78 and a pharmaceutically acceptable excipient.
80. In certain embodiments a method is provided for the treatment of a BRD9-mediated disorder comprising administering an effective amount of crystalline form of any of embodiments 64-78 or a composition of embodiment 79 to a host in need thereof.
81. The method of embodiment 80, wherein the host is a human.
82. In certain embodiments a process is provided to prepare a compound of formula:

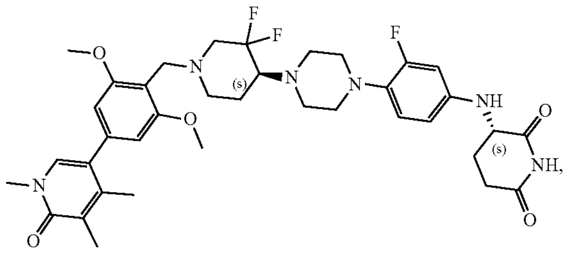 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

wherein the process comprises steps of:

a. reacting a N-protected piperazine with 1,2-difluoro-4-nitro-benzene in the presence of a first base in a first solvent to afford a N-protected 4-(2-fluoro-4-nitro-phenyl)piperazine of structure (a):

(a)

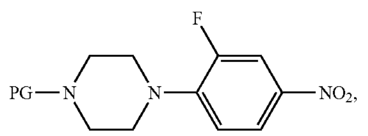

wherein each PG is independently a protecting group;

b. removing the protecting group from the N-protected 4-(2-fluoro-4-nitro-phenyl)piperazine of structure (a) in a second solvent to afford 4-(2-fluoro-4-nitro-phenyl)piperazine of structure (b):

(b)

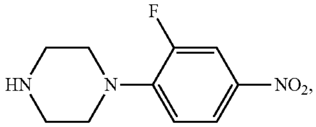

or its acid-addition salt, wherein the acid-addition salt is formed through protonation of one or both piperazine nitrogen atoms with a first organic or inorganic acid;

c. reacting 4-(2-fluoro-4-nitro-phenyl)piperazine of structure (b) or its acid-addition salt with a N-protected 3,3-difluoro-4-oxo-piperidine in a third solvent to afford a N-protected 1-(3,3-difluoro-1,2,3,6-tetrahydropyridin-4-yl)-4-(2-fluoro-4-nitrophenyl) piperazine of structure (c):

(c)

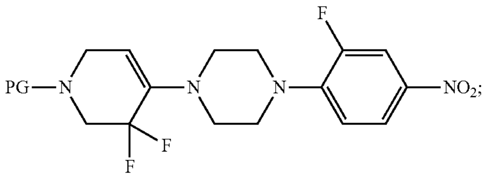

d. reacting the N-protected 1-(3,3-difluoro-1,2,3,6-tetrahydropyridin-4-yl)-4-(2-fluoro-4-nitrophenyl)piperazine of structure (c) with a first reducing agent for reduction of imine bond in a fourth solvent to afford a N-protected 1-(3,3-difluoropiperidin-4-yl)-4-(2-fluoro-4-nitrophenyl)piperazine of structure (d):

(d)

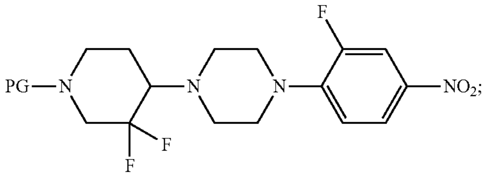

e. chiral separating the N-protected 1-(3,3-difluoropiperidin-4-yl)-4-(2-fluoro-4-nitrophenyl)piperazine of structure (d) by a chiral chromatography to afford a N-protected (R)-3,3-difluoro-4-(4-(2-fluoro-4-nitrophenyl)piperazin-1-yl)piperidine of structure (e1) and a N-protected (S)-3,3-difluoro-4-(4-(2-fluoro-4-nitrophenyl)piperazin-1-yl)piperidine of structure (e2):

(e1)

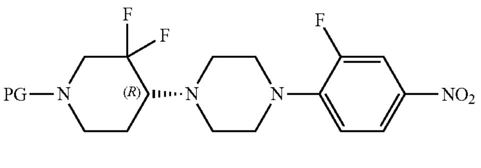

and

-continued (e2)

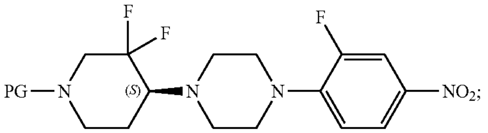

f. reducing the nitro group in the N-protected (S)-3,3-difluoro-4-(4-(2-fluoro-4-nitrophenyl)piperazin-1-yl)piperidine of structure (e2) with a second reducing agent to convert the nitro group into an amino group and to afford a N-protected 4-[4-(4-amino-2-fluoro-phenyl)piperazin-1-yl]-3,3-difluoro-piperidine of structure (f):

f

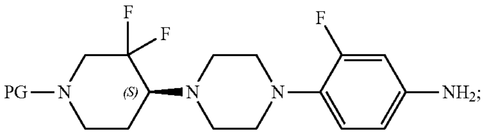

g. reacting the N-protected 4-[4-(4-amino-2-fluoro-phenyl)piperazin-1-yl]-3,3-difluoro-piperidine of structure (f) with 3-bromopiperidine-2,6-dione in the presence of a second base in a fifth solvent to afford a N-protected (4S)-4-(4-(4-((2,6-dioxopiperidin-3-yl)amino)-2-fluorophenyl)piperazin-1-yl)-3,3-difluoropiperidine of structure (g):

(g)

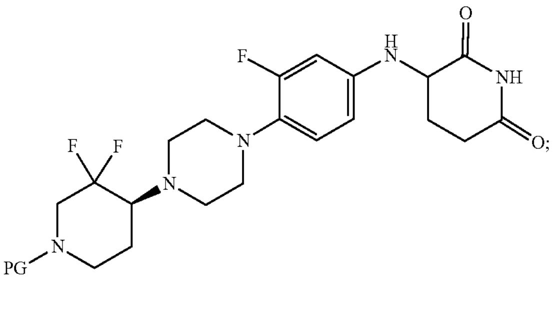

h. chiral separating the N-protected (4S)-4-(4-(4-((2,6-dioxopiperidin-3-yl)amino)-2-fluorophenyl)piperazin-1-yl)-3,3-difluoropiperidine of structure (g) by a chiral chromatography to afford a N-protected (S)-4-(4-(4-(((S)-2,6-dioxopiperidin-3-yl)amino)-2-fluorophenyl)piperazin-1-yl)-3,3-difluoropiperidine of structure (h):

(h)

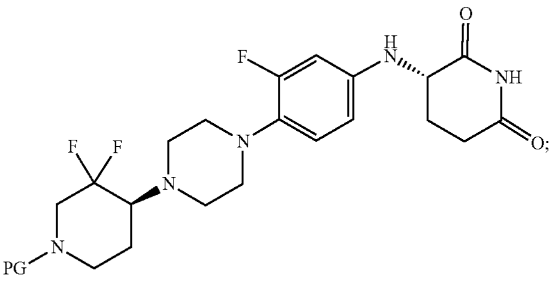

i. reacting the N-protected (S)-4-(4-(4-(((S)-2,6-dioxopiperidin-3-yl)amino)-2-fluorophenyl)piperazin-1-yl)-3,3-difluoropiperidine of structure (h) with a solution of a second organic or inorganic acid in a sixth solvent to afford (S)-3-((4-(4-((S)-3,3-difluoropiperidin-4-yl)piperazin-1-yl)-3-fluorophenyl)amino)piperidine-2,6-dione of structure (i):

(i)

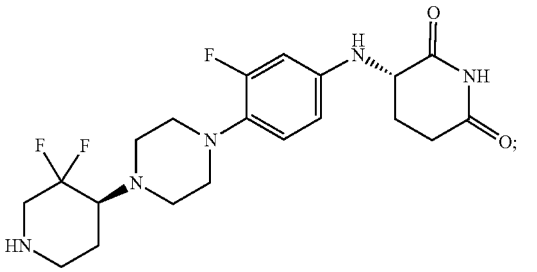

or its acid-addition salt; and j. reacting (S)-3-((4-(4-((S)-3,3-difluoropiperidin-4-yl)piperazin-1-yl)-3-fluorophenyl)amino)piperidine-2,6-dione of structure (i) or its acid-addition salt with 4-(1,4,5-trimethyl-6-oxo-1,6-dihydropyridin-3-yl)benzaldehyde in a seventh solvent in the presence of sodium triacetoxyborohydride and acetic acid to afford the compound of formula 1.

83. The process of embodiment 82, wherein the protecting group is tert-butyloxycarbonyl (BOC), benzyloxycarbonyl (Cbz), 9-fluorenylmethyloxycarbonyl (Fmoc) or 2-(triphenylsilyl)ethyloxycarbonyl (Tpseoc).

84. The process of any one of embodiments 82-83, wherein step (c) is carried out under reflux in the third solvent to remove water formed during the reaction.

85. The process of any one of embodiments 82-84, wherein step (g) is carried out in the presence of a phase transfer catalyst.

86. The process of any one of embodiments 82-85, wherein the process comprises steps of:

a. reacting tert-butyl piperazine-1-carboxylate with 1,2-difluoro-4-nitro-benzene in the presence of a first base in a first solvent to afford tert-butyl 4-(2-fluoro-4-nitro-phenyl) piperazine-1-carboxylate of formula:

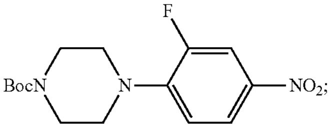 [SMILES: CC(C)(C)OC(=O)N1CCN(c2ccc([N+](=O)[O-])cc2F)CC1]

b. reacting tert-butyl 4-(2-fluoro-4-nitro-phenyl) piperazine-1-carboxylate of step (a) with a solution of a first organic or inorganic acid in a second solvent to afford 1-(2-fluoro-4-nitrophenyl)piperazine of formula:

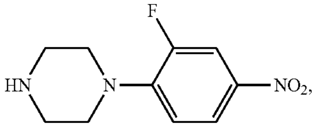 [SMILES: O=[N+]([O-])c1ccc(N2CCNCC2)c(F)c1]

or its acid-addition salt, wherein the acid-addition salt is formed through protonation of 1-(2-fluoro-4-nitrophenyl)piperazine with the first organic or inorganic acid;

c. reacting 1-(2-fluoro-4-nitrophenyl)piperazine or its acid-addition salt of step (b) with tert-butyl 3,3-difluoro-4-oxo-piperidine-1-carboxylate under reflux with toluene to remove water formed during the reaction and to afford tert-butyl 3,3-difluoro-4-(4-(2-fluoro-4-nitrophenyl)piperazin-1-yl)-3,6-dihydropyridine-1(2H)-carboxylate of formula:

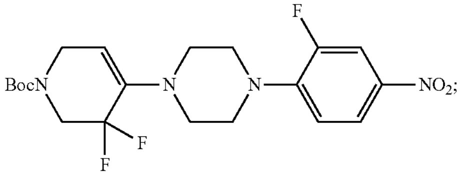

d. reacting tert-butyl 3,3-difluoro-4-(4-(2-fluoro-4-nitrophenyl)piperazin-1-yl)-3,6-dihydropyridine-1(2H)-carboxylate of step (c) with a first reducing agent for reduction of imine bond in a fourth solvent to afford tert-butyl-3,3-difluoro-4-[4-(2-fluoro-4-nitro-phenyl)piperazin-1-yl]piperidine-1-carboxylate of formula:

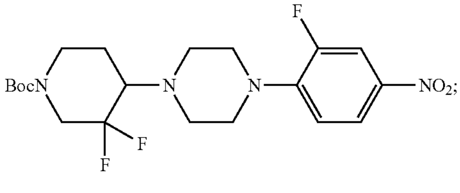

e. chiral separation of tert-butyl-3,3-difluoro-4-[4-(2-fluoro-4-nitro-phenyl)piperazin-1-yl]piperidine-1-carboxylate of step (d) by a chiral supercritical fluid chromatography to afford tert-butyl (R)-3,3-difluoro-4-(4-(2-fluoro-4-nitrophenyl)piperazin-1-yl)piperidine-1-carboxylate and tert-butyl (S)-3,3-difluoro-4-(4-(2-fluoro-4-nitrophenyl)piperazin-1-yl)piperidine-1-carboxylate of formulas:

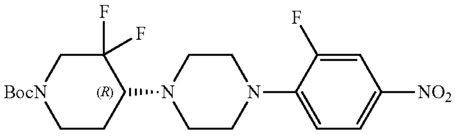
and

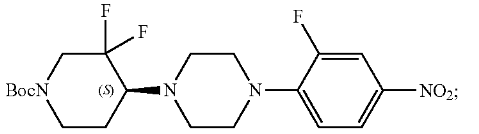

f. reducing the nitro group in tert-butyl (S)-3,3-difluoro-4-(4-(2-fluoro-4-nitrophenyl)piperazin-1-yl) piperidine-1-carboxylate of step (e) with a second reducing agent to convert the nitro group into an amino group and to afford tert-butyl 4-[4-(4-amino-2-fluoro-phenyl)piperazin-1-yl]-3,3-difluoro-piperidine-1-carboxylate of formula:

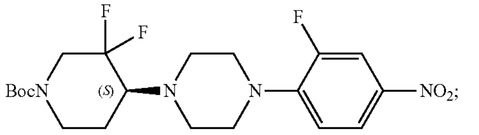

g. reacting tert-butyl 4-[4-(4-amino-2-fluoro-phenyl) piperazin-1-yl]-3,3-difluoro-piperidine-1-carboxylate of step (f) with 3-bromopiperidine-2,6-dione in the presence of a second base in a fifth solvent and in the presence of a phase transfer catalyst to afford tert-butyl (4S)-4-(4-(4-((2,6-dioxopiperidin-3-yl) amino)-2-fluorophenyl)piperazin-1-yl)-3,3-difluoropiperidine-1-carboxylate of formula:

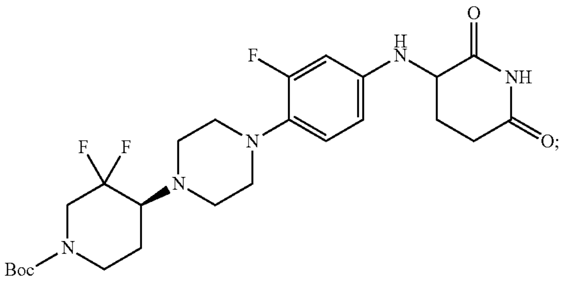 [SMILES: CC(C)(C)OC(=O)N1CC[C@H](N2CCN(c3ccc(NC4CCC(=O)NC4=O)cc3F)CC2)C(F)(F)C1]

h. chiral separation of tert-butyl (4S)-4-(4-(4-((2,6-dioxopiperidin-3-yl)amino)-2-fluorophenyl)piperazin-1-yl)-3,3-difluoropiperidine-1-carboxylate of step (g) by a chiral high-performance liquid chromatography to afford tert-butyl (S)-4-(4-(4-(((S)-2,6-dioxopiperidin-3-yl)amino)-2-fluorophenyl)piperazin-1-yl)-3, 3-difluoropiperidine-1-carboxylate of formula:

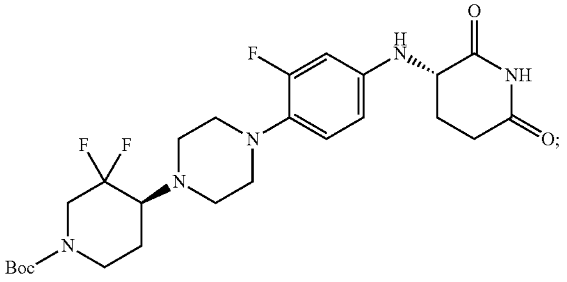 [SMILES: CC(C)(C)OC(=O)N1CC[C@H](N2CCN(c3ccc(N[C@H]4CCC(=O)NC4=O)cc3F)CC2)C(F)(F)C1]

i. reacting tert-butyl (S)-4-(4-(4-(((S)-2,6-dioxopiperidin-3-yl)amino)-2-fluorophenyl)piperazin-1-yl)-3,3-difluoropiperidine-1-carboxylate of step (h) with a solution of a second organic or inorganic acid in a sixth solvent to afford (S)-3-((4-(4-((S)-3,3-difluoropiperidin-4-yl)piperazin-1-yl)-3-fluorophenyl) amino)piperidine-2,6-dione of formula:

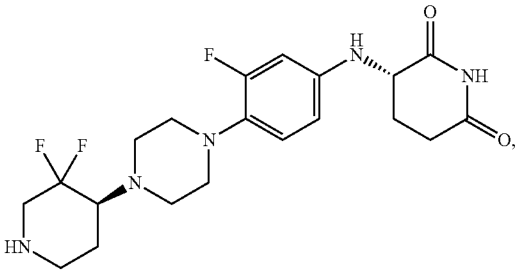 [SMILES: O=C1CC[C@H](Nc2ccc(N3CCN([C@H]4CCNCC4(F)F)CC3)c(F)c2)C(=O)N1]

or its acid-addition salt; and j. reacting (S)-3-((4-(4-((S)-3,3-difluoropiperidin-4-yl) piperazin-1-yl)-3-fluorophenyl)amino)piperidine-2,6-dione or its acid-addition salt of step (i) with 4-(1,4,5-trimethyl-6-oxo-1,6-dihydropyridin-3-yl) benzaldehyde in a seventh solvent in the presence of sodium triacetoxyborohydride and acetic acid to afford the compound of formula 1.

87. The process of any of embodiments 85-86, wherein the phase transfer catalyst is tetrabutylammonium iodide.

88. The process of any one of embodiments 82-87, wherein:

i. the first base is cesium carbonate and the first solvent is dimethylformamide;

ii. the first organic or inorganic acid is hydrochloric acid dissolved in dioxane and the second solvent is dioxane;

iii. the third solvent is toluene;

iv. the first reducing agent for reduction of imine bond is sodium cyanoborohydride and the fourth solvent is a mixture of acetic acid, methanol and dichloromethane;

v. the second reducing agent is hydrogen gas, wherein hydrogen gas is used in the presence of a 10% palladium on carbon catalyst;

vi. the second base is sodium bicarbonate, the fifth solvent is acetonitrile vii. the second organic or inorganic acid is hydrochloric acid and the sixth solvent is isopropyl acetate; and viii. the seventh solvent is dimethylacetamide.

89. In certain embodiments a compound is provided for use in the treatment of an unresectable cancer mediated by BRD9 in a human, wherein the compound is of formula:

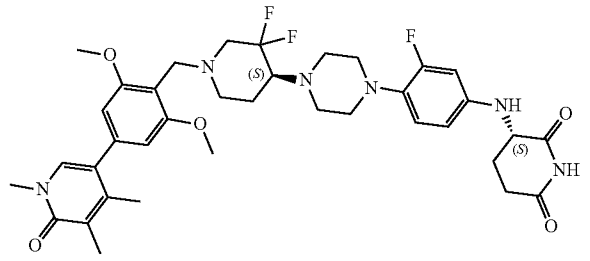

or a pharmaceutically acceptable salt thereof.

90. The compound of embodiment 89, wherein the cancer is relapsed.

91. The compound of embodiment 89 or 90, wherein the cancer is refractory.

92. The compound of any one of embodiments 89-91, wherein the cancer is a SMARCB1-perturbed cancer.

93. The compound any one of embodiments 89-92, wherein the cancer is selected from synovial sarcoma, malignant rhabdoid tumor, atypical teratoid rhabdoid tumor, cribriform neuroepithelial tumor, renal medullary carcinoma, epithelioid sarcoma, epithelioid malignant peripheral nerve sheath tumor, schwannomas in familial schwannomatosis, chordoma, myoepithelial carcinoma, and sinonasal carcinoma.

94. The compound any one of embodiments 89-92, wherein the cancer is synovial sarcoma.

95. The compound any one of embodiments 89-92, wherein the cancer is a soft tissue sarcoma.

96. The compound any one of embodiments 89-92, wherein the cancer is a clear cell renal cell carcinoma.

97. The compound any one of embodiments 89-96, wherein one or more additional therapeutically active agents are administered.

98. In certain embodiments a compound is provided for use in the treatment of a cancer mediated by BRD9 in a human, wherein the compound is of formula:

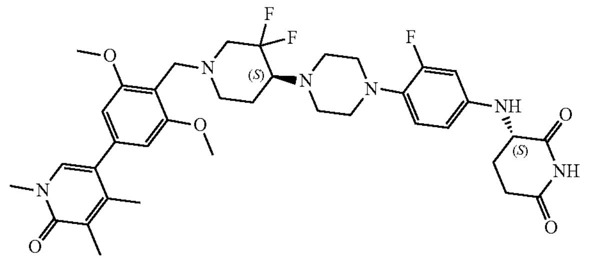

or a pharmaceutically acceptable salt thereof, wherein the cancer is an epithelioid malignant peripheral nerve sheath tumor, schwannomas in familial schwannomatosis, atypical malignant teratoid rhabdoid tumor, or cribriform neuroepithelial tumor.

99. The compound of embodiment 98, wherein one or more additional therapeutically active agents are administered.

100. In certain embodiments a compound is provided for use in the treatment of a cancer mediated by BRD9 in a human, comprising administering to the human an effective amount of a compound of Formula:

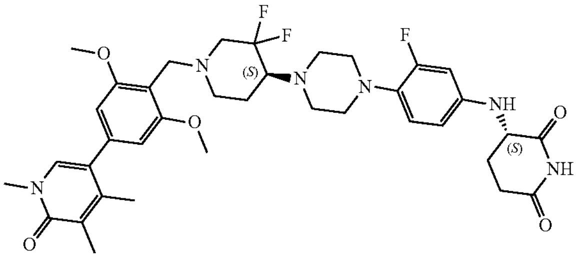

or a pharmaceutically acceptable salt thereof, wherein one or more additional therapeutic agents selected from ixazomib, anlotinib, itacitinib, cixutumumab, ixabepilone, exatecan mesylate, brostallicin, tazemetostat, and sapanisertib are also administered.

101. In certain embodiments a compound is provided for use in the treatment of a cancer mediated by BRD9 in a human, wherein the compound is of formula:

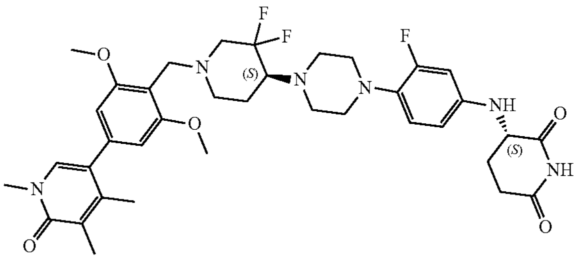

or a pharmaceutically acceptable salt thereof, wherein an additional chemotherapeutic regimen is administered and that regimen is selected from:

n. sintilimab, doxorubicin, and ifosfamide;

o. cixutumumab and doxorubicin;

p. cixutumumab and temsirolimus;

q. lurbinectedin and irinotecan;

r. sorafenib and dacarbazine;

s. pazopanib and gemcitabine;

t. doxorubicin and ribociclib;

u. tazemetostat, itraconazole, and rifampin;

v. cyclophosphamide and fludarabine;

w. ifosfamide, carboplatin, and etoposide;

x. doxorubicin, vincristine, and cyclophosphamide;

y. doxorubicin hydrochloride, etoposide, and ifosfamide; and z. trofosfamide, idarubicin, and etoposide.

102. In certain embodiments a compound is provided for use in the treatment of interferon-mediated inflammation in a human, wherein the compound is of formula:

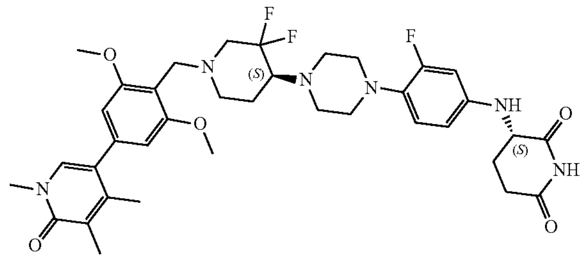

or a pharmaceutically acceptable salt thereof.

103. In certain embodiments a crystalline form is provided of any one of embodiments 15-29 or 64-78 or a pharmaceutical composition of any one of embodiments 31-33 or 79 for use in the treatment of a BRD9-mediated disorder.

104. The crystalline form of embodiment 103, wherein the disorder is a synovial sarcoma.

105. The crystalline form of embodiment 103, wherein the disorder is a SMARCB1-perturbed cancer.

106. The crystalline form of embodiment 103, wherein the disorder is selected from a poorly differentiated chordoma; a rare soft tissue malignancy; multiple myeloma; acute myeloid leukemia; a malignant rhabdoid tumor or an atypical teratoid or rhabdoid tumor; an epithelioid sarcoma; a renal medullary carcinoma; epithelioid malignant peripheral nerve sheath tumor; a myoepithelial carcinoma; an extra-skeletal myxoid chondrosarcoma; a chordoma; pancreatic undifferentiated rhabdoid carcinoma; a sinonasal basaloid carcinoma; a malignant rhabdoid tumor located in or on the brain or spinal cord; a cribriform neuroepithelial tumor located in or on the brain; a renal medullary carcinoma located in or on the kidney; an epithelioid sarcoma located in or on the skin, subcutaneous tissue, extremities, deep tissue, perineum, or proximal limb girdles; classic epithelioid sarcoma; proximal epithelioid sarcoma; epithelioid malignant peripheral nerve sheath tumor located in or on the dermis, subcutaneous tissue, or deep soft tissue; schwannoma in familial schwannomatosis located in or on a peripheral nerve or spinal nerve root; myoepithelial carcinoma located in or on a soft tissue or viscera; sinonasal carcinoma located in or on the sinonasal region; a synovial sarcoma located in or on deep soft tissues of extremities; and an atypical teratoid rhabdoid tumor located in or on the kidney, a soft tissue, or viscera.

107. The crystalline form of any one of embodiments 103-106, wherein the crystalline form is administered in combination with doxorubicin, ifosfamide, carboplatin, etoposide or cyclophosphamide.

108. In certain embodiments a use of a compound is provided in the treatment of an unresectable cancer mediated by BRD9 in a human, wherein the compound is of formula:

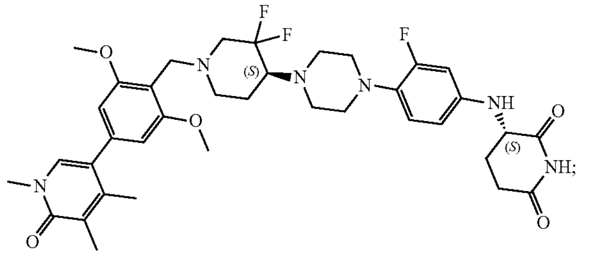

or a pharmaceutically acceptable salt thereof.

109. In certain embodiments a use of a compound is provided in the manufacture of a medicament for the treatment of an unresectable cancer mediated by BRD9 in a human, wherein the compound is of formula:

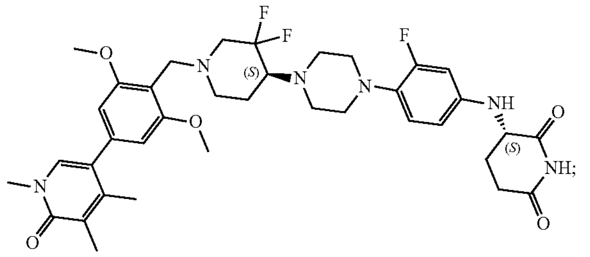

or a pharmaceutically acceptable salt thereof.

110. The use of embodiment 108 or 109, wherein the cancer is relapsed.

111. The use of embodiment 108 or 109, wherein the cancer is refractory.

112. The use of any one of embodiments 108-111, wherein the cancer is a SMARCB1-perturbed cancer.

113. The use of any one of embodiments 108-111, wherein the cancer is selected from synovial sarcoma, malignant rhabdoid tumor, atypical teratoid rhabdoid tumor, cribriform neuroepithelial tumor, renal medullary carcinoma, epithelioid sarcoma, epithelioid malignant peripheral nerve sheath tumor, schwannomas in familial schwannomatosis, chordoma, myoepithelial carcinoma, and sinonasal carcinoma.

114. The use of any one of embodiments 108-111, wherein the cancer is synovial sarcoma.

115. The use of any one of embodiments 108-111, wherein the cancer is a soft tissue sarcoma.

116. The use of any one of embodiments 108-111, wherein the cancer is a clear cell renal cell carcinoma.

117. The use of any one of embodiments 108-116, wherein one or more additional therapeutically active agents are administered.

118. In certain embodiments a use of a compound is provided in the treatment of a cancer mediated by BRD9 in a human, wherein the compound is of formula:

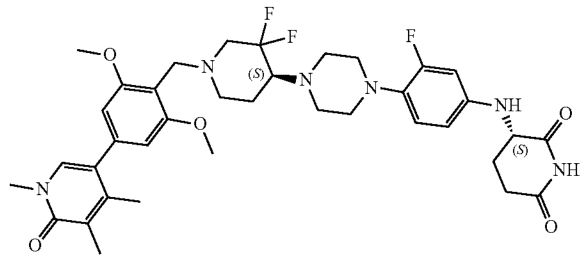

or a pharmaceutically acceptable salt thereof, wherein the cancer is an epithelioid malignant peripheral nerve sheath tumor, schwannomas in familial schwannomatosis, atypical malignant teratoid rhabdoid tumor, or cribriform neuroepithelial tumor.

119. In certain embodiments a use of a compound is provided in the manufacture of a medicament for the treatment of a cancer mediated by BRD9 in a human, wherein the compound is of formula:

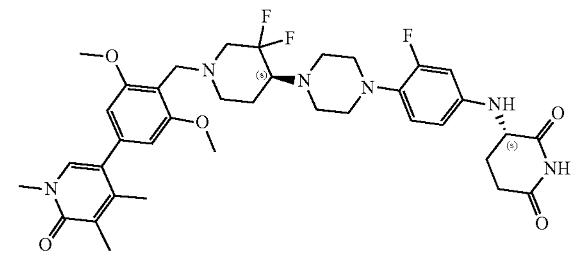 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof, wherein the cancer is an epithelioid malignant peripheral nerve sheath tumor, schwannomas in familial schwannomatosis, atypical malignant teratoid rhabdoid tumor, or cribriform neuroepithelial tumor.

120. The use of embodiment 118 or 119, wherein one or more additional therapeutically active agents are administered.

121. In certain embodiments a use of a compound is provided in the treatment of a cancer mediated by BRD9 in a human, comprising administering to the human an effective amount of a compound of Formula:

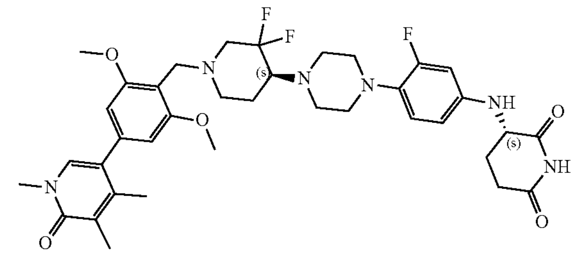 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof, wherein one or more additional therapeutic agents selected from ixazomib, anlotinib, itacitinib, cixutumumab, ixabepilone, exatecan mesylate, brostallicin, tazemetostat, and sapanisertib are also administered.

122. In certain embodiments a use of a compound is provided in the manufacture of a medicament for the treatment of a cancer mediated by BRD9 in a human, comprising administering to the human an effective amount of a compound of Formula:

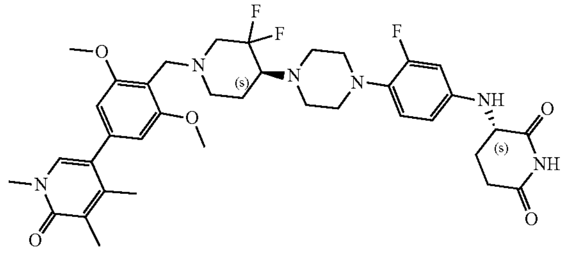 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof, wherein one or more additional therapeutic agents selected from ixazomib, anlotinib, itacitinib, cixutumumab, ixabepilone, exatecan mesylate, brostallicin, tazemetostat, and sapanisertib are also administered.

123. In certain embodiments a use of a compound is provided in the treatment of a cancer mediated by BRD9 in a human, wherein the compound is of formula:

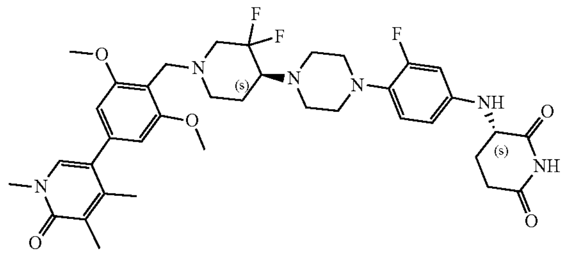 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof, wherein an additional chemotherapeutic regimen is administered and that regimen is selected from:

a. sintilimab, doxorubicin, and ifosfamide;

b. cixutumumab and doxorubicin;

c. cixutumumab and temsirolimus;

d. lurbinectedin and irinotecan;

e. sorafenib and dacarbazine;

f. pazopanib and gemcitabine;

g. doxorubicin and ribociclib;

h. tazemetostat, itraconazole, and rifampin;

i. cyclophosphamide and fludarabine;

j. ifosfamide, carboplatin, and etoposide;

k. doxorubicin, vincristine, and cyclophosphamide;

l. doxorubicin hydrochloride, etoposide, and ifosfamide; and m. trofosfamide, idarubicin, and etoposide.

124. In certain embodiments a use of a compound is provided in the manufacture of a medicament for the treatment of a cancer mediated by BRD9 in a human, wherein the compound is of formula:

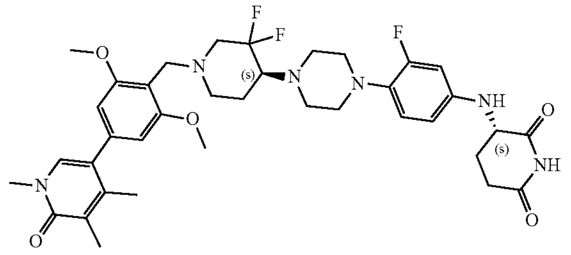 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof, wherein an additional chemotherapeutic regimen is administered and that regimen is selected from:

a. sintilimab, doxorubicin, and ifosfamide;
b. cixutumumab and doxorubicin;
c. cixutumumab and temsirolimus;
d. lurbinectedin and irinotecan;
e. sorafenib and dacarbazine;
f. pazopanib and gemcitabine;
g. doxorubicin and ribociclib;
h. tazemetostat, itraconazole, and rifampin;
i. cyclophosphamide and fludarabine;
j. ifosfamide, carboplatin, and etoposide;
k. doxorubicin, vincristine, and cyclophosphamide;
l. doxorubicin hydrochloride, etoposide, and ifosfamide; and
m. trofosfamide, idarubicin, and etoposide.

125. In certain embodiments a use of a compound is provided in the treatment of interferon-mediated inflammation in a human, wherein the compound is of formula:

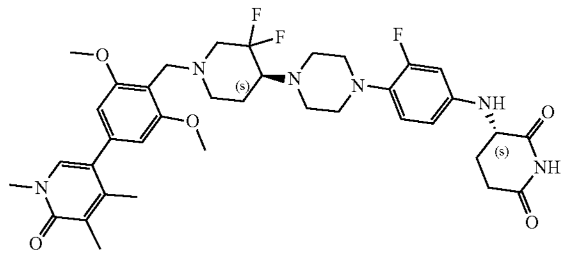 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof.

126. In certain embodiments a use of a compound is provided in the manufacture of a medicament for the treatment of interferon-mediated inflammation in a human, wherein the compound is of formula:

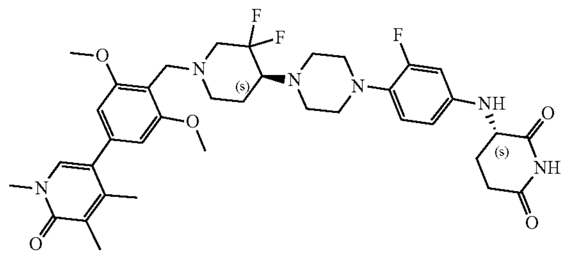 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof.

127. In certain embodiments a use of a crystalline form is provided of any one of embodiments 15-29 or 64-78 or a pharmaceutical composition of any one of embodiments 31-33 or 79 in the treatment of a BRD9-mediated disorder.

128. In certain embodiments a use of a crystalline form of any one of embodiments 15-29 or 64-78 or a pharmaceutical composition of any one of embodiments 31-33 or 79 in the manufacture of a medicament for the treatment of a BRD9-mediated disorder.

129. The use of embodiment 127 or 128, wherein the disorder is a synovial sarcoma.

130. The use of embodiment 127 or 128, wherein the disorder is a SMARCB1-perturbed cancer.

131. The use of embodiment 127 or 128, wherein the disorder is selected from a poorly differentiated chordoma; a rare soft tissue malignancy; multiple myeloma; acute myeloid leukemia; a malignant rhabdoid tumor or an atypical teratoid or rhabdoid tumor; an epithelioid sarcoma; a renal medullary carcinoma; epithelioid malignant peripheral nerve sheath tumor; a myoepithelial carcinoma; an extra-skeletal myxoid chondrosarcoma; a chordoma; pancreatic undifferentiated rhabdoid carcinoma; a sinonasal basaloid carcinoma; a malignant rhabdoid tumor located in or on the brain or spinal cord; a cribriform neuroepithelial tumor located in or on the brain; a renal medullary carcinoma located in or on the kidney; an epithelioid sarcoma located in or on the skin, subcutaneous tissue, extremities, deep tissue, perineum, or proximal limb girdles; classic epithelioid sarcoma; proximal epithelioid sarcoma; epithelioid malignant peripheral nerve sheath tumor located in or on the dermis, subcutaneous tissue, or deep soft tissue; schwannoma in familial schwannomatosis located in or on a peripheral nerve or spinal nerve root; myoepithelial carcinoma located in or on a soft tissue or viscera; sinonasal carcinoma located in or on the sinonasal region; a synovial sarcoma located in or on deep soft tissues of extremities; and an atypical teratoid rhabdoid tumor located in or on the kidney, a soft tissue, or viscera.

132. The use of any one of embodiments 127-131, wherein the crystalline form is administered in combination with doxorubicin, ifosfamide, carboplatin, etoposide or cyclophosphamide.

133. In certain embodiments a pharmaceutical composition is provided comprising a compound for use in the treatment of an unresectable cancer mediated by BRD9 in a human, wherein the compound is of formula:

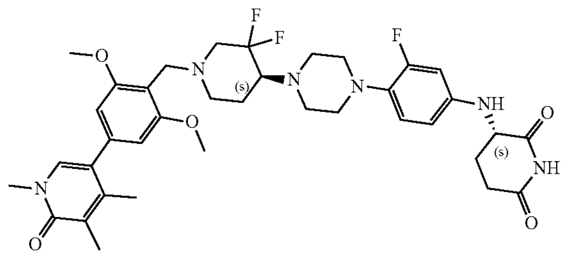 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof.

134. The pharmaceutical composition of embodiment 133, wherein the cancer is relapsed.

135. The pharmaceutical composition of embodiment 133 or 134, wherein the cancer is refractory.

136. The pharmaceutical composition of any one of embodiments 133-135, wherein the cancer is a SMARCB1-perturbed cancer.
137. The pharmaceutical composition of any one of embodiments 133-135, wherein the cancer is selected from synovial sarcoma, malignant rhabdoid tumor, atypical teratoid rhabdoid tumor, cribriform neuroepithelial tumor, renal medullary carcinoma, epithelioid sarcoma, epithelioid malignant peripheral nerve sheath tumor, schwannomas in familial schwannomatosis, chordoma, myoepithelial carcinoma, and sinonasal carcinoma.
138. The pharmaceutical composition of any one of embodiments 133-135, wherein the cancer is synovial sarcoma.
139. The pharmaceutical composition of any one of embodiments 133-135, wherein the cancer is a soft tissue sarcoma.
140. The pharmaceutical composition of any one of embodiments 133-135, wherein the cancer is a clear cell renal cell carcinoma.
141. The pharmaceutical composition of any one of embodiments 133-140, wherein one or more additional therapeutically active agents are administered.
142. In certain embodiments a pharmaceutical composition is provided comprising a compound for use in the treatment of a cancer mediated by BRD9 in a human, wherein the compound is of formula:

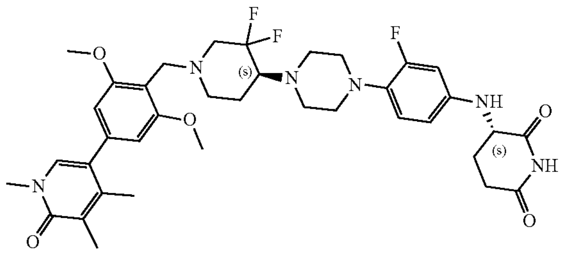 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof, wherein the cancer is an epithelioid malignant peripheral nerve sheath tumor, schwannomas in familial schwannomatosis, atypical malignant teratoid rhabdoid tumor, or cribriform neuroepithelial tumor.

143. The pharmaceutical composition of embodiment 142, wherein one or more additional therapeutically active agents are administered.
144. In certain embodiments a pharmaceutical composition is provided comprising a compound for use in the treatment of a cancer mediated by BRD9 in a human, comprising administering to the human an effective amount of a compound of Formula:

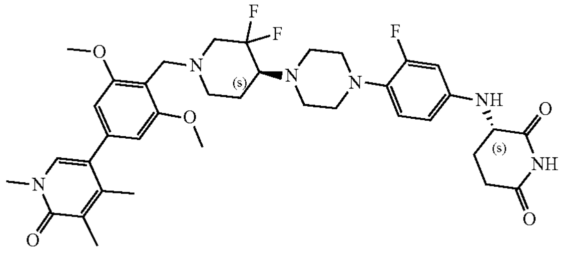 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof, wherein one or more additional therapeutic agents selected from ixazomib, anlotinib, itacitinib, cixutumumab, ixabepilone, exatecan mesylate, brostallicin, tazemetostat, and sapanisertib are also administered.

145. In certain embodiments a pharmaceutical composition is provided comprising a compound for use in the treatment of a cancer mediated by BRD9 in a human, wherein the compound is of formula:

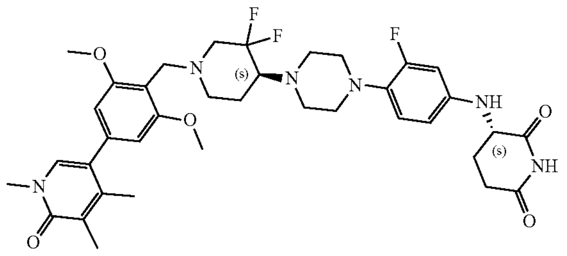 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof, wherein an additional chemotherapeutic regimen is administered and that regimen is selected from:

a. sintilimab, doxorubicin, and ifosfamide;
b. cixutumumab and doxorubicin;
c. cixutumumab and temsirolimus;
d. lurbinectedin and irinotecan;
e. sorafenib and dacarbazine;
f. pazopanib and gemcitabine;
g. doxorubicin and ribociclib;
h. tazemetostat, itraconazole, and rifampin;
i. cyclophosphamide and fludarabine;
j. ifosfamide, carboplatin, and etoposide;
k. doxorubicin, vincristine, and cyclophosphamide;
l. doxorubicin hydrochloride, etoposide, and ifosfamide; and
m. trofosfamide, idarubicin, and etoposide.

146. In certain embodiments a pharmaceutical composition is provided comprising a compound for use in the treatment of interferon-mediated inflammation in a human, wherein the compound is of formula:

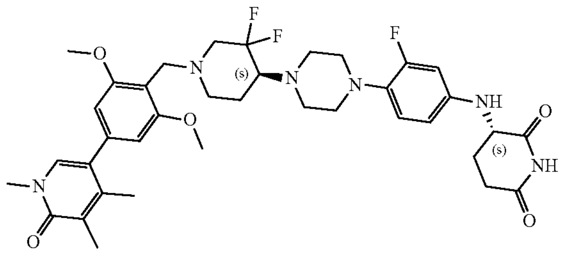 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof.

147. In certain embodiments a pharmaceutical composition is provided of any one of embodiments 31-33 or 79 for use in the treatment of a BRD9-mediated disorder.
148. The pharmaceutical composition of embodiment 147, wherein the disorder is a synovial sarcoma.
149. The pharmaceutical composition of embodiment 147, wherein the disorder is a SMARCB1-perturbed cancer.
150. The pharmaceutical composition of embodiment 147, wherein the disorder is selected from a poorly differentiated chordoma; a rare soft tissue malignancy; multiple myeloma; acute myeloid leukemia; a malignant rhabdoid tumor or an atypical teratoid or rhabdoid tumor; an epithelioid sarcoma; a renal medullary carcinoma; epithelioid malignant peripheral nerve sheath tumor; a myoepithelial carcinoma; an extra-skeletal myxoid chondrosarcoma; a chordoma; pancreatic undifferentiated rhabdoid carcinoma; a sinonasal basaloid carcinoma; a malignant rhabdoid tumor located in or on the brain or spinal cord; a cribriform neuroepithelial tumor located in or on the brain; a renal medullary carcinoma located in or on the kidney; an epithelioid sarcoma located in or on the skin, subcutaneous tissue, extremities, deep tissue, perineum, or proximal limb girdles; classic epithelioid sarcoma; proximal epithelioid sarcoma; epithelioid malignant peripheral nerve sheath tumor located in or on the dermis, subcutaneous tissue, or deep soft tissue; schwannoma in familial schwannomatosis located in or on a peripheral nerve or spinal nerve root; myoepithelial carcinoma located in or on a soft tissue or viscera; sinonasal carcinoma located in or on the sinonasal region; a synovial sarcoma located in or on deep soft tissues of extremities; and an atypical teratoid rhabdoid tumor located in or on the kidney, a soft tissue, or viscera.

151. The pharmaceutical composition of any one of embodiments 147-150, wherein the crystalline form is administered in combination with doxorubicin, ifosfamide, carboplatin, etoposide or cyclophosphamide.

X. Data

Example 1 HiBiT Assay

Selected compounds were tested in a BRD9 degradation assay using the HiBit Method.

Materials

Dulbecco's modified Eagle medium (DMEM) without phenol red and fetal bovine serum (FBS) were purchased from Gibco (Grand Island, NY, USA). Nano-Glo® HiBiT Lytic Assay System was purchased from Promega (Madison, WI, USA). 293T.166 (BRD9-HiBiT) cell line, endogenously expressing BRD9 with HiBiT fusion tag via CRISPR and ectopically expressing LgBiT tag, was purchased from Promega (Madison, WI, USA). 293T.167 (BRD7-HiBiT) cell line, endogenously expressing BRD7 with HiBiT fusion tag via CRISPR and ectopically expressing LgBiT tag, was purchased from Promega (Madison, WI, USA). 293T.92 (BRD4-HiBiT) cell line, endogenously expressing BRD4 with HiBiT fusion tag via CRISPR and ectopically expressing LgBiT tag, was generated in-house. Cell culture flasks and 384-well microplates were acquired from VWR (Radnor, PA, USA).

BRD9 Degradation Analysis

BRD9 degradation was determined based on quantification of luminescent signal using Nano-Glo® HiBiT Lytic Assay kit. Test compounds were added to the 384-well plate from a top concentration of 10 μM with 11 points, half log titration in duplicates. 293T.166 cells were added into 384-well plates at a cell density of 10,000 cells per well. The plates were kept at 37° C. with 5% CO2 for 2 hours. BRD7 and BRD4 degradation was similarly determined with 293T.167 cells and 293T.92 cells, respectively. The cells treated in the absence of the test compound were the negative control and the cells without Nano-Glo® HiBiT Lytic reagent were the positive control. After 2-hour incubation, Nano-Glo® HiBiT Lytic Assay reagents were added to the cells. Luminescence was acquired on EnVision® Multilabel Reader (Catalog No. 2104-0010, Perkin Elmer Inc., Dumfries, VA, USA).

Table 1 shows the activity of Compounds 1-5 in the BRD9 HiBit degradation assay wherein:

TABLE 1

| BRD9 Degradation Data | | |
|---|---|---|
| Cmpd # | Structure | HiBiT-Degradation 293T.166 BRD9 2.0 hours (DC50) [nM] |
| 1 | 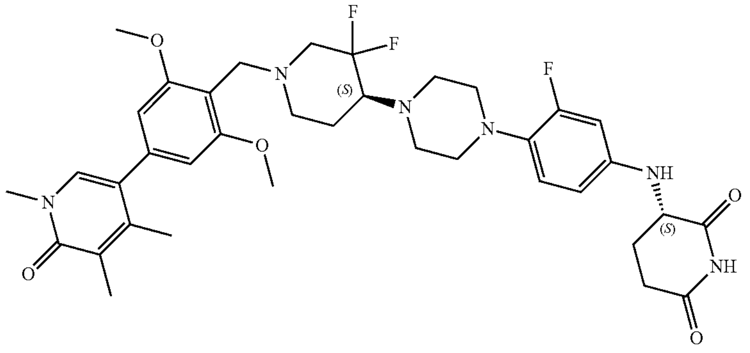 | +++ |

TABLE 1-continued
| BRD9 Degradation Data | | |
|---|---|---|
| Cmpd # | Structure | HiBiT-Degradation 293T.166 BRD9 2.0 hours (DC50) [nM] |
| 2 | 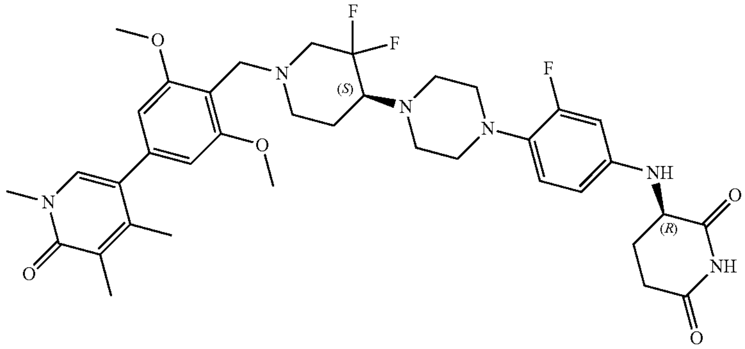 | +++ |
| 3 | 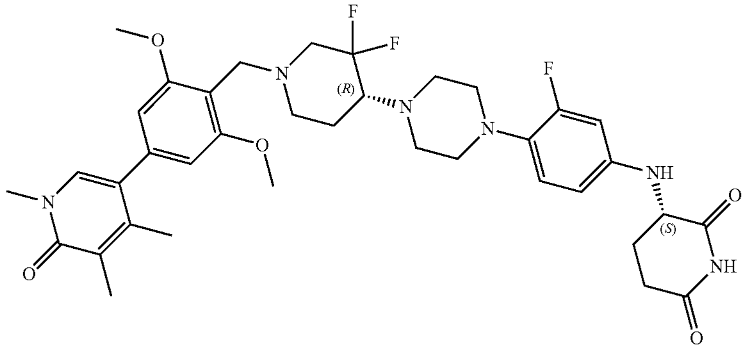 | +++ |
| 4 | 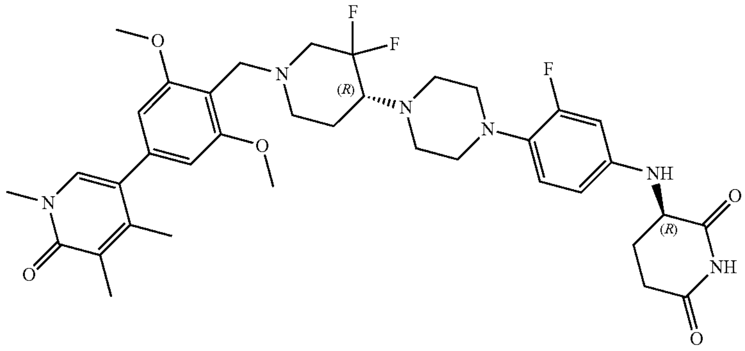 | +++ |

TABLE 1-continued

| BRD9 Degradation Data | | |
|---|---|---|
| Cmpd # | Structure | HiBiT-Degradation 293T.166 BRD9 2.0 hours (DC50) [nM] |
| 5 | 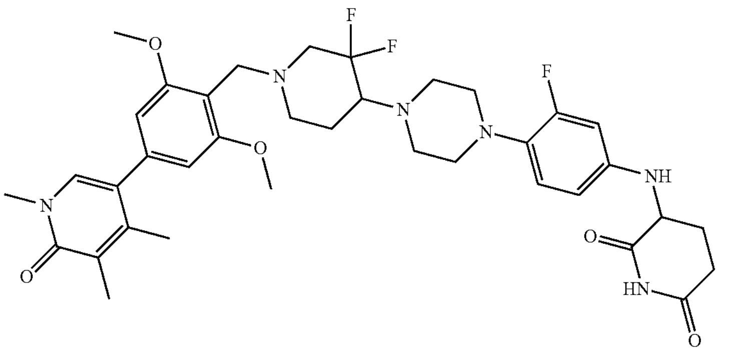 [SMILES: COc1cc(-c2cn(C)c(=O)c(C)c2C)cc(OC)c1CN1CCC(N2CCN(c3ccc(NC4CCC(=O)NC4=O)cc3F)CC2)C(F)(F)C1] | +++ |

"+++" represents a DC50 value of less than 100 nM;
"++" represents a DC50 value of 100 nM-500 nM; and
"+" represents a DC50 value of greater than 500 nM-800 nM.

Example 2 Pharmacology and Chemical Properties of Compound 1

Plasma Protein Binding Assay in Mouse, Rat, Dog, Monkey, and Human Plasma

Plasma protein binding (PPB) of Compound 1 was evaluated in plasma from mice, rats, dogs, cynomolgus monkeys, and humans using ultracentrifugation.

Frozen plasma from CD-1 mice, Sprague-Dawley rats, beagle dogs, cynomolgus monkeys, and humans was purchased and stored at ≤−30° C. On the day of study, plasma samples of CD-1 mice, Sprague-Dawley rats, beagle dogs, cynomolgus monkeys and humans were thawed under running cold tap water and centrifuged to remove any particulates.

10 mM stock solutions of Compound 1, warfarin (high-bound QC compound), and atenolol (low-bound QC compound) in dimethyl sulfoxide (DMSO) were prepared and stored at 4° C. For the internal standard, telmisartan, a 1 mg/mL solution was prepared by dissolving 1.4 mg of telmisartan in 1.4 mL of DMSO, and stored at 4° C.

The 10 mM stock solution of each test compound was used to prepare 400 μM intermediate stocks in methanol. Then, a 2 μM working stock of each test compound was prepared for plasma from each species (mouse, rat, dog, monkey, and human) by spiking 12 μL of the 400 μM intermediate stock for each test compound into 2400 μL of thawed and prepared plasma from a test species.

400 μL of blank plasma for each species was transferred to a 0.5 mL Beckman tube (Part No. 343776, Beckman Coulter Life Sciences, Indianapolis, IN, USA) and centrifuged for 3 hours at 627000×g at 37° C. The supernatant was removed and kept at room temperature.

To prepare for ultracentrifugation, the rotor of the centrifuge was placed into an incubator and warmed up to 37° C. before centrifugation. The vacuum switch of the OPTIMA™ MAX-TL Ultracentrifuge (Beckman Coulter Life Sciences, Indianapolis, IN, USA) was turned on and the vacuum was reduced to less than 10 microns to warm up the system. The ultracentrifuge's parameters were set to the following: Temperature—37° C.; Time—3 hours; and Speed—627000×g. For each species and each test compound, 2.4 mL of working stock was mixed and pre-incubated for 45 minutes at 37° C. Then, 60 μL was separated and precipitated with 200 μL of acetonitrile containing internal standard and labeled as (T0), and 0.4 mL (triplicates) were transferred to Beckman 2 mL tubes (Part No. 344625, Beckman Coulter Life Sciences, Indiana, IN, USA).

For each species and each test compound, the triplicate 0.4 mL sample tubes were centrifuged for 3 hours at 627000×g at 37° C. Remaining volume was incubated for 45 min & 3 hr at 37° C. for stability checking. At 45 minutes, 60 μL was separated, precipitated with 200 μL of acetonitrile containing internal standard and labelled as (T45). After completion of 3 hours, 60 μL of incubated samples were separated, precipitated with acetonitrile containing internal standard, and labeled as (T3).

After completing the 3 hours of centrifugation, 30 μl of the top fraction of supernatant from each sample tube was removed (free fraction) and precipitated with acetonitrile containing internal standard (labeled as top sample).

After removing 30 μL of the top fraction, remaining top and bottom layer were mixed thoroughly to make a uniform mixture. From this mixture, 30 μL of bottom sample was collected and precipitated with acetonitrile containing internal standard (labelled as bottom sample).

Matrix matching was done for crashed stability samples (TO, T45 and T3 samples) by adding 30 μL of a 50:50 mixture of blank plasma supernatant and phosphate-buffered saline (PBS), and for top and bottom samples, by adding 30 μL of blank plasma (kept at room temperature).

All the stability samples and centrifuged samples were vortexed at 1000 rpm for 5 minutes and centrifuged at 4000 rpm for 10 minutes. Supernatant from each sample was separated, diluted 2-fold with water, and analyzed in LC-MS/MS.

Samples (supernatant-free fraction and total plasma) were analyzed by LCMS-MS (no standards). Percent free, or percent unbound, (% FU) was calculated using the equation below:

% FU=(Peak area in free fraction-top/peak area ratio in total plasma)*100

Percent bound was calculated using the following equation: % Bound=100-% Unbound. Percent remaining was calculated using the following equation: % Remaining=100*$T_{3.0\ hr}/T_{0\ hr}$.

The results of the study are shown in Table 2 below.

TABLE 2

PPB in Mouse, Rat, Dog, Monkey, and Human Plasma

| | Compound 1 (average, n = 3) | | | Warfarin (average, n = 3) | | | Atenolol (average, n = 3 ) | | |
|---|---|---|---|---|---|---|---|---|---|
| | % FU | % Bound | % Remaining at 3 hours | % FU | % Bound | % Remaining at 3 hours | % FU | % Bound | % Remaining at 3 hours |
| Mouse | 3.39 | 96.61 | 84.69 | 4.10 | 95.90 | 107.21 | 118.02 | −18.02 | 125.31 |
| Rat | 9.71 | 90.29 | 88.73 | 0.77 | 99.23 | 88.82 | 84.60 | 15.40 | 85.83 |
| Dog | 6.46 | 93.54 | 99.38 | 4.69 | 95.31 | 111.42 | 112.42 | −12.42 | 75.82 |
| Monkey | 5.14 | 94.86 | 99.14 | 0.67 | 99.33 | 115.61 | 107.98 | −7.98 | 124.51 |
| Human | 6.7 | 93.30 | 66.87 | 0.80 | 99.20 | 91.67 | 104.26 | −4.26 | 90.68 |

Hepatocyte Stability Assay with Mouse, Rat, Dog, Monkey, and Human Hepatocytes

The metabolic stability of Compound 1 was evaluated using cryopreserved hepatocytes from mice, rats, dogs, cynomolgus monkeys, and humans.

Cryopreserved hepatocytes from CD-1 mice, Sprague-Dawley rats, beagle dogs, cynomolgus monkeys, and human were purchased (ThermoFisher Scientific, Waltham, MA, USA) and stored in a cryostorage liquid nitrogen Dewar.

10 mM stock solutions of test compounds (Compound 1 and propranolol (QC compound)) in dimethyl sulfoxide (DMSO) were prepared. 50 μL of 1 mM intermediate solutions for each test compound was prepared by adding 5 μL of 10 mM stock solution to 45 μL of a 1:1 mixture of water and acetonitrile. A 2 μM working stocks for each test compound were prepared in incubation media, InvitroGRO™ KHB (Bio IVT, Westbury, NY, USA), by adding 2 μL of 1 mM intermediate stock to 998 μL of incubation media.

For the internal standard, telmisartan, a 1 mg/mL solution was prepared by dissolving 1.4 mg of telmisartan in 1.4 mL of DMSO, and stored at 4° C.

To thaw the hepatocytes, InvitroGRO™ HT thawing medium (BioIVT, Westbury, NY, USA) was prewarmed to 37° C., and 48 mL of warmed thawing medium was transferred to a sterile 50 mL conical tube. The hepatocyte vial was removed from the liquid nitrogen Dewar, and gently thawed in a water bath at 37° C. for 1-2 minutes, then the contents of the vial were emptied into a conical tube with prewarmed InvitroGRO HT medium. 1 mL of prewarmed InvitroGRO HT medium was added to each emptied hepatocyte vial to resuspend any remaining cells, and the contents were pipetted into the hepatocyte suspension. The tube containing the hepatocyte suspension was centrifuged at 50*g for 5 minutes. The supernatant was removed carefully, and the remaining pellet was resuspended by adding 1 mL of incubation media, InvitroGRO KHB, and gently shaking until there were no clumps.

Cell viability was determined using the trypan blue method. 25 μL of hepatocyte cell suspension was added to a trypan blue (TB) solution (containing 775 μL InvitroGRO KHB and 200 μL of Trypan Blue). Cell count was taken using a hemacytometer.

For mouse hepatocytes, 200 μL of hepatocytes ($0.8\times10^6$ cells/mL) were added to the wells of a 48 well plate (Catalog No. 92048, TPP Techno Plastic Products AG, Trasadingen, Switzerland) and pre-incubated for 30 minutes at 37° C. For rat, dog, monkey, and hepatocytes, 200 μL of hepatocytes ($2\times10^6$ cells/mL) were added to the wells of a 48 well plate (Catalog No. 92048, TPP Techno Plastic Products AG, Trasadingen, Switzerland) and pre-incubated for 30 minutes at 37° C.

For all species of hepatocytes, once the pre-incubation period was complete, 200 μL of 2 μM working stock of test compound was added to the wells of the plate, and the plate was vortexed on a Vibramax™ 100 (P/N 544-21200-00, Heidolph Instruments GmbH & Co. KG, Schwabach, Germany) at 500 rpm in a 37° C. CO2 incubator (Model No. 51026280, ThermoFisher Scientific, Waltham, MA, USA). At each time point of 0, 15, 30, 60, 90, and 120 minutes, 50 μL of incubation mixture was precipitated with 200 μL of acetonitrile containing internal standard.

At the end of the experiment, the samples were centrifuged at 4000 rpm for 10 minutes. The supernatant was collected and diluted with an equal amount of water, and vortexed for 5 minutes at 900 rpm in MixMate® (Model No. 5353, Eppendorf SE, Hamburg, Germany).

The supernatant samples were submitted for LC-MS/MS analysis.

Calculations of the results included the following:

$$CLint\ \text{cells}\ (\mu L/\text{min/million cell}) = ABS\ (Kel/\text{cell density}) * 1000$$

$$CLint\ \text{in}\ vivo\ (\text{mL/min/kg body wt.}) = (CLint\ \text{protein} * \text{Hepatocellularity} * \text{Liver factor}) / 1000$$

$$CLinvivo\ \text{well stirred model (mL/min/kg body wt.)} = [(CLint\ \text{in}\ vivo * QH) / (CLint\ invivo + QH)]$$

The cell density, hepatocellularity, liver factor, and QH for each species of hepatocytes are set forth in Table 3. The results summary for each of the hepatocyte species evaluated are shown in Table 4 to Table 8.

TABLE 3

| Cell Density, Hepatocellularity, Liver Factor, and QH for Each Species | | | | | | |
|---|---|---|---|---|---|---|
| | Mouse | Rat | Dog | Monkey | Human | |
| Cell Density | 0.4 | 1 | 1 | 1 | 1 | 106 cells/mL |
| Hepato-cellularity | 120 | 120 | 240 | 120 | 120 | million cells/g liver |
| Liver factor | 88 | 40 | 32 | 30 | 25.7 | g liver/kg BW |
| QH | 90 | 70 | 35 | 44 | 20 | mL/min/kg BW |

TABLE 4

Mouse Hepatocyte Stability Assay

| Compound ID | $T_{1/2}$ (min.) | CL int cells (μL/min/$10^6$ cells) | CLh int in vivo (mL/min/Kg body wt.) | CLhb (mL/min/kg body wt.) scaled well stirred |
|---|---|---|---|---|
| Compound 1 | >120 | 4.26 | 44.94 | 30.0 |
| Propranolol | 16.28 | 106.46 | 1124.22 | 83.3 |

TABLE 5

Rat Hepatocyte Stability Assay

| Compound ID | $T_{1/2}$ (min.) | CL int cells (μL/min/$10^6$ cells) | CLh int in vivo (mL/min/Kg body wt.) | CLhb (mL/min/kg body wt.) scaled well stirred |
|---|---|---|---|---|
| Compound 1 | >120 | 3.70 | 17.76 | 14.2 |
| Propranolol | 10.58 | 65.50 | 314.38 | 57.3 |

TABLE 6

Dog Hepatocyte Stability Assay

| Compound ID | $T_{1/2}$ (min.) | CL int cells (μL/min/$10^6$ cells) | CLh int in vivo (mL/min/Kg body wt.) | CLhb (mL/min/kg body wt.) scaled well stirred |
|---|---|---|---|---|
| Compound 1 | >120 | 1.49 | 11.48 | 8.6 |
| Propranolol | 23.20 | 29.87 | 229.43 | 30.4 |

TABLE 7

Monkey Hepatocyte Stability Assay

| Compound ID | $T_{1/2}$ (min.) | CL int cells (μL/min/$10^6$ cells) | CL int in vivo (mL/min/Kg body wt.) | CLhb (mL/min/kg body wt.) scaled well stirred |
|---|---|---|---|---|
| Compound 1 | 44.16 | 15.70 | 56.51 | 24.7 |
| Propranolol | 13.84 | 50.07 | 180.26 | 35.4 |

* % Qh for Compound 1 was 56.2, and % Qh for Propranolol was 80.4.

TABLE 8

Human Hepatocyte Stability Assay

| Compound ID | $T_{1/2}$ (min.) | CL int cells (μL/min/$10^6$ cells) | CL int in vivo (mL/min/Kg body wt.) | CLhb (mL/min/kg body wt.) scaled well stirred |
|---|---|---|---|---|
| Compound 1 | >120 | 4.67 | 14.40 | 8.4 |
| Propranolol | 45.37 | 15.28 | 47.12 | 14.0 |

SyncroPatch hHERG Assay

The effects of Compound 1 on the hERG potassium channels were evaluated using the automated patch clamp method (SyncroPatch® 384PE, Nanion Technologies GmbH, Munich, Germany).

CHO cells stably expressing hERG potassium channels (Sophion Bioscience, Inc. Bedford, MA, USA) were used for this test. The cells were cultured in a humidified and air-controlled (5% CO2) incubator at 37° C. The CHO hERG cell culture medium was 500 mL Ham's F-12 medium (Catalog No. 31765035, Invitrogen, Waltham, MA, USA), 50 mL HyClone™ Fetal Bovine Serum (Catalog No. SV30087.03, Cytiva, Marlborough, MA, USA), 1 mL Geneticin™ (G418 Sulfate, 50 mg/mL)) (Catalog No. 10131027, Invitrogen, Waltham, MA, USA), and 1 mL Hygromycin B (50 mg/mL) (Catalog No. 10687010, Invitrogen, Waltham, MA, USA).

The CHO cells were at least two days after plating and more than 75% confluent were used. Before testing, cells were harvested using TrypLE™ and resuspended in the physiological solution at the room temperature.

The solutions in Table 9 were used for the electrophysiological recordings. The physiological solution and external solution were prepared at least one month prior to the experiment. The intracellular solution was prepared in batches, aliquoted, and stored at 4° C. until use.

TABLE 9

Composition of Physiological, External, and Internal Solutions

| Reagent | Physiological Solution (mM) | External Solution (mM) | Internal Solution (mM) |
|---|---|---|---|
| NaCl | 140 | 80 | 10 |
| KCl | 4 | 4 | 10 |
| KF | — | — | 110 |
| $CaCl_2$ | 2 | 2 | — |
| $MgCl_2$ | 1 | 1 | — |
| Glucose | 5 | 5 | — |
| NMDG | — | 60 | — |
| HEPES | 10 | 10 | 10 |
| EGTA | — | — | 10 |
| pH | 7.4 with NaOH | 7.4 with NaOH | 7.2 with KOH |
| Osmolarity | ~298 mOsm | ~289 mOsm | ~280 mOsm |

Test compounds, Compound 1 and control compound amitriptyline, were dissolved in 100% DMSO to obtain stock solutions for different test concentrations. The stock solutions were further diluted into external solution to achieve final concentrations for testing. A visual check for precipitation was conducted before testing. Final DMSO concentration in external solution was not more than 0.30% for the test compounds.

The voltage command protocol started from a holding potential of −80 mV. Then, the voltage was first stepped to −50 mV for 80 ms for leak subtraction, and then stepped to +20 mV for 4,800 ms to open hERG channels. After that, the voltage was stepped back down to −50 mV for 5,000 ms, causing a "rebound" or tail current, which was measured and collected for data analysis. Finally, the voltage was stepped back to the holding potential of −80 mV for 1,000 ms. This voltage command protocol was repeated every 20,000 msec, and performed continuously during the test of vehicle control and test compounds.

This SyncroPatch hERG assay was conducted at room temperature. The Setup, Prime Chip, Catch and Seal Cells, Amplifier Settings, Voltage and Application Protocols were established with Biomek Software (Nanion Technologies GmbH, Munich, Germany). One addition of 40 μL of vehicle was applied, followed by a baseline period of 300 s. Then 40 μL doses of test compounds were added. The exposure of test compound at each concentration was no less than 300 s. The recording for the whole process passed quality control or the well was abandoned and the compound was retested, all automatically set by PatchControl (Nanion Technologies, Munich, Germany). Five concentrations (0.30 μM, 1.00 μM, 3.00 μM, 10.00 μM and 30.00 μM) were tested for each compound. A minimum of 2 replicates per concentration were obtained.

Data analysis was carried out using DataControl® (Nanion Technologies GmbH, Munich, Germany), EXCEL 2013 (Microsoft Corporation, Redmond, WA, USA) and GraphPad Prism 5.0 (GraphPad Software, LLC, San Diego, CA, USA).

Within each recording well, percent of control values were calculated for each test compound concentration current response based on peak current in presence of reference control (current response/peak current)×100%. The Dose-Response curves were fit to the standard Hill equation as shown below:

$$I_{post\,cpd}/I_{pre\,cpd} = \text{Bottom} + (\text{Top} - \text{Bottom})/(1 + 10 \wedge ((\text{Log}IC_{50} - X) * HillSlope))$$

where X is the logarithm of concentration, $I_{post\ cpd}/I_{pre\ cpd}$ is the normalized peak current amplitude, Top is 1, and Bottom is equal to 0. Curve-fitting and IC50 calculations were performed by GraphPad Prism 5.0. If the inhibition obtained at the lowest concentration tested was over 50%, or at the highest concentration tested was less than 50%, we reported the IC50 as less than lowest concentration, or higher than highest concentration, respectively.

Figure 33A:
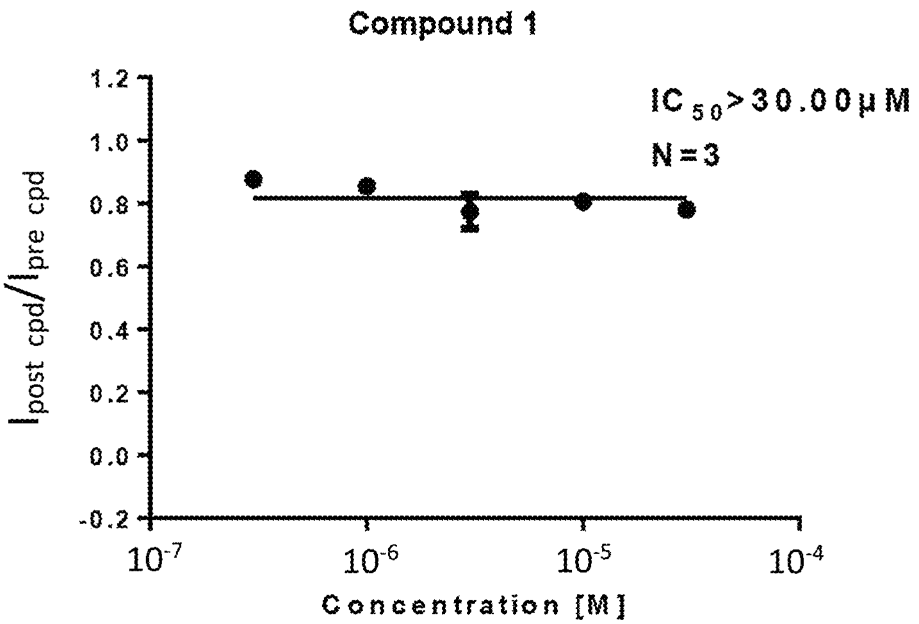
FIG. 33A and FIG. 33B are graphs demonstrating the effect of various concentrations of Compound 1 and control compound amitriptyline, respectively, on hERG potassium channels in a patch clamp assay. The experimental procedure is provided in Example 2.
Figure 33B:
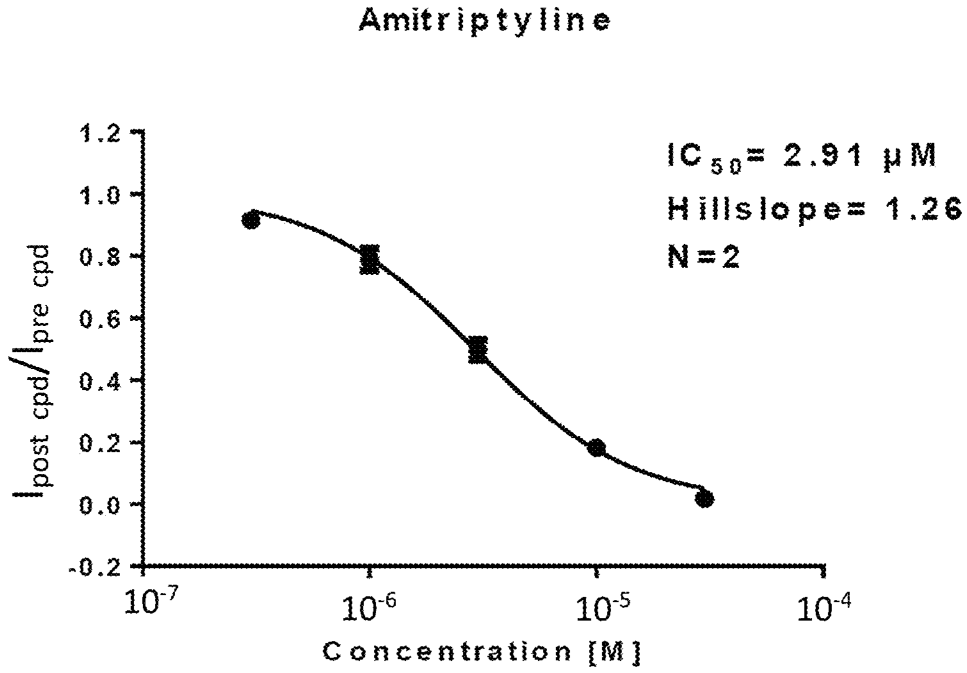

The results of this hERG assay are shown in Table 10 and Table 11 below, and in FIG. 33A and FIG. 33B.

TABLE 10

Compound 1 and Amitriptyline Concentration, POI, and SD

| | Concentration (M) | POI (%) | SD |
|---|---|---|---|
| Compound 1 | 3.00E−07 | 12.42 | 2.16 |
| | 1.00E−06 | 14.61 | 3.11 |
| | 3.00E−06 | 22.59 | 7.61 |
| | 1.00E−05 | 19.49 | 3.44 |
| | 3.00E−05 | 21.92 | 4.75 |
| Amitriptyline | 3.00E−07 | 8.48 | 2.15 |
| | 1.00E−06 | 21.15 | 4.95 |
| | 3.00E−06 | 50.15 | 5.61 |
| | 1.00E−05 | 81.81 | 4.59 |
| | 3.00E−05 | 98.26 | 1.65 |

TABLE 11

Summary of $IC_{50}$ of Test Compounds on Whole Cell hERG Currents

| | $IC_{50}$ (μM) | HillSlope | N |
|---|---|---|---|
| Compound 1 | 2.91 | 1.26 | 2 |
| Amitriptyline | >30.00 | — | 3 |

Competition Assay to Determine Binding Constant of Compound 1 to BRD9

An AlphaLISA® (Perkin Elmer Inc., Dumfries, VA, USA) displacement assay was used to determine the binding affinity of Compound 1 to purified bromodomain of BRD9 protein.

Human histidine-tagged (His-tag) bromodomain of BRD9 was expressed in *E. coli* and purified, with a concentration of 1.1 mg/mL. The bromodomain of BRD9 was labeled with an AlphaLISA® donor bead (Catalog No. AS101R, Perkin Elmer Inc., Dumfries, VA, USA) attached via a His-tag on the protein. A potent BRD9 ligand was chemically modified to attach a biotin tag. The biotin tag was subsequently used to attach a streptavidin-labeled AlphaLISA® acceptor bead (Catalog No. AL125M, Perkin Elmer Inc., Dumfries, VA, USA).

Determination of the binding constant ($K_d$) of Compound 1 to the bromodomain of BRD9 was carried out using an AlphaLISA® competition assay, where binding of Compound 1 to BRD9 was measured via loss of signal upon displacement of biotinylated BRD9 ligand tagged with the AlphaLISA® acceptor bead.

Compounds were dispensed (ECHO® 550 Liquid Handler, Labcyte Inc., San Jose, CA, USA) from serially diluted DMSO stock supplied by Frontier Scientific Services, Inc. (Newark, DE, USA) in low dead volume plates into gray 384-well light gray AlphaPlates (Catalog No. 6005359, Perkin Elmer Inc., Dumfries, VA, USA) using acoustic technology to 1% of total reaction volume. Compounds were arranged vertically in rows A through P. Concentration series were horizontal: columns 1-11, and then duplicates in columns 12-22. Columns 23 and 24 were reserved for 100% (no test compound, hence maximum signal) and 0% controls (no protein, hence only background signal), respectively.

Compound binding to BRD9 was measured by displacement of biotinylated BRD9 ligand probe ($K_d$=7.5 μM), labeled with an acceptor AlphaLISA® bead.

A 10 μL mixture containing 50 nM BRD9 and 10 nM of probe in 50 mM HEPES (pH 7.4) (Catalog No. BBH-74, Boston Bioproducts, Inc., Milford, MA, USA), 200 mM NaCl, 1 mM TCEP Catalog No. 77720, Thermo Fisher Scientific, Waltham, MA, USA), 0.05% Pluronic Acid F-127 (Catalog No. P6866, Invitrogen, Waltham, MA, USA), 0.1% BSA (Catalog No. 15260-037, Gibco, Grand Island, NY, USA), and 2 mM Imidazole (Catalog No. 68268-100 ml-F, Sigma-Aldrich, Inc., St. Louis, MO, USA) was added to wells containing compound (columns 1-22). Control wells contained 50 nM BRD9 plus 10 nM of probe (column 23) or 10 nM of probe only (column 24). The plate was incubated for 30 minutes at room temperature. Plates were read on an EnVision® multimode plate reader (Catalog No. 2104-0010, Perkin Elmer Inc., Dumfries, VA, USA) with an appropriate AlphaLISA® filter set.

Compounds were all soluble up to 99 μM by Nephelometry.

Compound 1 was tested in the assay in duplicate on three independent occasions.

Response (normalized signal), R, for each well containing the test compounds was calculated using the averaged signal from negative and positive control wells:

$$R = 100\% \times (S - N)/(P - N),$$

where S is the Alpha-signal in the well, and P and N are averaged values of positive (column 23) and negative (column 24) controls.

Normalized signal was then fitted to a logistic function to extract the $IC_{50}$ values.

$$R = R_{min} + (R_{max} - R_{min}) \Big/ \left(1 + \left(\frac{IC_{50}}{[BiDAC]}\right)^h\right),$$

where $R_{min}$ and $R_{max}$ correspond to the top and the bottom of the curve, and h is a Hill coefficient.

Binding constant $K_d$ was calculated using competitive binding model and a binding $K_d$ of 7.5 for the probe (Remillard et al., 2017; Theodoulou et al., 2016).

Compound 1 competed with fluorescence probe for binding to bromodomain of BRD9. A competitive single site binding model fit to the duplicate data yielded $K_d$ values for each of individual test occasion.

Data fitting was done globally for the duplicates and the average value for the duplicates reported. $K_d$ values for Compound 1 were obtained by fitting experimental data from each individual experiment. Individual test occasion data for Compound 1 $K_d$ were 157 nM, 131 nM, and 129 nM.

Figure 34:
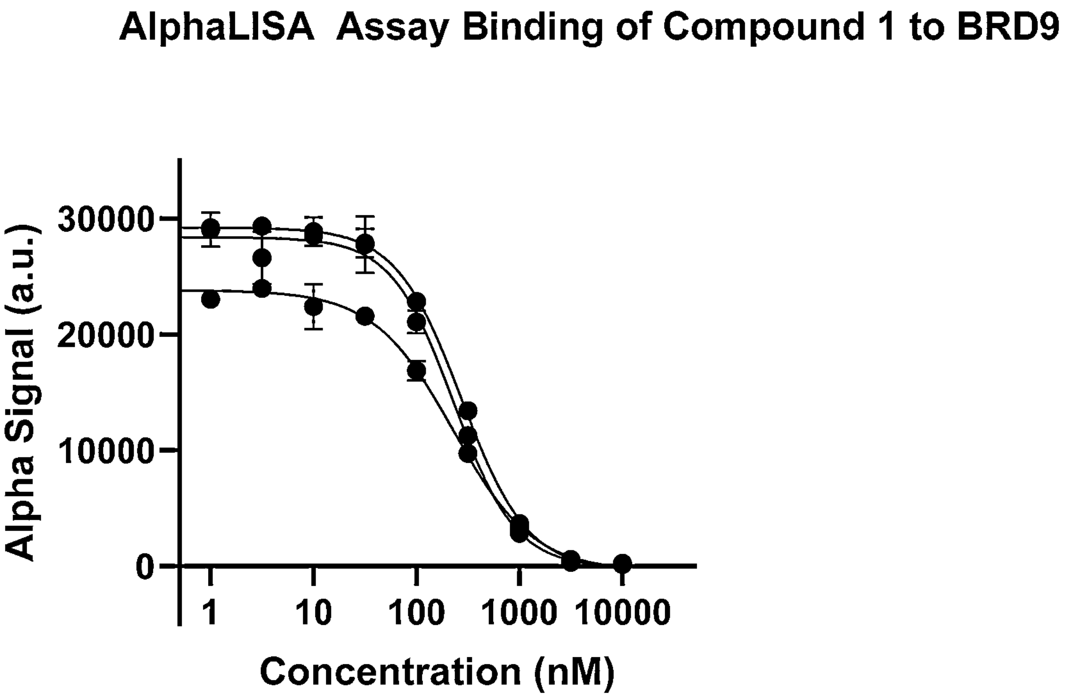
FIG. 34 is a graph demonstrating the binding of Compound 1 to BRD9 in an AlphaLISA® binding competition assay. Compound 1 competed with fluorescence probe for binding to BRD9. Error bars represent the standard deviation (SD) between duplicates run on the same occasion. The experimental procedure is provided in Example 2 and mean $K_d$ value and SD (n=3) are shown in Table 12.

Binding of Compound 1 to BRD9 was demonstrated by the displacement of Alpha-acceptor labeled probe as shown in FIG. 34. Table 12 shows the binding affinity ($K_d$) for Compound 1 to the BRD9 was determined to be 139 nM (geometric mean) with a geometric standard deviation of 1.12.

TABLE 12

Compound 1 Binding Affinity to BRD9

| Sample | $K_d$ (nM) (geometric mean) | $K_d$ geometric standard deviation |
|---|---|---|
| Compound 1 | 139 | 1.12 |

Fluorescence Polarization Assay

Fluorescence polarization (FP) competition experiments were used to determine the binding affinity of Compound 1 to purified CRBN-DDB1 protein. The binding of Compound 1 to CRBN-DDB1 was demonstrated by the displacement of fluorescently labeled CRBN-DDB1 binding compound.

Human Histidine (His) CRBN and non-tag DDB1 (CRBN-DDB1 (5.64 mg/mL in 25 mM HEPES, 300 mM NaCl, 1 mM TCEP, pH 7.5)) was purchased from Wuxi Biortus Biosciences Co., Ltd. (Jiangsu, China) and stored at −80° C. until use. Potent CRBN-DDB1 ligand was chemically labeled with the commercially available fluorophore Alexa Fluor™ 647 (Invitrogen, Waltham, MA, USA) following manufacturer's instructions. Fluorescently labelled CRBN-DDB1 binding compound at 0.3 mM in DMSO was stored at −20° C.

The determination of the binding constant ($K_d$) of Compound 1 to CRBN-DDB1 was carried out using an established, sensitive and quantitative in vitro fluorescence polarization (FP) binding assay (Nasir & Jolley, 1999). Control compound, pomalidomide (Catatlog No. 109806, ChemSuttle, Burlingame, CA, USA), was run on the same plate as Compound 1.

Compounds were dispensed (ECHO® 550 Liquid Handler, Labcyte Inc., San Jose, CA, USA) from serially diluted DMSO stock supplied by Frontier Scientific Services, Inc. (Newark, DE, USA) in low dead volume plates into black 384-well compatible FP plates (Catalog No. 3821, Corning, Glendale, CA, USA) using acoustic technology to 1% of total reaction volume. Compounds were arranged vertically in rows A through P. Concentration series were horizontal: columns 1-11, and then duplicates in columns 12-22. Columns 23 and 24 are reserved for 0% (5 nM probe) and 100% controls (protein at 1.5 uM with 5 nM probe), respectively.

Compound binding to CRBN-DDB1 was measured by displacement of fluorescently labelled CRBN-DDB1 binding compound with a $K_d$ of 72 nM.

A 20 μL mixture containing 150 nM CRBN-DDB1 and 5 nM probe dye in 50 mM HEPES, pH 7.4, 200 mM NaCl, 1 mM TCEP and 0.05% Pluronic Acid F-127 was added to wells containing compound and incubated at room temperature for 1.5 hours. Control wells with 100% bound probe contained 1.5 μM of CRBN-DDB1. Matching control plates excluding CRBN-DDB1 were used to correct for background fluorescence (Shapiro et al., 2009). Plates were read on an EnVision® multimode plate reader (Catalog No. 2104-0010, Perkin Elmer Inc., Dumfries, VA, USA) with Cy5 polarization filters and mirror.

Compounds were all soluble up to 99 μM by Nephelometry.

Compound 1 and control compound were tested in the FP assay in duplicate on three independent occasions. Matching control plates excluding CRBN-DDB1 were used to correct S (perpendicular) and P (parallel) values for background fluorescence according to Shapiro et al (Shapiro et al., 2009).

The corrected S and P values were used together with the gain (G) to calculate fluorescence polarization with the following equation:

$$FP = 1000 \times (S - G \times P)/(S + G \times P)\mu$$

The fractional amount of bound probe to CRBN-DDB1 as a function of compound concentration was fitted according to Wang 1995 to obtain binding constant ($K_d$) of competitor compound (Z.-X. Wang, 1995).

Data fitting was done globally for the duplicates and the geometric mean for the duplicates reported. Three replicates for Compound 1 and control compound were run. Compound 1 competed with fluorescence probe for binding to CRBN-DDB1. A competitive single site binding model fit to the duplicate data yielded $K_d$ values for each of individual test occasion. Individual test occasion data $K_d$ values were 2.1 μM, 1.6 μM, and 2.3 μM.

Figure 35:
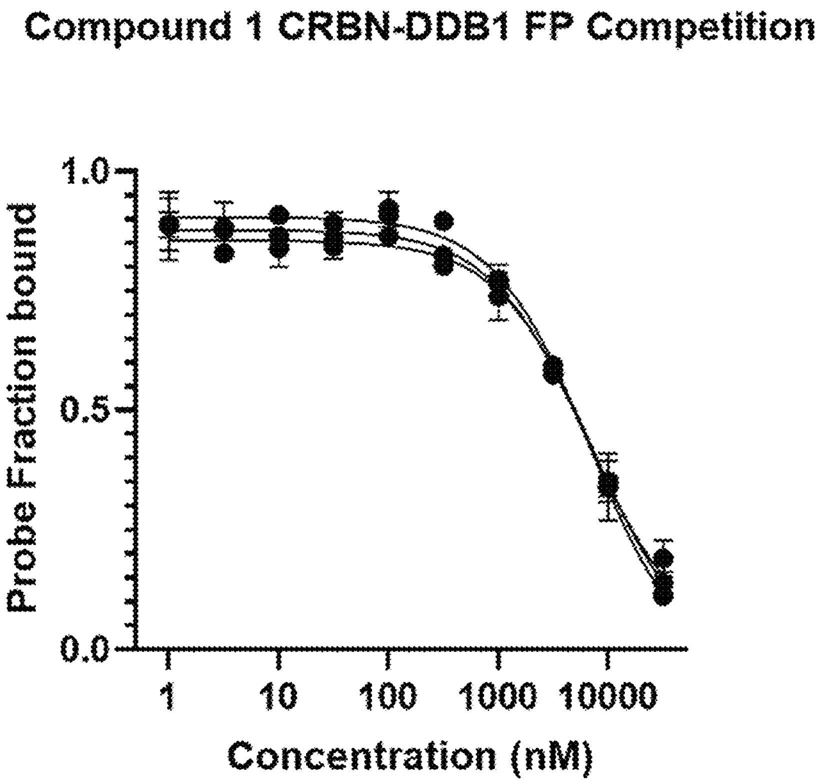
FIG. 35 is a graph demonstrating the binding Compound 1 binding to CRBN-DDB1 in a fluorescence polarization competition binding assay. Compound 1 competed with Alexa Fluor™ 647 fluorescence probe for binding to CRBN-DDB1. Error bars represent the standard deviation (SD) between duplicates run on the same occasion. The experimental procedure is provided in Example 2 and mean $K_d$ value and SD (n=3) are shown in Table 13.

Binding of Compound 1 to CRBN-DDB1 was demonstrated by the displacement of fluorescently labeled CRBN-DDB1 binding compound as shown in FIG. 35. Table 13 shows the binding affinity ($K_d$) for Compound 1 to the CRBN-DDB1 domain of E3 ligase was determined to be 2.0 μM (geometric mean) with geometric mean standard deviation of 1.2.

TABLE 23

| Compound 1 Binds to CRBN-DDB1 | | |
|---|---|---|
| Sample | $K_d$ (μM) (geometric mean) | $K_d$ geometric standard deviation |
| Compound 1 | 2.0 | 1.2 |

BRD9 Degradation by Compound 1 or Compound 2 in HEK293T.166 Cell Line

This assay evaluates the degradation of BRD9 induced by treatment with Compound 1 or Compound 2 as measured by luminescence using Nano-Glo® HiBiT Lytic Assay System in HEK293 cells CRISPR-edited to endogenously express HiBiT tagged BRD9 and exogenously express LgBiT protein.

Nano-Glo® HiBiT Lytic Assay System was purchased from Promega (Catalog No. N3050, Madison, WI, USA). BRD9-HiBiT HEK293 cells were purchased from Promega (Catalog No. CS302348, Madison, WI, USA). The cells were maintained in Dulbecco's modified Eagle medium (DMEM) without phenol red (Catalog No. 12430112, ThermoFisher Scientific, Waltham, MA, USA) supplemented with 10% fetal bovine serum (FBS) (Catalog No. 16000-044, Gibco, Grand Island, NY, USA) at 37° C. in an atmosphere of 5% $CO_2$ in air. The HiBiT polypeptide tag was introduced into the C-terminus of the endogenous BRD9 locus by CRISPR-Cas9 and the LgBiT protein was introduced via Lentiviral infection to produce the modified HEK293T.166 cell line. The HiBiT polypeptide and LgBiT protein allow reconstitution of NanoBiT enzyme in the cells. The Nano-Glo® HiBiT Lytic Substrate was then added and activated by the NanoBiT enzyme following cell lysis to produce a luminescent signal that is directly proportional to the amount of HiBiT-tagged BRD9.

The HEK293T.166 cells were routinely sub-cultured to maintain cell density between 30-80% confluence, not to exceed 20 passages. Cells were washed with PBS pH 7.4 (Catalog No. 10010049, ThermoFisher Scientific, Waltham, MA, USA), trypsinized for 5 minutes at 37° C., and resuspended in fresh growth media without phenol red. An aliquot was diluted 2× with Trypan Blue solution 0.4% (Catalog No. 15250061, ThermoFisher Scientific, Waltham, MA, USA) and cell count determined. Cell concentration was adjusted with growth media without phenol red to $3.3\times10^5$ cells/mL.

Compound 1 or Compound 2 was prepared by dissolving neat compounds in DMSO (Catalog No. D8418, Sigma-Aldrich, Inc., St. Louis, MO, USA) to generate 10 mM stock solution and stored at −20° C. The 10 mM DMSO stock solution of Compound 1 or Compound 2 was serially diluted (half log) in DMSO to generate 11-point dose series (10000, 3165, 1000, 316, 100, 31.6, 10, 3.2, 1, 0.32, 0.1 μM) in an acoustic ready 384-well low dead volume microplate (Catalog No. LP-0200, Beckman Coulter Life Sciences, Indianapolis, IN, USA). Using an Echo 550 Acoustic Liquid Handler (Beckman Coulter Life Sciences, Indianapolis, IN, USA), 2.5 nL of serially diluted compound solutions and 27.5 nL DMSO were dispensed in duplicate to each 384-well TC-treated microplate (Catalog No. 3571, Corning, Glendale, CA, USA). 30 nL DMSO was transferred to all control wells.

30 μL of HEK293T.166 cells suspended in growth media without phenol red at $3.3\times10^5$ cells/mL (10000 cells/well) were dispensed using a Multidrop Combi Reagent Dispenser (Catalog No. 5840300, ThermoFisher Scientific, Waltham, MA, USA) to each well of columns 1-23 of 384-well TC-treated microplates containing duplicate concentration range of test compounds and DMSO controls. 30 μL of media was dispensed to column 24 as background positive control (P). Plates were spun briefly at 1000 rpm and cells were incubated at 37° C., 5% $CO_2$ for 2 hours. Final concentration of DMSO was 0.1% for all samples.

Cellular BRD9 protein level was determined based on quantification of HiBiT using Nano-Glo® HiBiT Lytic Assay System (Promega). 30 μL Nano-Glo Lytic Assay reagents were added to each well and luminescence was acquired on EnVision® Multilabel Reader (Catalog No. 2104-0010, Perkin Elmer Inc., Dumfries, VA, USA). Cells treated in the absence of the test compound (0.1% DMSO vehicle) were the negative control (N) and wells containing only media were the positive control (P).

Percent response of compound-treated samples (T) were calculated by normalizing to the DMSO treated negative (N) controls on the same microtiter plate after background (i.e., positive control) signal subtraction:

$$\text{Response }\% = 100\times(\text{Signal}(T) - \text{Average }(P))/(\text{Average }(N) - \text{Average }(P)).$$

Curve fit and $DC_{50}$ (concentration that degrades 50% BRD9) determination was performed by 4 parametric logistic fit analysis using software such as GraphPad Prism software (GraphPad Software, LLC, San Diego, CA, USA). The fit was performed through minimization of the root mean squared error between observed and calculated values of the four-parameter logistic equation using the simplex optimizer of the Apache Commons Math library. Boundary conditions for the fit parameters were set as: top was constrained to be between 80% and 120% response, bottom to be between 0% and 80% response, Hill slope between −3 and −0.3, inflection point unrestricted. $DC_{50}$ values were computed as the concentrations where the fitted curves cross the 50% response level. Averages and standard deviations were computed from replicates of the experiment.

Figure 36:
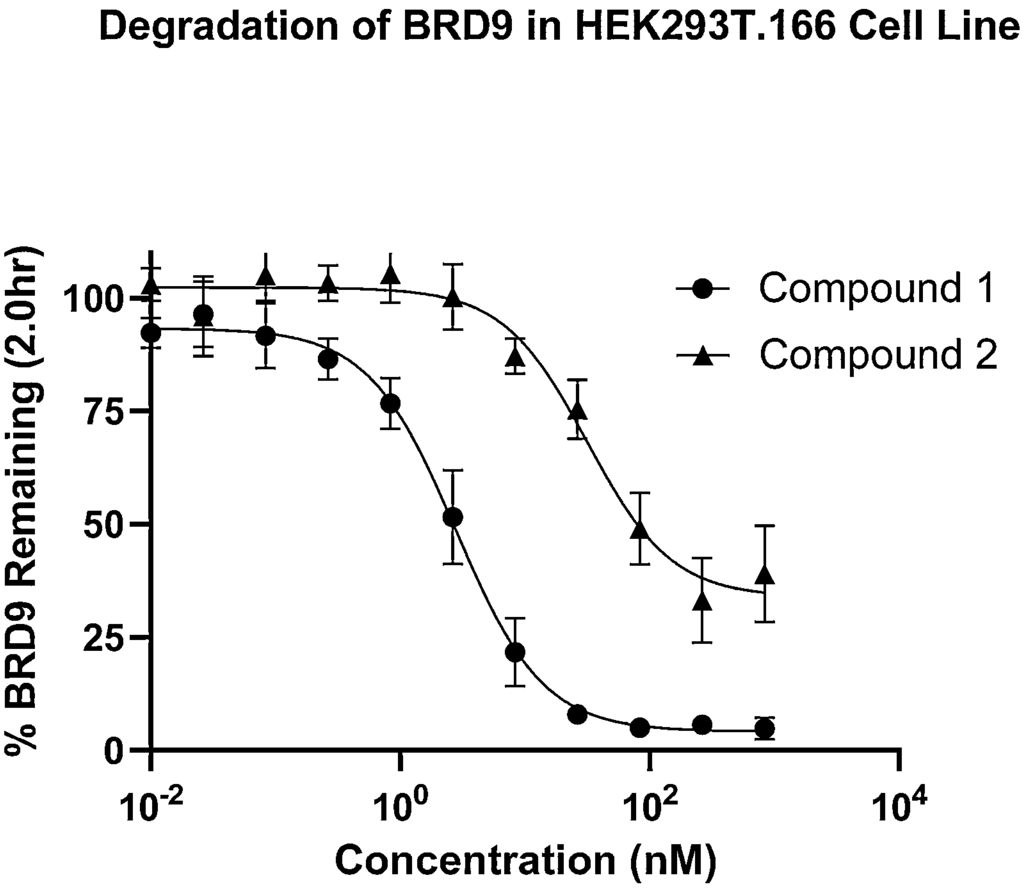
FIG. 36 depicts BRD9 degradation in HEK293T.166 cells modified to express HiBiT-tagged BRD9 measured by luminescence after 2-hour treatment with Compound 1 or Compound 2. The experimental procedure is provided in Example 2.

The results are shown in Table 14, Table 15, and FIG. 36. Data in FIG. 36 and Table 14 are expressed as the mean±SD for three independent experiments each performed in duplicate. Data in Table 14 are the geometric mean and 95% confidence interval of $DC_{50}$ values and the arithmetic mean±SD for $E_{max}$ values.

TABLE 34

| Statistics of BRD9-HiBiT Degradation in 293T.166 Cells at 2 Hours | | | |
|---|---|---|---|
| | Geometric Mean $DC_{50}$ (nM) | Geometric Mean $DC_{50}$ 95% CI (nM) | Mean $E_{max}$ (%) ± SD |
| Compound 1 | 2.66 | 1.26 to 5.63 | 4.14 ± 1.15 |
| Compound 2 | 85.4 | N.D. | 33.1 ± 9.92 |

TABLE 45

Percent Activity of Compound 1 and Compound 2 in BRD9-HiBiT Degradation in 293T.166 Cells at 2 Hours

| | % BRD9 Remaining Relative to Vehicle Control at 2 hr | | | |
|---|---|---|---|---|
| | Compound 1 | | Compound 2 | |
| Concentration (nM) | Mean | SD | Mean | SD |
| 0.010 | 92.3 | 3.3 | 103.0 | 3.6 |
| 0.032 | 96.4 | 7.3 | 95.9 | 8.8 |
| 0.100 | 91.6 | 7.1 | 105.0 | 5.6 |
| 0.315 | 86.4 | 4.6 | 103.3 | 4.0 |
| 0.997 | 76.7 | 5.6 | 105.4 | 6.4 |
| 3.15 | 51.6 | 10.4 | 100.2 | 7.3 |
| 10.0 | 21.7 | 7.5 | 87.1 | 3.8 |
| 31.7 | 7.9 | 0.9 | 75.4 | 6.5 |
| 100 | 5.0 | 1.3 | 49.0 | 8.0 |
| 316 | 5.7 | 1.7 | 33.1 | 9.4 |
| 999 | 4.8 | 2.4 | 39.0 | 10.7 |

BRD9 degradation in HEK293T.166 cells, modified to express HiBiT-tagged BRD9, was measured by luminescence after 2-hour treatment with Compound 1 or Compound 2. Compound 1 induced significant degradation of BRD9, resulting in >9500 maximal degradation and $DC_{50}$, or the concentration at which 50% protein is degraded, of 2.66 nM after 2-hour treatment. BRD9 degradation by Compound 2 was weaker in comparison, resulting in approximately 700% degradation and DC50 of 85.4 nM after 2 hours (20->30-fold weaker than Compound 1) (P=0.01).

BRD9 Degradation in Yamato-SS Cells (Endogenous)

The purpose of this study was to evaluate the detection of BRD9 in a human cell line and susceptibility to degradation by Compound 1.

Previously frozen YAMATO-SS human cells (provided by the RIKEN BRC through the National BioResource Project of the MEXT/AMED, Japan (cat #RCB3577)) were thawed. Upon thawing, the cells were transferred to a 15 mL conical tube containing 10 mL of warm RPMI-1640 medium (Catalog No. C2400500BT, Gibco, Grand Island, NY, USA) supplemented with 10% FBS (Catalog No. SV30087.03, Cytiva, Marlborough, MA, USA) and spun down for 5 minutes at 1200 rpm. An aliquot was diluted 2× with Trypan Blue solution 0.4% (Catalog No. 15250061, ThermoSischer Scientific, Waltham, MA, USA) and cell count was determined.

Compound 1 was prepared by dissolving neat compound in DMSO (Catalog No. D8418, Sigma-Aldrich, Inc., St. Louis, MO, USA) to 10 mM stock concentration and stored at −20° C. until usage. Upon usage, this stock solution was then diluted to 0.1 μM, 1 μM, 10 μM, 100 μM, 1000 μM and 10000 μM working solutions.

YAMATO-SS cells were seeded in a well plate, 600 thousand cells per well in 2 mL RPMI-1640 media supplemented with 10% FBS. 2 μL of DMSO and 2 μL of a dose range of 0.1 μM, 1 μM, 10 μM, 100 μM, 100 μM and 10000 μM Compound 1 was then added to a separate well. The final concentration of DMSO was 0.1% for both DMSO alone, and 30 μM Compound 1 treated wells. These cells were then placed in an incubator at 37° C., 5% $CO_2$ for 4 hours and 24 hours.

At the end of drug treatment, cells were collected into 2.0 mL MμlTI™ SafeSeal™ microcentrifuge tubes (Catalog No. 53550, Sorenson BioScience Inc., Murray, UT, USA) and spun down for 30 seconds at 14,000 rpm. Cells were resuspended in ice-cold PBS, spun down for 30 seconds at 14,000 rpm and resuspended in 100 μl RIPA Lysis and Extraction Buffer (Catalog No. BP-415-250 ml, Boston Bioproducts, Inc., Milford, MA, USA) supplemented with 2× Halt™ Protease and Phosphatase Inhibitor Cocktail (Catalog No. PI78444, ThermoFischer Scientific, Waltham, MA, USA) at 20 μM per 1000 μM RIPA Buffer.

Samples were boiled for 5 minutes and placed on ice for 30 minutes. Samples were spun down for 10 minutes at 14,000 rpm. Supernatants were transferred to a new 2.0 mL microcentrifuge tube and total protein concentrations were measured using Pierce™ BCA Protein Assay Kit (Catalog No. 23225, ThermoFischer Scientific, Waltham, MA USA).

After total protein quantification, all samples were diluted to a fixed μg/μL of protein in 6× loading buffer (Catalog No. BP-111R, Boston Bioproducts, Inc., Milford, MA, USA) for a final concentration of 40 μg of total protein in 1× loading buffer per lane. Volumes of each lane were normalized using DI water.

Samples were boiled for 5 minutes and run on duplicate 4-15% acrylamide gels at 120V until the loading buffer was at the bottom of the gel. The protein was transferred out of the gel using the BioRad Turbo Transfer unit on to nitrocellulose membranes (Catalog No. 1704271, Bio-Rad Laboratories, Hercules, CA, USA). Membranes were removed from the transfer and blocked for 1 hour at room temperature in Intercept® LiCor TBS blocking buffer (Catalog No. 927-66003, Li-Cor Biosciences, Lincoln, NE, USA). One membrane was used for blotting BRD9 and endogenous control Vinculin (Catalog No. SAB4200080, Sigma-Aldrich, Inc., St. Louis, MO, USA). The BRD9 (E9R2I) Rabbit antibody (Catalog No. 58906, Cell Signaling Technology, Inc., Danvers, MA, USA) was diluted 1:1000 and vinculin antibody was diluted 1:10000 in Intercept® LiCor TBS blocking buffer and added to the membrane. The membrane was incubated at 4° C. overnight on a plate rocker.

The following day, the membrane was washed three times by submerging each blot in TBS-T (Catalog No. IBB-885, Boston Bioproducts, Inc., Milford, MA, USA) and rocking on a plate rocker for 5 minutes. After each wash fresh TBS-T was added to the blots. After the third wash, anti-mouse 680 and anti-rabbit secondary antibodies 800 (Catalog Nos. 926-68070 and 926-32211, Li-Cor Biosciences, Lincoln, NE, USA) were diluted 1:10000 in Intercept® LiCor TBS blocking buffer and added to the membrane. The membrane incubated in secondary antibodies for 1 hour at room temperature. The membrane was then washed three times by submerging each blot in TBS-T and rocking on a plate rocker for 5 minutes. After each wash fresh TBS-T was added to the blots. A fourth wash in PBS for 5 minutes was used last before scanning with the LiCor instrument.

For analysis, protein band intensities were quantified in the LiCor Image studio software (Li-Cor Biosciences, Lincoln, NE, USA). BRD9 band intensities were normalized to the corresponding Vinculin band. Band intensities were then normalized to DMSO treated samples and plotted in Prism as % of control.

Figure 37:
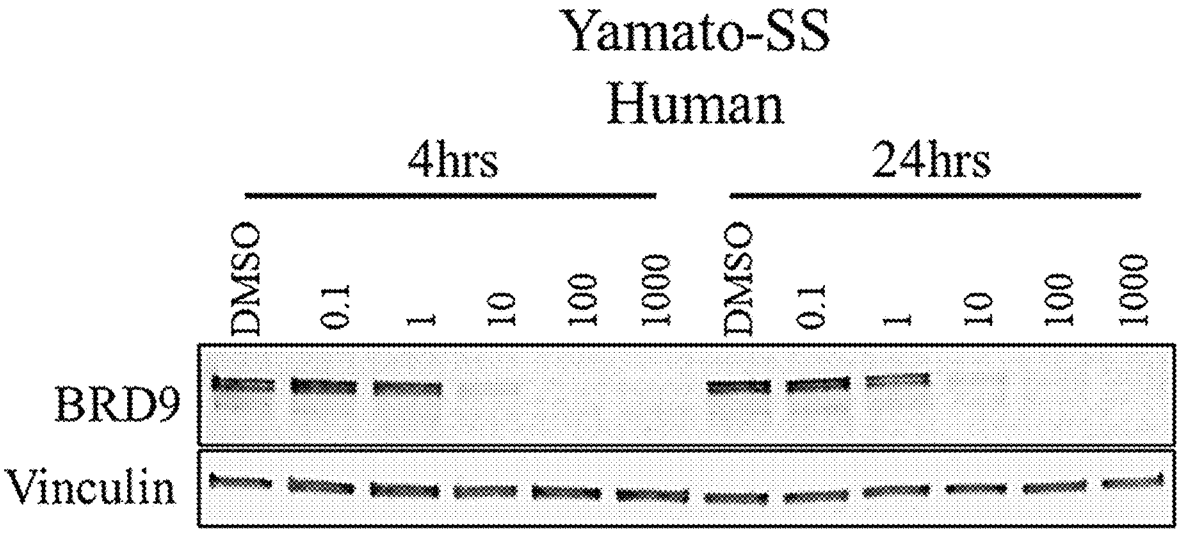
FIG. 37 is a western blot depicting BRD9 degradation by Compound 1 in Yamato-SS human cells. The experimental procedure is provided in Example 2.

The resulting Western Blot is shown in FIG. 37.

Table 16 shows that Compound 1 treatment induced degradation of BRD9 in human YAMATO-SS cells had an Emax of 1.2% and a $DC_{50}$ of 2.1 nM at 4 hours, and an Emax of 3.4% and $DC_{50}$ of 2.3 nM at 24 hours.

TABLE 16

| Percent BRD9 Detected inYamato-SS Cells After Compound 1 Treatment | | | |
|---|---|---|---|
| Cell line (species) | Time | $DC_{50}$ (nM) | $E_{max}$(%) |
| Yamato-SS (human) | 4 hr | 2.1 | 1.2% |
| | 24 hr | 2.3 | 3.4% |

BRD7 Degradation Assay

This assay evaluates the degradation of Bromodomain Containing 7 (BRD7) induced by treatment with Compound 1 as measured by luminescence using Nano-Glo® HiBiT Lytic Assay System in HEK293 cells CRISPR-edited to endogenously express HiBiT tagged BRD7.

Nano-Glo® HiBiT Lytic Assay System was purchased from Promega (Catalog No. N3050, Madison, WI, USA). BRD7-HiBiT HEK293 cells were purchased from Promega (Catalog No. CS302346, Madison, WI, USA). The cells were maintained in Dulbecco's modified Eagle medium (DMEM) (Catalog No. 12430112, ThermoFisher Scientific, Waltham, MA, USA) supplemented with 10% fetal bovine serum (FBS) (Catalog No. 16000-044, Gibco, Grand Island, NY, USA) at 37° C. in an atmosphere of 5% $CO_2$ in air. The HiBiT polypeptide tag was introduced into the C-terminus of the endogenous BRD7 locus by CRISPR-Cas9 and the LgBiT protein was introduced via Lentiviral infection to produce the modified HEK293T.167 cell line. The HiBiT polypeptide and LgBiT protein allow reconstitution of NanoBiT enzyme in the cells. The Nano-Glo® HiBiT Lytic Substrate was then added and activated by the NanoBiT enzyme following cell lysis to produce a luminescent signal that is directly proportional to the amount of HiBiT-tagged BRD7.

The HEK293T.167 cells were routinely sub-cultured to maintain cell density between 30-80% confluence, not to exceed 20 passages. Cells were washed with PBS pH 7.4 (Catalog No. 10010049, ThermoFisher Scientific, Waltham, MA, USA), trypsinized for 5 minutes at 37° C., and resuspended in fresh growth media without phenol red. An aliquot was diluted 2× with Trypan Blue solution 0.4% (Catalog No. 15250061, ThermoFisher Scientific, Waltham, MA, USA) and cell count determined. Cell concentration was adjusted with growth media without phenol red to $3.3\times10^5$ cells/mL.

Compound 1 was prepared by dissolving neat compounds in DMSO (Catalog No. D8418, Sigma-Aldrich, Inc., St. Louis, MO, USA) to generate 10 mM stock solution and stored at −20° C. The 10 mM DMSO stock solution of Compound 1 was serially diluted (half log) in DMSO to generate 11-point dose series (10000, 3165, 1000, 316, 100, 31.6, 10, 3.2, 1, 0.32, 0.1 μM) in an acoustic ready 384-well low dead volume microplate (Catalog No. LP-0200, Beckman Coulter Life Sciences, Indianapolis, IN, USA). Using an Echo 550 Acoustic Liquid Handler (Beckman Coulter Life Sciences, Indianapolis, IN, USA), 30 nL of serially diluted compound solutions were dispensed in duplicate to each 384-well TC-treated microplate (Catalog No. 3571, Corning, Glendale, CA, USA). 30 nL DMSO was transferred to all control wells.

30 μL of HEK293T.167 cells suspended in growth media without phenol red at $3.3\times10^5$ cells/mL (10000 cells/well) were dispensed using a Multidrop Combi Reagent Dispenser (Catalog No. 5840300, ThermoFisher Scientific, Waltham, MA, USA) to each well of columns 1-23 of 384-well TC-treated microplates containing duplicate concentration range of test compounds and DMSO controls. 30 μL of media was dispensed to column 24 as background positive control (P). Plates were spun briefly at 1000 rpm and cells were incubated at 37° C., 5% $CO_2$ for 24 hours. Final concentration of DMSO was 0.1% for all samples.

Cellular BRD7 protein level was determined based on quantification of HiBiT using Nano-Glo® HiBiT Lytic Assay System (Promega). 30 μL Nano-Glo Lytic Assay reagents were added to each well and luminescence was acquired on EnVision® Multilabel Reader (Catalog No. 2104-0010, Perkin Elmer Inc., Dumfries, VA, USA). Cells treated in the absence of the test compound (0.1% DMSO vehicle) were the negative control (N) and wells containing only media were the positive control (P).

Percent response of compound-treated samples (T) were calculated by normalizing to the DMSO treated negative (N) controls on the same microtiter plate after background (i.e., positive control) signal subtraction:

$$\text{Response \%} = 100\times(\text{Signal}(T)-\text{Average}(P))/(\text{Average}(N)-\text{Average}(P)).$$

Curve fit and $DC_{50}$ (concentration that degrades 50% BRD7) determination was performed by 4 parametric logistic fit analysis using software such as GraphPad Prism software (GraphPad Software, LLC, San Diego, CA, USA). The fit was performed through minimization of the root mean squared error between observed and calculated values of the four-parameter logistic equation using the simplex optimizer of the Apache Commons Math library. Boundary conditions for the fit parameters were set as: top was constrained to be between 80% and 120% response, bottom to be between 0% and 80% response, Hill slope between −3 and −0.3, inflection point unrestricted. $DC_{50}$ values were computed as the concentrations where the fitted curves cross the 50% response level. Averages and standard deviations were computed from replicates of the experiment.

Figure 38:
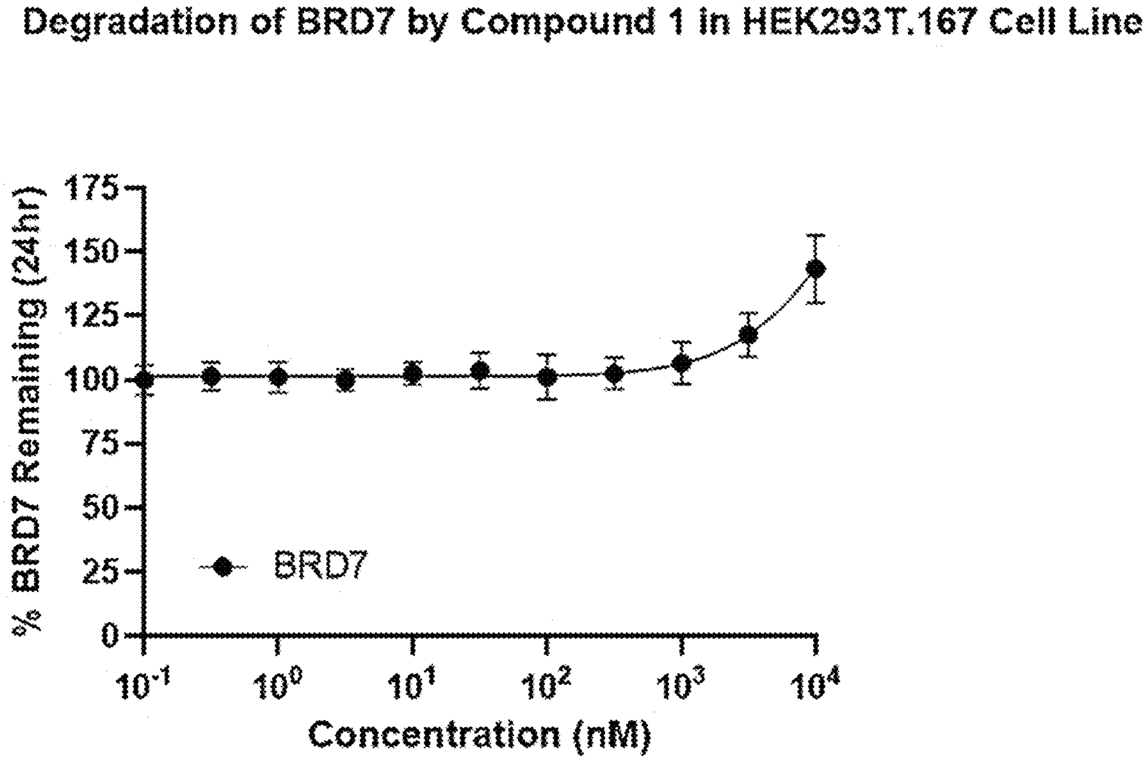
FIG. 38 depicts BRD7 degradation in HEK293T.167 cells modified to express HiBiT-tagged BRD7 measured by luminescence after 24-hour treatment with Compound 1. Compound 1 had no significant effect on the degradation of BRD7 at concentrations up to 10 μM after 24 hours. The experimental procedure is provided in Example 2.

The results are shown in Table 17, Table 18, and FIG. 38. Data in FIG. 38 and Table 18 are expressed as the mean±SD for three independent experiments each performed in duplicate. Data in Table 17 are the geometric mean and 95% confidence interval of $DC_{50}$ values and the arithmetic mean±SD for $E_{max}$ values.

TABLE 17

| Statistics of BRD7-HiBiT Degradation in 293T.167 Cells at 24 Hours | | | |
|---|---|---|---|
| | Mean $DC_{50}$ (nM) | $DC_{50}$ 95% CI (nM) | Mean $E_{max}$ (%) ± SD |
| Compound 1 | >10000 | N.A. | 97.6 ± 6.41 |

TABLE 18

| Percent Activity of Compound 1 in BRD7-HiBiT Degradation in 293T.167 Cells at 24 Hours | | |
|---|---|---|
| | % BRD7 Remaining Relative to Vehicle Control at 24 hr Compound 1 | |
| Concentration (nM) | Mean | SD |
| 0.101 | 99.8 | 5.7 |
| 0.318 | 101.3 | 5.5 |
| 1.01 | 101.0 | 6.0 |
| 3.17 | 99.8 | 4.3 |

TABLE 18-continued

| Percent Activity of Compound 1 in BRD7-HiBiT Degradation in 293T.167 Cells at 24 Hours | | |
|---|---|---|
| | % BRD7 Remaining Relative to Vehicle Control at 24 hr Compound 1 | |
| Concentration (nM) | Mean | SD |
| 10.0 | 102.4 | 4.4 |
| 31.7 | 103.4 | 7.1 |
| 100 | 101.0 | 8.8 |
| 317 | 102.3 | 6.2 |
| 1000 | 106.3 | 8.2 |
| 3161 | 117.4 | 8.5 |
| 9990 | 143.3 | 13.3 |

BRD7 degradation was measured in response to Compound 1 in HEK293 cell line modified to express HiBiT-tagged BRD7. Compound 1 had no significant effect on the degradation of BRD7 at concentrations up to 10 μM after 24 hours.

BRD4 Degradation Assay

This assay evaluates the degradation of Bromodomain Containing 4 (BRD4) induced by treatment with Compound 1 as measured by luminescence using Nano-Glo® HiBiT Lytic Assay System in HEK293 cells CRISPR-edited to endogenously express HiBiT tagged BRD4.

Nano-Glo® HiBiT Lytic Assay System was purchased from Promega (Catalog No. N3050, Madison, WI, USA). 293T cells were obtained from ATCC (Catalog No. CRL-3216, Manassas, VA, USA), and maintained in Dulbecco's modified Eagle medium (DMEM) (Catalog No. 12430112, ThermoFisher Scientific, Waltham, MA, USA) supplemented with 10% fetal bovine serum (FBS) (Catalog No. 16000-044, Gibco, Grand Island, NY, USA) at 37° C. in an atmosphere of 5% $CO_2$ in air. The HiBiT polypeptide tag was introduced into the N-terminus of the endogenous BRD4 locus by CRISPR-Cas9 to produce the modified HEK293T.92 cell line. The HiBiT polypeptide allows reconstitution of NanoBiT enzyme following cell lysis and addition of the complementing LgBiT polypeptide that activates substrate to produce a luminescent signal that is directly proportional to the amount of HiBiT-tagged BRD4.

The HEK293T.92 cells were routinely sub-cultured to maintain cell density between 30-80% confluence, not to exceed 20 passages. Cells were washed with PBS pH 7.4 (Catalog No. 10010049, ThermoFisher Scientific, Waltham, MA, USA), trypsinized for 5 minutes at 37° C., and resuspended in fresh growth media without phenol red. An aliquot was diluted 2× with Trypan Blue solution 0.4% (Catalog No. 15250061, ThermoFisher Scientific, Waltham, MA, USA) and cell count determined. Cell concentration was adjusted with growth media without phenol red to $5.0\times10^5$ cells/mL.

Compound 1 was prepared by dissolving neat compounds in DMSO (Catalog No. D8418, Sigma-Aldrich, Inc., St. Louis, MO, USA) to generate 10 mM stock solution and stored at −20° C. The 10 mM DMSO stock solution of Compound 1 was serially diluted (half log) in DMSO to generate 11-point dose series (10000, 3165, 1000, 316, 100, 31.6, 10, 3.2, 1, 0.32, 0.1 μM) in an acoustic ready 384-well low dead volume microplate (Catalog No. LP-0200, Beckman Coulter Life Sciences, Indianapolis, IN, USA). Using an Echo 550 Acoustic Liquid Handler (Beckman Coulter Life Sciences, Indianapolis, IN, USA), 30 nL of serially diluted compound solutions were dispensed in duplicate to each 384-well TC-treated microplate (Catalog No. 3571, Corning, Glendale, CA, USA). 30 nL DMSO was transferred to all control wells.

30 μL of 293T.92 cells suspended in growth media without phenol red at $5.0\times10^5$ cells/mL (15000 cells/well) were dispensed using a Multidrop Combi Reagent Dispenser (Catalog No. 5840300, ThermoFisher Scientific, Waltham, MA, USA) to each well of columns 1-23 of 384-well TC-treated microplates containing duplicate concentration range of test compounds and DMSO controls. 30 μL of media was dispensed to column 24 as background positive control (P). Plates were spun briefly at 1000 rpm and cells were incubated at 37° C., 5% $CO_2$ for 24 hours. Final concentration of DMSO was 0.1% for all samples.

Cellular BRD4 protein level was determined based on quantification of HiBiT using Nano-Glo® HiBiT Lytic Assay System (Promega). 30 μL Nano-Glo Lytic Assay reagents were added to each well and luminescence was acquired on EnVision® Multilabel Reader (Catalog No. 2104-0010, Perkin Elmer Inc., Dumfries, VA, USA). Cells treated in the absence of the test compound (0.1% DMSO vehicle) were the negative control (N) and wells containing only media were the positive control (P).

Percent response of compound-treated samples (T) were calculated by normalizing to the DMSO treated negative (N) controls on the same microtiter plate after background (i.e., positive control) signal subtraction:

$$\text{Response }\% = 100\times(\text{Signal}(T) - \text{Average }(P))/(\text{Average }(N) - \text{Average }(P)).$$

Curve fit and $DC_{50}$ (concentration that degrades 50% BRD4) determination was performed by 4 parametric logistic fit analysis using software such as GraphPad Prism software (GraphPad Software, LLC, San Diego, CA, USA). The fit was performed through minimization of the root mean squared error between observed and calculated values of the four-parameter logistic equation using the simplex optimizer of the Apache Commons Math library. Boundary conditions for the fit parameters were set as: top was constrained to be between 80% and 120% response, bottom to be between 0% and 80% response, Hill slope between −3 and −0.3, inflection point unrestricted. $DC_{50}$ values were computed as the concentrations where the fitted curves cross the 50% response level. Averages and standard deviations were computed from replicates of the experiment.

Figure 39:
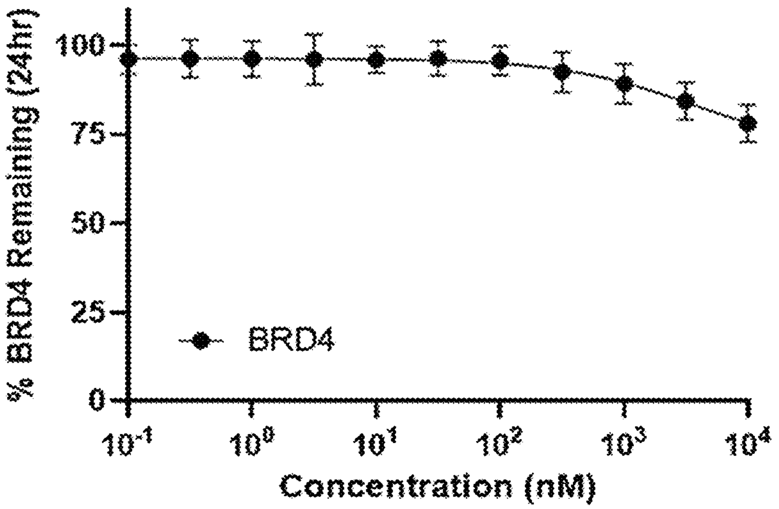
FIG. 39 depicts BRD4 degradation in HEK293T.92 cells modified to express HiBiT-tagged BRD4 measured by luminescence after 24-hour treatment with Compound 1. Compound 1 had no significant effect on the degradation of BRD4 at concentrations up to 10 μM after 24 hours. The experimental procedure is provided in Example 2.

The results are shown in Table 19, Table 20, and FIG. 39. Data in FIG. 39 and Table 19 are expressed as the mean±SD for three independent experiments each performed in duplicate. Data in Table 19 are the geometric mean and 95% confidence interval of $DC_{50}$ values and the arithmetic mean±SD for $E_{max}$ values.

TABLE 19

| Statistics of BRD4-HiBiT Degradation in 293T.92 Cells at 24 Hours | | | |
|---|---|---|---|
| | Mean $DC_{50}$ (nM) | $DC_{50}$ 95% CI (nM) | Mean $E_{max}$ (%) ± SD |
| Compound 1 | >10000 | N.A. | 78.1 ± 3.41 |

TABLE 20

Percent Activity of Compound 1 in BRD4-HiBiT Degradation in 293T.92 Cells at 24 Hours

| Concentration (nM) | % BRD4 Remaining Relative to Vehicle Control at 24 hr Compound 1 Mean | SD |
|---|---|---|
| 0.101 | 96.1 | 4.0 |
| 0.318 | 96.3 | 5.3 |
| 1.01 | 96.3 | 5.0 |
| 3.17 | 96.1 | 7.0 |
| 10.0 | 96.0 | 3.7 |
| 31.7 | 96.4 | 4.9 |
| 100 | 95.8 | 4.1 |
| 317 | 92.5 | 5.6 |
| 1000 | 89.2 | 5.6 |
| 3161 | 84.4 | 5.3 |
| 9990 | 78.1 | 5.2 |

BRD4 degradation was measured in response to Compound 1 in HEK293T cell line modified to express HiBiT-tagged BRD4. Compound 1 had no significant effect on the degradation of BRD4 at concentrations up to 10 μM after 24 hours.

SW982 In Vitro Viability Assay

This assay evaluated the inhibitory effect of Compound 1 on growth of SW982, a soft-tissue sarcoma cell line bearing the wild-type BAF complex, in a 144-hour in vitro viability assay.

SW982 cells were obtained from ATCC (Catalog No. HTB-93, Manassas, VA, USA) and maintained in DMEM medium (Catalog No. 12430112, ThermoFisher Scientific, Waltham, MA, USA) supplemented with 10% fetal bovine serum (FBS) (Catalog No. 16000-044, Gibco, Grand Island, NY, USA) at 37° C. in an atmosphere of 5% $CO_2$ in air. The cells were routinely sub-cultured to maintain cell density between $3\times10^5$-$1.5\times10^6$ cells/mL, not to exceed 20 passages. The cells growing in an exponential growth phase were harvested by centrifugation at 1000 rpm and resuspended in fresh growth media. An aliquot was diluted 2× with Trypan Blue solution 0.4% (Catalog No. 15250061, ThermoFisher Scientific, Waltham, MA, USA) and cell count was determined. Cell concentration was adjusted with growth media to $1.0\times10^4$ cells/mL.

Compound 1 was prepared by dissolving neat compound in DMSO (Catalog No. D8418, Sigma-Aldrich, Inc., St. Louis, MO, USA) to generate 10 mM stock solution and stored at −20° C. 10 mM DMSO stock solution was serially diluted (half log) in DMSO to generate 10-point dose series (10000, 3160, 1000, 316, 100, 31.6, 10, 3.16, 1, 0.32 μM) in acoustic ready 384-well low dead volume microplates (Catalog No. LP-0200, Beckman Coulter Life Sciences, Indianapolis, IN, USA). 50 nL of serially diluted compound solutions were dispensed using the Echo 550 Acoustic Liquid Handler Handler (Beckman Coulter Life Sciences, Indianapolis, IN, USA) in duplicate to each 384-well black TC-treated microplate (Catalog No. 3571, Corning, Glendale, CA, USA). 50 nL DMSO was transferred to all control wells.

50 μL SW982 cells suspended in growth media at $1.0\times10^4$ cells/mL (500 cells/well) were dispensed using a Multidrop Combi Reagent Dispenser (Catalog No. 5840300, ThermoFisher Scientific, Waltham, MA, USA) to each well of 384-well black TC-treated microplates containing duplicate concentration range of test compounds and DMSO controls. Plates were spun briefly at 1000 rpm and cells were incubated at 37° C., 5% $CO_2$ for 144 hours. Final concentration of DMSO was 0.1% for all samples.

Additional cell plates (T0plates) were prepared by dispensing cells into a blank 384-well black TC-treated microplate to represent cytostatic controls and processed for viability detection immediately after cell dispensing.

SW982 cell viability was determined based on quantification of ATP using CellTiter-Glo® 2.0 luminescent assay kit (Catalog No. G9243, Promega, Madison, WI, USA), which signals the presence of metabolically active cells. On Day 0 (Time 0) and Day 6 (144 hours) 25 μL CellTiter-Glo® reagent was added to each well of cell plates except the wells in column 24 and the luminescence was measured after 4 hours incubation at room temperature using an EnVision® Multilabel Reader (Catalog No. 2104-0010, Perkin Elmer Inc., Dumfries, VA, USA). Column 24 (cells without CellTiter-Glo® addition) was used as plate background or positive control (P). Cytostatic control value ($C_{T0}$) was computed from T0 plate read using untreated cell signals ($U_{T=0}$) and positive control signals ($P_{T=0}$) as below.

$$C_{T0} = \text{Average}\,(U_{T=0} - \text{Average}\,(P_{T=0}))$$

Percent response of compound-treated samples at a time point T were calculated by normalizing the signal with P and DMSO treated negative (N) controls on the same microtiter plate and the $C_{T0}$ control:

$$R1_T = 100\times (\text{Signal}_T - \text{Average}\,(P_T) - C_{T0})/(\text{Average}\,(N_T - \text{Average}\,(P_T)) - C_{T0})$$

$$R2_T = 100\times(\text{Signal}_T - \text{Average}\,(P_T) - C_{T0})/C_{T0}$$

$$\text{Response }\%_T = \text{if } R2_T < 0\text{: } R2_T\text{; else: } R1_T$$

The Response % is thus 100% if the CellTiter-Glo® signal equals that of the DMSO treated controls (i.e., normal cell growth), 0% if it equals that of untreated cell at T0 (i.e., cytostasis), and −100% if it equals the no CellTiter-Glo® reagent controls (i.e., complete cytotoxicity).

Figure 40:
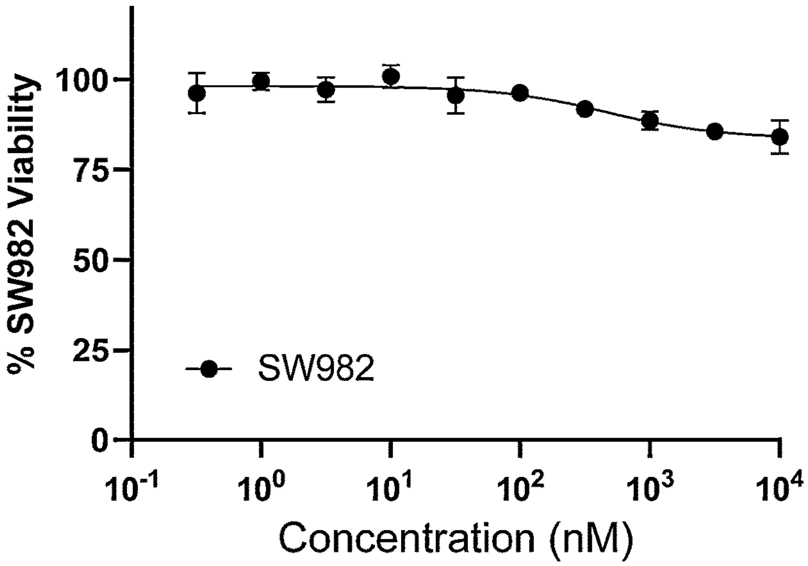
FIG. 40 depicts the growth inhibition of SW982, a soft-tissue cell line bearing wild-type BAF complex, after 144-hour treatment with Compound 1. Treatment of SW982 cells with Compound 1 resulted in in <20% growth inhibition at the highest concentration tested. The experimental procedure is provided in Example 2.

Curve fit and $GI_{50}$ determination was performed by 4 parametric logistic fit analysis using software such as GraphPad Prism software (GraphPad Software, LLC, San Diego, CA, USA). The fit was performed through minimization of the root mean squared error between observed and calculated values of the four-parameter logistic equation using the simplex optimizer of the Apache Commons Math library. Boundary conditions for the fit parameters were set as: top was constrained to be between 80% and 120% response, bottom to be between 0% and 80% response, Hill slope between −3 and −0.3, inflection point unrestricted. $GI_{50}$ values were computed as the concentrations where the fitted curves cross the 50% response level. Averages and standard deviations were computed from replicates of the experiment The results are shown in Table 21, Table 22, and FIG. 40. Data in FIG. 40 and Table 22 are expressed as the mean±SD from 3 independent experiments each containing duplicate samples. Data in Table 21 are the geometric mean and 95% confidence interval of $GI_{50}$ values and the arithmetic mean±SD for $E_{max}$ values determined for the indicated number of independent experiments.

TABLE 21

| Statistics for Growth Inhibition of SW982 Cells After 144-Hour Treatment with Compound 1 | | | |
|---|---|---|---|
| | Geometric Mean $GI_{50}$ | Geometric $GI_{50}$ 95% CI (nM) | Mean $E_{max}$ (%) ± SD |
| Compound 1 | >10000 | N.A. | 84.2 ± 4.6 |

TABLE 22

| Percent Cell Viability of SW982 Cells Following 144-Hour Treatment with Compound 1 | | |
|---|---|---|
| | % SW982 Viability Relative to Vehicle Control at 144 hr Compound 1 | |
| Concentration (nM) | Mean | SD |
| 0.318 | 96.2 | 5.5 |
| 1.01 | 99.6 | 2.4 |
| 3.17 | 97.2 | 3.4 |
| 10.0 | 101.0 | 3.2 |
| 31.7 | 95.7 | 5.0 |
| 100 | 96.4 | 1.9 |
| 317 | 91.9 | 1.3 |
| 1000 | 88.6 | 2.5 |
| 3161 | 85.7 | 2.1 |
| 9990 | 84.2 | 4.6 |

Cellular viability of SW982, a soft-tissue sarcoma cell line bearing the wild-type BAF complex, was measured after 144-hour treatment with Compound 1. Treatment of SW982 cells with Compound 1 resulted in <20% growth inhibition at the highest concentration tested.

IKZF1 Degradation Assay

This assay evaluated the degradation of the transcription factor, Ikaros (IKZF1), following treatment with Compound 1 as measured by luminescence using Nano-Glo© HiBiT Lytic Assay System in NCIH929 cells CRISPR-edited to endogenously express HiBiT tagged IKZF1.

Nano-Glo® HiBiT Lytic Assay System was purchased from Promega (Catalog No. N3050, Madison, WI, USA). NCIH929 cells were obtained from ATCC (Catalog No. CRL-9068, Manassas, VA, USA), and maintained in RPMI1640 medium (Catalog No. 11835030, ThermoFischer Scientific, Waltham, MA, USA) supplemented with 10% heat inactivated FBS (Catalog No. 16000-044, Gibco, Grand Island, NY, USA) and 0.05 mM 2-mercaptoethanol (Catalog No. 21985-023, Gibco, Grand Island, NY, USA) at 37° C. in an atmosphere of 5% $CO_2$ in air. The HiBiT polypeptide tag was introduced into the N-terminus of the endogenous IKZF1 locus by CRISPR-Cas9 to produce the modified NCIH929.11 cell line. The HiBiT polypeptide allows reconstitution of NanoBiT enzyme following cell lysis and addition of the complementing LgBiT polypeptide that activates substrate to produce a luminescent signal that is directly proportional to the amount of HiBiT-tagged IKZF1.

The NCIH929.11 cells were routinely sub-cultured to maintain cell density between $3\times10^5$ to $1.5\times10^6$ cells/mL, not to exceed 10 passages. The cells growing in an exponential growth phase were harvested by centrifugation at 1000 rpm and resuspended in fresh growth media without phenol red. An aliquot was diluted 2× with Trypan Blue solution 0.4% (Catalog No. 15250061, ThermoFisher Scientific, Waltham, MA, USA) and cell count determined. Cell concentration was adjusted with growth media without phenol red to $5\times10^5$ cells/mL.

Compound 1 and pomalidomide were prepared by dissolving neat compounds in DMSO (Catalog No. D8418, Sigma-Aldrich, Inc., St. Louis, MO, USA) to generate 10 mM stock solution and stored at −20° C. The 10 mM DMSO stock solutions were serially diluted (half log) in DMSO to generate 11-point dose series (10000, 3165, 1000, 316, 100, 31.6, 10, 3.2, 1, 0.32, 0.1 μM) in an acoustic ready 384-well low dead volume microplate (Catalog No. LP-0200, Beckman Coulter Life Sciences, Indianapolis, IN, USA). Using an Echo 550 Acoustic Liquid Handler (Beckman Coulter Life Sciences, Indianapolis, IN, USA), 30 nL of serially diluted compound solutions were dispensed in duplicate to each 384-well TC-treated microplate (Catalog No. 3571, Corning, Glendale, CA, USA). 30 nL DMSO was transferred to all control wells.

30 μL of NCIH929.11 cells suspended in growth media without phenol red at $5\times10^5$ cells/mL (15000 cells/well) were dispensed using a Multidrop Combi Reagent Dispenser (Catalog No. 5840300, ThermoFisher Scientific, Waltham, MA, USA) to each well of columns 1-23 of 384-well white TC-treated microplates (Catalog No. 3570, Corning, Glendale, CA, USA) containing duplicate concentration range of test compounds and DMSO controls. 30 μL of media was dispensed to column 24 as background positive control (P). Plates were spun briefly at 1000 rpm and cells were incubated at 37° C., 5% $CO_2$ for 1.5 to 24 hours. Final concentration of DMSO was 0.1% for all samples.

Cellular IKZF1 protein level was determined based on quantification of HiBiT using Nano-Glo® HiBiT Lytic Assay System (Promega). 30 μL Nano-Glo Lytic Assay reagents were added to each well and luminescence was acquired on EnVision® Multilabel Reader (Catalog No. 2104-0010, Perkin Elmer Inc., Dumfries, VA, USA). Cells treated in the absence of the test compound (0.1% DMSO vehicle) were the negative control (N) and wells containing only media were the positive control (P).

Percent response of compound-treated samples (T) were calculated by normalizing to the DMSO treated negative (N) controls on the same microtiter plate after background (i.e., positive control) signal subtraction:

$$\text{Response }\% = 100\times(\text{Signal}(T)-\text{Average}(P))/(\text{Average}(N)-\text{Average}(P)).$$

Curve fit and $DC_{50}$ (concentration that degrades 50% IKZF1) determination was performed by 4 parametric logistic fit analysis using software such as GraphPad Prism software (GraphPad Software, LLC, San Diego, CA, USA). The fit was performed through minimization of the root mean squared error between observed and calculated values of the four-parameter logistic equation using the simplex optimizer of the Apache Commons Math library. Boundary conditions for the fit parameters were set as: top was constrained to be between 80% and 120% response, bottom to be between 0% and 80% response, Hill slope between −3 and −0.3, inflection point unrestricted. $DC_{50}$ values were computed as the concentrations where the fitted curves cross the 50% response level. Averages and standard deviations were computed from replicates of the experiment.

Figure 41:
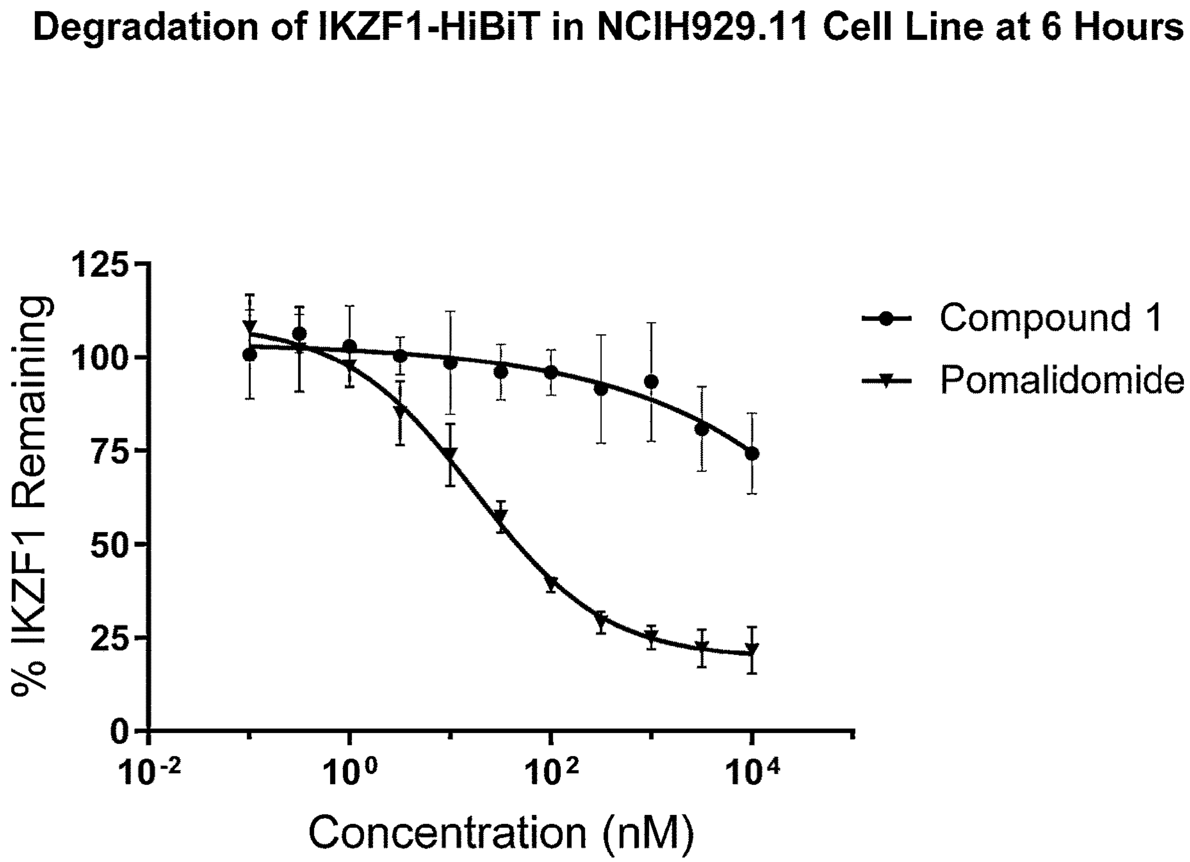
FIG. 41 depicts IKZF1 degradation in NCIH929.11, a multiple myeloma cell line modified to express HiBiT-tagged IKZF1, measured by luminescence after 6-hour treatment with Compound 1 or Pomalidomide. The experimental procedure is provided in Example 2.

The results are shown in Table 23, Table 24, and FIG. 41. Data in FIG. 41 and Table 24 are expressed as the mean±SD for three independent experiments each performed in duplicate. Data in Table 23 are the geometric mean and 95% confidence interval of $DC_{50}$ values and the arithmetic mean±SD for $E_{max}$ values.

TABLE 23

Statistics of IKZF1-HiBiT Degradation in NCIH929.11 Cells at 6 Hours by Compound 1 and Pomalidomide

| | Mean DC50 (nM) | DC50 95% CI (nM) | Mean Emax (%) ± SD |
|---|---|---|---|
| Compound 1 | NA | NA | 74.2 ± 8.2* |
| Pomalidomide | 44.4 | 30.7-64.2 | 20.8 ± 3.2 |

*P = 0.002 vs. DMSO-treated controls

TABLE 24

IKZ1-HiBiT Degradation in NCIH929.11 Cells at 6 Hours Following Treatment with Compound 1 or Pomalidomide

| | % IKZF1 Remaining Relative to Vehicle Control at 6 hr | | | |
|---|---|---|---|---|
| | Compound 1 | | Pomalidomide | |
| Concentration (nM) | Mean | SD | Mean | SD |
| 0.101 | 100.8 | 12.0 | 107.9 | 8.8 |
| 0.318 | 106.4 | 5.1 | 102.2 | 11.4 |
| 1.01 | 102.9 | 10.9 | 97.4 | 5.5 |
| 3.17 | 100.4 | 5.2 | 84.9 | 8.5 |
| 10.0 | 98.5 | 13.9 | 73.9 | 8.3 |
| 31.7 | 96.0 | 7.6 | 57.3 | 4.2 |
| 100 | 95.9 | 6.1 | 39.2 | 1.9 |
| 317 | 91.5 | 14.6 | 29.1 | 2.9 |
| 1000 | 93.3 | 16.0 | 25.1 | 3.1 |
| 3161 | 80.8 | 11.2 | 22.1 | 5.1 |
| 9990 | 74.2 | 10.7 | 21.6 | 6.4 |

IKZF1 degradation was measured in response to Compound 1 or pomalidomide in NCIH929 multiple myeloma cell line modified to express HiBiT-tagged IKZF1. Compound 1 had no significant effect on degradation of IKZF1 at concentrations up to 1 μM and induced 25%0 degradation of IKZF1 at 10 μM, while positive control, pomalidomide, induced 8000 degradation of IKZF1 with a DC50 of 44.4 nM at 6 hours.

SALL4 Degradation Assay

This assay evaluated the off-target degradation of the cereblon neosubstrate, Sal-like protein 4 (SALL4), induced by treatment with Compound 1 as measured by luminescence using Nano-Glo® HiBiT Lytic Assay System in KELLY cells CRISPR-edited to endogenously express HiBiT tagged SALL4.

Nano-Glo® HiBiT Lytic Assay System was purchased from Promega (Catalog No. N3050, Madison, WI, USA). KELLY neuroblastoma cells were obtained from DSMZ (Catalog No. ACC-355, Leibniz Institute DSMZ-German Collection of Microorganisms and Cell Cultures GmbH, Braunschweig, Germany), and maintained in RPMI medium (Catalog No. 11835030, ThermoFischer Scientific, Waltham, MA, USA) supplemented with 10% heat inactivated FBS (Catalog No. 16000-044, Gibco, Grand Island, NY, USA) at 37° C. in an atmosphere of 5% $CO_2$ in air. The HiBiT polypeptide tag was introduced into the C-terminus of the endogenous SALL4 locus by CRISPR-Cas9 to produce the modified KELLY.2 cell line. The HiBiT polypeptide allows reconstitution of NanoBiT enzyme following cell lysis and addition of the complementing LgBiT polypeptide that activates substrate to produce a luminescent signal that is directly proportional to the amount of HiBiT-tagged SALL4.

KELLY.2 cells were routinely sub-cultured to maintain cell density between 30-80% confluence, not to exceed 10 passages. Cells were washed with PBS, trypsinized for 5 minutes at 37° C., and resuspended in fresh growth media without phenol red. An aliquot was diluted 2× with Trypan Blue solution 0.4% (Catalog No. 15250061, ThermoFisher Scientific, Waltham, MA, USA) and cell count determined. Cell concentration was adjusted with growth media without phenol red to $2\times10^5$ cells/mL.

Compound 1 and control compound, pomalidomide (HY-10984, MedChemExpress, Monmouth Junction, NJ, USA), were prepared by dissolving neat compounds in DMSO (Catalog No. D8418, Sigma-Aldrich, Inc., St. Louis, MO, USA) to generate 10 mM stock solution and stored at −20° C. The 10 mM DMSO stock solutions of test compounds were serially diluted (half log) in DMSO to generate 11-point dose series (10000, 3167, 1000, 316, 100, 31.6, 10, 3.2, 1, 0.32, 0.1 μM) in an acoustic ready 384-well low dead volume microplate (Catalog No. LP-0200, Beckman Coulter Life Sciences, Indianapolis, IN, USA). Using an Echo 550 Acoustic Liquid Handler (Beckman Coulter Life Sciences, Indianapolis, IN, USA), 30 nL of serially diluted compound solutions were dispensed in duplicate to each 384-well TC-treated microplate (Catalog No. 3571, Corning, Glendale, CA, USA). 30 nL DMSO was transferred to all control wells.

30 μL of KELLY.2 cells suspended in growth media without phenol red at $2\times10^5$ cells/mL (6000 cells/well) were dispensed using a Multidrop Combi Reagent Dispenser (Catalog No. 5840300, ThermoFisher Scientific, Waltham, MA, USA) to each well of columns 1-23 of 384-well white TC-treated microplates (Catalog No. 3570, Corning, Glendale, CA, USA) containing duplicate concentration range of test compounds and DMSO controls. 30 μL of media was dispensed to column 24 as background positive control (P). Plates were spun briefly at 1000 rpm and cells were incubated at 37° C., 5% $CO_2$ for 6 hours. Final concentration of DMSO was 0.1% for all samples.

Cellular SALL4 protein level was determined based on quantification of HiBiT using Nano-Glo® HiBiT Lytic Assay System (Promega). 30 μL Nano-Glo Lytic Assay reagents were added to each well and luminescence was acquired on EnVision® Multilabel Reader (Catalog No. 2104-0010, Perkin Elmer Inc., Dumfries, VA, USA). Cells treated in the absence of the test compound (0.1% DMSO vehicle) were the negative control (N) and wells containing only media were the positive control (P).

Percent response of compound-treated samples (T) were calculated by normalizing to the DMSO treated negative (N) controls on the same microtiter plate after background (i.e., positive control) signal subtraction:

$$\text{Response }\% = 100\times(\text{Signal}(T) - \text{Average }(P))/(\text{Average }(N) - \text{Average }(P)).$$

Curve fit and $DC_{50}$ (concentration that degrades 50% SALL4) determination was performed by 4 parametric logistic fit analysis using software such as GraphPad Prism software (GraphPad Software, LLC, San Diego, CA, USA). The fit was performed through minimization of the root mean squared error between observed and calculated values of the four-parameter logistic equation using the simplex optimizer of the Apache Commons Math library. Boundary conditions for the fit parameters were set as: top was constrained to be between 80% and 120% response, bottom to be between 0% and 80% response, Hill slope between −3 and −0.3, inflection point unrestricted. $DC_{50}$ values were computed as the concentrations where the fitted curves cross the 50% response level. Averages and standard deviations were computed from replicates of the experiment.

Figure 42:
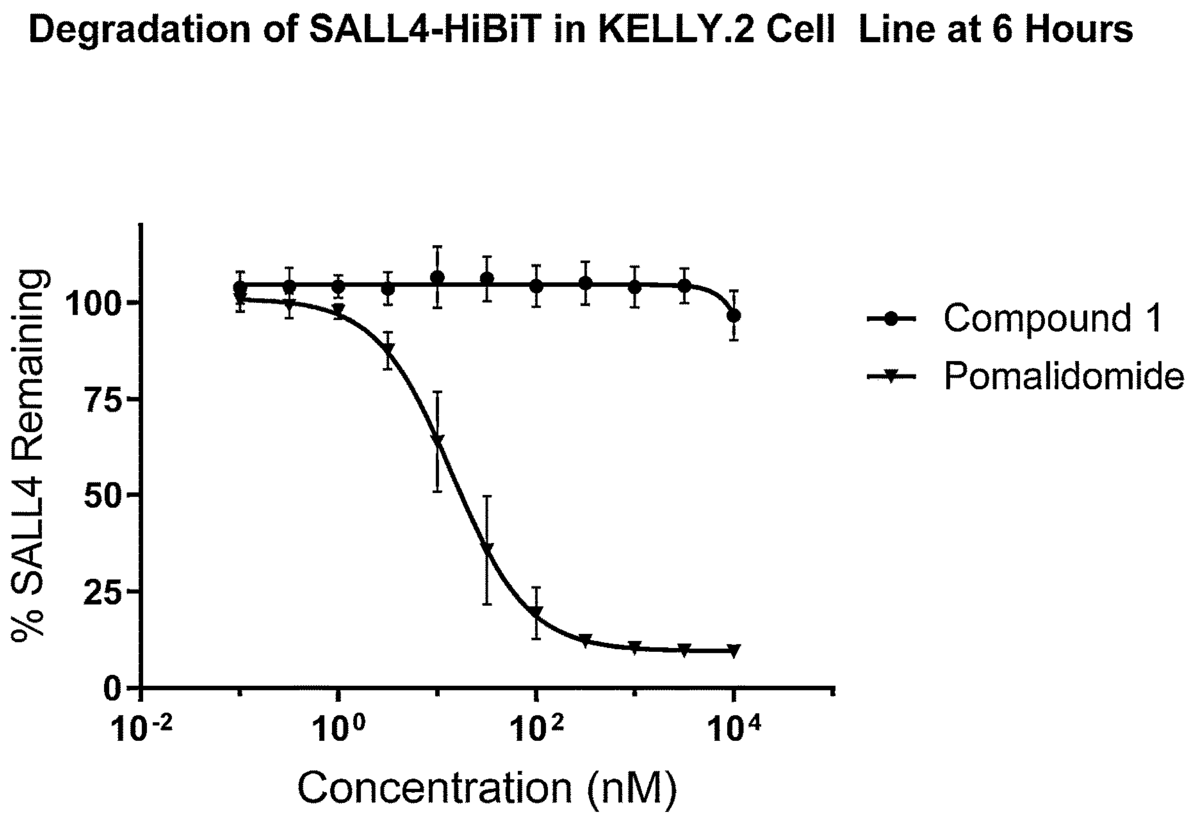
FIG. 42 depicts degradation of SALL4-HiBiT in KELLY.2 cells measured by luminescence after 6-hour treatment with Compound 1 or Pomalidomide. Compound 1 had no significant effect on degradation of SALL4 at concentrations up to 10 μM while positive control, pomalidomide, induced 90% degradation of SALL4 with a $DC_{50}$ of 18 nM at 6 hours. The experimental procedure is provided in Example 2.

The results are shown in Table 25, Table 26, and FIG. 42. Data in FIG. 42 and Table 26 are expressed as the mean±SD for three independent experiments each performed in duplicate. Data in Table 25 are the geometric mean and 9500 confidence interval of $DC_{50}$ values and the arithmetic mean±SD for $E_{max}$ values.

TABLE 25

Statistics of SALL4-HiBiT Degradation in KELLY.2 Cells at 6 Hours by Compound 1 and Pomalidomide

| | Mean $DC_{50}$ (nM) | $DC_{50}$ 95% CI (nM) | Mean Emax (%) ± SD |
|---|---|---|---|
| Compound 1 | NA | NA | 98.9 ± 2.1 |
| Pomalidomide | 18 | 3.6-87 | 9.5 ± 1.5 |

TABLE 26

Percent Activity of SALL4-HiBiT Degradation in KELLY.2 Cells at 6 Hours Following Treatment with Compound 1 or Pomalidomide

| | % SALL4 Remaining Relative to Vehicle Control at 6 hr | | | |
|---|---|---|---|---|
| | Compound 1 | | Pomalidomide | |
| Concentration (nM) | Mean | SD | Mean | SD |
| 0.101 | 103.8 | 4.1 | 100.7 | 3.1 |
| 0.318 | 104.1 | 4.9 | 99.2 | 3.3 |
| 1.01 | 104.1 | 3.0 | 97.6 | 2.0 |
| 3.17 | 103.7 | 4.3 | 87.5 | 4.9 |
| 10.0 | 106.5 | 7.9 | 63.9 | 13.0 |
| 31.7 | 106.1 | 5.8 | 35.7 | 14.0 |
| 100 | 104.2 | 5.3 | 19.3 | 6.7 |
| 317 | 105.0 | 5.6 | 12.1 | 1.7 |
| 1000 | 104.0 | 5.4 | 10.3 | 1.3 |
| 3161 | 104.4 | 4.5 | 9.6 | 1.3 |
| 9990 | 96.6 | 6.4 | 9.5 | 1.5 |

SALL4 degradation was measured in response to Compound 1 in KELLY.2 cell line modified to express HiBiT-tagged SALL4. Compound 1 had no significant effect on degradation of SALL4 at concentrations up to 10 μM while positive control, pomalidomide, induced 9000 degradation of SALL4 with a $DC_{50}$ of 18 nM at 6 hours.

GSPT1 Degradation Assay

This assay evaluated the off-target degradation of the cereblon neosubstrate, Eukaryotic peptide chain release factor GTP-binding subunit ERF3A (GSPT1), induced by treatment with Compound 1 as measured by luminescence using Nano-Glo HiBiT® Lytic Assay System in 293T cells CRISPR-edited to endogenously express HiBiT tagged GSPT1.

Nano-Glo® HiBiT Lytic Assay System was purchased from Promega (Catalog No. N3050, Madison, WI, USA). HEK293T cells were obtained from ATCC (Catalog No. CRL-3216, Manassas, VA, USA), and maintained in DMEM medium (Catalog No. 11995065, ThermoFischer Scientific, Waltham, MA, USA) supplemented with 10% heat inactivated FBS (Catalog No. 16000-044, Gibco, Grand Island, NY, USA) at 37° C. in an atmosphere of 5% $CO_2$ in air. The HiBiT polypeptide tag was introduced into the N-terminus of the endogenous GSPT1 locus by CRISPR-Cas9 to produce the HEK293T.114 modified cell line. The HiBiT polypeptide allows reconstitution of NanoBiT enzyme following cell lysis and addition of the complementing LgBiT polypeptide that activates substrate to produce a luminescent signal that is directly proportional to the amount of HiBiT-tagged GSPT1.

HEK293T.114 cells were routinely sub-cultured to maintain cell density between 30-80% confluence, not to exceed 20 passages. Cells were washed with PBS, trypsinized for 5 minutes at 37° C., and resuspended in fresh growth media without phenol red. An aliquot was diluted 2× with Trypan Blue solution 0.4% (Catalog No. 15250061, ThermoFisher Scientific, Waltham, MA, USA) and cell count determined. Cell concentration was adjusted with growth media without phenol red to $2\times10^5$ cells/mL.

Compound 1 and control compound, CC-885 (Axon 2645, Axon MedChem LLC, Reston, VA, USA), were prepared by dissolving neat compounds in DMSO (Catalog No. D8418, Sigma-Aldrich, Inc., St. Louis, MO, USA) to generate 10 mM stock solution and stored at −20° C. The 10 mM DMSO stock solutions of Compound 1 or CC0885 were serially diluted (half log) in DMSO to generate 11-point dose series (10000, 3160, 1000, 316, 100, 31.6, 10, 3.2, 1, 0.32, 0.1 μM) in an acoustic ready 384-well low dead volume microplate (Catalog No. LP-0200, Beckman Coulter Life Sciences, Indianapolis, IN, USA). Using an Echo 550 Acoustic Liquid Handler (Beckman Coulter Life Sciences, Indianapolis, IN, USA), 30 nL of serially diluted compound solutions were dispensed in duplicate to each 384-well black TC-treated microplate (Catalog No. 3571, Corning, Glendale, CA, USA). 30 nL DMSO was transferred to all control wells.

30 μL of HEK293T.114 cells suspended in growth media without phenol red at $2\times10^5$ cells/mL (6000 cells/well) were dispensed using a Multidrop Combi Reagent Dispenser (Catalog No. 5840300, ThermoFisher Scientific, Waltham, MA, USA) to each well of columns 1-23 of 384-well black TC-treated microplates containing duplicate concentration range of test compounds and DMSO controls. 30 μL of media was dispensed to column 24 as background positive control (P). Plates were spun briefly at 1000 rpm and cells were incubated at 37° C., 5% $CO_2$ for 6 hours. Final concentration of DMSO was 0.1% for all samples.

Cellular GSPT1 protein level was determined based on quantification of HiBiT using Nano-Glo® HiBiT Lytic Assay System (Promega). 30 μL Nano-Glo Lytic Assay reagents were added to each well of columns 1-23 and luminescence was acquired on EnVision® Multilabel Reader (Catalog No. 2104-0010, Perkin Elmer Inc., Dumfries, VA, USA). Column 24 (cells without Nano-Glo reagent addition) was used as plate background or positive control (P). Cells treated in the absence of the test compound (0.1% DMSO vehicle) were the negative control (N)/

Percent response of compound-treated samples (T) were calculated by normalizing to the DMSO treated negative (N) controls on the same microtiter plate after background (i.e., positive control) signal subtraction:

Response % =

$$100\times(\text{Signal}(T)-\text{Average}(P))/(\text{Average}(N)-\text{Average}(P)).$$

Curve fit and $DC_{50}$ (concentration that degrades 50% GSPT1) determination was performed by 4 parametric logistic fit analysis using software such as GraphPad Prism software (GraphPad Software, LLC, San Diego, CA, USA). The fit was performed through minimization of the root mean squared error between observed and calculated values of the four-parameter logistic equation using the simplex optimizer of the Apache Commons Math library. Boundary conditions for the fit parameters were set as: top was constrained to be between 80% and 120% response, bottom to be between 0% and 80% response, Hill slope between −3 and −0.3, inflection point unrestricted. $DC_{50}$ values were computed as the concentrations where the fitted curves cross the 50% response level. Averages and standard deviations were computed from replicates of the experiment.

Figure 43:
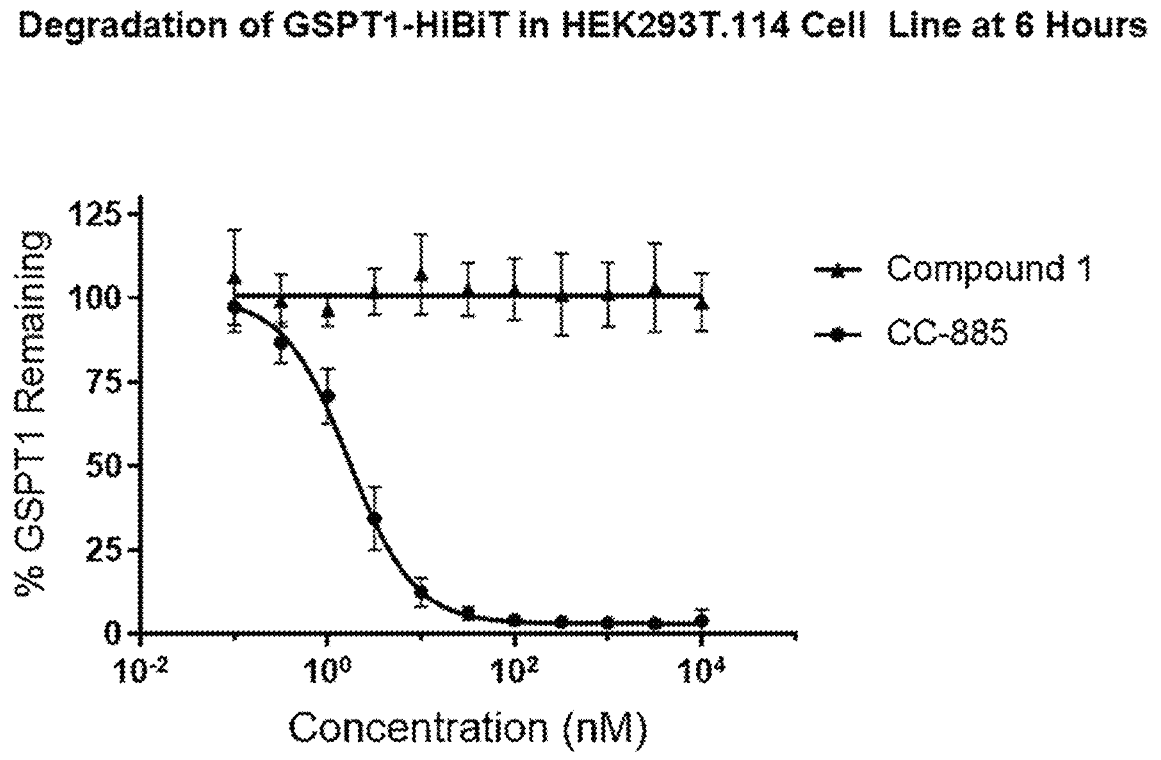
FIG. 43 depicts degradation of GSPT1-HiBiT in HEK293T.114 cells measured by luminescence after 6-hour treatment with Compound 1 or CC-885. Compound 1 had no significant effect on degradation of GSPT1 at concentrations up to 10 μM while positive control, CC-85, induced >95% degradation of GSPT1 with a $DC_{50}$ of 1.93 nM at 6 hours. The experimental procedure is provided in Example 2.

The results are shown in Table 27, Table 28, and FIG. 43. Data in FIG. 43 and Table 28 are expressed as the mean±SD for three independent experiments each performed in duplicate. Data in Table 27 are the geometric mean and 9500 confidence interval of $DC_{50}$ values and the arithmetic mean±SD for $E_{max}$ values.

TABLE 27

Statistics of GSPT1-HiBiT Degradation in HEK293T.114 Cells at 6 Hours by Compound 1 and CC-885

| | Geometric Mean $DC_{50}$ (nM) | Geometric Mean $DC_{50}$ 95% CI (nM) | Mean $E_{max}$ (%) ± SD |
|---|---|---|---|
| Compound 1 | >10000 | NA | 93.9 ± 5.85 |
| CC-885 | 1.93 | 1.15-3.25 | 92.85 ± 1.30 |

TABLE 28

Percent Activity of GSPT1-HiBiT Degradation in HEK293T-114 Cells at 6 Hours Following Treatment with Compound 1 or CC-885

| | % GSPT1 Remaining | | | |
|---|---|---|---|---|
| | Compound 1 | | CC-885 | |
| Concentration (nM) | Mean | SD | Mean | SD |
| 0.100 | 97.4 | 7.4 | 106.2 | 14.2 |
| 0.316 | 86.7 | 6.0 | 99.3 | 7.7 |
| 1.00 | 70.8 | 8.2 | 96.4 | 4.8 |
| 3.15 | 34.4 | 9.4 | 101.9 | 6.8 |
| 10.0 | 12.4 | 4.3 | 107.2 | 12.1 |
| 31.5 | 6.0 | 1.9 | 102.5 | 7.8 |
| 100 | 4.0 | 1.4 | 102.6 | 9.1 |
| 317 | 3.5 | 1.4 | 100.9 | 12.2 |
| 1000 | 3.2 | 1.5 | 101.1 | 9.6 |
| 3161 | 3.0 | 1.1 | 103.2 | 13.3 |
| 9990 | 3.8 | 3.2 | 98.8 | 8.6 |

GSPT1 degradation was measured in response to Compound 1 or CC-885 in HEK293T.114 cell line modified to express HiBiT-tagged GSPT1. Compound 1 had no significant effect on degradation of GSPT1 at concentrations up to 10 μM while positive control, CC-885, induced >95% degradation of GSPT1 with a $DC_{50}$ of 1.93 nM at 6 hours.

HepG2 In Vitro Viability Assay

This assay assessed the general cytotoxicity of Compound 1 using the human hepatocarcinoma cell line HepG2. HepG2 cells were treated with Compound 1 for 72 hours and cellular viability was measured following the addition of CellTiter-Glo® 2.0 reagent (Promega) according to manufacturer's instructions. Agents were solubilized in DMSO and tested in the HepG2 cell line at concentrations ranging from 0.3 nM to 10 μM.

HepG2 cells were obtained from ATCC (Catalog No. HB-8065, Manassas, VA, USA) and maintained in MEM medium (Catalog No. 11095080, ThermoFisher Scientific, Waltham, MA, USA) supplemented with 10% heat inactivated fetal bovine serum (FBS) (Catalog No. 16000-044, Gibco, Grand Island, NY, USA) at 37° C. in an atmosphere of 5% $CO_2$ in air. The cells were routinely sub-cultured to maintain cell density between $3\times10^5$-$1.5\times10^6$ cells/mL, not to exceed 20 passages. Cells were washed with PBS, trypsinized for 5 min at 37° C., and resuspended in growth media. An aliquot was diluted 2× with Trypan Blue solution 0.4% (Catalog No. 15250061, ThermoFisher Scientific, Waltham, MA, USA) and cell count was determined. Cell concentration was adjusted with growth media to $1.0\times10^4$ cells/mL.

Compound 1 was prepared by dissolving neat compound in DMSO (Catalog No. D8418, Sigma-Aldrich, Inc., St. Louis, MO, USA) to generate 10 mM stock solution and stored at −20° C. 10 mM DMSO stock solution of Compound 1 was serially diluted (half log) in DMSO to generate 10-point dose series (10000, 3333, 1000, 333, 100, 33.3, 10, 3.3, 1, 0.3 μM) in acoustic ready 384-well low dead volume microplates (Catalog No. LP-0200, Beckman Coulter Life Sciences, Indianapolis, IN, USA). Using an Echo 550 Acoustic Liquid Handler Handler (Beckman Coulter Life Sciences, Indianapolis, IN, USA), 50 nL of serially diluted compound solutions were dispensed directly in quadruplicate to each 384-well black TC-treated microplate (Catalog No. 3571, Corning, Glendale, CA, USA). 50 nL DMSO was transferred to all control wells.

50 μL HepG2 cells suspended in growth media at $1.0\times10^4$ cells/mL (500 cells/well) were dispensed using a Multidrop Combi Reagent Dispenser (Catalog No. 5840300, ThermoFisher Scientific, Waltham, MA, USA) to each well of 384-well black TC-treated microplates containing quadruplicate concentration range of test compound and DMSO controls. Plates were incubated at 37° C., 5% $CO_2$ for 72 hours. Final concentration of DMSO was 0.1% for all samples.

Additional cell plates (T0plates) were prepared by dispensing cells into a blank 384-well black TC-treated microplate to represent cytostatic controls and processed for viability detection immediately after cell dispensing.

HepG2 cell viability was determined based on quantification of ATP using CellTiter-Glo® 2.0 luminescent assay kit (Catalog No. G9243, Promega, Madison, WI, USA), which signals the presence of metabolically active cells. On Day 0 (Time 0) and Day 3 (72 hours) 25 μL CellTiter-Glo® reagent was added to each well of cell plates except the wells in column 24 and the luminescence was measured after 4 hours incubation at room temperature using an EnVision® Multilabel Reader (Catalog No. 2104-0010, Perkin Elmer Inc., Dumfries, VA, USA). Column 24 (cells without CellTiter-Glo® addition) was used as plate background or positive control (P).

Cytostatic control value ($C_{T0}$) was computed from TO plate read using untreated cell signals ($U_{T=0}$) and positive control signals ($P_{T=0}$) as below.

$$C_{T0} = \text{Average}\,(U_{T=0} - \text{Average}\,(P_{T=0}))$$

Percent response of compound-treated samples at a time point T were calculated by normalizing the signal with P and DMSO treated negative (N) controls on the same microtiter plate and the $C_{T0}$ control:

$$R1_T = 100\times$$
$$(\text{Signal}_T - \text{Average}\,(P_T) - C_{T0}) / (\text{Average}\,(N_T - \text{Average}\,(P_T)) - C_{T0})$$
$$R2_T = 100\times(\text{Signal}_T - \text{Average}\,(P_T) - C_{T0}) / C_{T0}$$
$$\text{Response } \%_T = \text{if } R2_T < 0\text{: } R2_T\text{; else: } R1_T$$

The Response % is thus 100% if the CellTiter-Glo® signal equals that of the DMSO treated controls (i.e., normal cell growth), 0% if it equals that of untreated cell at TO (i.e., cytostasis), and −100% if it equals the no CellTiter-Glo® reagent controls (i.e., complete cytotoxicity).

Figure 44:
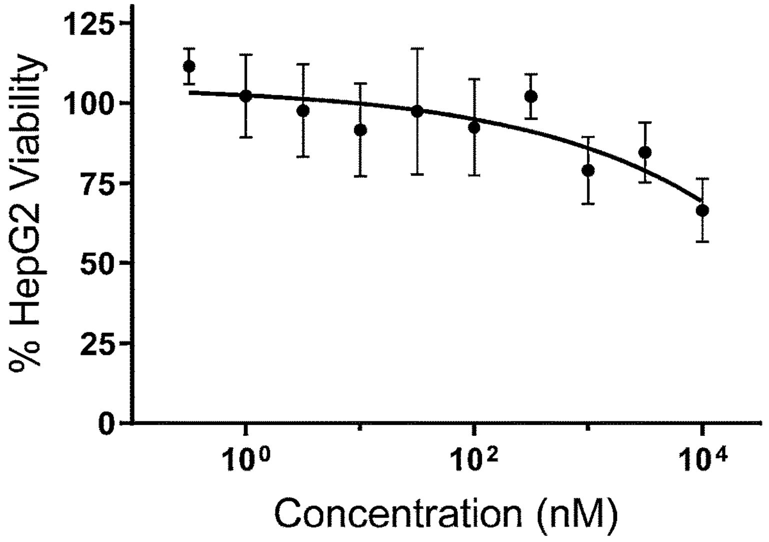
FIG. 44 depicts the cellular viability of HepG2 cells following 72-hour treatment with Compound 1. The experimental procedure is provided in Example 2.

Curve fit and $GI_{50}$ determination was performed by 4 parametric logistic fit analysis using software such as GraphPad Prism software (GraphPad Software, LLC, San Diego, CA, USA). The fit was performed through minimization of the root mean squared error between observed and calculated values of the four-parameter logistic equation using the simplex optimizer of the Apache Commons Math library. Boundary conditions for the fit parameters were set as: top was constrained to be between 80% and 120% response, bottom to be between 0% and 80% response, Hill slope between −3 and −0.3, inflection point unrestricted. $GI_{50}$ values were computed as the concentrations where the fitted curves cross the 50% response level. Averages and standard deviations were computed from replicates of the experiment The results are shown in Table 29 and FIG. 44. Data in FIG. 44 and Table 29 are expressed as the mean±SD from 3 independent experiments each with n=2.

TABLE 29

HepG2 Viability Following 72-Hour Treatment with Compound 1

| Concentration (nM) | HepG2 % Viability Mean | SD |
|---|---|---|
| 0.32 | 111.4 | 5.6 |
| 1.01 | 102.2 | 12.9 |
| 3.17 | 97.7 | 14.5 |
| 10.0 | 91.6 | 14.4 |
| 31.7 | 97.4 | 19.6 |
| 100 | 92.5 | 14.9 |
| 317 | 102.1 | 7.0 |
| 1000 | 79.0 | 10.4 |
| 3161 | 84.6 | 9.4 |
| 9990 | 66.6 | 9.9 |

Cellular viability of HepG2 cells was measured using CellTiter-Glo® reagent following 72-hour treatment with Compound 1. No significant effect on viability was observed with Compound at concentrations up to 3.3 μM. Compound 1 treatment at 10 μM inhibited growth of HepG2 cells by 33.4±9.9% relative to 0.1% DMSO controls (p<0.0001).

Cellular viability was measured in response to Compound 1 in the HepG2 cell line to assess general toxicity. Compound 1 had no effect on the growth of HepG2 cells at concentrations up to 3.3 μM and minimal growth inhibition (33.4±9.9%) at 10 μM.

Pharmacokinetic Study of Compound 1 in Male CD1 Mice

The pharmacokinetic (PK) profile in plasma of Compound 1 was determined in male CD1 mice following single dose intravenous (IV) (2 mg/kg) and per os (PO) (10 mg/kg) administration. This study was performed under non-GLP conditions, and unless otherwise stated, all analytical reagents were at least standard laboratory reagent grade, and deionized water was prepared at the study site.

The characteristics of Compound 1 used in this study were as follows: molecular weight of base, 710.78; molecular weight of Compound 1 with salt, 824.81; purity on as is basis, 99.28%.

All animals were housed in cages with clean bedding and maintained and monitored for good health and at the discretion of the laboratory animal veterinarian. Certified rodent diet was provided, and water was available ad libitum. Environmental controls for the animal room were set to maintain a temperature of 22 to 25° C., humidity of 40-70% relative humidity, and a 12-hour light/12-hour dark cycle.

Normal healthy animals certified by the attending veterinarian were selected and acclimatized for a minimum of three days prior to initiation of the study. Animals were identified by body markings. The study design variables are set forth in Table 30 below.

TABLE 30

| Study Variables | Group 1 | Group 2 |
|---|---|---|
| Animal Species/Strain/ Sex (Std Body Weight) | Mouse/CD1/Male (30 g) | |
| Test Item | Compound 1 | |
| Number of Animals | Total 3 animals | Total 3 animals |
| Route of Administration | IV | PO |
| Feeding Condition | Fasted state | |
| Dose (mg/kg) | 2 | 10 |
| Dose Volume (mL/kg) | 5 | 5 |
| Concentration (mg/mL) | 0.4 | 2 |
| Formulation Vehicle | DMSO (5%) + 20% HPBCD in Water (95%) | |
| Sample Collection/Type | Blood/saphenous vein (serial sampling) | |
| Anti-coagulant/% | Sodium citrate (200 mM, pH 4.79)/~6% v/v | |
| Time points (h) | Plasma—0.033, 0.33, 1, 2, 4, 8, 24 | Plasma—0.033, 0.33, 1, 2, 4, 8, 24 |

Test animals were weighed prior to drug administration, and the standard weight of the animals used was 30 grams. The animals were divided into two groups, IV group and PO group, with each group containing 3 test animals each and 2 spare animals. The IV dose was administered by intravenous injection into the tail vein and PO dose was administered via oral gavage. The dosing volume was 5 mL/kg body weight for both groups. The dosing concentration was 0.4 mg/mL for the IV group and 2 mg/mL for the PO group. The animals were in fasted state during the study.

For both dosing groups, blood was collected from the saphenous vein (serial sampling) for plasma isolation at 0.033, 0.33, 1, 2, 4, 6, 8, and 24 hour timepoints. The anti-coagulant solution used was 6% (v/v) sodium citrate (200 mM, pH 4.79).

For sample collection, the mice were restrained, and the back of the hind leg was shaved until the saphenous vein was visible. The hind limb was immobilized, and slight pressure was applied gently above the knee joint. While taking aseptic precautions, the vein was punctured using a 20 G needle and ~20-30 μL of blood was collected in pre-labeled pre-chilled tubes. After blood collection from each animal, the sample from that animal was recorded in the sample collection sheet.

After collection of each blood sample, the blood sample was stored on ice prior to centrifugation. Blood samples were centrifuged within 0.5 hours of collection to separate plasma. Centrifugation was conducted at 2500×g for 15 minutes at 4° C. The plasma was separated and transferred to pre-labeled micro-centrifuge tubes and promptly frozen at −80° C.±10° C. and stored until bioanalysis was performed. Each sample was identified by test compound, group, animal number, and collection time point.

A fit-for-purpose bioanalytical method was developed for analyzing the plasma samples. One set of nine standards was run before the sample batch and was used for plotting the calibration curve. Quality control (QC) samples were prepared at a minimum of three concentrations, i.e., LQC (not more than 5 times to that of lowest standard concentration), HQC (not less than 75% of the highest standard concentration), and MQC (between the low and high concentration).

A minimum of 6 QC samples were prepared (three concentrations in duplicate). One set of QC (LQC, MQC and HQC) samples were analyzed before and after the sample batch.

Samples were analyzed by Exion AD (Sciex, Framingham, MA, USA) high-pressure liquid chromatography (HPLC) system followed by tandem mass spectroscopy analysis (MS/MS) with Q TRAP 4500 (Sciex, Framingham, MA). The samples were resolved on a Kinetex® EVO C18 4.5*50 mm, 5 μm column (Phenomenex, Inc., Torrance, CA, USA).

For the mobile phase, 10 mM ammonium acetate with 0.1% formic acid in Milli-Q® water (EMD Millipore, Burlington, MA, USA) was used as aqueous reservoir (A) and acetonitrile:methanol (50:50, v/v) was used as organic reservoir (B). The flow rate was set at 1 mL/min. The LC gradient program included initial conditions of 95% A/5% B at 0.01 min, with a switch to 15% A/85% B at 1.00 min and hold, then switch to 95% A/5% B at 2.60 min and with a hold until 3.50 min at 95% A/5% B.

A positive electrospray ionization (ESI) method was used for detecting analytes and internal standard by mass spectroscopy. The MRM conditions were Q1 m/z 711.0, Q3 m/z 286.0, declustering potential (DP) 80 V, collision energy (CE) 32 eV, and Collision Cell Exit Potential (CXP) 15. Other MS/MS conditions included Collision Gas (CAD) 8, Curtain Gas (CUR) 25, Nebulizer Gas (GS1) 50, Heater Gas (GS2) 50, Ion spray voltage (V) 5500, Temperature (TEM) 550, and Interface Heater (ihe) ON.

Pharmacokinetic parameters were calculated for mean concentrations by non-compartmental model with Phoenix® software version 8.1 (Certara, Princeton, NJ, USA).

Figure 45:
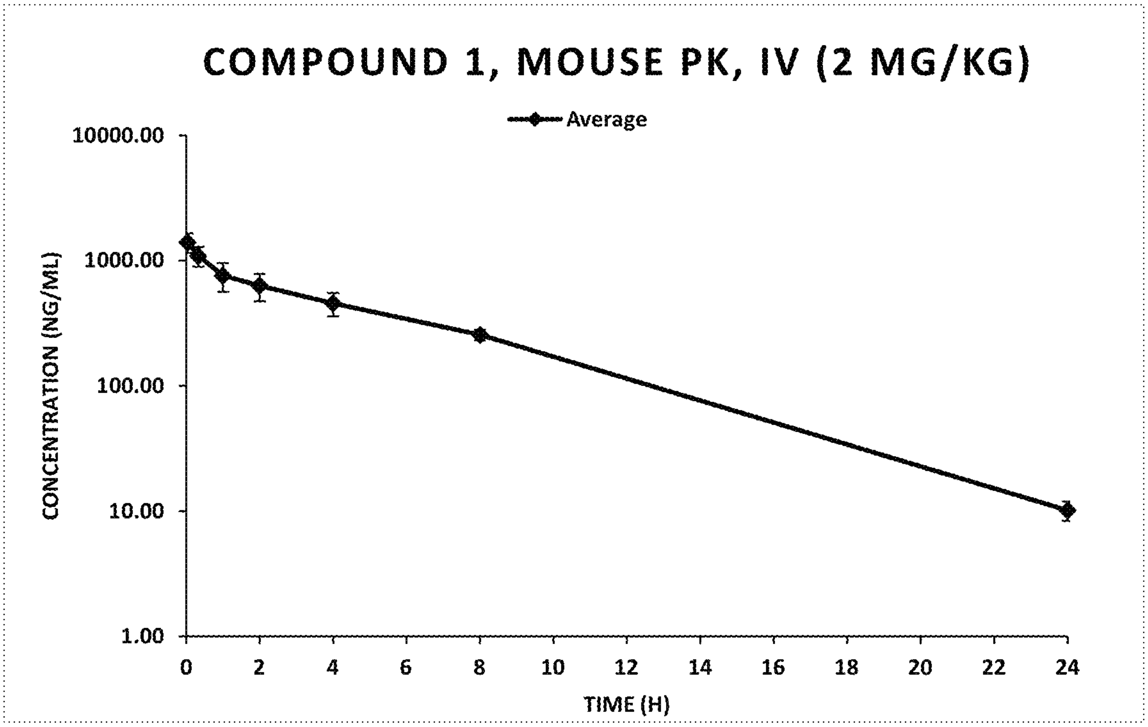
FIG. 45 shows the pharmacokinetic profile of Compound 1 following 2 mg/kg IV dosing in male CD1 mice. The experimental procedure is provided in Example 2.
Figure 46:
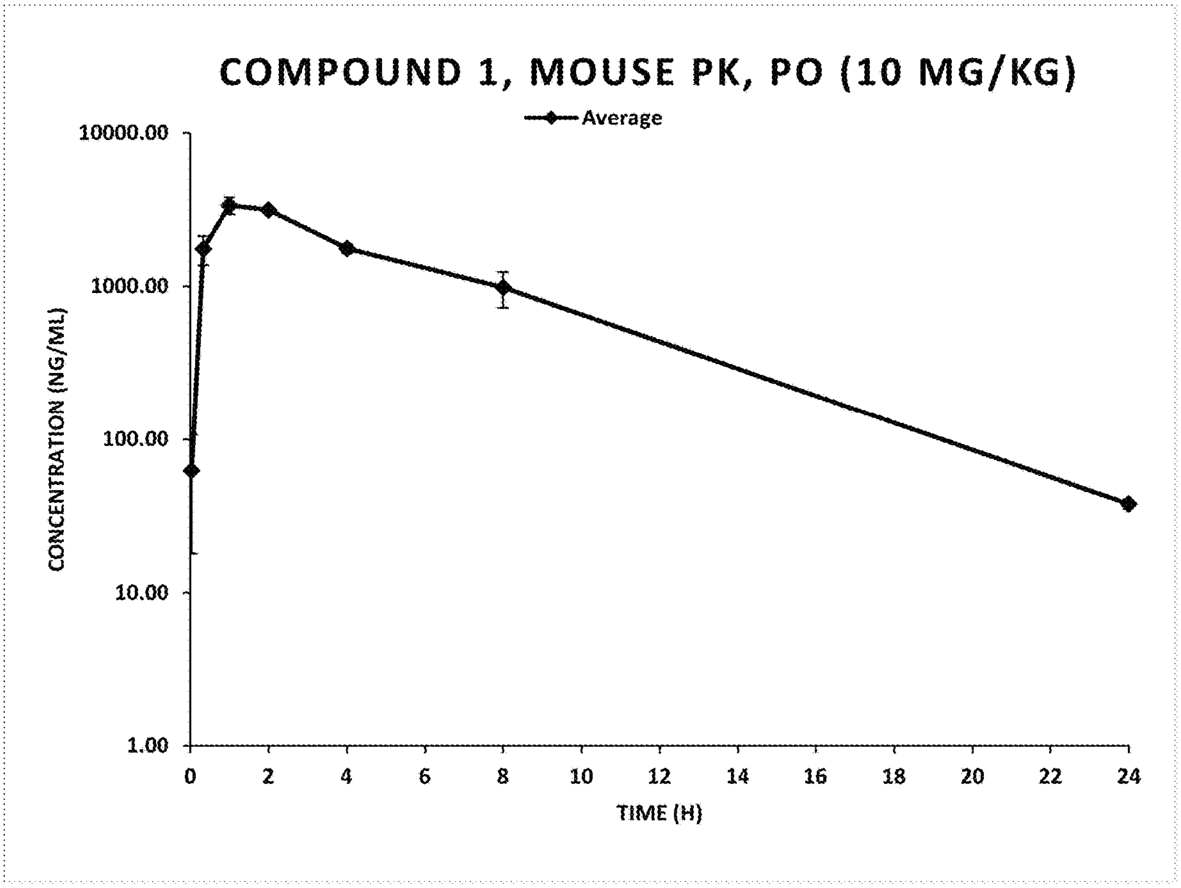
FIG. 46 shows the pharmacokinetic profile of Compound 1 following 10 mg/kg PO dosing in male CD1 mice. The experimental procedure is provided in Example 2.

The results of this PK study in male CD1 mice are shown in Tables 31-34 below and FIG. 45 and FIG. 46.

TABLE 31

Plasma Concentration Time Profile following 2 mg/kg IV dosing of Compound1 in Male CD1 Mice

| Time | Plasma Concentration (ng/mL) @ 2 mpk IV | | | Average | |
|---|---|---|---|---|---|
| (h) | Mouse-1 | Mouse-2 | Mouse-3 | (ng/mL) | SD |
| 0.033 | 1688.87 | 1282.85 | 1230.25 | 1400.66 | 250.98 |
| 0.33 | 1295.96 | 1069.92 | 907.03 | 1090.97 | 195.32 |
| 1 | 947.12 | 778.91 | 554.87 | 760.30 | 196.78 |
| 2 | 809.01 | 530.20 | 551.12 | 630.11 | 155.28 |
| 4 | 567.16 | 402.36 | 398.41 | 455.98 | 96.31 |
| 8 | 257.14 | 230.84 | 279.05 | 255.68 | 24.13 |
| 24 | 11.51 | 8.14 | 10.81 | 10.16 | 1.78 |

TABLE 32

Plasma Concentration Time Profile following 10 mg/kg PO dosing of Compound 1 in Male CD1 Mice

| Time | Plasma Concentration (ng/mL) @ 10 mpk IV | | | Average | |
|---|---|---|---|---|---|
| (h) | Mouse-1 | Mouse-2 | Mouse-3 | (ng/mL) | SD |
| 0.033 | 113.39 | 45.23 | 29.34 | 62.66 | 44.65 |
| 0.33 | 2096.21 | 1350.89 | 1805.33 | 1750.81 | 375.64 |
| 1 | 2892.08 | 3702.63 | 3513.39 | 3369.37 | 424.04 |
| 2 | 3152.08 | 3236.77 | 3069.59 | 3152.81 | 83.59 |
| 4 | 1884.53 | 1775.48 | 1635.06 | 1765.03 | 125.06 |
| 8 | 1167.19 | 1094.97 | 687.92 | 983.36 | 258.39 |
| 24 | 38.20 | 40.19 | 35.09 | 37.83 | 2.57 |

TABLE 33

Calculated pharmacokinetic parameters following 2 mg/kg IV dosing of Compound 1 in Male CD1 Mice

| | Dose: 2 mg/kg IV | | | | | | |
|---|---|---|---|---|---|---|---|
| Values | $C_0$ (ng/ml) | $T_{1/2}$ (h) | Vdss (L/kg) | CI (ml/min/kg) | $AUC_{last}$ (h*ng/ml) | $AUC_{inf}$ (h*ng/mL) | $MRT_{last}$ (h) |
| Mean | 1440.307 | 3.654 | 2.012 | 6.201 | 5394.715 | 5448.340 | 5.149 |
| SD | 259.58 | 0.15 | 0.38 | 0.85 | 797.69 | 803.29 | 0.42 |

TABLE 34

Calculated pharmacokinetic parameters following 10 mg/kg PO dosing of Compound 1 in Male CD1 Mice

| | Dose: 10 mg/kg PO | | | | | | |
|---|---|---|---|---|---|---|---|
| Values | $C_{max}$ (ng/mL) | $T_{max}$ (h) | $T_{1/2}$ (h) | $AUC_{last}$ (h*ng/ml) | $AUC_{last}$ (h*ng/ml) | $MRT_{last}$ (h) | % F |
| Mean | 3456.036 | 1.333 | 3.544 | 19992.143 | 20185.396 | 5.379 | 74.118 |
| SD | 279.72 | 0.58 | 0.09 | 1917.97 | 1925.22 | 0.35 | 7.11 |

Pharmacokinetic Study of Compound 1 in Male Sprague Dawley Rats

The pharmacokinetic (PK) profile in plasma of Compound 1 was determined in male Sprague Dawley rats following single dose intravenous (IV) (2 mg/kg) and per os (PO) (10 mg/kg) administration. This study was performed under non-GLP conditions, and unless otherwise stated, all analytical reagents were at least standard laboratory reagent grade, and deionized water was prepared at the study site.

The characteristics of Compound 1 used in this study were as follows: molecular weight of base, 710.78; molecular weight of Compound 1 with salt, 824.81; purity on as is basis, 99.28%.

All animals were housed in cages with clean bedding and maintained and monitored for good health and at the discretion of the laboratory animal veterinarian. Certified rodent diet was provided, and water was available ad libitum. Environmental controls for the animal room were set to maintain a temperature of 22 to 25° C., humidity of 40-70% relative humidity, and a 12-hour light/12-hour dark cycle.

Normal healthy animals certified by the attending veterinarian were selected and acclimatized for a minimum of three days prior to initiation of the study. Animals were identified by body markings.

The rats were anaesthetized with a single dose of ketamine 50 mg/kg i.p. plus xylazine 6 mg/kg i.p. The right jugular was exposed, and a loose ligature was placed caudally, and the cranial end of the vein was ligated. A small incision was made between the ligatures into which a catheter (polyethylene 50 tubing with an internal diameter of 0.58 mm and outer diameter of 0.96 mm) was inserted. The catheter was secured in place by tying the loose ligature around the catheterized vessel. A small incision was made in the scapular region to serve as the exit site of the catheter. The catheter was subcutaneously tunneled and exteriorized through the scapular incision. A stay suture was placed in the scapular area. Patency was tested, and the catheter was filled with a locking solution (heparinized saline) and sealed with a stainless-steel plug. The incision was then sutured with sterile suturing material. Anti-septic solution was applied to the sutured site and the animal was placed back in its home cage. The animals were closely observed throughout the recovery period of 24 hours. The rats were freely moving in the cage (one rat per cage).

The study design variables are set forth in Table 35 below.

TABLE 35

| Study Variables | Group 1 | Group 2 |
|---|---|---|
| Animal Species/Strain/ Sex (Std Body Weight) | Rat/Sprague Dawley/Male (190 g) | |
| Test Item | Compound 1 | |
| Number of Animals | Total 3 animals | Total 3 animals |
| Route of Administration | IV | PO |
| Feeding Condition | Fasted state | |
| Dose (mg/kg) | 2 | 10 |
| Dose Volume (mL/kg) | 5 | 5 |
| Concentration (mg/mL) | 0.4 | 2 |
| Formulation Vehicle | DMSO (5%) + 20% HPβCD in Water (95%) | |
| Sample Collection/Type | Blood/jugular vein (serial sampling) | |
| Anti-coagulant/% | Sodium citrate (200 mM, pH 4.79)/~6% v/v | |
| Time points | Plasma-0.033, 0.33, 1, 2, 4, 8, 24 h | Plasma -0.033, 0.33, 1, 2, 4, 8, 24 h |

Test animals were weighed prior to drug administration, and the standard weight of the animals used was 190 grams. The animals were divided into two groups, IV group and PO group, with each group containing 3 test animals each and 2 spare animals. The IV dose was administered by intravenous injection into the tail vein and PO dose was administered via oral gavage needle. The dosing volume was 5 mL/kg body weight for both groups. The dosing concentration was 0.4 mg/mL for the IV group and 2 mg/mL for the PO group. The animals were in fasted state during the study.

For both dosing groups, blood was collected from the jugular vein (serial sampling) for plasma isolation at 0.033, 0.33, 1, 2, 4, 6, 8, and 24 hour timepoints. The anti-coagulant solution used was 6% (v/v) sodium citrate (200 mM, pH 4.79).

For sample collection, the animals were held to remove the first two drops of blood from the cannula to ensure removal of any excess heparinized saline before collection of blood. The external catheter was connected to a syringe and 0.20-0.30 mL of blood was collected in the syringe and transferred to a pre-labeled, pre-chilled tube. Blood volume was replaced by administering to the animal an equal volume of saline through the jugular vein. After blood collection from each animal, the sample from that animal was recorded in the sample collection sheet.

After collection of each blood sample, the blood sample was stored on ice prior to centrifugation. Blood samples were centrifuged within 20 minutes of collection to separate plasma. Centrifugation was conducted at 2500×g for 15 minutes at 4° C. The plasma was separated and transferred to pre-labeled micro-centrifuge tubes and promptly frozen at −80° C.±10° C. and stored until bioanalysis was performed. Each sample was identified by test compound, group, animal number, and collection time point.

A fit-for-purpose bioanalytical method was developed for analyzing the plasma samples. One set of nine standards was run before the sample batch and was used for plotting the calibration curve. Quality control (QC) samples were prepared at a minimum of three concentrations, i.e., LQC (not more than 5 times to that of lowest standard concentration), HQC (not less than 75% of the highest standard concentration), and MQC (between the low and high concentration).

A minimum of 6 QC samples were prepared (three concentrations in duplicate). One set of QC (LQC, MQC and HQC) samples were analyzed before and after the sample batch.

Samples were analyzed by Exion AD (Sciex, Framingham, MA, USA) high-pressure liquid chromatography (HPLC) system followed by tandem mass spectroscopy analysis (MS/MS) with Q TRAP 4500 (Sciex, Framingham, MA, USA). The samples were resolved on a Kinetex® EVO C18 4.5*50 mm, 5 μm column (Phenomenex, Inc., Torrance, CA, USA).

For the mobile phase, 10 mM ammonium acetate with 0.1% formic acid in Milli-Q® water (EMD Millipore, Burlington, MA, USA) was used as aqueous reservoir (A) and acetonitrile:methanol (50:50, v/v) was used as organic reservoir (B). The flow rate was set at 1 mL/min. The LC gradient program included initial conditions of 95% A/5% B at 0.01 min, with a switch to 15% A/85% B at 1.00 min and hold, then switch to 95% A/5% B at 2.60 min and with a hold until 3.50 min at 95% A/5% B.

A positive electrospray ionization (ESI) method was used for detecting analytes and internal standard by mass spectroscopy. The MRM conditions were Q1 m/z 711.0, Q3 m/z 286.0, declustering potential (DP) 80 V, collision energy (CE) 32 eV, and Collision Cell Exit Potential (CXP) 15. Other MS/MS conditions included Collision Gas (CAD) 8, Curtain Gas (CUR) 25, Nebulizer Gas (GS1) 50, Heater Gas (GS2) 50, Ion spray voltage (V) 5500, Temperature (TEM) 550, and Interface Heater (ihe) ON.

Pharmacokinetic parameters were calculated for mean concentrations by non-compartmental model with Phoenix® software version 8.1 (Certara, Princeton, NJ, USA).

Figure 47:
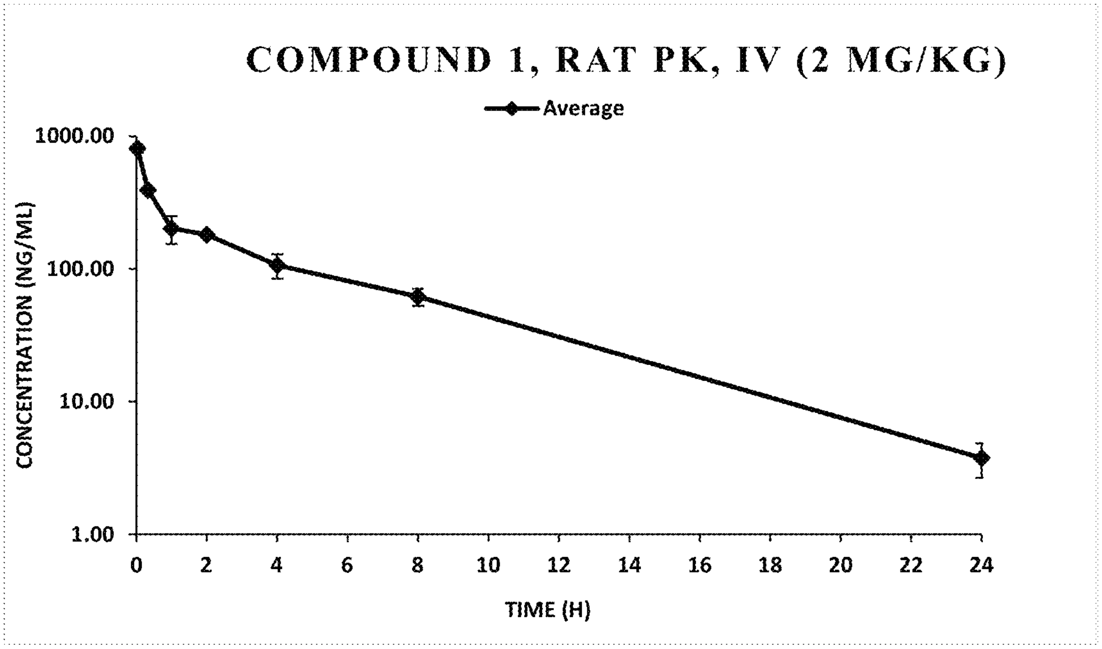
FIG. 47 shows the pharmacokinetic profile of Compound 1 following 2 mg/kg IV dosing in male Sprague Dawley rats. The experimental procedure is provided in Example 2.
Figure 48:
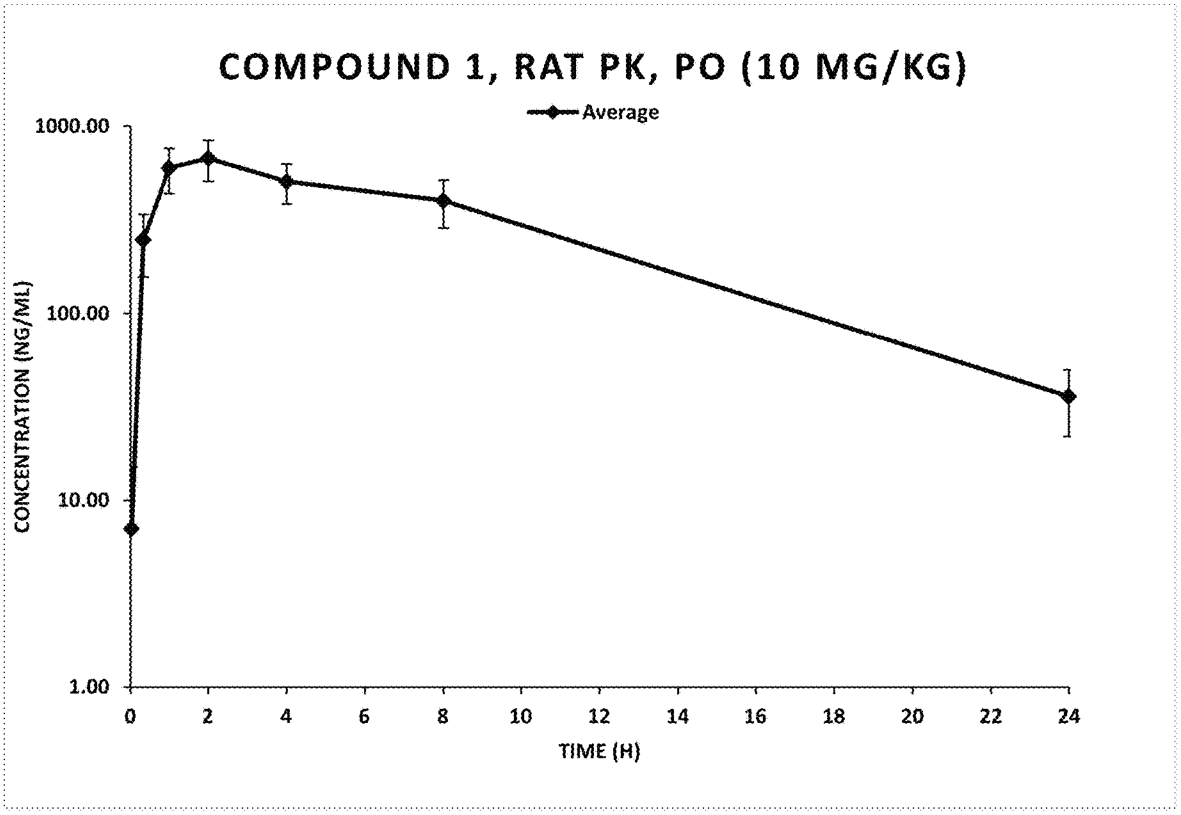
FIG. 48 shows the pharmacokinetic profile of Compound 1 following 10 mg/kg PO dosing in male Sprague Dawley rats. The experimental procedure is provided in Example 2.

The results of this PK study in male Sprague Dawley rats are shown in Tables 36-39 below and FIG. 47 and FIG. 48.

TABLE 36

Plasma Concentration Time Profile following 2 mg/kg IV dosing of Compound 1 in Male Sprague Dawley Rats

| Time (h) | Plasma Concentration (ng/mL) @ 2 mpk IV Rats-1 | Rats-2 | Rats-3 | Average (ng/mL) | SD |
|---|---|---|---|---|---|
| 0.033 | 853.54 | 827.34 | 751.46 | 810.78 | 53.02 |
| 0.33 | 384.75 | 387.61 | 411.63 | 394.66 | 14.76 |
| 1 | 157.74 | 253.11 | 196.32 | 202.39 | 47.98 |
| 2 | 185.90 | 175.63 | 182.50 | 181.34 | 5.23 |
| 4 | 125.25 | 82.15 | 113.01 | 106.80 | 22.21 |
| 8 | 51.42 | 66.27 | 68.01 | 61.90 | 9.12 |
| 24 | 4.54 | 2.51 | 4.24 | 3.76 | 1.10 |

TABLE 37

Plasma Concentration Time Profile following 10 mg/kg PO dosing of Compound 1 in Male Sprague Dawley Rats

| Time (h) | Plasma Concentration (ng/mL) @ 10 mpk IV Rat-1 | Rat-2 | Rat-3 | Average (ng/mL) | SD |
|---|---|---|---|---|---|
| 0.033 | 2.98 | 16.39 | 1.81 | 7.06 | 8.10 |
| 0.33 | 214.99 | 177.44 | 349.71 | 247.38 | 90.59 |
| 1 | 647.84 | 416.26 | 728.94 | 597.68 | 162.26 |
| 2 | 560.21 | 864.30 | 594.30 | 672.94 | 166.60 |
| 4 | 226.67* | 592.56 | 419.66 | 506.11 | 122.26 |
| 8 | 304.16 | 527.27 | 369.64 | 400.36 | 114.68 |
| 24 | 21.49 | 49.29 | 36.76 | 35.84 | 13.92 |

*Outlier: Aberrant value

TABLE 38

Calculated pharmacokinetic parameters following 2 mg/kg IV dosing of Compound 1 in Male Sprague Dawley Rats

| Values | Dose: 2 mg/kg IV $C_0$ (ng/ml) | $T_{1/2}$ (h) | Vdss (L/kg) | CI (ml/min/kg) | $AUC_{last}$ (h*ng/mL) | $AUC_{inf}$ (h*ng/ml) | $MRT_{last}$ (h) |
|---|---|---|---|---|---|---|---|
| Mean | 878.68 | 3.97 | 6.70 | 21.64 | 1520.41 | 1542.28 | 4.82 |
| SD | 67.16 | 0.32 | 0.26 | 0.89 | 60.54 | 64.79 | 0.24 |

TABLE 39

| Calculated pharmacokinetic parameters following 10 mg/kg PO dosing of Compound 1 in Male Sprague Dawley Rats | | | | | | | |
|---|---|---|---|---|---|---|---|
| | Dose: 10 mg/kg PO | | | | | | |
| Values | $C_{max}$ (ng/mL) | $T_{max}$ (h) | $T_{1/2}$ (h) | $AUC_{last}$ (h*ng/ml) | $AUC_{inf}$ (h*ng/ml) | $MRT_{last}$ (h) | % F |
| Mean | 747.03 | 1.33 | 5.12 | 6293.07 | 6562.63 | 7.34 | 82.78 |
| SD | 109.36 | 0.58 | 0.49 | 1343.89 | 1454.93 | 0.55 | 17.68 |

Example 3 Antitumor Activity of Compound 1 in CRT_SARC_00310 Patient Derived Xenograft (PDX) Model of Synovial Sarcoma To evaluate the efficacy potential of Compound 1 in a PDX model of synovial sarcoma, NOG (NOD/Shi-scidIL2rgnull) female mice bearing CRT_SARC_00310 synovial sarcoma (SS18-SSX2 fusion) tumor xenografts (Certis Oncology, San Diego, CA, USA) were treated with an oral daily regimen of vehicle or Compound 1. Animals were administered vehicle or Compound 1 at 1, 3, 10, 30, or 50 mg/kg once per day for 28 days (FIG. 1).

Figure 2:
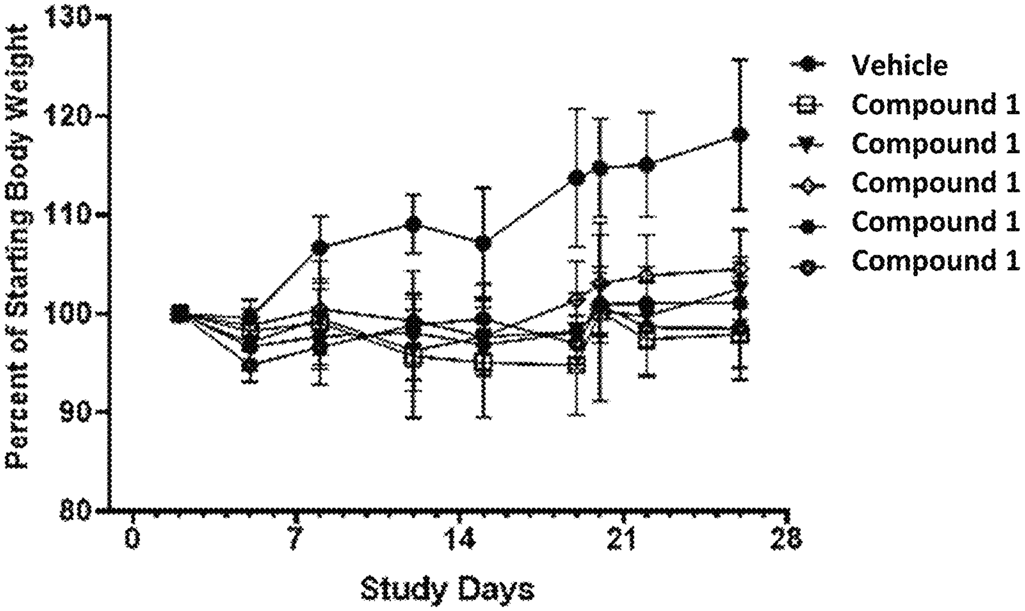
FIG. 2 is a graph demonstrating the effect of Compound 1 at various doses on female NOG (NOD/Shi-scid IL2rgnull) mice bearing an established CRT_SARC_00310 synovial sarcoma body weight at start of study, day 0 measurement. Data are expressed as mean±SD. The experimental procedure is provided in Example 3.

Tumor growth inhibition was calculated using the Day 21 MRI measurement data as this is the last day an n=7 vehicle mice remained on study. The lowest tested dose of Compound 1 (1 mg/kg/day) gave minimal tumor growth inhibition (TGI) of 81% (P=0.0016). Escalating doses of Compound 1 led to improvements in efficacy with TGI of 91% (P=0.0007), 90%, 90% (P=0.0004), and 86% (P=0.0037) for doses 3, 10, 30, and 50 mg/kg/day, respectively). Dosing group 10 mg/kg QD p value was not calculated because MRI data was not available for 4 of 8 mice due to technical reasons; n=8 animals remained on study in this group for next measurement at day 28. Compound 1 was well tolerated with no group exhibiting greater than 7% body weight loss (FIG. 2).

Figure 3:
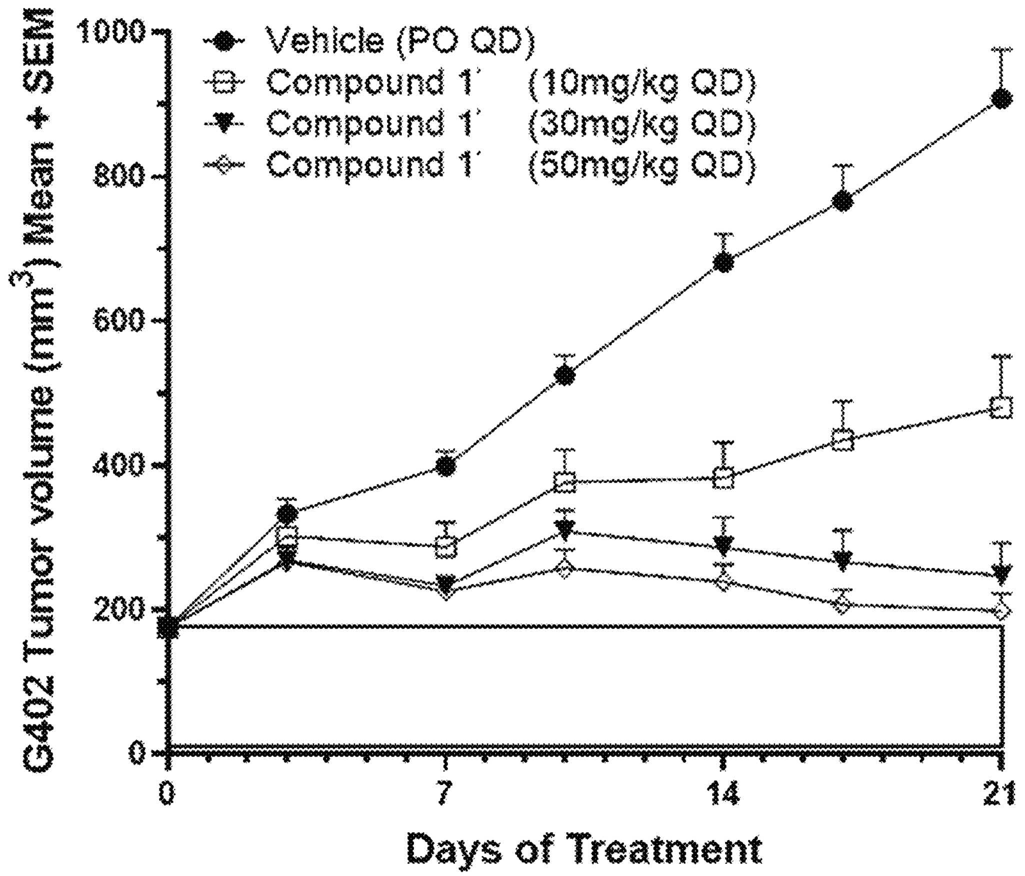
FIG. 3 is a graph demonstrating the effect of Compound 1 at various doses on BALB/c nude female mice bearing established G402 xenografts. The mice were orally administered vehicle or Compound 1 (10 mg/kg, 30 mg/kg, or 50 mg/kg) daily as indicated. Efficacy data is expressed as mean tumor volumes±SEM. The experimental procedure is provided in Example 4.
Figure 4:
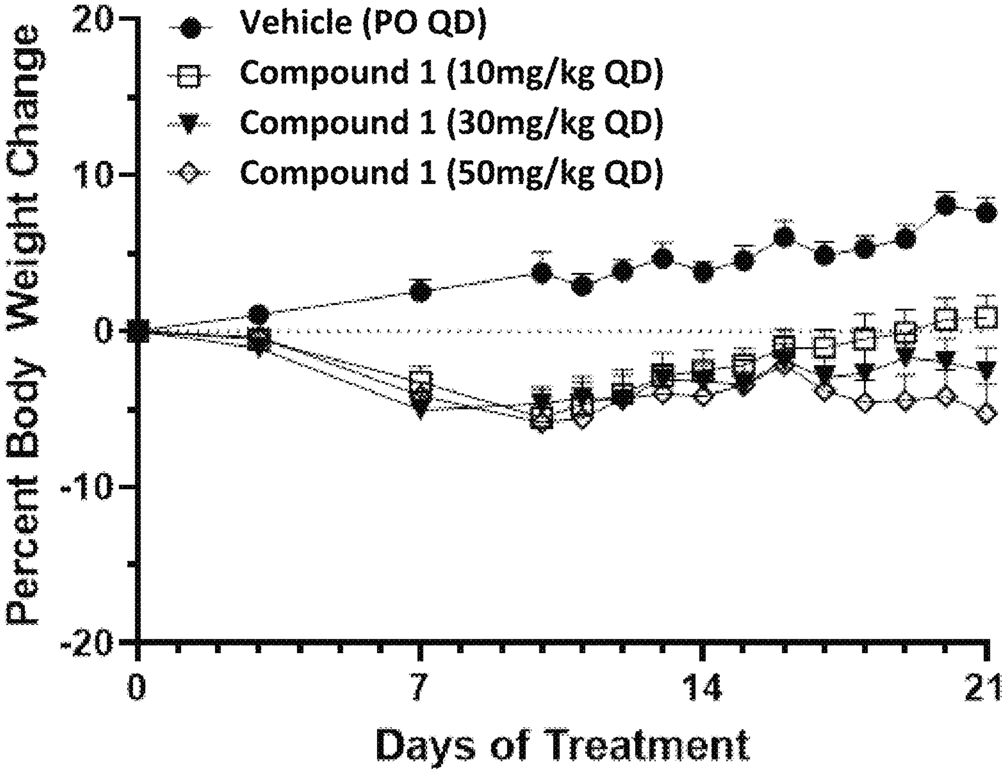
FIG. 4 is a graph demonstrating the effect of Compound 1 at various doses on BALB/c nude female mice bearing established G402 xenografts. The mice were orally administered vehicle or Compound 1 (10 mg/kg, 30 mg/kg, or 50 mg/kg) daily as indicated. Body weight data are derived from Study Report and are expressed as percent of predosing body weight measured on Day 0±SEM. The experimental procedure is provided in Example 4.

Example 4 Antitumor Activity of Compound 1 in the G402 Malignant Rhabdoid Tumor (MRT) Xenograft Model To evaluate the efficacy potential of Compound 1 in the malignant rhabdoid tumor setting, BALB/c nude female mice bearing G402 tumor xenografts (WuXi AppTec, Shanghai, China) were treated with a daily regimen of escalating doses of Compound 1 (10 mg/kg, 30 mg/kg, or 50 mg/kg) or vehicle via oral gavage for 21 days (FIG. 3). Compound 1 was tolerated in this study with all mice except two losing no greater than 8% body weight (FIG. 4). One mouse in the 10 mg/kg QD group showed over 15% body weight loss and was given 4-day dosing holiday at which point body weight recovered and mouse was back on study and gained weight during the duration of treatment. One mouse in the 50 mg/kg QD group also experienced accumulating body weight loss to end the study at −17.3% but was never taken off study. Compound 1 was efficacious in the G402 xenograft model with TGI of 73% (P=<0.0001) and 78% (P=<0.0001) for doses 30 mg/kg/day and 50 mg/kg/day, respectively. TGI and One-way ANOVA analyses were performed on day 21, the last day all animals were on study.

The G402 tumor cells were maintained in vitro in McCoy's 5a medium supplemented with 10% fetal bovine serum and 1% Penicillin-Streptomycin at 37° C. in an atmosphere of 5% $CO_2$ in air. The tumor cells were routinely subcultured twice weekly. The cells growing in an exponential growth phase were harvested and counted for tumor inoculation.

Each mouse was inoculated subcutaneously at the right flank with G402 cells ($10\times10^6$) in 0.2 mL of PBS supplemented with Matrigel (PBS:Matrigel=1:1) for tumor development. For efficacy part, the treatments were started when the average tumor volume reaches 175 $mm^3$.

Example 5 Morphic Form Evaluation of Compound 1

The following techniques were used to generate the results presented in this Example and in Section II.

Approximate Solubility at 25° C. and 50° C.

About 5 mg of Compound 1 free form Pattern E was weighed to a 2 mL glass vial and aliquots of 20 μL of each solvent were added to determine solubility at 25° C. Max. volume of each solvent added was 1 mL. Approximate solubility was determined by visual observation.

About 10 mg of Compound 1 free form Pattern E, was weighed to a 2 mL glass vial and aliquots of 20 μL of each solvent were added to determine solubility at 50° C. Max. volume of each solvent added was 1 mL. Approximate solubility was determined by visual observation.

Equilibration with Solvents at 25° C. for 2 Weeks

Based on approximate solubility, about 20 mg of Compound 1 free form Pattern E was equilibrated in suitable amount of solvent at 25° C. for 2 weeks with a stirring plate at a rate of 400 rpm. Obtained suspension was filtered through a 0.45 μm nylon membrane filter by centrifugation at 14,000 rpm for 5 min. Solid parts (wet cakes) were investigated by XRPD immediately. Some samples with Form K were exposure to ambient condition and investigated by XRPD again.

Equilibration with Solvents at 50° C. for 1 Week

Based on approximate solubility results, about 30 mg of Compound 1 free form Pattern E was equilibrated in suitable amount of solvent at 50° C. for 1 week with a stirring plate at a rate of 400 rpm. The obtained suspension was filtered through a 0.45 μm nylon membrane filter by centrifugation at 14,000 rpm for 5 min. Solid parts (wet cakes) were investigated by XRPD immediately. For samples with different XRPD results, additional analysis including HPLC, DSC, TGA, $^1$H-NMR and KF was performed. Some samples with Form K were exposure to ambient condition and investigated by XRPD again.

Equilibration Under a Temperature Cycle

Based on approximate solubility results, about 30 mg of Compound 1 free form Pattern E was equilibrated in suitable amount of solvent under a temperature cycle between 5° C. to 50° C. at a heating/cooling rate of 0.2° C./min for 10 cycles. Obtained suspension was filtered through a 0.45 μm nylon membrane filter by centrifugation at 14,000 rpm for 5 min. Solid parts (wet cakes) were investigated by XRPD immediately. For samples with different XRPD results, additional analysis including HPLC, DSC, TGA, $^1$H-NMR and KF was performed. Some samples with Form K were exposure to ambient condition and investigated by XRPD again.

Crystallization at Room Temperature by Slow Evaporation

Based on approximate solubility results, about 10 mg of Compound 1 free form Pattern E was dissolved in suitable amount of solvents. Obtained suspensions or solutions were centrifuged. Obtained clear solutions were slowly evaporated under ambient condition. Solid residues were examined for their polymorphic form.

Crystallization Under Nitrogen Flow by Fast Evaporation

Based on approximate solubility results, about 10 mg of Compound 1 free form Pattern E was dissolved in suitable amount of solvents. Obtained suspensions or solutions were centrifuged to get clear solutions. Then clear solutions were fast evaporated under a dry nitrogen flow. Solid residues were examined for their polymorphic form.

Crystallization from Hot Saturated Solutions by Slow Cooling

Based on approximate solubility results, about 20 mg of Compound 1 free form Pattern E was dissolved in the minimal amount of selected solvents at 50° C. Obtained solutions were centrifuged to get clear solutions. Then clear solutions were cooled to 5° C. at a rate of 0.1° C./min. Samples with no precipitates were put in −20° C. freezer for crystallization. Precipitates were collected by centrifuged. Solid parts (wet cakes) were investigated by XRPD.

Crystallization from Hot Saturated Solutions by Fast Cooling

Based on approximate solubility results, about 20 mg of Compound 1 free form Pattern E was dissolved in the minimal amount of selected solvents at 50° C. Obtained solutions were centrifuged to get clear solutions. Then clear solutions were put into an ice bath and agitated. Samples with no precipitates were put in −20° C. freezer for crystallization. Precipitates were collected by filtration. The solid part (wet cake) were investigated by XRPD.

Crystallization by Addition of Anti-Solvent

Based on approximate solubility results, about 20 mg of Compound 1 free form Pattern E was dissolved in the minimal amount of good solvent. Anti-solvent was added into the obtained solutions slowly. Precipitates were collected by centrifuged. The solid part (wet cake) were investigated by XRPD.

Crystallization by Vapor Diffusion

Based on approximate solubility results, about 20 mg of Compound 1 free form Pattern E was dissolved in the minimal amount of good solvent in 2 mL glass vial without lid. Then the 2 mL lid less vial was placed to 8 mL vial. To the 8 mL vial was added anti-solvent. Then the 8 mL vial was capped and placed at ambient condition. Precipitates were collected by centrifugation filtration through a 0.45 μm nylon membrane filter at 14,000 rpm for 5 min. Solid parts (wet cakes) were investigated by XRPD.

Crystallization by Heat-Cool DSC

Polymorphic behavior of Compound 1 free form was investigated by two different heat-cool DSC cycles using free form Pattern E. A Tzero pan and a Tzero hermetic lid with a pin hole were used for this experiment. Cycle 1: 30° C. to 180° C. at 10° C./min; 180° C. to −20° C. at 20° C./min; reheat to 250° C. at 10° C./min. Cycle 2: 30° C. to 180° C. at 10° C./min; 180° C. to −20° C. at 2° C./min; reheat to 250° C. at 10° C./min.

Variable Temperature XRPD (VT-XRPD) Experiments

To investigate form conversion behavior, variable temperature XRPD experiments were conducted for hydrate Pattern A, hydrate Pattern C, hydrate Pattern F and heterosolvate Pattern L.

Based on DSC and TGA results, variable temperature XRPD was conducted for Pattern A, at different temperatures, including 25° C., 110° C. and 25° C.

Based on DSC and TGA results, variable temperature XRPD was conducted for Pattern B, at different temperatures, including 25° C., 80° C., 130° C. and 25° C. The sample after heating-cooling was placed at 25° C./75% RH condition for 1 day and investigated by XRPD.

Based on DSC and TGA results, variable temperature XRPD was conducted for Pattern C, at different temperatures, including 25° C., 110° C. and 25° C.

Based on DSC and TGA results, variable temperature XRPD was conducted for Pattern F at different temperatures, including 25° C., 110° C. and 25° C. The sample after heating-cooling was placed at 25° C./75% RH condition for 1 day and investigated by XRPD.

Based on DSC and TGA results, variable temperature XRPD was conducted for Pattern L, at different temperatures, including 25° C., 100° C., 140° C., 180° C. and 25° C. The sample after heating-cooling was placed at 25° C./92% RH condition for 24 h and investigated by XRPD.

Variable Humidity XRPD (VH-XRPD) Experiments

Based on DVS results, variable humidity XRPD was conducted for Pattern A at different humidity conditions, including 40%, 70%, 90%, 70%, 40%, 20%, 0%, 40% RH conditions.

Based on DVS results, variable humidity XRPD was conducted for Pattern N, at different humidity conditions, including 40%, 70%, 90%, 70%, 40%, 20%, 0%, 40% RH conditions.

Characterization of Polymorphs

New crystalline forms obtained were characterized by XRPD, TGA, DSC, $^{1}$H-NMR, KF, etc.

Preparation and Characterization of Important Polymorphs

Preparation of Pattern G

About 200 mg of Compound 1 free form Pattern E, was equilibrated in 2 mL of toluene at 50° C. with a stirring plate at a rate of 400 rpm. About 5 mg of Pattern G was added into the mixture as seeds. Obtained suspension was equilibrated at 50° C. for 1 day, then the suspension was centrifuged. Based on XRPD result, about 160 mg of Pattern G was obtained as white solids in a yield of 80.0%. This batch Pattern G was used for competitive water activity and competitive experiments.

Preparation of Pattern A

About 500 mg of Compound 1 free form Pattern A was equilibrated in 3.2 mL of acetone/water (v:v=36:64) under a temperature cycle between 5° C. to 50° C. in a heating-cooling rate of 0.2° C./min for 5 cycles. About 5 mg of Pattern A, was added into the suspension as seeds. Obtained suspension was equilibrated at 5° C. for 1 day, then the suspension was centrifuged. Based on XRPD result, about 400 mg of Pattern A, was obtained as white solids in a yield of 80.0%. Pattern A was used for competitive water activity experiments.

Preparation of Pattern L

Method 1: About 100 mg of Compound 1 free form Pattern A was added in 500M1 of 2-MeTHF. The suspension was filtered to obtain clear solution. Solids were precipitated from clear solution after stirring at 25° C. for 2 hours. Precipitations were centrifuged and obtained solids were analyzed by XRPD.

Method 2: About 100 mg of Compound 1 free form Pattern A was added in 500M1 of 2-MeTHF. The solution with few solids was equilibrated at 25° C. for 1 day with a stirring plate at a rate of 400 rpm. Obtained suspension was centrifuged and obtained solids were analyzed by XRPD.

Method 3: About 100 mg of Compound 1 free form Pattern A was added in 300M1 of 2-MeTHF. Obtained suspension was equilibrated at 25° C. for 1 day with a stirring plate at a rate of 400 rpm. The suspension was centrifuged and obtained solids were analyzed by XRPD.

Competitive Water Activity Study

Competitive Water Activity Among Hydrates

Competitive water activity experiments for hydrates were conducted to investigate the thermodynamically stable hydrate in different ranges of water activity. Pattern A, Pattern C, Pattern D, and Pattern E, were equilibrated at 25° C. in 7 different water activities with acetone/water mixtures for 7 days. Obtained suspensions were centrifuged and obtained solids were analyzed by XRPD immediately.

Competitive Water Activity of Hydrate Pattern a and Anhydrate Pattern G

Competitive water activity experiments at 25° C. were conducted for hydrate Pattern A and anhydrate Pattern G. Pattern A, and Pattern G, were equilibrated at 25° C. in 6 different water activities with acetone/water mixtures. Obtained suspensions were stirred at 25° C. for 3 days and 7 days. Obtained suspensions were centrifuged and obtained solids were analyzed by XRPD immediately.

Competitive Water Activity of Hydrate Pattern a and Anhydrate Pattern M

Competitive water activity experiments at 25° C. were conducted for hydrate Pattern A and anhydrate Pattern M. Pattern A, and Pattern M were equilibrated at 25° C. in 6 different water activities with acetone/water mixtures. Obtained suspension was stirred at 25° C. for 3 days and 7 days. Obtained suspensions were centrifuged and obtained solids were analyzed by XRPD immediately.

Competitive Equilibration Experiment

Competitive equilibration experiments were conducted at 25° C. to investigate the thermodynamically stable anhydrate. 5 mg of Pattern G, and 5 mg of Pattern H, were added to about 200 μL of saturated solution in selected solvents. Obtained suspension was stirred at 25° C. for 7 days. Obtained suspensions were centrifuged and obtained solids were analyzed by XRPD immediately.

Results

Approximate Solubility at 25° C. and 50° C.

TABLE 40

Approximate solubility at 25° C. and 50° C.

| Solvent | Solubility (mg/mL), 25° C. (Target conc. = 250 mg/mL) | Solubility (mg/mL), 50° C. (Target conc. = 500 mg/mL) |
|---|---|---|
| Pattern E | | |
| Water | <5 | <10 |
| Methanol | 8-13 | 18-22 |
| Ethanol | 6-8 | 16-25 |
| Acetone | 20-25 | 100-200 |
| Acetonitrile | 5-6 | <10 |
| THF | >250 | >500 |
| Ethyl acetate | 6-8 | 14-20 |
| MTBE | <5 | <10 |
| Heptane | <5 | <10 |
| Methanol/water (v:v = 95:5) | 8-13 | 14-20 |
| DCM | 125-250 | // |
| 1,4-Dioxane | >250 | >500 |
| Toluene | <5 | <10 |
| DMSO | >250 | >500 |
| 2-MeTHF | 83-125 | 250-500 |

Explanation

"//": Not conducted

Equilibration with Solvents at 25° C. for 2 Weeks

TABLE 41

Equilibration with solvents at 25° C. for 2 weeks

| Solvent | XRPD |
|---|---|
| Pattern E | |
| Methanol | +Pattern K |
| Ethanol | +Pattern A |
| Acetone | +Pattern B |
| Acetonitrile | +Pattern B |
| Ethyl acetate | +Pattern F |
| 2-MeTHF | +Pattern B |
| Toluene | +Pattern K |
| THF/heptane (v:v = 1:1) | +Pattern B |
| 1,4-dioxane/heptane (v:v = 1:1) | +Pattern B |
| DCM/heptane (v:v = 1:1) | +Pattern F |
| Solvent | XRPD |
| Pattern E | |
| Acetone/water (v: v = 92:8) a.w.* = 0.50 | +Pattern B |
| Acetone/water (v: v = 76:24) a.w.* = 0.70 | +Pattern B |
| Acetone/water (v: v = 36:64) a.w.* = 0.90 | +Pattern K |
| DMSO/water (v: v = 64:36) a.w.* = 0.50 | +Physical mixture of Pattern B and Pattern F |
| DMSO/water (v: v = 23:77) a.w.* = 0.91 | +Pattern K |

Explanation

"+": Form change detected

"*": The water activity of a binary solvent system is calculated based on UNIFAC method (UNIQUAC Functional-group Activity Coefficients).

Equilibration with Solvents at 50° C. for 1 Week

TABLE 42

Equilibration with solvents at 50° C. for 1 week

| Solvent | XRPD | Notes |
|---|---|---|
| Pattern E | | |
| Methanol | +Physical mixture of Pattern E and Pattern F | |
| Ethanol | +Pattern F | |
| Acetone | +Pattern B | DSC: Dehydrate from 30.0° C.; Onset: 150.0° C., 24 J/g TGA: ~7.3% at 100° C.$^1$H-NMR: 0.9% residual acetone |
| Acetonitrile | +Pattern F | |
| Ethyl acetate | +Pattern F | |

TABLE 42-continued

| Equilibration with solvents at 50° C. for 1 week | | |
|---|---|---|
| Solvent | XRPD | Notes |
| 2-MeTHF | +Pattern B | |
| Toluene | +Pattern G | DSC: Onset: 196.2° C., 75 J/g TGA: ~0.6% at 190° C. $^{1}$H-NMR: No residual solvent |
| THF/heptane (v:v = 1:1) | +Pattern B | |
| 1,4-Dioxane/heptane (v:v = 1:1) | +Pattern B | |
| DCM/heptane (v:v = 1:1) | +Physical mixture of Pattern B and Pattern F | |
| Acetone/water (v: v = 92:8) a.w.* = 0.50 | +Pattern B | |
| Acetone/water (v: v = 76:24) a.w.* = 0.71 | +Pattern B | |
| Acetone/water (v: v = 36:64) a.w.* = 0.90 | +Pattern K | Under ambient condition changes to Pattern A |
| DMSO/water (v: v = 64:36) a.w.* = 0.53 | +Pattern B | |
| DMSO/water (v: v = 23:77) a.w.* = 0.91 | +Pattern K | |

Explanation
"+": Form change detected
"*": The water activity of a binary solvent system is calculated based on UNIFAC method (UNIQUAC Functional-group Activity Coefficients)

Equilibration Under a Temperature Cycle

TABLE 43

| Equilibration under a temperature cycle | | |
|---|---|---|
| Solvent | XRPD | Comments |
| | Pattern E | |
| Methanol | +Pattern B | |
| Ethanol | +Pattern F | High crystallinity DSC: Dehydrate from 30.0° C.; Onset: 109.8° C., 0.9 J/g; 155.1° C., 29 J/g TGA: ~6.1% at 100° C. $^{1}$H-NMR: 0.8% residual Ethanol |
| Acetone | +Pattern B | |
| Acetonitrile | +Pattern B | High crystallinit DSC: Dehydrate from 30.0°C; Onset: 153.1°C, 29J/g TGA: ~6.5% at 100° C. $^{1}$H-NMR: 0.9% residual ACN |
| Ethyl acetate | +Pattern F | |
| 2-MeTHF | +Pattern F | |
| Toluene | +Pattern A | |
| THF/heptane (v:v = 1:1) | +Pattern F | |
| 1,4-Dioxane/heptane (v: v = 1:1) | +Pattern B | |
| DCM/heptane (v:v = 1:1) | +Pattern F | |
| Acetone/water (v: v = 92:8) | +Pattern B | |
| Acetone/water (v: V = 76:24) | +Pattern A | High crystallinity DSC: Dehydrate from 30.0° C.; Onset: 151.0° C., 27 J/g TGA: ~4.7% at 100° C., ~0.9% at 160° C. $^{1}$H-NMR: 0.4% residual acetone |
| Acetone/water (v: v = 36:64) | +Pattern K | Under ambient condition: Pattern A |
| DMSO/water (v: v = 64:36) | +Pattern F | |

TABLE 43-continued

| Equilibration under a temperature cycle | | |
|---|---|---|
| Solvent | XRPD | Comments |
| DMSO/water (v: v = 23:77) | +Physical mixture of Pattern B and Pattern F | |

Explanation
"+": Form change detected

Crystallization at Room Temperature by Slow Evaporation

TABLE 44

| Crystallization at room temperature by slow evaporation | | |
|---|---|---|
| Solvents | XRPD | Comments |
| Methanol | AF | |
| Ethanol | // | Gel-like sample |
| Acetone | Physical mixture of Pattern F and Pattern B | |
| Acetonitrile | Pattern A | |
| Ethyl acetate | Pattern F | High crystallinity DSC: Dehydrate from 30.0° C.; Onset: 110.9° C., 2 J/g, 153.1° C., 24 J/g |
| 2-MeTHF | // | Gel-like sample |
| THF | // | Jelly-like sample |
| DCM | AF | |
| 1,4-dioxane | // | Gel-like sample |
| Methanol/water (v: v = 95:5) | AF | |

Explanation
"//": Not carried out
"AF": Amorphous form

Crystallization Under Nitrogen Flow by Fast Evaporation

TABLE 45

| Crystallization under nitrogen flow by fast evaporation | | |
|---|---|---|
| Solvents | XRPD | Comments |
| Methanol | AF | |
| Ethanol | // | Gel-like sample |
| Acetone | // | Gel-like sample |
| Acetonitrile | Pattern B | |
| Ethyl acetate | // | Gel-like sample |
| 2-MeTHF | // | Gel-like sample |
| THF | // | Gel-like sample |
| DCM | // | Gel-like sample |
| 1,4-dioxane | // | Gel-like sample |
| Methanol/water (v:v = 95:5) | AF | |

Explanation
"AF": Amorphous form
"//": Not carried out

Crystallization from Hot Saturated Solutions by Slow Cooling

TABLE 46

| Crystallization from hot saturated solutions by slow cooling | | |
|---|---|---|
| Solvents | XRPD | Comments |
| Methanol | // | Clear solution |
| Ethanol | Pattern F | Low crystallinity |
| Acetone | Pattern B | |
| Ethyl acetate | // | Clear solution Add Pattern G as seeds slurry for 5 days: |

TABLE 46-continued

| Crystallization from hot saturated solutions by slow cooling | | |
|---|---|---|
| Solvents | XRPD | Comments |
| | | Pattern F + an additional peak |
| 2-MeTHF | // | Clear solution Add Pattern G as seeds slurry for 5 days Pattern G |

Explanation
"//": Not carried out

Crystallization from Hot Saturated Solutions by Fast Cooling

TABLE 48

| Crystallization from hot saturated solutions by fast cooling | | |
|---|---|---|
| Solvents | XRPD | Comments |
| Methanol | // | Clear solution |
| Ethanol | Pattern F | Low crystallinity |
| Acetone | Pattern B | |
| Ethyl acetate | Pattern F | |
| 2-MeTHF | // | Clear solution Add Pattern G as seeds slurry for 5 days Pattern G |

Explanation
"//": Not carried out

Crystallization by Addition of Anti-Solvent

TABLE 48

| Crystallization by addition of anti-solvent | | | |
|---|---|---|---|
| Solvents/ Volume (Ml) | Anti-solvent/ Volume(Ml) | XRPD | Comments |
| DCM/200 | Heptane/400 | AF | Add Pattern G as seeds slurry for 5 days Pattern F |
| THF/40 | Heptane/160 | AF | Add Pattern G as seeds slurry for 5 days: Pattern G |
| 1,4-dioxane/200 | Heptane/400 | Pattern F | Low crystallinity |
| 2-MeTHF/110 | Heptane/200 | AF | Add Pattern G as seeds slurry for 5 days: Pattern G |
| DCM/200 | MTBE/400 | Pattern F | Low crystallinity |
| 2-MeTHF/200 | MTBE/200 | // | Oil-like sample |

Explanation
"//": Not carried out
"AF": Amorphous form

Crystallization by Vapor Diffusion

TABLE 49

Crystallization by vapor diffusion

| Solvents/ Volume (Ml) | Anti-solvent/ Volume(Ml) | XRPD | Comments |
|---|---|---|---|
| 1,4-Dioxane/50 | MTBE/600 | // | Gum-like sample |
| THF/50 | MTBE/600 | // | Gum-like sample |
| 2-MeTHF/120 | MTBE/1080 | // | Gum-like sample |

Explanation
"//": Not carried out

Crystallization by Heat-Cool DSC

TABLE 50

Crystallization by heat-cool DSC

| Heating rate | Thermal events |
|---|---|
| Cycle 1: 30° C. to 180° C. at 10° C./min; 180° C. to −20° C. at 20° C./min; reheat to 250° C. at 10° C./min. | Heat to 180° C.: Dehydrate from 30.0° C.; Onset: 154.6° C.; Re-heat to 250° C.: Glass transition: 135.6° C.; Delta Cp: 0.3 J/(g · ° C.) |
| Cycle 2: 30° C. to 180° C. at 10° C./min; 180° C. to −20° C. at 2° C./min; reheat to 250° C. at 10° C./min. | Heat to 180° C.: Dehydrate from 30.0° C.; Onset: 154.6° C.; Re-heat to 250° C.: Glass transition: 135.7° C.; Delta Cp: 0.5 J/(g · ° C.) |

Variable Temperature XRPD (VT-XRPD) Experiments

TABLE 51

Variable temperature XRPD (VT-XRPD) experiments

| Pattern | Temperature | XRPD |
|---|---|---|
| Pattern A | 25° C. | Pattern A |
| | Heat to 110° C. | Metastable Pattern J |
| | Cool to 25° C. | Metastable Pattern J |
| | 25° C./50% RH hold 2 h | Pattern A |
| Pattern B | 25° C. | Pattern B |
| | Heat to 80° C. | Similar to Pattern H |
| | 80° C. hold 1 h | Similar to Pattern H |
| | Heat to 130° C. | Similar to Pattern H |
| | Cool to 25° C. | Similar to Pattern H |
| | 25° C./50% RH hold 2 h | Similar to Pattern H |
| | 25° C./75% RH hold 1 day | Similar to Pattern H |
| Pattern C | 25° C. | Pattern C |
| | Heat to 110° C. | Metastable Pattern I |
| | Cool to 25° C. | Metastable Pattern I |
| | 25° C./50% RH hold 2 h | Pattern C |
| Pattern F | 25° C. | Pattern F |
| | Heat to 110° C. | Pattern H |
| | Cool to 25° C. | Pattern H |
| | 25° C./50% RH hold 2 h | Low crystallinity, similar to Pattern H |
| | 25° C./75% RH hold 1 day | Similar to Pattern H |
| Pattern L | 25° C. | Pattern L |
| | Heat to 100° C. | Pattern L |
| | Heat to 140° C. | Similar to Pattern L |
| | Heat to 180° C. | Similar to Pattern M |
| | Cool to 25° C. | Pattern M |
| | 25° C./92.5% RH hold 1 day | Pattern M |

Variable Humidity XRPD (VH-XRPD) Experiments

TABLE 52

Variable humidity XRPD (VH-XRPD) experiments

| Pattern | Humidity | XRPD |
|---|---|---|
| Pattern A | 40% RH | Pattern A |
| | 70% RH | Metastable Pattern K |
| | 90% RH | Metastable Pattern K |
| | 70% RH | Metastable Pattern K |
| | 40% RH | Pattern A |
| | 20% RH | Pattern A |
| | 0% RH | Pattern J |
| | 0% RH hold 6 h | Pattern J |
| | 0% RH hold 2 days | Pattern J |
| | 40% RH | Pattern A |
| Pattern N | 40% RH | Pattern N |
| | 70% RH | Pattern N |
| | 90% RH | Pattern N |
| | 70% RH | Pattern N |
| | 40% RH | Pattern N |
| | 20% RH | Pattern N |
| | 0% RH | Pattern N |
| | 40% RH | Pattern N |

TABLE 53

Water activity study of Form A, Form C, Form D, and Form E

| Polymorph | Pattern A, Pattern C, Pattern D, and Pattern E | |
|---|---|---|
| Solvents | a.w.* | XRPD-7 days |
| Acetone | 0.0 | Pattern B |
| Acetone/water (v:v = 99.5:0.5) | 0.1 | Pattern B |
| Acetone/water (v:v = 97:30) | 0.3 | Pattern B |
| Acetone/water (v:v = 92:8) | 0.5 | Pattern B |
| Acetone/water (v:v = 76:24) | 0.7 | Pattern K |
| Acetone/water (v:v = 36:64) | 0.9 | Pattern K |
| Water | 1.0 | Pattern K |

Explanation
"*": The water activity of a binary solvent system is calculated based on UNIFAC method (UNIQUAC Functional-group Activity Coefficients).

TABLE 54

| Competitive water activity study of hydrate Pattern A and anhydrate Pattern G | | | | |
|---|---|---|---|---|
| Polymorph | Pattern A and Pattern G | | | |
| Solvents | a.w.* | XRPD-3 days | XRPD-7 days | Comments |
| Acetone | 0.0 | Pattern B | Pattern N | |
| Acetone/water (v:v = 98:2) | 0.2 | Pattern B | Pattern N | Pattern N: DSC: Dehydration: 153.8° C.; Recrystallization: 166.5° C. Melting onset: 221.1° C., 58 J/g; KF: 5.9% by weight |
| Acetone/water (v:v = 95:5) | 0.4 | Pattern B | Pattern N | $^1$H-NMR: No residual solvent |
| Acetone/water (v:v = 86:14) | 0.6 | Pattern B | Pattern B | // |
| Acetone/water (v:v = 60:40) | 0.8 | Pattern K | Pattern K | // |
| Water | 1.0 | Physical mixture of Pattern A and Pattern G | Pattern K | // |

Explanation
"//": Not carried out.
"*": The water activity of a binary solvent system is calculated based on UNIFAC method (UNIQUAC Functional-group Activity Coefficients).

TABLE 55

| Water activity study of hydrate Pattern A and anhydrate Pattern M | | | |
|---|---|---|---|
| Polymorph | Pattern A and Pattern M | | |
| Solvents | a.w.* | XRPD-3 days | XRPD-7 days |
| Acetone | 0.0 | Pattern N | Pattern N |
| Acetone/water (v:v = 98:2) | 0.2 | Pattern N | Pattern N |
| Acetone/water (v:v = 95:5) | 0.4 | Pattern N | Pattern N |
| Acetone/water (v:v = 86:14) | 0.6 | Pattern N | Pattern N |
| Acetone/water (v:v = 60:40) | 0.8 | Pattern K | Pattern A |
| Water | 1.0 | Pattern K | Pattern A |

Explanation
"//": Not carried out.
"*": The water activity of a binary solvent system is calculated based on UNIFAC method (UNIQUAC Functional-group Activity Coefficients).

TABLE 56

| Competitive equilibration experiment at 25° C. | |
|---|---|
| Polymorph | Pattern G and Pattern H |
| Solvent | XRPD |
| Ethanol | Low crystallinity, difficult to differentiate |
| Acetone | Pattern B |
| Ethyl acetate | Pattern F |
| Toluene | Pattern G |

Example 6 Single Crystal Structure of Compound 1

Figure 21:
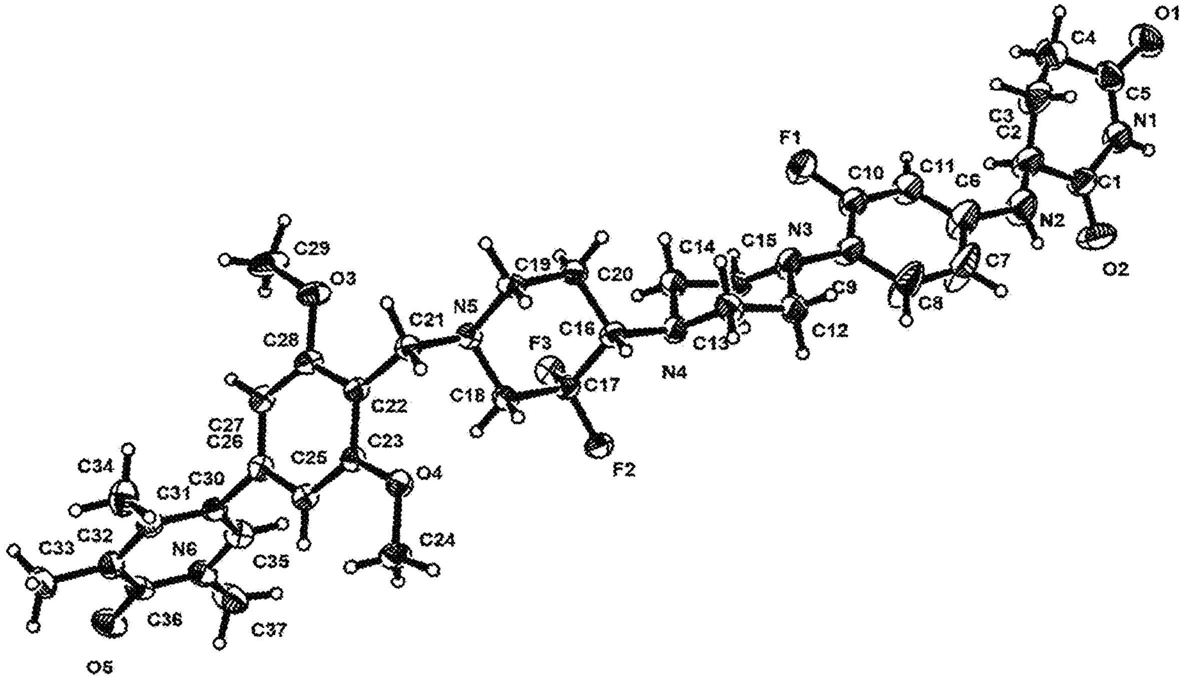
FIG. 21 depicts a single crystal structure of Compound 1 corresponding to Form O.

A total of 13481 reflections were collected in the 2theta range from 5.068 to 133.16. The 5 limiting indices were: −41<=h<=42, −8<=k<=9, −16<=1<=15; which yielded 5817 unique reflections (Rint=0.0284). The structure was solved using SHELXT (Sheldrick, G. M. 2015. Acta Cryst. A71, 3-8) and refined using SHELXL (against F2) (Sheldrick, G. M. 2015. Acta Cryst. C71, 3-8). The total number of refined parameters was 465, compared with 5817 data. All reflections were included in the refinement. The goodness of fit on $F^2$ was 1.036 with a final R value for [I>2σ (I)] $R_1$=0.0346 and $wR_2$=0.0916. The largest differential peak and hole were 0.27 and −0.21 $Å^{-3}$, respectively. ORTEP structure depicted in FIG. 21.

| | |
|---|---|
| Crystal Size | 0.10 × 0.10 × 0.10 mm3 |
| Radiation Type | Cu Kα (λ = 1.54184 Å) |
| Crystal system | monoclinic |
| Space Group | C2 |
| Cell Size | a = 35.5077(8) Å<br>b = 7.59150(10) Å<br>c = 13.4959(3) Å<br>α = 90°<br>β = 100.895(2)°<br>γ = 90° |
| Cell Volume | V = 3572.34(12) $Å^3$ |
| Cell Formula Units | Z = 4 |
| Crystal Density | Dc = 1.322 g/$cm^3$ |
| Crystal F(000) | 1504.0 |
| Absorption Coefficient mu | μ(Cu Kα) = 0.829 mm − 1 |
| Limiting Indices | −41 <= h <= 42<br>−8 <= k <= 9<br>−16 <= 1 <= 15 |
| Cell Measurement Temperature | T = 107(10) K. |
| 2□ range for data collection | 5.068 to 133.16° |
| Goodness-of-fit on F^2 | 1.036 |
| Final R indices [I > 2sigma(I)] | R1 = 0.0346, wR2 = 0.0916 |
| R indices (all data) | R1 = 0.0363, wR2 = 0.0926 |
| Largest diff. peak and hole | 0.27 and −0.21 e.$Å^{-3}$ |
| Reflections collected/unique | 13481/5817 [R(int) = 0.0284] |
| Flack parameter | 0.10(5) |

TABLE 57

Atomic coordinates (×10^4) and equivalent isotropic displacement parameters (Å^2 × 10^3).

| Atom | x | y | z | U(eq) |
|---|---|---|---|---|
| F(3) | 3700.9(5) | 1586(2) | 4746.5(12) | 35.3(4) |
| F(1) | 4171.8(4) | 7233(2) | 1427.2(13) | 38.4(4) |
| F(2) | 3394.6(4) | 1046(2) | 3218.7(13) | 40.2(4) |
| O(5) | 1542.1(6) | −1359(3) | 9632.4(15) | 36.4(5) |
| O(4) | 3699.4(5) | −3175(3) | 7598.3(15) | 35.6(5) |
| O(3) | 2740.9(5) | −3323(3) | 4676.4(14) | 36.5(5) |
| O(1) | 6793.6(6) | 12838(4) | 2159.3(16) | 45.7(5) |
| N(3) | 4494.8(6) | 4797(3) | 2869.9(16) | 28.0(5) |
| N(4) | 4248.6(6) | 1382(3) | 3382.0(16) | 25.7(4) |
| N(5) | 3712.3(6) | −2183(3) | 5175.3(16) | 26.2(5) |
| N(6) | 1881.1(7) | −461(3) | 8461.2(18) | 32.1(5) |
| N(1) | 6220.9(7) | 12169(3) | 1197.2(17) | 34.4(5) |
| N(2) | 5299.7(7) | 10665(3) | 1727(2) | 37.5(6) |
| O(2) | 5648.8(8) | 11639(4) | 189.1(17) | 64.4(8) |
| C(8) | 4549.1(7) | 7437(4) | 1865(2) | 29.1(6) |
| C(35) | 1802.2(8) | −1703(4) | 9147(2) | 30.4(6) |
| C(9) | 4715.1(8) | 6199(4) | 2577(2) | 28.4(6) |
| C(23) | 2826.8(8) | −3057(4) | 5703(2) | 30.2(6) |
| C(17) | 3650.8(8) | 315(4) | 4007(2) | 27.5(6) |
| C(31) | 2294.9(8) | −3591(4) | 8662(2) | 32.0(6) |
| C(6) | 5118.9(8) | 9170(4) | 2015(2) | 31.2(6) |
| C(20) | 4274.0(7) | −1233(3) | 4491(2) | 27.1(6) |
| C(28) | 3317.4(8) | −2987(4) | 7190(2) | 30.2(6) |
| C(19) | 4046.5(7) | −2793(4) | 4770(2) | 27.9(5) |
| C(12) | 4362.4(8) | 3466(4) | 2086(2) | 28.4(6) |
| C(22) | 3217.0(7) | −3204(3) | 6145(2) | 28.4(6) |
| C(33) | 2023.3(8) | −3287(4) | 9250(2) | 31.4(6) |
| C(30) | 2362.6(8) | −2263(4) | 7962(2) | 31.6(6) |
| C(7) | 4735.1(8) | 8863(4) | 1573(2) | 31.1(6) |
| C(13) | 4074.4(7) | 2243(4) | 2437.7(19) | 27.4(5) |
| C(5) | 5850.3(9) | 11567(4) | 1028(2) | 37.0(7) |
| C(16) | 4029.8(7) | −96(3) | 3676(2) | 24.7(5) |
| C(21) | 3517.6(8) | −3705(3) | 5536(2) | 29.0(6) |
| C(15) | 4670.6(8) | 3908(4) | 3802(2) | 33.3(6) |
| C(27) | 3041.7(8) | −2641(4) | 7773(2) | 33.3(6) |

TABLE 57-continued

| Atomic coordinates (×10ˆ4) and equivalent isotropic displacement parameters (Aˆ2 × 10ˆ3). | | | | |
|---|---|---|---|---|
| Atom | x | y | z | U(eq) |
| C(25) | 2549.3(8) | −2730(4) | 6281(2) | 32.7(6) |
| C(14) | 4383.4(8) | 2712(4) | 4155(2) | 30.6(6) |
| C(18) | 3454.6(7) | −1253(3) | 4377(2) | 26.7(5) |
| C(10) | 5098.9(8) | 6509(4) | 2998(2) | 32.6(6) |
| C(26) | 2657.4(8) | −2525(4) | 7317(2) | 32.9(6) |
| C(37) | 2156.0(8) | −761(4) | 7883(2) | 33.9(6) |
| C(11) | 5298.2(8) | 7979(4) | 2733(2) | 33.8(6) |
| C(3) | 5875.7(8) | 11899(4) | 2869(2) | 34.6(6) |
| C(1) | 6468.0(8) | 12320(4) | 2128(2) | 32.8(6) |
| C(4) | 5713.0(8) | 10806(4) | 1941(2) | 33.2(6) |
| C(2) | 6311.2(8) | 11815(4) | 3044(2) | 33.4(6) |
| C(36) | 1656.7(9) | 1167(4) | 8349(3) | 41.6(7) |
| C(24) | 2354.7(8) | −3052(5) | 4173(2) | 40.6(7) |
| C(29) | 3805.3(9) | −3175(5) | 8681(2) | 40.2(7) |
| C(32) | 2507.0(9) | −5298(5) | 8694(3) | 45.2(8) |
| C(34) | 1932(1) | −4555(4) | 10027(2) | 41.8(7) |

Example 7 Salt Evaluation of Compound 1

About 5 mg of Compound 1 free form was weighed to a 2 mL glass vial and aliquots of 20 μL of each solvent were added to get a clear solution at 25° C. Max volume of each solvent added was 1 mL. Approximate solubility was determined by visual observation.

TABLE 58

| Approximate solubility of Compound 1 at 25° C. | |
|---|---|
| Solvent | Solubility (mg/mL, 25° C.) (Target conc. = 250 mg/mL) |
| Water | <5 |
| Methanol | 10-17 |
| Ethanol | 5-6 |
| Acetone | 17-25 |
| Acetonitrile | 6-7 |
| Tetrahydrofuran | >250 |
| Ethyl acetate | 5-6 |
| Methyl tert-butyl ether | <5 |
| Heptane | <5 |
| Methanol/Water (v:v = 95:5) | 8-13 |

Based on the pKa of free form, 14 acids were selected for evaluation in acetone and methanol. About 30 mg of Compound 1 free form and 1 or 2 equivalents of salt forming agents 5 were weighed into 2 mL glass vials. 200 μL of acetone or methanol was added. Obtained suspensions or clear solutions were stirred at 50° C. for 2 hours, then chilled to 25° C. and stirred for 2 days. To avoid degradation, experiments with strong acids were conducted without heating. Samples were stirred at 25° C. for 2 days. Obtained suspensions were taken out and centrifuged. Then wet cakes were dried at 25° C. under vacuum for 2 h. Obtained solids were analyzed by XRPD and results were summarized. Only free form, amorphous form and gum-like samples were obtained.

To obtain crystalline salts, another two solvents including ethyl acetate and acetonitrile were added as solvents. About 30 mg of Compound 1 free form and 1 or 2 equivalents of salt forming agents were weighed into 2 mL glass vials. 400 μL of ethyl acetate or 300 μL of acetonitrile was added. Samples were stirred at 25° C. for 2 days. Obtained solids were analyzed by XRPD and results were summarized. Only free form, amorphous form and gum-like samples were obtained.

Nicotinamide and urea were selected as crystallization agents for cocrystal evaluation. Acetone, methanol, ethyl acetate and acetonitrile were used as solvents. About 30 mg of Compound 1 free form, and 1 equivalent of crystallization agent were weighed into 2 mL glass vials. 200 L of acetone, 200 μL of methanol, 400 L of ethyl acetate or 300 L of acetonitrile was added. Obtained suspensions were stirred at 25° C. for 2 days. Obtained solids were analyzed by XRPD and results were summarized.

TABLE 59

| Counter-ions or crystallization agent used for salt and cocrystal evaluation | | |
|---|---|---|
| Counter-ions/ cocrystalization agents | pKa(s) | M.W. |
| Hydrochloric acid | −6.0 | 36.5 |
| Sulfuric acid | −3.0, 1.9 | 98.1 |
| Phosphoric acid | 2.0, 7.1,12.3 | 98.0 |
| Methanesulfonic acid | −1.2 | 96.1 |
| Maleic acid | 1.9, 6.2 | 116.1 |
| Fumaric acid | 3.0, 4.4 | 116.1 |
| L-Tartaric acid | 3.0, 4.4 | 150.1 |
| Citric acid | 3.1, 4.8, 6.4 | 192.3 |
| L-Malic acid | 3.5, 5.1 | 134.1 |
| Succinic acid | 4.2, 5.6 | 118.1 |
| Adipic acid | 4.4, 5.4 | 146.1 |
| Hippuric acid | 3.5 | 179.2 |
| p-Toluenesulfonic acid | −1.3 | 172.2 |
| Trifluoroacetic acid | −0.3 | 114.0 |
| Urea | N/A | 60.06 |
| Nicotinamide | N/A | 122.13 |

TABLE 60

| Results | | | | | |
|---|---|---|---|---|---|
| Ions | Amount | A Acetone | B MeOH | C EA | D ACN |
| Free form | // | −Free form Pattern B* | −Free form Pattern B* | −Free form Pattern B* | −Free form Pattern B* |
| Hydrochloric acid | 2.10 equiv. | Gum-like sample | Clear solution | −Free form Pattern B*, low crystallinity | Gum-like sample |
| Sulfuric acid | 2.10 equiv. | Gum-like sample AF Sulfate salt* Equilibration for another 8 days: AF | Clear solution | AF | Gum-like sample |

TABLE 60-continued

| | | Results | | | |
|---|---|---|---|---|---|
| Ions | Amount | A Acetone | B MeOH | C EA | D ACN |
| Sulfuric acid | 1.05 equiv. | Gum-like sample | Clear solution | −Free form Pattern A* | Gum-like sample |
| Phosphoric acid | 2.10 equiv. | Gum-like sample | −Free form Pattern C | | |
| Methanesul fonic acid | 2.10 equiv. | Gum-like sample | Clear solution | AF MSA salt* Equilibration for another 8 days: AF | Gum-like sample |
| Maleic acid | 2.10 equiv. | Gum-like sample | Clear solution | // | // |
| Fumaric acid | 2.10 equiv. | Clear solution | −Free form Pattern C | // | // |
| Fumaric acid | 1.05 equiv. | Clear solution | −Free form Pattern C | // | // |
| L-Tartaric acid | 2.10 equiv. | Gum-like sample | −Free form Pattern C | // | // |
| L-Tartaric acid | 1.05 equiv. | Gum-like sample | −Free form Pattern C | // | // |
| Citric acid | 2.10 equiv. | Gum-like sample | Clear solution | // | // |
| L-Malic acid | 2.10 equiv. | Clear solution | −Free form Pattern C | // | // |
| Succinic acid | 2.10 equiv. | Clear solution | −Free form Pattern C | // | // |
| Adipic acid | 2.10 equiv. | Clear solution | −Free form Pattern C | // | // |
| Hippuric acid | 2.10 equiv. | Physical mixture of free form Pattern A* and free form Pattern C* | −Free form Pattern C | // | // |
| p-Toluenesul fonic acid | 2.10 equiv. | Gum-like sample | Clear solution | AF* + free form Pattern A* Equilibration for 8 days: AF | Gum-like sample |
| Trifluoroac etic acid | 2.10 equiv. | Clear solution | Clear solution | Clear solution | Clear solution |
| Urea | 1.05 equiv. | Clear solution | −Free form Pattern C | −Free form Pattern B* | +Urea cocrystal Pattern P |
| Nicotinami de | 1.05 equiv. | Clear solution | −Free form Pattern C | −Free form Pattern B* | −Free form Pattern B* |

Explanation
"+": Salt/cocrystal hits
"−": Free form, counter ions, or physical mixtures
"AF": Amorphous form
"//": Not conducted
"*": Salt formation was confirmed by $^1$H-NMR Clear solutions obtained from equilibration experiments were cooled to 5° C. and stirred at 5° C. for 3 days. Supernatants obtained from equilibration experiments were cooled to 5° C. and stirred at 5° C. for 3 days. Then obtained suspensions were centrifuged at 5° C. and solids were dried under vacuum at 25° C. for 2 h. Obtained solids were analyzed by XRPD and results were summarized in Table 61. No crystalline salt was obtained.

TABLE 61

| | Results (cooling) | | | |
|---|---|---|---|---|
| Counter-ions | A Acetone | B MeOH | C EA | D ACN |
| 2.10 equiv. Hydrochloric acid | Clear Solution | Clear Solution | // | // |
| 2.10 equiv. Sulfuric acid | Clear Solution | Clear Solution | // | // |
| 1.05 equiv. Sulfuric acid | Clear Solution | Clear Solution | // | // |
| 2.10 equiv. Methanesulfonic acid | // | Clear Solution | // | // |

TABLE 61-continued

| Results (cooling) | | | | |
|---|---|---|---|---|
| Counter-ions | A Acetone | B MeOH | C EA | D ACN |
| 2.10 equiv. Maleic acid | // | Clear Solution | // | // |
| 2.10 equiv. Fumaric acid | Clear Solution | // | // | // |
| 1.05 equiv. Fumaric acid | Clear Solution | // | // | // |
| 2.10 equiv. Citric acid | // | Clear Solution | // | // |
| 2.10 equiv. L-Malic acid | Clear Solution | // | // | // |
| 2.10 equiv. Succinic acid | Clear Solution | // | // | // |
| 2.10 equiv. Adipic acid | –Physical mixture of free form Pattern A* and free form Pattern C* | // | // | // |
| 2.10 equiv. p-Toluenesulfonic acid | // | Clear Solution | // | // |
| 2.10 equiv. Trifluoroacetic acid | Clear Solution | Clear Solution | Clear Solution | Clear Solution |
| 1.05 equiv. Urea | –Free form Pattern B* | // | // | // |
| 1.05 equiv. Nicotinamide | –Free form Pattern B* | // | // | // |

Explanation
"–": Free form, counter ions, or physical mixtures
"//": Not conducted Half volume of each clear solution obtained from cooling experiments in Table 62 was evaporated in a fume hood. Only gum-like samples were obtained.

TABLE 62

| Results (slow evaporation) | | | | |
|---|---|---|---|---|
| Counter-ions | A Acetone | B MeOH | C EA | D ACN |
| 2.10 equiv. Hydrochloric acid | // | Gum-like sample | // | // |
| 2.10 equiv. Sulfuric acid | // | Gum-like sample | // | // |
| 1.05 equiv. Sulfuric acid | // | Gum-like sample | // | // |
| 2.10 equiv. Methanesulfonic acid | // | Gum-like sample | // | // |
| 2.10 equiv. Maleic acid | // | Gum-like sample | // | // |
| 2.10 equiv. Fumaric acid | Gum-like sample | // | // | // |
| 1.05 equiv. Fumaric acid | Gum-like sample | // | // | // |
| 2.10 equiv. Citric acid | // | Gum-like sample | // | // |

TABLE 62-continued

| Results (slow evaporation) | | | | |
|---|---|---|---|---|
| Counter-ions | A Acetone | B MeOH | C EA | D ACN |
| 2.10 equiv. L-Malic acid | Gum-like sample | // | // | // |
| 2.10 equiv. Succinic acid | Gum-like sample | // | // | // |
| 2.10 equiv. Adipic acid | Gum-like sample | // | // | // |
| 2.10 equiv. p-Toluenesulfonic acid | // | Gum-like sample | // | // |
| 2.10 equiv. Trifluoroacetic acid | Gum-like sample | Gum-like sample | Gum-like sample | Gum-like sample |

Explanation
"//": Not conducted

For half volume of each clear solution obtained from cooling experiments in Table 61, anti-solvent was added slowly. Obtained solids were analyzed by XRPD and results were summarized in Table 63. No crystalline hits were obtained.

TABLE 63

| Results (anti-solvent addition) | | | | |
|---|---|---|---|---|
| Counter-ions | A Acetone | B MeOH | C EA | D ACN |
| 2.10 equiv. Hydrochloric acid | +200 μL ACN Gel-like sample | +400 μL MTBE Gel-like sample | // | // |

TABLE 63-continued

| Results (anti-solvent addition) | | | | |
|---|---|---|---|---|
| Counter-ions | A Acetone | B MeOH | C EA | D ACN |
| 2.10 equiv. Sulfuric acid | +200 μL ACN Gel-like sample | +200 μL MTBE Gel-like sample | // | // |
| 1.05 equiv. Sulfuric acid | +200 μL ACN Gel-like sample | +200 μL MTBE Gel-like sample | // | // |
| 2.10 equiv. Methanesulfonic acid | +200 μL ACN Gel-like sample | +200 μL MTBE, Gel-like sample | // | // |
| 2.10 equiv. Maleic acid | // | +200 μL MTBE Gel-like sample | // | // |
| 2.10 equiv. Fumaric acid | +200 μL MTBE Gel-like sample | // | // | // |
| 1.05 equiv. Fumaric acid | +200 μL MTBE, Gel-like sample | // | // | // |
| 2.10 equiv. Citric acid | // | +200 μL MTBE Gel-like sample | // | // |
| 2.10 equiv. Succinic acid | +200 μL ACN Gel-like sample | // | // | // |
| 2.10 equiv. p-Toluenesulfonic acid | +200 μL EA Gel-like sample | +400 μL MTBE Gel-like sample | // | // |
| 2.10 equiv. Trifluoroacetic acid | +400 μL MTBE Clear solution | +200 μL MTBE, Gel-like sample | +200 μL MTBE suspension XRPD: AF* Equilibration for 8 days: AF | +200 μL MTBE Gel-like sample |

Explanation
"AF": Amorphous form
"//": Not conducted
"*": Salt formation was confirmed by $^1$H-NMR Amorphous salts from above experiments were re-equilibrated at 25° C. for crystallization. Obtained solids were analyzed by XRPD and results were summarized in Table 64. No crystalline salt hits were obtained.

TABLE 64

| Results (re-equilibration for 8 days) | |
|---|---|
| Counter-ions | Acetone |
| 2.10 equiv. Hydrochloric acid | +100 μL ACN, Gel-like sample |
| 2.10 equiv. Sulfuric acid | +100 μL EA: AF Equilibration for 8 days: AF |
| 1.05 equiv. Sulfuric acid | +200 μL EA, Free form Pattern B* |
| 2.10 equiv. Methanesulfonic acid | +200 μL EA, Gel-like sample |

Preparation of the Urea Cocrystal Form P

About 500 mg of the free form Pattern A* and 1 equivalent of urea were weighed into an 8 mL glass vial. 4.2 mL of acetonitrile was added into the sample. Obtained suspensions were stirred at 25° C. About 5 mg of the urea cocrystal Form P was added into suspensions as seeds and stirred at 25° C. for 2 days.

Obtained suspensions were taken out and centrifuged. Solids were dried at 25° C. under vacuum for 2 h first and then placed at 25° C./60% RH for another 1 day to remove residual ACN. Obtained off-white solids were analyzed by XRPD. About 300 mg the urea cocrystal Pattern P was obtained as off-white solids in a yield of 60%.

Solubility Study

About 10 mg of the Compound 1 free form Pattern A* and the urea cocrystal Pattern P, were weighted in glass vials. 5 mL of aqueous media including pH 1.0 HCl solution (0.1N); pH 4.5 acetate buffer (50 mM); SGF (pH 1.8); FeSSIF-v1 (pH 5.0) and FaSSIF-v1 (pH 6.5) were added, respectively. After stirring at 37° C. at a rate of 300 rpm for 2 h, they were tested by pH meter and then supernatant of suspensions were analyzed by UPLC. Residual solids were characterized by XRPD to identify its physical form. The rest of samples were stirred at 37° C. at a rate of 300 rpm for 24 h. Then they were tested by pH meter and then supernatant of suspensions were analyzed by UPLC. Physical form of residual solids was characterized by XRPD.

TABLE 65

| Solubility study | | | | |
|---|---|---|---|---|
| | Solubility at 37° C., target concentration: 10 mg/5 mL of free form, LOQ: 50 μg/mL<br>Free form Pattern A* | | | |
| | 2 h | | 24 h | |
| Experiment | Solubility/ mg/mL (pH) | XRPD | Solubility/ mg/mL (pH) | XRPD |
| pH 1.0 (0.1N HCl) | >2<br>pH: 1.0 | // | >2<br>pH: 1.0 | // |
| pH 4.5, 50 mM acetate buffer | 0.26<br>pH: 4.5 | No form change | 0.12<br>pH: 4.5 | No form change |
| SGF, pH 1.8 | >2<br>pH: 2.4 | // | >2<br>pH: 2.4 | // |
| FeSSIF-v1, pH 5.0 | 0.17<br>pH: 5.0 | No form change | 0.21<br>pH: 5.0 | Free form Pattern A* + an additional peak |
| FaSSIF-v1, pH 6.5 | <LOQ<br>pH: 6.5 | No form change | 0.08<br>pH: 6.5 | No form change |

| | Solubility at 37° C., target concentration: 10 mg/5 mL of free form, LOQ: 50 μg/mL<br>Urea cocrystal Pattern P | | | |
|---|---|---|---|---|
| | 2 h | | 24 h | |
| Experiment | Solubility/ mg/mL (pH) | XRPD | Solubility/ mg/mL (pH) | XRPD |
| pH 1.0 (0.1N HCl) | >2<br>pH: 1.0 | // | >2<br>pH: 1.0 | // |
| pH 4.5, 50 mM acetate buffer | 0.24<br>pH: 4.6 | Dissociate to free form Pattern D<br>// | 0.14<br>pH: 4.5 | Dissociate to free form Pattern D |
| SGF, pH 1.8 | >2<br>pH: 2.4 | // | >2<br>pH: 2.4 | // |
| FeSSIF-v1, pH 5.0 | 0.28<br>pH: 5.0 | Dissociate to free form Pattern D | 0.34<br>pH: 4.9 | Dissociate to free form Pattern D |
| FaSSIF-v1, pH 6.5 | <LOQ<br>pH: 6.5 | Dissociate to free form Pattern D | <LOQ<br>pH: 6.5 | Dissociate to free form Pattern D |

TABLE 66

| Hygroscopicity | | | | | | | | |
|---|---|---|---|---|---|---|---|---|
| | Free form Pattern A* Hydrate | | | | Urea cocrystal Pattern P Hydrate | | | |
| Humidity | 1st sorp. (%) | 1st de-sorp. (%) | 2nd sorp. (%) | 2nd de-sorp. (%) | 1st sorp. (%) | 1st de-sorp. (%) | 2nd sorp. (%) | 2nd de-sorp. (%) |
| 0% RH | // | 0.0 | 0.0 | // | // | 0.0 | 0.0 | // |
| 10% RH | // | 1.1 | 1.0 | // | // | 2.2 | 1.2 | // |
| 20% RH | // | 1.8 | 1.5 | // | // | 3.1 | 2.8 | // |
| 30% RH | // | 4.5 | 2.1 | // | // | 3.7 | 3.3 | // |
| 40% RH | 4.6 | 6.3 | 3.6 | 6.6 | 4.0 | 4.2 | 3.7 | 4.2 |
| 50% RH | 5.2 | 8.5 | 5.8 | 8.5 | 4.2 | 4.5 | 4.1 | 4.5 |
| 60% RH | 6.9 | 9.4 | 7.7 | 9.4 | 4.4 | 4.7 | 4.4 | 4.7 |
| 70% RH | 9.1 | 9.7 | 9.3 | 9.7 | 4.7 | 5.0 | 4.8 | 5.0 |
| 80% RH | 9.8 | 1.0 | 9.8 | 10.0 | 5.1 | 5.2 | 5.1 | 5.3 |
| 90% RH | 10.3 | 10.3 | 10.2 | 10.3 | 5.6 | 5.8 | 5.6 | 5.8 |
| 95% RH | 10.6 | 10.6 | 10.5 | 10.5 | 7.1 | 7.1 | 7.3 | 7.3 |
| Hygro-scopicity | Slightly hygroscopic in <60% RH; Hygroscopic, 6.0% water uptake from 40% RH to 95% RH | | | | Slightly hygroscopic in <90% RH, 1.6% water uptake from 40% RH to 90% RH; Hygroscopic, 3.1% water uptake from 40% RH to 95% RH; | | | |

TABLE 66-continued

| | | |
|---|---|---|
| XRPD after DVS test | Pattern A* + one additional peak; Crystallinity decrease slightly | No form change |

Example 8 Determination of Compound 1 Selectivity in Synovial Sarcoma HSSYII Cells using Global Proteomics Global protein expression was performed in Yamato-SS and HSSYII synovial sarcoma cell lines after 4-hour treatment with Compound 1 (100 nM). The Yamato-SS cell line was provided by the RIKEN BRC through the National BioResource Project of the MEXT/AMED, Japan (cat #RCB3577), and the HS-SY-II cell line was provided by the RIKEN BRC through the National BioResource Project of the MEXT/AMED, Japan (cat #RCB2231). A total of 8,608 proteins in Yamato-SS cells and 9,013 proteins in HSSYII cells were quantified, and only BRD9 levels significantly changed upon treatment with Compound 1. In Yamato-SS cells, when compared with the dimethyl sulfoxide (DMSO) control, BRD9 protein level was decreased by 66.5% (13 peptides identified; $E_{max}$=33.5%; p value=5.0E-6) and ADAMST1 was also observed to be decreased by 66.3% (4 peptides identified; $E_{max}$=33.7%; p value=1.9E-4), though with less statistical significance than BRD9. In HSSYII cells, when compared with the DMSO control, BRD9 protein level was decreased by 66.7% (7 peptides identified; $E_{max}$=33.3%; p value==4.6E-7) and was the only protein found to have a statistically significant $E_{max}$ less than or equal to 50%. Taken together these data show that Compound 1 is a highly selective and potent degrader in multiple disease model cell lines.

Figure 25:
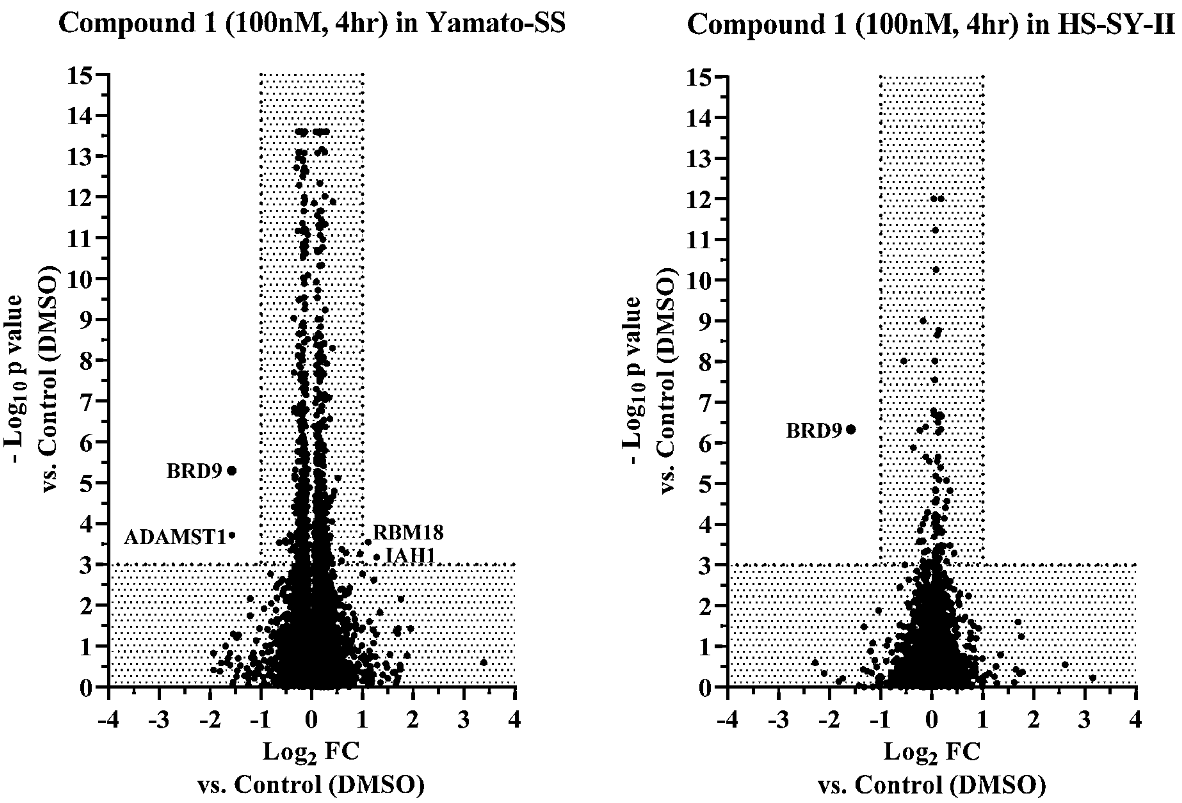
FIG. 25 depicts the results of global proteomics experiment. Compound 1 was incubated for four hours at 100 nM concentration as described in Example 8 in Yamato-SS and HSSYII cell lines.

Both Yamato-SS and HSSYII cell lines were treated with Compound 1 at 100 nM for 4 hours and analyzed by multiplexed quantitative proteomics. The x-axis illustrates the totality of the proteomics data and is labeled as fold change (FC) of Compound 1 vs vehicle in a Log 2 transformation scale. The statistical significance (T-test of treated vs. DMSO with Benjamini-Hochberg correction applied) of the observed changes is shown in the y-axis as negative Log 10 of the P-value. The horizontal dashed line marks the statistical significance (P-value ≤0.001) and the vertical line marks fold change ≥2. The results are shown in FIG. 25.

Example 9 Determination of Compound 1 Dose Proportional Exposure in a Cell Derived Model Compound 1 was tested in the Yamato-SS human synovial sarcoma model. The Yamato-SS cell line was provided by the RIKEN BRC through the National BioResource Project of the MEXT/A MED, Japan (cat #RCB3577). Compound 1 was administered to BALB/c nude mice bearing Yamato-SS tumors on day 1 with PO. Compound 1 was dosed at 0.3, 1, 3, 10, 30 or 50 mg/kg with samples collected at 1, 4, 12, 24, and 48 hours post-dose. For multiple doses part, Compound 1 was administered from day 1 and dosed PO daily for one week. Compound 1 was dosed at 3 or 50 mg/kg.

The Yamato-SS cells were maintained in vitro in DMEM medium supplemented with 20% fetal bovine serum and 1% Penicillin Streptomycin at 37° C. in an atmosphere of 5% $CO_2$ in air. The cells were routinely subcultured twice weekly. The cells growing in an exponential growth phase were harvested and counted for tumor inoculation.

Each mouse was inoculated subcutaneously at the right flank with Yamato-SS cells ($10\times10^6$) in 0.2 mL of PBS supplemented with Matrigel (PBS:Matrigel=1:1) for tumor development. The treatments were started when the average tumor volume reaches 341 $mm^3$ for PKPD study.

Prior to the onset of drug treatment, mice were measured for tumor size in two dimensions using a caliper, and the tumor volume ($mm^3$) was calculated using formula $V=0.5\ a\times b^2$ where a and b are the long and short diameters of the tumor in mm, respectively. Mice were randomized into different treatment groups based on the tumor volume.

Plasma was collected at 1, 4, and 24 hours post single dose treatment with Compound 1 for PK. The whole blood was collected and put into tubes with 15 μL of 0.5 M EDTA-$K_2$. The anticoagulant blood samples were centrifuged at 2,500 g at 4° C. for 15 min. The plasma samples were separated into 2 aliquots and kept at −80° C. before bioanalysis. WBC samples were collected at the indicated time points for PD and kept at −80° C. before bioanalysis.

Figure 26:
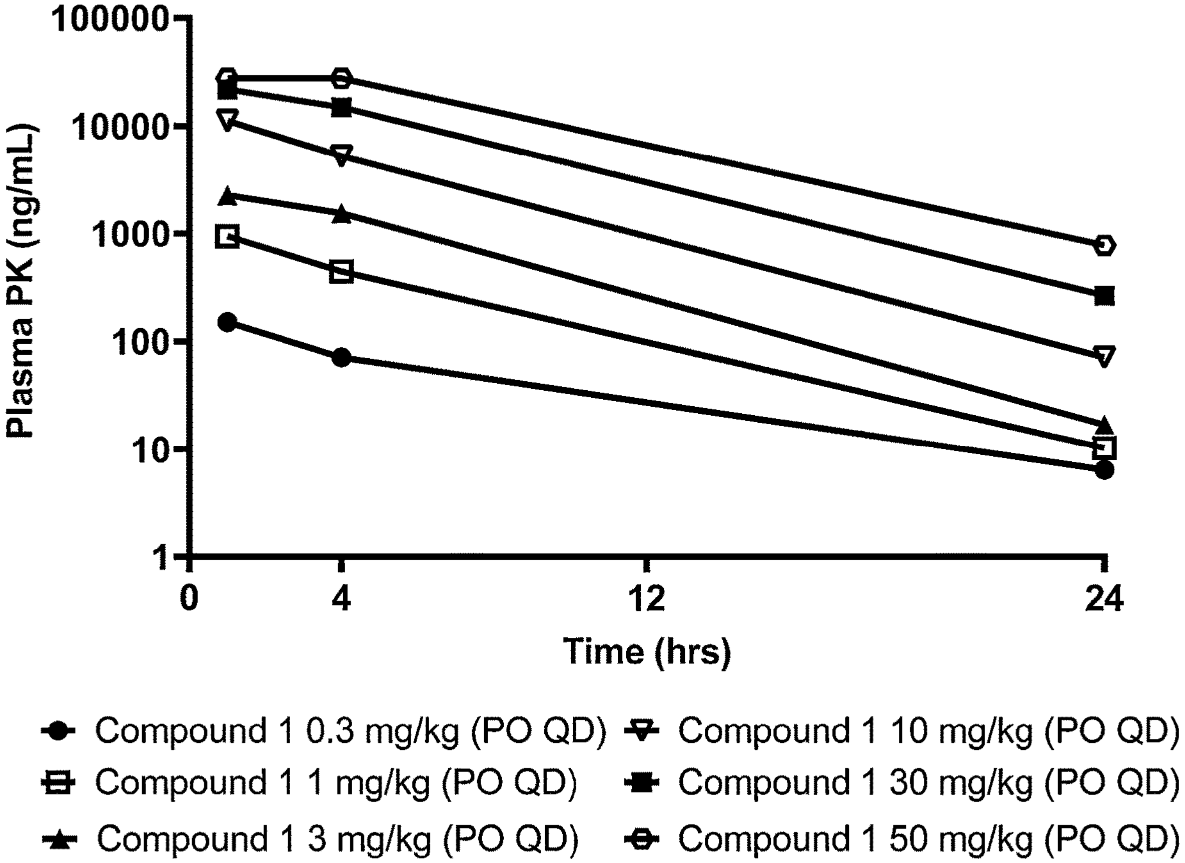
FIG. 26 and FIG. 27 depict the dose proportional exposure of Compound 1 in a Yamato-SS model. The x-axis is time measured in hours and the y-axis is logarithmically scaled tumor concentration measured in ng/g. The experimental procedure is provided in Example 9.
Figure 27:
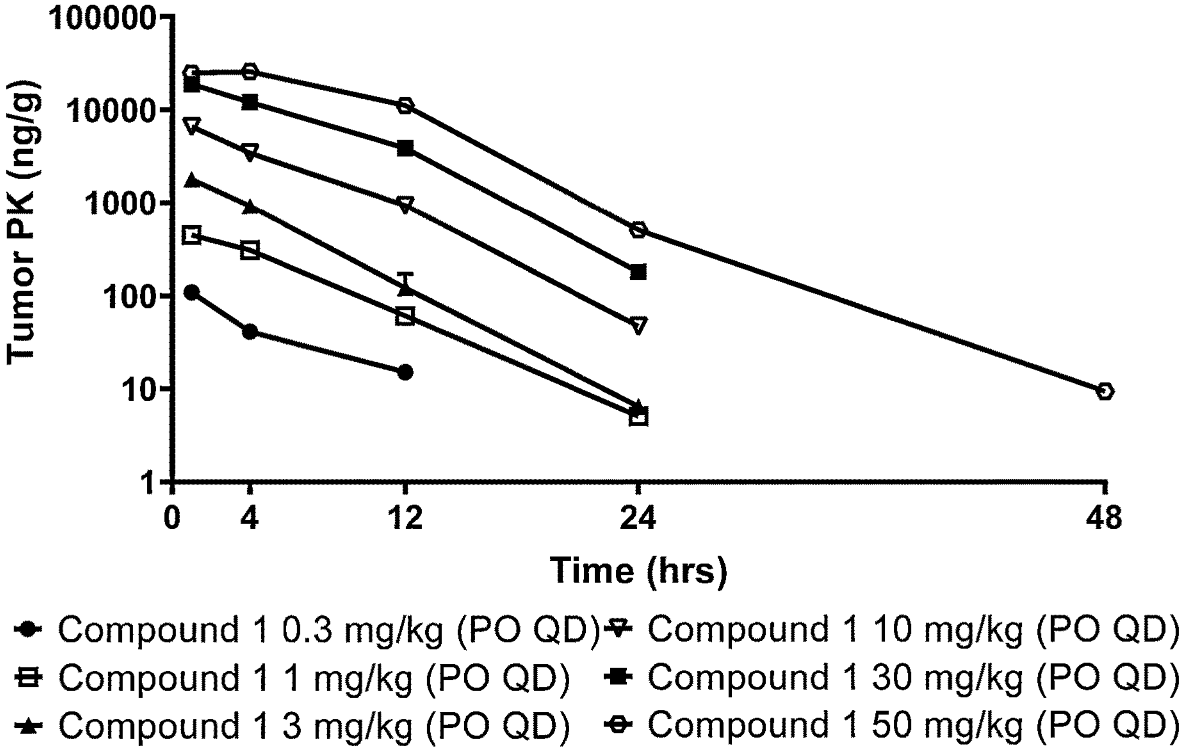

Tumor samples were collected in liquid nitrogen at 1, 4, 12, 24, and 48 hour time points for PK and PD and kept at −80° C. before bioanalysis. The harvested plasma and tumor were processed for pharmacokinetics analysis by LC-MS/MS with a concentration range of 0.5-10,000 ng/mL using an LC-MS/MS API 4000-003. The resulting data is shown in FIGS. 26 and 27.

Example 10 PDX SA13412 Tumor Model

Compound 1 was tested in the synovial sarcoma PDX model SA13412 (Crown Bioscience, San Diego, CA, USA). For efficacy portion, 8 animals per group were administered vehicle or Compound 1 orally at 1, 3, 10, 30, or 50 mg/kg once per day for 29 days. For pharmacodynamic portion, 6 animals per group were administered vehicle or Compound 1 orally at 1, 3, 10, 30, 50 mg/kg once per day for 18 days where tumor samples were then harvested.

Animals were shaved and ear tagged prior to injection. Frozen tumor chunks of SA13412 were thawed in a 37° C. water bath. Five total animals were inoculated with tumor chunks on both front flanks of female NSG mice. Each mouse received a single injection of buprenorphine 30 minutes before tumor chunk implantation. A sterile trocar was loaded with a 2×2 mm tumor fragment using forceps. The mice were anesthetized using isoflurane and the injection area were wiped thoroughly 2-3 times with a betadine-soaked gauze pad followed by 2-3 times with an alcohol-soaked gauze pad or swab. The trocar was inserted and the obturator depressed to release the fragment into the subcutaneous space. The trocar was slowly removed by using forceps to hold the skin in place while guiding the trocar out. The mice were then removed from the nose cone to recover from anesthesia and placed in a heated empty cage to recover. Mice were monitored until fully recovered from anesthesia prior to returning the mouse to their cage. Once the tumor volume reached 700 to 1000 $mm^3$, warm tumors were harvested and processed for tumor chunk inoculation.

After harvesting the warm tumors, the tumors were placed in a petri dish over ice in a biosafety cabinet, and washed with sterile cold PBS. Connective tissue, fat, excess skin and necrotic tissue were removed. Using a sterile scalpel, the tumor was sliced into 2-3 mm squared tumor fragments. The tumor fragments were transferred to a petri dish over ice and washed in cold PBS.

Mice were ear tagged and shaved prior to injection. Each mouse received a single injection of buprenorphine 30 minutes before tumor chunk implantation. A sterile trocar was loaded with a 2×2 mm tumor fragment using forceps. The mice were anesthetized using isoflurane and the injection area was wiped thoroughly 2-3 times with a betadine-soaked gauze pad followed by 2-3 times with an alcohol-soaked gauze pad or swab. The trocar was inserted and the obturator depressed to release the fragment into the front flank of the mouse. The trocar was slowly removed by using forceps to hold the skin in place while guiding the trocar out. The mice were then removed from the nose cone to recover from anesthesia and placed in a heated empty cage to recover. Mice were monitored until fully recovered from anesthesia prior to returning the mouse to their cage. The randomization started when the mean tumor size reached approximately 150 $mm^3$. A total of 84 mice were enrolled in the study and allocated into 6 groups, with 14 mice per group. Randomization was performed based on "Matched distribution" method (Study Director™ software).

Tumor volumes were measured 2 times per week after randomization in two dimensions using a caliper, and the volume was expressed in $mm^3$ using the formula: $V=(L\times W\times W)/2$, where V is tumor volume, L is tumor length (the longest tumor dimension) and W is tumor width (the longest tumor dimension perpendicular to L). Dosing as well as tumor and body weight measurements were conducted in a Laminar Flow Cabinet. The body weights and tumor volumes were measured by using Study Director™ software.

Figure 28:
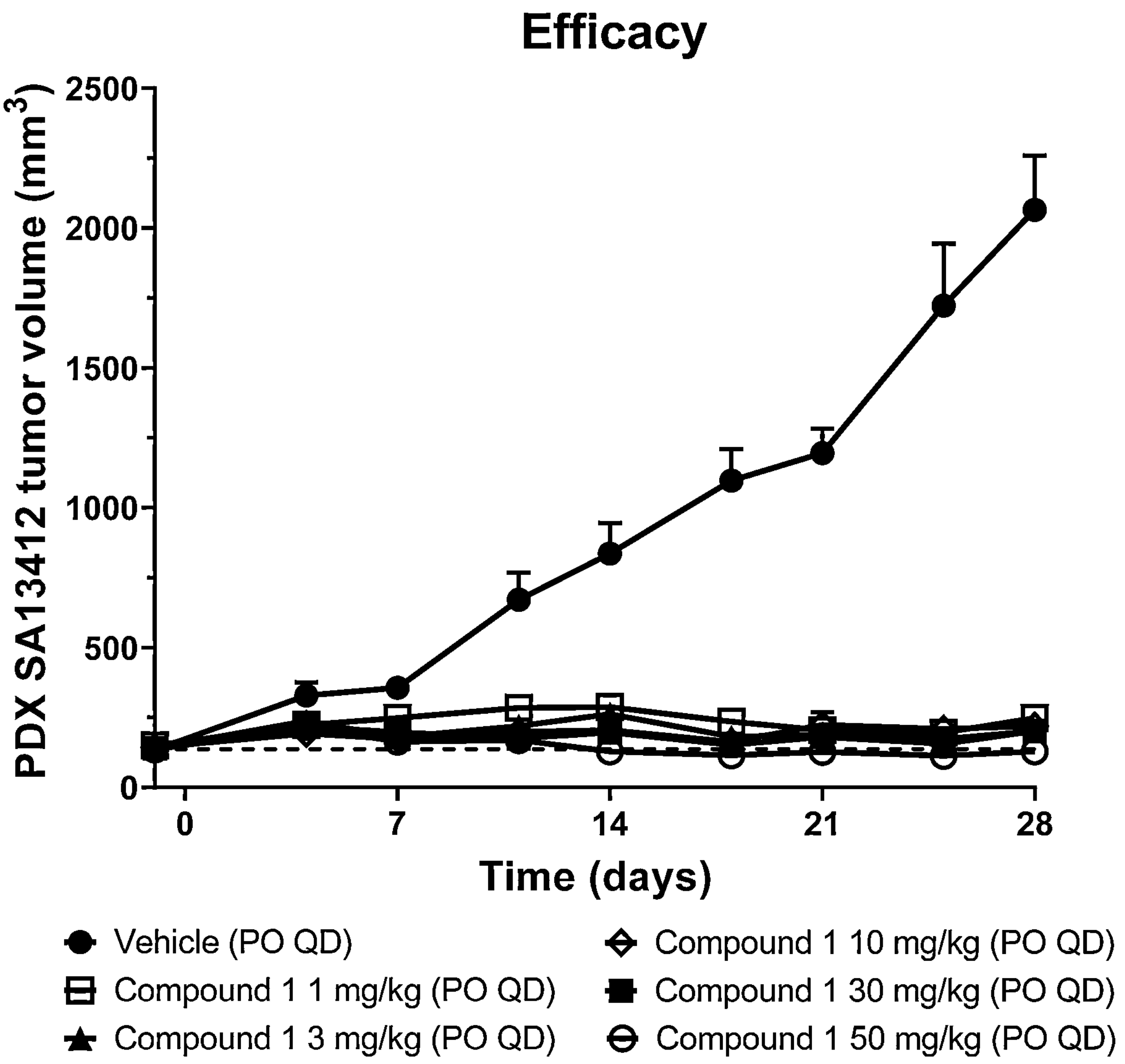
FIG. 28 depicts the robust efficacy response of Compound 1 in a SA13412 PDX model. The y-axis is tumor volume measured in $mm^3$ and the x-axis is time measured in days. The experimental procedure is provided in Example 10.

Tumors were collected at 4 hr post-last dose. The resulting data is shown in FIG. 28.

Pharmacodynamics

Figure 29:
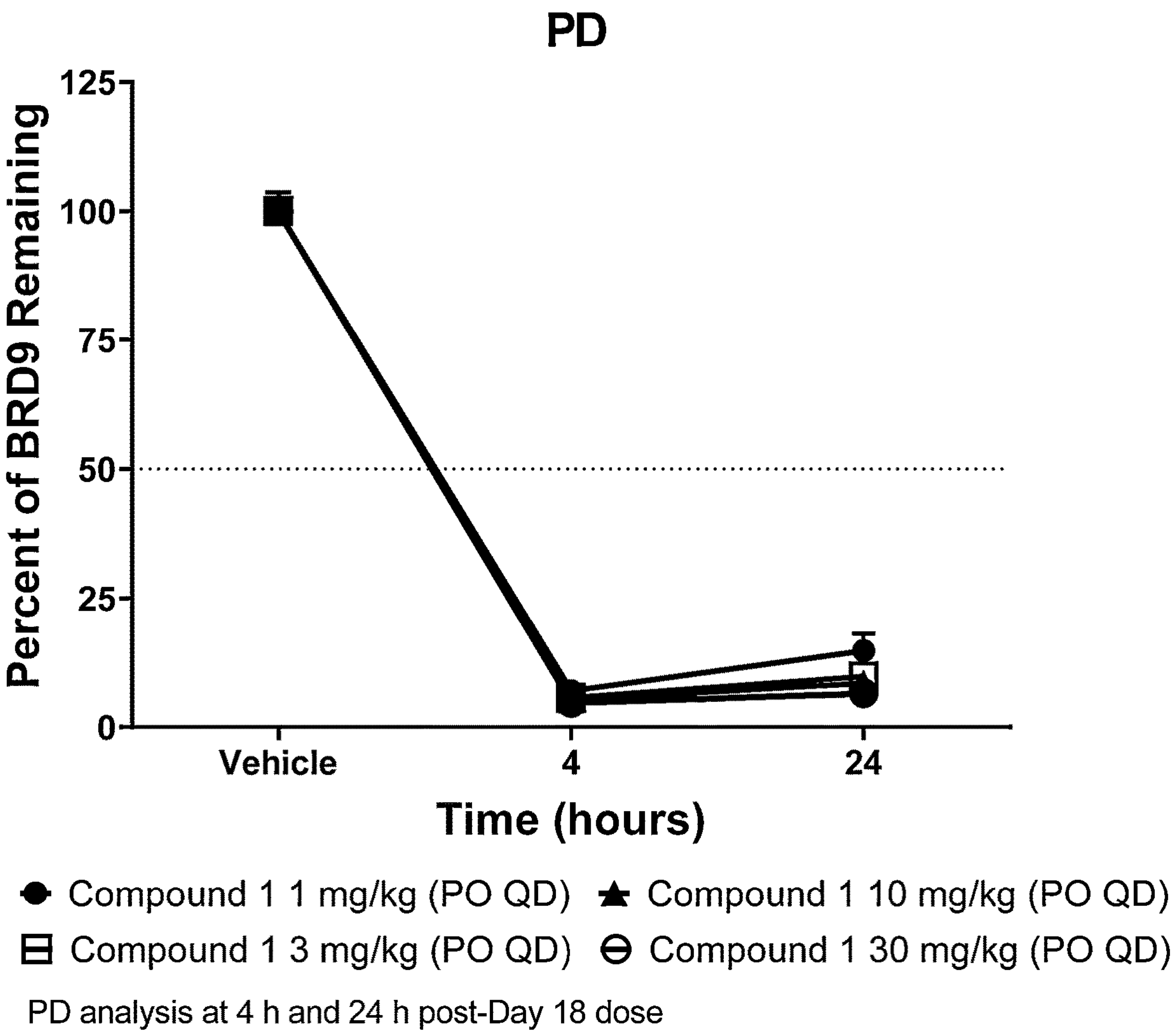
FIG. 29 depicts the percent of BRD9 remaining after dosing Compound 1 in a SA13412 PDX model. The y-axis is the amount of BRD9 remaining measured in percent and the x-axis is time measured in hours. The experimental procedure is provided in Example 10.

Final dose was on Day 18. Tumors were collected for PD at 4 hr post-dose (Day 18) and 24 hr post-dose (Day 19). The resulting data is shown in FIG. 29.

Protein Extraction & Protein Quantification

1) Take the snap-frozen tissues out from −80° C. freezer.
2) Cut up to about 30-100 mg of tissue. Place the tissues in a 2 mL microcentrifuge tube, and add 400 μL of RIPA Buffer (contains 1% Protease Inhibitor Cocktail and 1% Phosphatase Inhibitor Cocktail 2).
3) Grind tumors with Freeze grinder at 50 Hz for 5 min.
4) Keep the tissue lysates on ice for 30 min.
5) Centrifuge at 15,000 rpm at 4° C. for 10 min; gently transfer the supernatants to a new microcentrifuge tube kept on ice.
6) Measure protein concentrations by Pierce™ BCA Protein Assay Kit.
7) According to the result of BCA protein quantification, dilute all samples to the same final concentration (at 2 μg/μL) using RIPA buffer plus 4× LDS Sample Buffer and 10× Sample Reducing Agent. Heat the samples at 100° C. for 10 min.
8) Proceed to Western blotting or keep the denatured samples in the −80° C. refrigerator for long term storage.

Western Blotting

1) Load protein samples to NuPAGE® Novex 4-12% Bis-Tris gel, 10 μL per slot.
2) Electrophoresis with MES running buffer, 80 V for 30 min and then 120 V for 60 min.
3) Transfer protein to NC (nitrocellulose) membranes with iBlot® 2 Gel Transfer Device, P3, 7 min.
4) Cut the membrane and keep the interest parts, wash the membranes with 5-10 mL 1× TBS, once for 5 min.
5) Block the non-specific protein by 5-10 mL Intercept™ (TBS) Blocking Buffer at room temperature, 1 h.
6) Wash the membrane with 5-10 mL 1× TBST two times for 5 min each.
7) Incubate membrane with 5-10 mL diluted primary antibody (BRD9 antibody was diluted at a ratio of 1:1000, Vinculin antibody was diluted at a ratio of 1:10000) in Intercept™ (TBS) Blocking Buffer at 4° C., with gentle agitation overnight.
8) Wash the membrane with 5-10 mL 1× TBST three times for 10 min each.
9) Incubate membrane with 5-10 mL IRDye® 680RD Goat anti-Mouse IgG and IRDye® 800CW Goat Anti-Rabbit IgG secondary antibody (generally 1:10000) with gentle agitation in the dark for 1 h at room temperature.
10) Wash the membrane with 5-10 mL 1× TBST three times for 10 min each.
11) Wash the membranes with 5-10 mL 1× TBS two times for 5 min each.
12) Detect fluorescence signal by Odyssey CLx Imaging System.

Intensity of individual bands were quantified using Image Studio Lite Ver 5.2 software.

Example 11 CRT_SARC_310 Model os Synovial Sarcoma

Compound 1 was tested in the CRT_SARC_310 patient xenograft model of Synovial Sarcoma (Certis Oncology, San Diego, CA, USA). All agents were administered to NOG mice bearing CRT_SARC_310 tumors on day 0 and dosed PO daily for four weeks. Compound 1 was dosed at 1, 3, 10, 30, or 50 mg/kg. The last day all mice were on study was Day 28 when the vehicle control group had a MTV of 2291.9 $mm^3$.

Animals are anesthetized via isoflurane induction. The surgical site is shaved and prepared using aseptic technique to scrub the skin, alternating surgical scrub and alcohol-soaked gauze. Artificial tears are applied to the eyes. Animal is laid in left lateral recumbency. A medial incision is made with surgical scissors along the thigh. The skin surrounding the incision site is blunt dissected to gain visibility of the muscles. With a scalpel, a small pocket between the biceps femoris muscle and vastus lateralis is opened, and a tumor fragment of a 13.5 $mm^3$ volume is inserted. The muscle is then released and the bicep femoris and vastus lateralis muscles are sutured using absorbable sutures, sealing the tumor fragment in place. The wound is closed by suture. Post-operative analgesic is administered.

Prior to the onset of drug treatment, mice were measured for tumor growth using the Aspect Imaging M3 MRI, and the tumor volume ($mm^3$) was calculated quantified using VivoQuant software. Mice were randomized into different treatment groups based on the tumor volume and imaged weekly thereafter.

The major endpoint was to see if the tumor growth could be delayed or mice could be cured. The tumor size was then used for calculations of T/C value. The T/C value (in percent) is an indication of antitumor effectiveness; T and C are the mean volumes of the treated and control groups, respectively on specified day.

TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Figure 30:
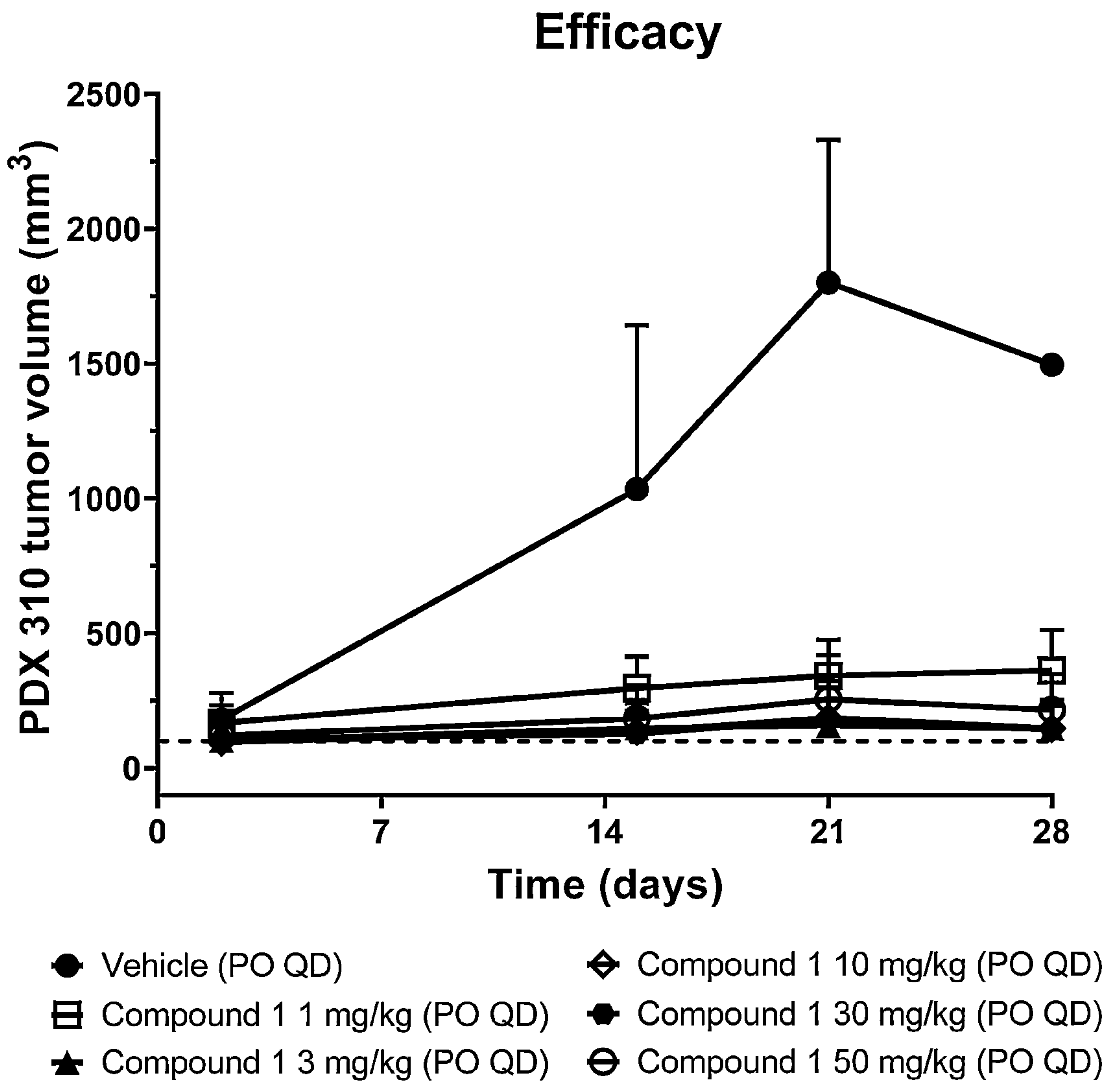
FIG. 30 depicts the robust efficacy response of Compound 1 in a 310 PDX model. The y-axis is tumor volume measured in $mm^3$ and the x-axis is time measured in days. The experimental procedure is provided in Example 11.

Tumors were collected at 4 hr post-last dose. The resulting data is shown in FIG. 30.

Example 12 PDX SA13412 Tumor Model—Durability of Response

Compound 1 was tested in the synovial sarcoma PDX model SA13412 (Crown Bioscience, San Diego, CA, USA). Mice were administered Compound 1 orally at 50 mg/kg/day either as once daily, twice daily, or three times daily treatment. The last day of treatment for vehicle mice was day 35 when mean tumor volume was 1529.51 $mm^3$. Treatment mice continued dosing to day 89 with an additional 51-day observation period.

Female NOD/SCID mice were inoculated with single cell suspensions dual rear flank. Once the tumor volume reached approximately 700 to 1000 $mm^3$, warm tumors were harvested and processed for tumor chunk inoculation.

After harvesting the warm tumors, the tumors were placed in a petri dish over ice in a biosafety cabinet, and washed with sterile cold PBS. Connective tissue, fat, excess skin and necrotic tissue were removed. Using a sterile scalpel, the tumors were sliced into 2-3 mm squared tumor fragments. The tumor fragments were transferred to a petri dish over ice and washed in cold PBS.

Mice were ear tagged and shaved prior to injection. Each mouse received a single injection of buprenorphine 30 minutes before tumor chunk implantation. A sterile trocar was loaded with a 2×2 mm tumor fragment using forceps. The mice were anesthetized using isoflurane and the injection area were wiped thoroughly 2-3 times with a betadine-soaked gauze pad followed by 2-3 times with an alcohol-soaked gauze pad or swab. The trocar was inserted and the obturator depressed to release the fragment into the front flank of the mouse. The trocar was slowly removed by using forceps to hold the skin in place while guiding the trocar out. The mice were be removed from the nose cone to recover from anesthesia and placed in a heated empty cage to recover. Mice were monitored until fully recovered from anesthesia prior to returning the mouse to their cage. The randomization started when the mean tumor size reached approximately 208.58-209.06 $mm^3$. A total of 32 mice were enrolled in the study and allocated into 4 groups with n=8 mice per group. Randomization was performed based on "Matched distribution" method (Study Director™ software).

Figure 31:
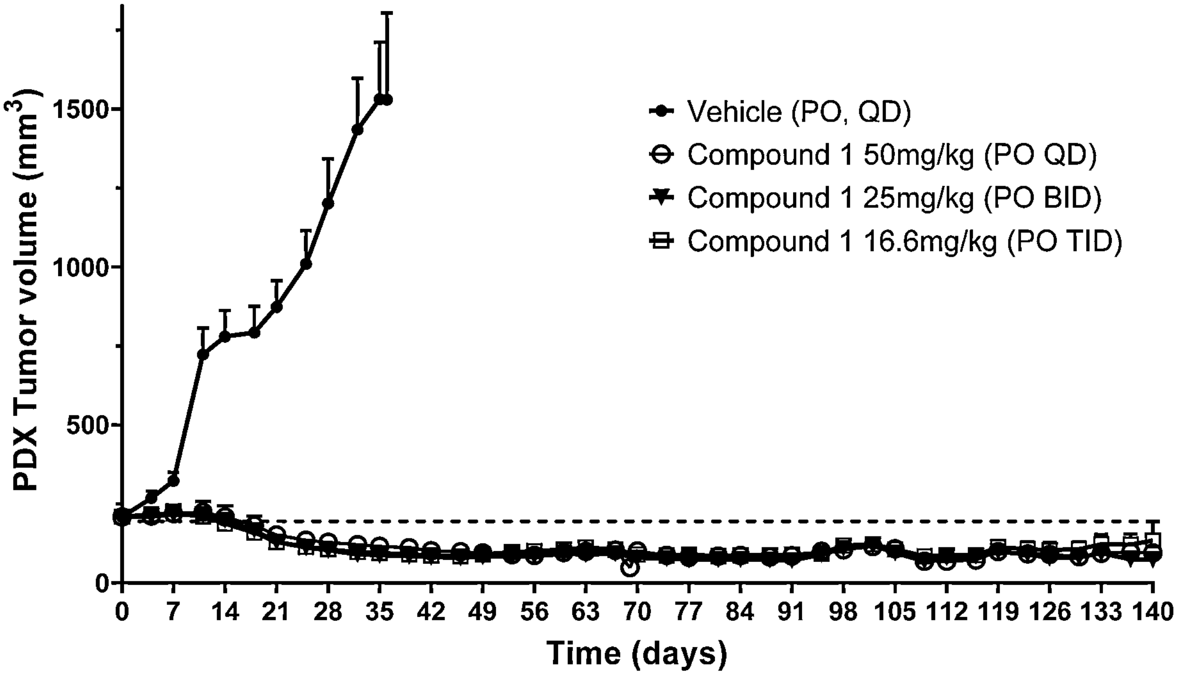
FIG. 31 depicts the antitumor effect of Compound 1 in a SA13412 PDX model over a prolonged period of time. The y-axis is tumor volume measured in $mm^3$ and the x-axis is time measured in days. The experimental procedure is provided in Example 12.
Figure 32:
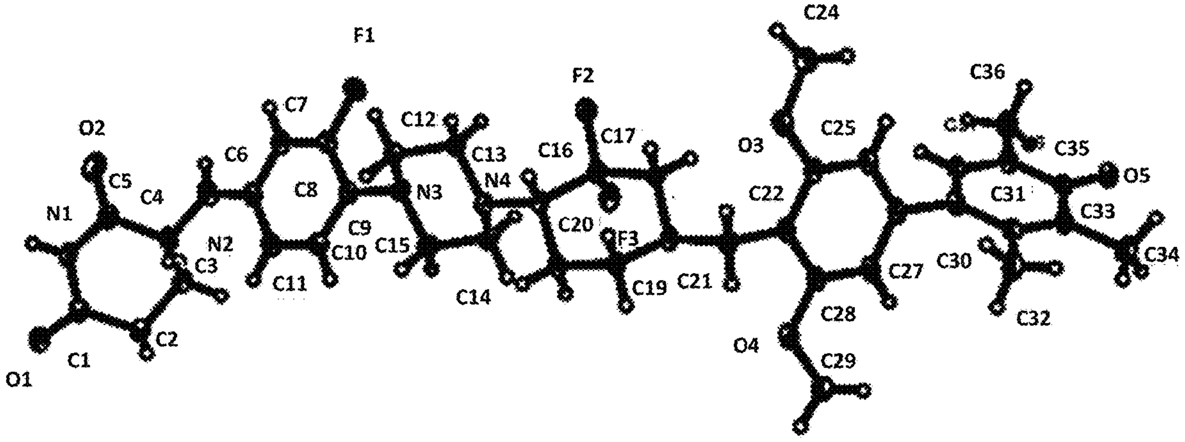
FIG. 32 depicts a single crystal structure of Compound 2.

Tumor volumes were measured 2 times per week after randomization in two dimensions using a caliper, and the volume was expressed in $mm^3$ using the formula: $V=(L\times W\times W)/2$, where V is tumor volume, L is tumor length (the longest tumor dimension) and W is tumor width (the longest tumor dimension perpendicular to L). Dosing as well as tumor and body weight measurements were conducted in a Laminar Flow Cabinet. The body weights and tumor volumes were measured by using Study Director™ software. The resulting data is shown in FIG. 31.

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modification may be made thereto without departing from the spirit or scope of the invention as defined in the appended claims. Additionally, those skilled in the art will recognize, or be able to ascertain using no more than routine experimentation, many equivalents to the specific embodiments and methods described herein. Such equivalents are intended to be encompassed by the scope of the present application.

We claim:

1. A method for the treatment of an unresectable cancer mediated by BRD9 in a human, comprising administering to the human an effective amount of a compound of Formula:

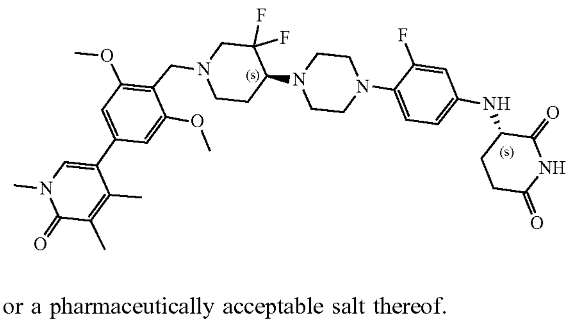

or a pharmaceutically acceptable salt thereof.

2. The method of claim 1, wherein the cancer is relapsed.

3. The method of claim 1, wherein the cancer is refractory.

4. The method of claim 1, wherein the cancer is a SMARCB1-perturbed cancer.

5. The method of claim 1, wherein the cancer is selected from synovial sarcoma, malignant rhabdoid tumor, atypical teratoid rhabdoid tumor, cribriform neuroepithelial tumor, renal medullary carcinoma, epithelioid sarcoma, epithelioid malignant peripheral nerve sheath tumor, schwannomas in familial schwannomatosis, chordoma, myoepithelial carcinoma, and sinonasal carcinoma.

6. The method of claim 1, wherein the cancer is synovial sarcoma.

7. The method of claim 1, wherein the cancer is a soft tissue sarcoma.

8. The method of claim 1, wherein the cancer is a clear cell renal cell carcinoma.

9. The method of claim 1, wherein the cancer is multiple myeloma.

10. The method of claim 1, wherein one or more additional therapeutically active agents are administered.

11. A method for the treatment of a cancer mediated by BRD9 in a human, comprising administering to the human an effective amount of a compound of Formula:

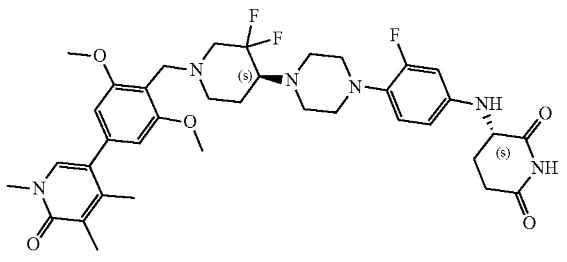 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof, wherein the cancer is an epithelioid malignant peripheral nerve sheath tumor, schwannomas in familial schwannomatosis, atypical malignant teratoid rhabdoid tumor, or cribriform neuroepithelial tumor.

12. The method of claim 11, wherein one or more additional therapeutically active agents are administered.

13. A method for preventing the recurrence of a BRD9 mediated disorder in a human comprising administering to the human an effective amount of a compound of Formula:

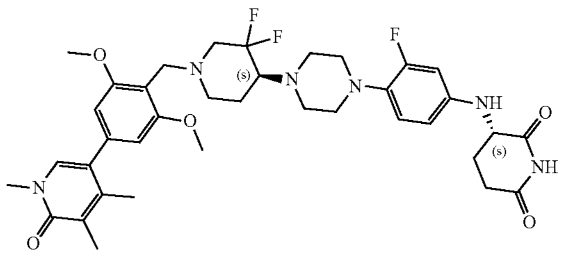 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof.

14. The method of claim 13, wherein the BRD9 mediated disorder is a cancer.

15. The method of claim 14, wherein the cancer is a SMARCB1-perturbed cancer.

16. The method of claim 14, wherein the cancer is selected from synovial sarcoma, malignant rhabdoid tumor, atypical teratoid rhabdoid tumor, cribriform neuroepithelial tumor, renal medullary carcinoma, epithelioid sarcoma, epithelioid malignant peripheral nerve sheath tumor, schwannomas in familial schwannomatosis, chordoma, myoepithelial carcinoma, and sinonasal carcinoma.

17. The method of claim 14, wherein the cancer is synovial sarcoma.

18. The method of claim 14, wherein the cancer is a soft tissue sarcoma.

19. The method of claim 14, wherein the cancer is a clear cell renal cell carcinoma.

20. The method of claim 14, wherein the cancer is multiple myeloma.

21. The method of claim 14, wherein one or more additional therapeutically active agents are administered.

* * * * *